United States Patent
Huang et al.

(10) Patent No.: US 10,493,060 B2
(45) Date of Patent: Dec. 3, 2019

(54) SPIROCYCLIC COMPOUNDS

(71) Applicant: ZENO ROYALTIES & MILESTONES, LLC, San Diego, CA (US)

(72) Inventors: Peter Qinhua Huang, San Diego, CA (US); Mehmet Kahraman, San Diego, CA (US); Deborah Helen Slee, Encinitas, CA (US); Kevin Duane Bunker, Escondido, CA (US); Chad Daniel Hopkins, San Diego, CA (US); Joseph Robert Pinchman, San Diego, CA (US); Sunny Abraham, San Diego, CA (US); Rakesh Kumar Sit, San Diego, CA (US); Daniel Lee Severance, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/354,949

(22) Filed: Mar. 15, 2019

(65) Prior Publication Data

US 2019/0201380 A1    Jul. 4, 2019

Related U.S. Application Data

(62) Division of application No. 15/563,926, filed as application No. PCT/US2016/025345 on Mar. 31, 2016.

(60) Provisional application No. 62/142,946, filed on Apr. 3, 2015.

(51) Int. Cl.

| | |
|---|---|
| *C07D 487/10* | (2006.01) |
| *A61K 31/4162* | (2006.01) |
| *C07D 471/10* | (2006.01) |
| *A61P 35/00* | (2006.01) |
| *A61K 31/416* | (2006.01) |

(52) U.S. Cl.
CPC ........ *A61K 31/4162* (2013.01); *A61K 31/416* (2013.01); *A61P 35/00* (2018.01); *C07D 471/10* (2013.01); *C07D 487/10* (2013.01)

(58) Field of Classification Search
None
See application file for complete search history.

(56) References Cited

U.S. PATENT DOCUMENTS

| | | |
|---|---|---|
| 2014/0135335 A1 | 5/2014 | Wang et al. |
| 2014/0275245 A1 | 9/2014 | Bunker |

FOREIGN PATENT DOCUMENTS

| | | |
|---|---|---|
| CN | 103130775 A | 6/2013 |
| CN | 105732636 A | 7/2016 |
| WO | WO 2008/063609 | 5/2008 |
| WO | WO 2010/027567 | 3/2010 |
| WO | WO 2011/071860 | 6/2011 |
| WO | WO 2013/033059 | 3/2013 |
| WO | WO 2016/161160 | 10/2016 |
| WO | WO 2018/067512 | 4/2018 |

OTHER PUBLICATIONS

Adjei, A.A., "The role of mitogen-activated ERK-kinase inhibitors in lung cancer therapy" Clin. Lung. Cancer (2005) 7(3):221-223.
Buonata et al., "ERK1/2 blockade prevents epithelial-mesenchymal transition in lung cancer cells and promotes their sensitivity to EGFR inhibition" Cancer Res (2014) 74(1):309-319.
Carlo-Stella et al., "Sorafenib inhibits lymphoma xenografts by targeting MAPK/ERK and AKT pathways in tumor and vascular cells" PLoS One (2013) 8(4):e61603.
Chambers et al., "Self-renewal of teratocarcinoma and embryonic stem cells" Oncogene (2004) 23(43):7150-7160.
Chen et al., "Glioma cell proliferation controlled by ERK activity-dependent surface expression of PDGFRA" PLoS One (2014) 9(1):e87281.
Chen et al., "Expression and prognostic role of MEKK3 and pERK in patients with renal clear cell carcinoma" Asian Pac J Cancer Prev (2015) 16(6):2495-2499.
Fang et al., "The MAPK signalling pathways and colorectal cancer" Lancet Oncol (2005) 6(5):322-327.
Hayes, et al., "Long-Term ERK Inhibition in KRAS-Mutant Pancreatic Cancer Is Associated with MYC Degradation and Senescence-like Growth Suppression" Cancer Cell (2016) 29(1):75-89 with Supplemental Information.
Huang et al., "Apelin-13 induces autophagy in hepatoma HepG2 cells through ERK1/2 signaling pathway-dependent upregulation of Beclin1" Oncol Lett (2016) 11(2):1051-1056.
Jimenez et al., "Mechanisms of Invasion in Head and Neck Cancer" Arch Pathol Lab Med (2015) 139(11):1334-1348.
Jin et al., "USO1 promotes tumor progression via activating Erk pathway in multiple myeloma cells" Biomed Pharmacother (2016) 78:264-271.
Khavari et al., "Ras/Erk MAPK signaling in epidermal homeostasis and neoplasia" Cell Cycle (2007) 6(23)2928-2931.
Maiello et al., "EGFR and MEK Blockade in Triple Negative Breast Cancer Cells" J Cell Biochem (2015) 116(12):2778-2785.
Milosevic et al., "Targeting RAS-MAPK-ERK and PI3K-AKT-mTOR signal transduction pathways to chemosensitize anaplastic thyroid carcinoma" Transl Res (2014) 164(5):411-423.

(Continued)

*Primary Examiner* — Heidi Reese

(74) *Attorney, Agent, or Firm* — Knobbe Martens Olson & Bear LLP

(57) ABSTRACT

Disclosed herein are spirocyclic compounds, together with pharmaceutical compositions and methods of ameliorating and/or treating a cancer described herein with one or more of the compounds described herein.

11 Claims, No Drawings

Specification includes a Sequence Listing.

(56) References Cited

OTHER PUBLICATIONS

Morris et al., "Discovery of a novel ERK inhibitor with activity in models of acquired resistance to BRAF and MEK inhibitors" Cancer Discov (2013) 3(7):742-750.

Noguchi et al., "Replacement treatment with microRNA-143 and -145 induces synergistic inhibition of the growth of human bladder cancer cells by regulating PI3K/Akt and MAPK signaling pathways" Cancer Lett (2013) 328(2):353-361.

Roberts et al., "Targeting the Raf-MEK-ERK mitogen-activated protein kinase cascade for the treatment of cancer" Oncogene (2007) 26(22):3291-3310.

Rodriguez-Berriguete et al., "Relationship between IL-6/ERK and NF-κB: a study in normal and pathological human prostate gland" Eur Cytokine Netw (2010) 21(4):241-250.

Serrano et al., "RAS/MAPK pathway hyperactivation determines poor prognosis in undifferentiated pleomorphic sarcomas" Cancer (2016) 122(1):99-107.

Sheppard et al., "Synergistic inhibition of ovarian cancer cell growth by combining selective PI3K/mTOR and RAS/ERK pathway inhibitors" Eur J Cancer (2013) 49(18):3936-3944.

Steelman et al., "Roles of the Ras/Raf/MEK/ERK pathway in leukemia therapy" Leukemia (2011) 25(7):1080-1094.

Vieira et al., "LGR5 regulates pro-survival MEK/ERK and proliferative Wnt/β-catenin signalling in neuroblastoma" Oncotarget (2015) 6(37):40053-40067.

Wang et al., "ERK inhibition rescues defects in fate specification of Nf1-deficient neural progenitors and brain abnormalities" Cell (2012) 150(4):816-830 with Supplemental Information.

International Search Report and Written Opinion dated May 23, 2016 for PCT Application No. PCT/US2016/025345, filed Mar. 31, 2016.

International Preliminary Report on Patentability dated Oct. 3, 2017 for PCT Application No. PCT/US2016/025345, filed Mar. 31, 2016.

Extended European Search Report dated Jul. 23, 2018 for EP Application No. 16774232.9, filed Mar. 31, 2016.

Search Report and Written Opinion completed Aug. 6, 2018 for SG Application No. 11201707911V, filed Mar. 31, 2016.

Office Action dated Sep. 19, 2018 for U.S. Appl. No. 15/563,926, filed Oct. 2, 2017.

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: ARTIFICIALLY SYNTHESIZED PEPTIDE
<220> FEATURE:
<221> NAME/KEY: VARIANT
<222> LOCATION: (14)...(14)
<223> OTHER INFORMATION: Xaa=Lysine-CONH2

<400> SEQUENCE: 1

Ile Pro Thr Thr Pro Ile Thr Thr Thr Tyr Phe Phe Phe Xaa
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: ARTIFICIALLY SYNTHESIZED PEPTIDE
<220> FEATURE:
<221> NAME/KEY: VARIANT
<222> LOCATION: (14)...(14)
<223> OTHER INFORMATION: Xaa=Lysine-5-carboxyfluorescein)-CONH2

<400> SEQUENCE: 2

Ile Pro Thr Thr Pro Ile Thr Thr Thr Tyr Phe Phe Phe Xaa
 1               5                  10
```

SPIROCYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

REFERENCE TO SEQUENCE LISTING

The present application is filed with a Sequence Listing in Electronic format. The Sequence Listing is provided as a file entitled ZENO001.txt, created Mar. 15, 2019, which is approximately 4 kb in size. The information in the electronic format of the sequence listing is incorporated herein by reference in its entirety.

BACKGROUND

Field

The present application relates to the fields of chemistry, biochemistry and medicine. More particularly, disclosed herein are spirocyclic compounds, together with pharmaceutical compositions, and methods of synthesizing the same. Also disclosed herein are methods of ameliorating and/or treating a cancer described herein with one or more of the compounds described herein.

Description

The RAS/MAPK pathway is activated in response to growth factor binding and regulates cellular growth, differentiation and survival in a variety of cell types. Activation of this pathway occurs via a cascade of protein phosphorylation events, which culminates in the phosphorylation and activation of ERK (ERK1 and/or ERK2). ERK lies downstream from the small GTPase RAS and the protein kinases RAF and MEK in the RAS/MAPK pathway. Following its activation by RAS, RAF phosphorylates MEK, which in turn phosphorylates ERK. Activated ERK phosphorylates other substrates that govern the transcriptional output of cells.

SUMMARY

Some embodiments disclosed herein relate to a compound of Formula (I), or a pharmaceutically acceptable salt thereof. Some embodiments disclosed herein related to compound that include a bicyclo[1.1.1]pentyl moiety.

Some embodiments described herein relate to a pharmaceutical composition, that can include an effective amount a compound of Formula (I), or a pharmaceutically acceptable salt thereof.

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein that can include contacting a malignant growth or a tumor, wherein the malignant growth or tumor is due to a cancer described herein.

Some embodiments described herein relate to a method for inhibiting the activity of ERK1 and/or ERK2 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a sample that includes a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of ERK1 and/or ERK2. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of ERK1 and/or ERK2.

Some embodiments described herein relate to a method for ameliorating or treating a cancer described herein that can include inhibiting the activity of ERK1 and/or ERK2 using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of ERK1 and/or ERK2. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of ERK1 and/or ERK2.

DETAILED DESCRIPTION

Inhibition of ERK can have therapeutic effects in the treatment of certain types of cancer. It has been shown that the RAS/MAPK/ERK pathway can be aberrantly activated in certain tumors via activating mutations in RAS and BRAF, and this activation has been implicated in the growth and pathologic behavior of certain cancer cells. Constitutive activation of this pathway has been observed in human cancers and has been associated with high rates of cancer cell proliferation. Tumor cells that harbor either BRAF or RAS mutations are generally dependent on the activity of the altered proteins for growth and survival, a phenomenon described as "oncogene addiction." Activating mutations of RAS have been reported in ~30% of all cancers, with some, such as pancreatic and colon cancer, harboring mutation rates of ~90% and ~50%, respectively. RAS mutations have been identified in ~15% of melanomas and ~30% of NSCLCs (non-small cell lung cancers). BRAF somatic mutations have been identified in 50-70% of malignant melanomas, where all mutations are within the kinase domain and a single substitution (V600E) accounts for 80% of mutations. Activating BRAF mutations have also been documented in a variety of human cancers, including colorectal cancer (~10%), NSCLC (2-3%), and thyroid cancer (~36%). The high frequency of mutations makes targeting this pathway a strategy for cancer therapy. Accordingly, there is a large unmet medical need for improved therapies in these diseases especially in the advanced, refractory setting.

Provided herein are compounds that can inhibit the kinase activity of ERK1 and/or the kinase activity of ERK2. The compounds described herein can also inhibit the phosphorylation of ERK1 and ERK2, and thus can be ERK inhibitors (for example, ERK1 inhibitors and/or ERK2 inhibitors). The compounds described herein may also effectively inhibit MAPK signaling through a dual mechanism, via inhibiting both the phosphorylation and activation of ERK by MEK, in addition to inhibiting ERK phosphorylation of RSK. As ERK inhibitors, the compounds described herein can be used to ameliorate and/or treat a variety of cancers, such as, lung cancer, pancreatic cancer, colon cancer, myeloid leukemia, thyroid cancer, myelodysplastic syndrome (MDS), bladder carcinoma, epidermal carcinoma, melanoma, breast cancer, prostate cancer, head and neck cancer, ovarian cancer, brain cancer, cancer of mesenchymal origin, sarcoma, tetracarcinoma, neuroblastoma, kidney carcinoma, hepatoma, non-Hodgkin's lymphoma, multiple myeloma and anaplastic thyroid carcinoma.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^{1a1}$, $R^{1a2}$, $R^{1b}$, $R^{2a}$, $R^{2b}$, $R^{2c}$, $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{4a}$, $R^{4b}$, $R^{5a}$, $R^{5b}$, $R^{5c}$, $R^{5d}$, $R^{5e}$, $R^{5f}$, $R^{5g}$, $R^{5h}$, $R^{5i}$, $R^{5j}$, $R^{5k}$, $R^{5l}$ and $R^6$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

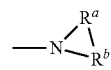

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, acylalkyl, hydroxy, alkoxy, alkoxyalkyl, aminoalkyl, amino acid, aryl, heteroaryl, heterocyclyl, aryl (alkyl), heteroaryl(alkyl), heterocyclyl(alkyl), hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, bicylco[2.1.1] heptane, adamantanyl, and norbornanyl; and examples of spiro cycloalkyl groups include spiro[3.3]heptane and spiro [4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one, two, three or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused or spiro fashion, as described herein with respect to "cycloalkyl." Additionally, any nitrogens in a heterocyclyl may be quaternized. Heterocyclyl or heteroalicyclic groups may be unsubstituted or substituted. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3,4-oxadiazol-2(3H)-one, 1,2,3-oxadiazol-5(2H)-one, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidone, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "acylalkyl" refers to an acyl connected, as a substituent, via a lower alkylene group. Examples include aryl-C(=O)—$(CH_2)_n$— and heteroaryl-C(=O)—$(CH_2)_n$—, where n is an integer in the range of 1 to 6.

As used herein, "alkoxyalkyl" refers to an alkoxy group connected, as a substituent, via a lower alkylene group. Examples include $C_{1-4}$ alkyl-O—$(CH_2)_n$—, wherein n is an integer in the range of 1 to 6.

As used herein, "aminoalkyl" refers to an optionally substituted amino group connected, as a substituent, via a lower alkylene group. Examples include $H_2N(CH_2)_n$—, wherein n is an integer in the range of 1 to 6.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chloro-fluoroalkyl, chloro-difluoroalkyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "$RC(=O)O-$" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "$-C(=O)OR$" group in which R can be the same as defined with respect to O-carboxy. An ester and C-carboxy may be substituted or unsubstituted.

A "thiocarbonyl" group refers to a "$-C(=S)R$" group in which R can be the same as defined with respect to O-carboxy. A thiocarbonyl may be substituted or unsubstituted.

A "trihalomethanesulfonyl" group refers to an "$X_3CSO_2-$" group wherein each X is a halogen.

A "trihalomethanesulfonamido" group refers to an "$X_3CS(O)_2N(R_A)-$" group wherein each X is a halogen, and $R_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

The term "amino" as used herein refers to a $-NH_2$ group.

As used herein, the term "hydroxy" refers to a $-OH$ group.

A "cyano" group refers to a "$-CN$" group.

The term "azido" as used herein refers to a $-N_3$ group.

An "isocyanato" group refers to a "$-NCO$" group.

A "thiocyanato" group refers to a "$-CNS$" group.

An "isothiocyanato" group refers to an "$-NCS$" group.

A "carbonyl" group refers to a $C=O$ group.

An "S-sulfonamido" group refers to a "$-SO_2N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "$RSO_2N(R_A)-$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "$-OC(=O)N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "$ROC(=O)N(R_A)-$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "$-OC(=S)-N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "$ROC(=S)N(R_A)-$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "$-C(=O)N(R_AR_B)$" group in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "$RC(=O)N(R_A)-$" group in which R and $R_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

A "urea" group refers to "$N(R)-C(=O)-NR_AR_B$ group in which R can be hydrogen or an alkyl, and $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A urea may be substituted or unsubstituted.

An "oxime" group refers to "$-C(=N-OH)R_A$" in which $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An oxime may be substituted or unsubstituted.

An "acyl hydrozone" refers to "$-C(=N-NH-acyl)-R_A$." in which the acyl portion has the structure as provided herein for "acyl", and $R_A$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An acyl hydrozone may be substituted or unsubstituted.

A "hydrazine" refers to "$-NHNR_AR_B$" in which $R_A$ and $R_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A hydrazine may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, "------" indicates a single or double bond, unless stated otherwise.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates, mesylates, trifluoroacetates and halogens (e.g., I, Br, and Cl). Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* 5$^{th}$ ed., John McMurry (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z, or a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds
Formula (I)

Some embodiments disclosed herein relate to a compound of Formula (I), or a pharmaceutically acceptable salt thereof, having the structure:

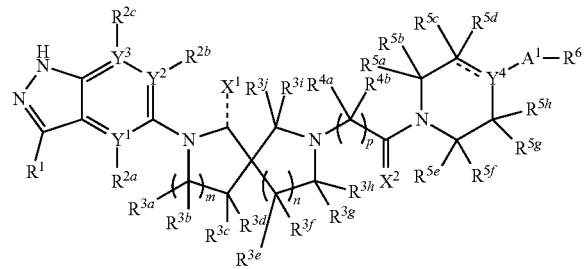

wherein: $R^1$ can be selected from hydrogen, an optionally substituted alkyl, an optionally substituted alkenyl, an optionally substituted cycloalkyl, an optionally substituted cycloalkenyl, an optionally substituted aryl, an optionally substituted heteroaryl, an optionally substituted heterocyclyl, an optionally substituted cycloalkyl(alkyl), an optionally substituted cycloalkenyl(alkyl), an optionally substituted aryl(alkyl), an optionally substituted heteroaryl(alkyl), an optionally substituted heterocyclyl(alkyl), hydroxy, an optionally substituted alkoxy, cyano, an optionally substituted C-carboxy, an optionally substituted N-amido, an optionally substituted urea, nitro, an optionally substituted sulfenyl, an optionally substituted haloalkyl, amino, an optionally substituted mono-substituted amino group, an optionally substituted di-substituted amino group and —$(CR^{1a1}R^{1a2})_q$-$R^{1b}$, wherein q can be 1, 2, 3, 4, 5 or 6, each $R^{1a1}$ and each $R^{1a2}$ each can be independently hydrogen, halogen or an unsubstituted alkyl, and $R^{1b}$ can be selected from hydroxy, an optionally substituted N-amido, an optionally substituted N-sulfinamido, an optionally substituted N-sulfonamido, an optionally substituted urea, an optionally substituted sulfenyl, amino, an optionally substituted mono-substituted amino group and an optionally substituted di-substituted amino group; $Y^1$, $Y^2$ and $Y^3$ can be independently C (carbon) or N (nitrogen), provided that when $Y^1$ is C (carbon), then $R^{2a}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group, and when $Y^1$ is N (nitrogen), then $R^{2a}$ is absent, provided that when $Y^2$ is C (carbon), then $R^{2b}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group, and when $Y^2$ is N (nitrogen), then $R^{2b}$ is absent, provided that when $Y^3$ is C (carbon), then $R^{2c}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group, and when $Y^3$ is N, then $R^{2c}$ is absent, each $R^{3a}$, each $R^{3b}$, $R^{3c}$, $R^{3d}$, each $R^{3e}$, each $R^{3f}$, $R^{3g}$, $R^{3h}$, $R^{3i}$ and $R^{3j}$ can be independently selected from hydrogen, halogen, an optionally substituted alkyl, an optionally substituted alkenyl, an optionally substituted alkynyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl) hydroxy, an optionally substituted alkoxy, an optionally substituted haloalkoxy, cyano, an optionally substituted N-amido, an optionally substituted C-carboxy, an optionally substituted oxime, an optionally substituted acyl hydrozone, an optionally substituted sulfenyl, an optionally substituted sulfinyl, an optionally substituted sulfonyl, amino, an optionally substituted mono-substituted amino group, an optionally substituted di-substituted amino group and —(CH$_2$)r-R$^{3k}$, wherein r can be 1, 2, 3, 4, 5 or 6, and R$^{3k}$ can be selected from halo, hydroxy, cyano, an optionally substituted heteroaryl, an optionally substituted alkoxy, an optionally substituted sulfenyl and an optionally substituted hydrazine; each R$^{4a}$ and each R$^{4b}$ can be independently hydrogen, deuterium or an optionally substituted alkyl; R$^{5a}$, R$^{5b}$, R$^{5c}$, R$^{5e}$, R$^{5f}$, R$^{5g}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy; or R$^{5b}$ and R$^{5c}$ can be taken together to form an optionally substituted cycloalkyl, an optionally substituted aryl or an optionally substituted heterocyclyl, and R$^{5a}$, R$^{5e}$, R$^{5f}$, R$^{5g}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy; or R$^{5f}$ and R$^{5g}$ can be taken together to form an optionally substituted cycloalkyl, an optionally substituted aryl or an optionally substituted heterocyclyl, R$^{5a}$, R$^{5b}$, R$^{5c}$, R$^{5e}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy; or R$^{5b}$ and R$^{5c}$ can be taken together to form an optionally substituted cycloalkyl, an optionally substituted aryl or an optionally substituted heterocyclyl, and R$^{5f}$ and R$^{5g}$ can be taken together to form an optionally substituted cycloalkyl, an optionally substituted aryl or an optionally substituted heterocyclyl, and R$^{5a}$, R$^{5e}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy; or R$^{5b}$ and R$^{5g}$ can be connected via Y$^5$, wherein Y$^5$ is (CR$^{5i}$R$^{5j}$)s, wherein s can be 1, 2 or 3, and each R$^{5i}$ and each R$^{5j}$ can be independently hydrogen, halogen or an unsubstituted alkyl, and R$^{5a}$, R$^{5c}$, R$^{5e}$, R$^{5f}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl (alkyl), an optionally substituted heteroaryl(alkyl), an optionally substituted heterocyclyl(alkyl) and an optionally substituted C-carboxy; R$^{5c}$ and R$^{5e}$ can be connected via Y$^6$, wherein Y$^6$ can be (CR$^{5k}$R$^{5l}$)t, wherein t can be 1, 2 or 3, and each R$^{5k}$ and each R$^{5l}$ can be independently hydrogen, halogen or an unsubstituted alkyl, and R$^{5a}$, R$^{5b}$, R$^{5f}$, R$^{5g}$ and R$^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy; R$^6$ can be an optionally substituted aryl, an optionally substituted heteroaryl or an optionally substituted heterocyclyl; A$^1$ can be selected from an optionally substituted C$_{3-10}$ cycloalkyl, an optionally substituted C$_{3-10}$ cycloalkenyl, an optionally substituted aryl, an optionally substituted heteroaryl and an optionally substituted heterocyclyl; X$^1$ can be hydrogen, O (oxygen) or S (sulfur), provided that when X$^1$ is hydrogen, then ------- can be a single bond, and when X$^1$ is O (oxygen) or S (sulfur), then ------- can be a double bond; X$^2$ can be O (oxygen) or S (sulfur); Y$^4$ can be C(Y$^{1a}$), C (carbon) or N (nitrogen), Y$^{1a}$ can be selected from hydrogen, halogen, unsubstituted C$_{1-4}$ alkyl and —O—C$_{1-4}$ alkyl; ------ can be a single or double bond; wherein when Y$^4$ is C(Y$^{1a}$) and ------ is a single bond, then R$^{5d}$ can be selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl (alkyl), an optionally substituted aryl(alkyl), an optionally substituted heteroaryl(alkyl), an optionally substituted heterocyclyl(alkyl) and an optionally substituted C-carboxy, wherein when Y$^4$ is C and ------ is a double bond, then R$^{5d}$ is absent, and wherein when Y$^4$ is N (nitrogen), then ------ is a single bond and R$^{5d}$ can be selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl (alkyl), an optionally substituted heteroaryl(alkyl), an optionally substituted heterocyclyl(alkyl) and an optionally substituted C-carboxy; m can be 0, 1 or 2; n can be 0, 1 or 2; and p can be 1, 2 or 3.

In some embodiments, R$^1$ can be hydrogen. In other embodiments, R$^1$ can be an optionally substituted alkyl, such as, an optionally substituted C$_{1-8}$ alkyl. Examples of C$_{1-8}$ alkyl groups include methyl, ethyl, n-propyl, iso-propyl, n-butyl, iso-butyl, tert-butyl, pentyl (branched and straight-chained), hexyl (branched and straight-chained), heptyl (branched and straight-chained) and octyl (branched and straight-chained). In still other embodiments, R$^1$ can be an optionally substituted alkenyl.

Cyclic moieties can be present at R$^1$. In some embodiments, R$^1$ can be an optionally substituted cycloalkyl. As an example, R$^1$ can be an optionally substituted C$_{4-8}$ cycloalkyl. In other embodiments, R$^1$ can be a substituted or unsubstituted C$_5$ cycloalkyl, for example, a substituted or unsubstituted bicyclo[1.1.1]pentane. In still other embodiments, R$^1$ can be an optionally substituted cycloalkenyl, such as an optionally substituted C$_{6-8}$ cycloalkenyl. In some embodiments, R$^1$ can be an optionally substituted aryl, for example, an optionally substituted phenyl or an optionally substituted naphthyl. In other embodiments, R$^1$ can be an optionally substituted heteroaryl, such as an optionally substituted monocyclic heteroaryl or an optionally substituted bicyclic heteroaryl. In still other embodiments, R$^1$ can be an optionally substituted heterocyclyl. Examples of optionally heterocyclyls include optionally substituted monocyclic heterocyclyls or optionally substituted bicyclic heterocyclyls. In yet still other embodiments, $R^1$ can be an optionally substituted cycloalkyl(alkyl). In some embodiments, $R^1$ can be an optionally substituted cycloalkenyl(alkyl). In other embodiments, $R^1$ can be an optionally substituted aryl(alkyl), for example, a substituted or unsubstituted benzyl. In still other embodiments, $R^1$ can be an optionally substituted heteroaryl (alkyl). In yet still other embodiments, $R^1$ can be an optionally substituted heterocyclyl(alkyl).

In other embodiments, $R^1$ can be hydroxy. In still other embodiments, $R^1$ can be an optionally substituted alkoxy. In yet still other embodiments, $R^1$ can be cyano. In some embodiments, $R^1$ can be an optionally substituted C-carboxy. In other embodiments, $R^1$ can be an optionally substituted N-amido. In still other embodiments, $R^1$ can be an optionally substituted urea. In yet still other embodiments, $R^1$ can be nitro. In some embodiments, $R^1$ can be an optionally substituted sulfenyl. In other embodiments, $R^1$ can be an optionally substituted haloalkyl. In still other embodiments, $R^1$ can be amino. In yet still other embodiments, $R^1$ can be an optionally substituted mono-substituted amino group. In some embodiments, $R^1$ can be an optionally substituted di-substituted amino group. In other embodiments, $R^1$ can be —$(CR^{1a1}R^{1a2})q$-$R^{1b}$, wherein q can be 1, 2, 3, 4, 5 or 6, each $R^{1a}$ and each $R^{1a2}$ can be independently hydrogen, halogen or an unsubstituted alkyl, and $R^{1b}$ can be selected from hydroxy, an optionally substituted N-amido, an optionally substituted N-sulfinamido, an optionally substituted N-sulfonamido, an optionally substituted urea, an optionally substituted sulfenyl, amino, an optionally substituted mono-substituted amino group and an optionally substituted di-substituted amino group. In some embodiments, $R^1$ can be —$(CH_2)q$-$R^{1b}$.

The 6-membered ring of

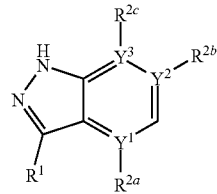

includes $Y^1$, $Y^2$ and $Y^3$. In some embodiments, $Y^1$, $Y^2$ and $Y^3$ can be independently C (carbon) or N (nitrogen). In some embodiments, $Y^1$ can be C (carbon), then $R^{2a}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group. In some embodiments, $Y^1$ can be C and $R^{2a}$ can be hydrogen. In other embodiments, $Y^1$ can be C and $R^{2a}$ can be halogen or an optionally substituted $C_{1-4}$ alkyl. In some embodiments, $Y^1$ can be N (nitrogen), then $R^{2a}$ is absent.

In some embodiments, $Y^2$ can be C (carbon), then $R^{2b}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group. In some embodiments, $Y^2$ can be C and $R^{2b}$ can be hydrogen. In other embodiments, $Y^2$ can be C and $R^{2b}$ can be halogen or an optionally substituted $C_{1-4}$ alkyl. In some embodiments, $Y^2$ can be N (nitrogen), then $R^{2b}$ is absent.

In some embodiments, $Y^3$ can be C (carbon), then $R^{2c}$ can be selected from hydrogen, halogen, an optionally substituted alkyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl), hydroxy, an optionally substituted alkoxy, cyano, nitro, an optionally substituted sulfenyl, amino, an optionally substituted mono-substituted amino group and an optionally substituted di-substituted amino group. In some embodiments, $Y^3$ can be C and $R^{2c}$ can be hydrogen. In other embodiments, $Y^3$ can be C and $R^{2c}$ can be halogen or an optionally substituted $C_{1-4}$ alkyl. In some embodiments, $Y^3$ can be N (nitrogen), then $R^{2c}$ is absent.

In some embodiments,

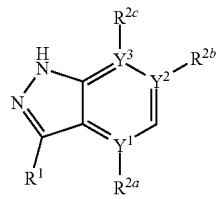

can be

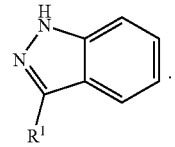

In other embodiments,

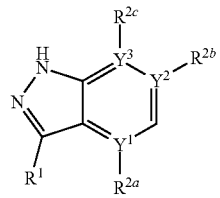

can be

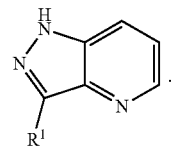

The size of each of the rings of the spiro-connected moiety of a compound of Formula (I) can independently vary. In some embodiments, m can be 0, such that ring is a 4-membered ring. In other embodiments, m can be 1, such that ring is a 5-membered ring. In still other embodiments, m can be 2, such that ring is a 6-membered ring. In some embodiments, n can be 0, such that ring is a 4-membered ring. In other embodiments, n can be 1, such that ring is a 5-membered ring. In still other embodiments, n can be 2, such that ring is a 6-membered ring.

In some embodiments, $X^1$ can be hydrogen and ------- can be a single bond. In other embodiments, $X^1$ can be O (oxygen) and ------- can be a double bond. In still other embodiments, $X^1$ can be S (sulfur) and ------- can be a double bond.

The spiro-connected moiety of a compound of Formula (I) can be substituted or unsubstituted. In some embodiments, each $R^{3a}$, each $R^{3b}$, $R^{3c}$, $R^{3d}$, each $R^{3e}$, each $R^{3f}$, $R^{3g}$, $R^{3h}$, $R^{3i}$ and $R^{3j}$ can be independently selected from hydrogen, halogen, an optionally substituted alkyl, an optionally substituted alkenyl, an optionally substituted alkynyl, an optionally substituted cycloalkyl, an optionally substituted aryl, an optionally substituted heteroaryl, an optionally substituted heterocyclyl, an optionally substituted cycloalkyl(alkyl), an optionally substituted aryl(alkyl), an optionally substituted heteroaryl(alkyl), an optionally substituted heterocyclyl(alkyl) hydroxy, an optionally substituted alkoxy, an optionally substituted haloalkoxy, cyano, an optionally substituted N-amido, an optionally substituted C-carboxy, an optionally substituted oxime, an optionally substituted acyl hydrozone, an optionally substituted sulfenyl, an optionally substituted sulfinyl, an optionally substituted sulfonyl, amino, an optionally substituted mono-substituted amino group, an optionally substituted di-substituted amino group and —(CH$_2$)r-R$^{3k}$, wherein r can be 1, 2, 3, 4, 5 or 6, and $R^{3k}$ can be selected from halo, hydroxy, cyano, an optionally substituted heteroaryl, an optionally substituted alkoxy, an optionally substituted sulfenyl and an optionally substituted hydrazine. When the spiro-connected moiety is substituted, 1, 2, 3, 4, 5 or more groups can be present. In some embodiments, each $R^{3a}$, each $R^{3b}$, $R^{3c}$, $R^{3d}$, each $R^{3e}$, each $R^{3f}$, $R^{3g}$, $R^{3h}$, $R^{3i}$ and $R^{3j}$ can be hydrogen. In other embodiments, at least one of each $R^{3a}$, each $R^{3b}$, $R^{3c}$, $R^{3d}$, each $R^{3e}$, each $R^{3f}$, $R^{3g}$, $R^{3h}$, $R^{3i}$ and $R^{3j}$ can be an optionally substituted $C_{1-4}$ alkoxy. In still other embodiments, at least one of each $R^{3a}$, each $R^{3b}$, $R^{3c}$, $R^{3d}$, each $R^{3e}$, each $R^{3f}$, $R^{3g}$, $R^{3h}$, $R^{3i}$ and $R^{3j}$ can be an optionally substituted $C_{1-4}$ sulfenyl.

In some embodiments, each $R^{4a}$ and each $R^{4b}$ can be each hydrogen. In other embodiments, one of each $R^{4a}$ and each $R^{4b}$ can be deuterium. In still other embodiments, one of each $R^{4a}$ and each $R^{4b}$ can be an optionally substituted $C_{1-6}$ alkyl.

Examples of the spiro-connected moiety of a compound of Formula (I) include, but are not limited to, the following:

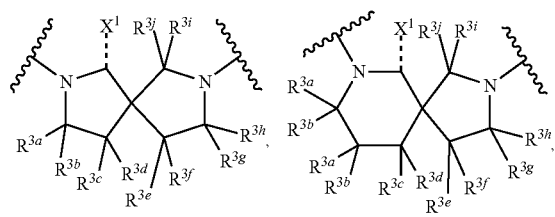

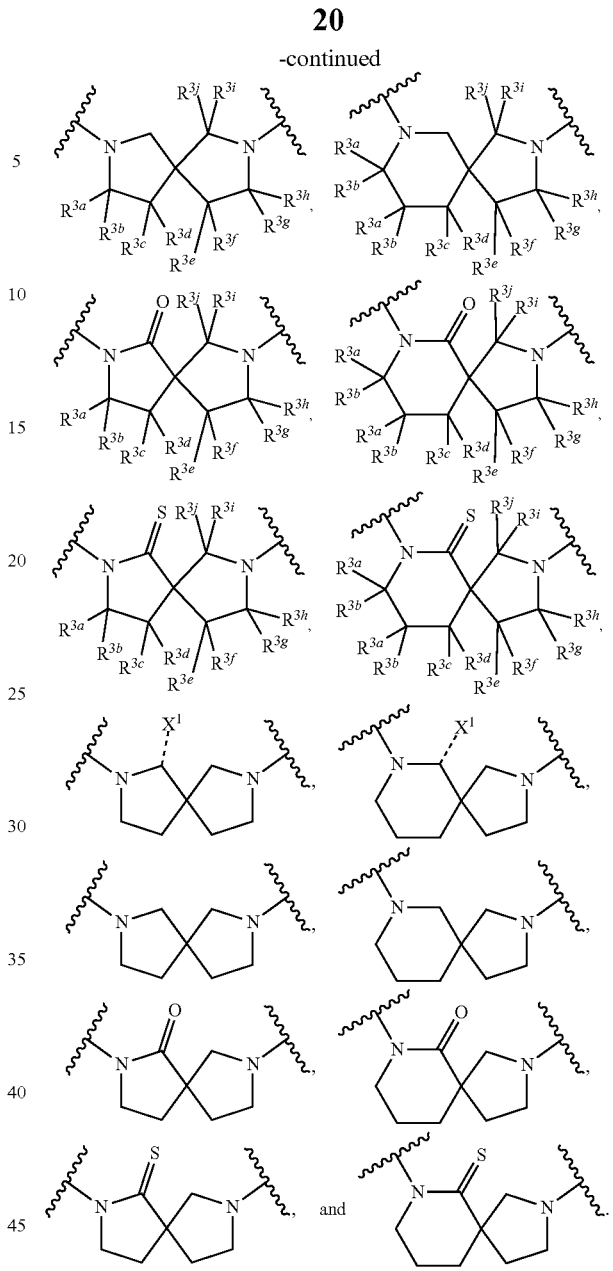

In some embodiments, p can be 1. In other embodiments, p can be 2. In still other embodiments, p can be 3. When p is 1, the methylene group can be unsubstituted or substituted. When p is 2, each carbon of the ethylene group can be unsubstituted or substituted. When p is 3, each carbon of the propylene group can be unsubstituted or substituted. In some embodiments, the methylene when p is 1, the ethylene when p is 2 and the propylene group when p is 3 can be independently substituted with an optionally substituted alkyl, for example, an optionally substituted $C_{1-4}$ alkyl.

In some embodiments, $Y^4$ can be C($Y^{1a}$), C (carbon) or N (nitrogen), ===== ===== can be a single or double bond, $Y^{1a}$ can be selected from hydrogen, halogen, unsubstituted $C_{1-4}$ alkyl and —O—$C_{1-4}$ alkyl and various groups can be present at $R^{5a}$, $R^{5b}$, $R^{5c}$, $R^{5d}$, $R^{5e}$, $R^{5f}$, $R^{5g}$ and $R^{5h}$. In some embodiments, $R^{5a}$, $R^{5b}$, $R^{5c}$, $R^{5e}$, $R^{5g}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy.

In some embodiments, $Y^4$ can be $C(Y^{1a})$, ═══ can be a single bond, and $R^{5d}$ can be selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy. In other embodiments, $Y^4$ can be C (carbon), ═══ can be a double bond, and $R^{5d}$ can be absent. In still other embodiments, $Y^4$ can be N (nitrogen), ═══ an be a single bond and $R^{5d}$ can be selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy.

In some embodiments, $R^{5b}$ and $R^{5c}$ can be taken together to form an optionally substituted cycloalkyl, an optionally substituted aryl or an optionally substituted heterocyclyl, and $R^{5a}$, $R^{5e}$, $R^{5g}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy. In other embodiments, $R^{5f}$ and $R^{5g}$ can be taken together to form an optionally substituted cycloalkyl, an optionally substituted aryl or an optionally substituted heterocyclyl, $R^{5a}$, $R^{5b}$, $R^{5c}$, $R^{5e}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy. In still other embodiments, $R^{5b}$ and $R^{5c}$ can be taken together to form an optionally substituted cycloalkyl, an optionally substituted aryl or an optionally substituted heterocyclyl, and $R^{5f}$ and $R^{5g}$ can be taken together to form an optionally substituted cycloalkyl, an optionally substituted aryl or an optionally substituted heterocyclyl, and $R^{5a}$, $R^{5e}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy.

In some embodiments, $R^{5b}$ and $R^{5g}$ can be connected via $Y^5$, wherein $Y^5$ can be $(CR^{5i}R^{5j})s$, wherein s can be 1, 2 or 3, and each $R^{5i}$ and each $R^{5j}$ can be independently hydrogen, halogen or an unsubstituted alkyl, and $R^{5a}$, $R^{5c}$, $R^{5e}$, $R^{5f}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy. In some embodiments, $Y^5$ can be $(CH_2)s$. In other embodiments, $R^{5c}$ and $R^{5e}$ can be connected via $Y^6$, wherein $Y^6$ can be $(CR^{5k}R^{5l})t$, wherein t can be 1, 2 or 3, and each $R^{5k}$ and $R^{5l}$ can be independently hydrogen, halogen or an unsubstituted alkyl, and $R^{5a}$, $R^{5b}$, $R^{5f}$, $R^{5g}$ and $R^{5h}$ can be independently selected from hydrogen, an optionally substituted alkyl, an optionally substituted alkenyl, an optionally substituted alkynyl, an optionally substituted cycloalkyl, an optionally substituted aryl, an optionally substituted heteroaryl, an optionally substituted cycloalkyl(alkyl), an optionally substituted aryl(alkyl), an optionally substituted heteroaryl(alkyl), an optionally substituted heterocyclyl(alkyl) and an optionally substituted C-carboxy. In some embodiments, $Y^6$ can be $(CH_2)t$.

Examples of

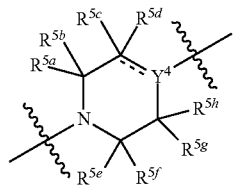

rings include, but are not limited to the following:

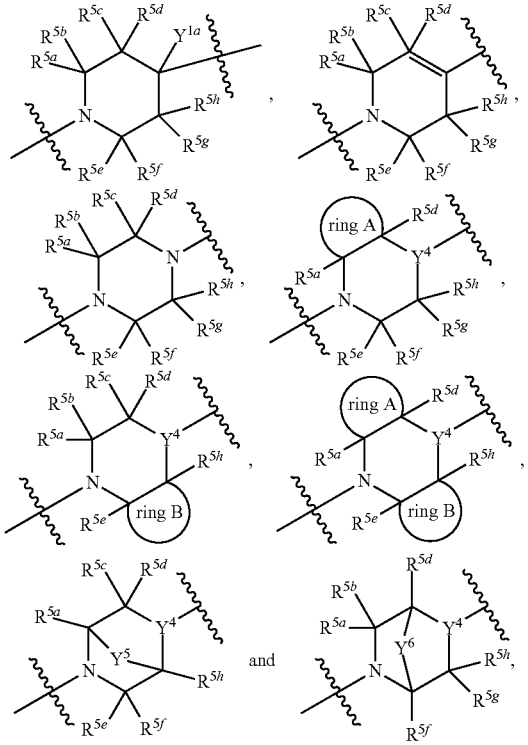

wherein ring A and ring B can be independently selected from an optionally substituted cycloalkyl, an optionally substituted aryl and an optionally substituted heterocyclyl.

In some embodiments, $A^1$ can be an optionally substituted $C_{3-10}$ cycloalkyl. As one example, $A^1$ can be an optionally substituted monocyclic $C_{5-10}$ cycloalkyl. As another example, $A^1$ can be an optionally substituted bicyclic $C_{3-10}$ cycloalkyl. In some embodiments, $A^1$ can be a substituted or unsubstituted bicyclo[1.1.1]pentane. In some embodiments, $A^1$ can be an optionally substituted $C_{3-10}$ cycloalkenyl. Examples of optionally substituted $C_{3-10}$ cycloalkenyls include an optionally substituted monocyclic $C_{5-10}$ cycloalkenyl and an optionally substituted bicyclic $C_{3-10}$ cycloalkenyl. In some embodiments, $A^1$ can be an optionally substituted aryl, such as an optionally substituted phenyl. In other embodiments, $A^1$ can be an optionally substituted heteroaryl, for example, such as an optionally substituted pyridine, an optionally substituted pyrimidine and an optionally substituted thiazole. In still other embodiments, $A^1$ can be an optionally substituted heterocyclyl. When $A^1$ is an optionally substituted heteroaryl, the heteroaryl can be an optionally substituted monocyclic heteroaryl or an optionally substituted bicyclic heteroaryl. When $A^1$ is an optionally substituted heterocyclyl, the heteroaryl can be an optionally substituted monocyclic heterocyclyl or an optionally substituted bicyclic heterocyclyl.

In some embodiments, $R^6$ can be an optionally substituted aryl, for example, an optionally substituted phenyl. In other embodiments, $R^6$ can be an optionally substituted heteroaryl. In still other embodiments, $R^6$ can be an optionally substituted heterocyclyl. Examples of suitable optionally substituted heteroaryls include optionally substituted monocyclic heteroaryls (such as an optionally substituted pyridine, an optionally substituted pyrimidine, an optionally substituted triazole, an optionally substituted isoxazole, an optionally substituted oxazole, an optionally substituted imidazole and an optionally substituted pyrazole) and an optionally substituted bicyclic heteroaryls; examples of optionally substituted heterocyclyls include optionally substituted monocyclic heterocyclyls and an optionally substituted bicyclic heterocyclyls. In some embodiments, $R^6$ can be an optionally substituted 1,3,4-oxadiazol-2(3H)-one or an optionally substituted 1,2,3-oxadiazol-5(2H)-one.

Examples of compounds of Formula (I), or pharmaceutically acceptable salts thereof, include the following:

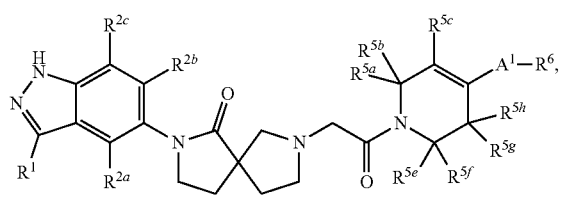

(Ia)

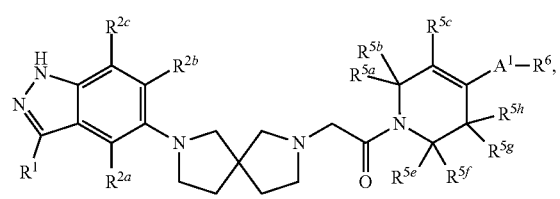

(Ib)

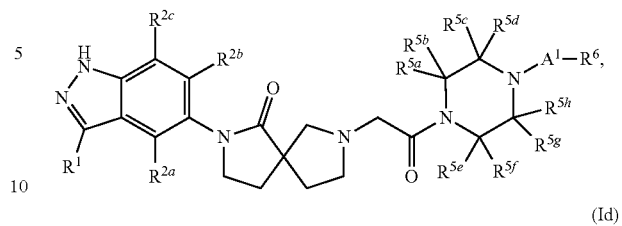

(Ic)

(Id)

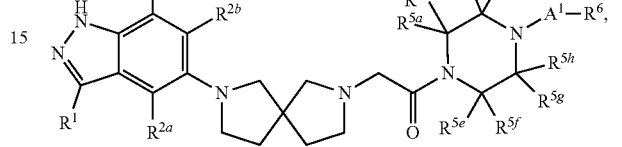

(Ie)

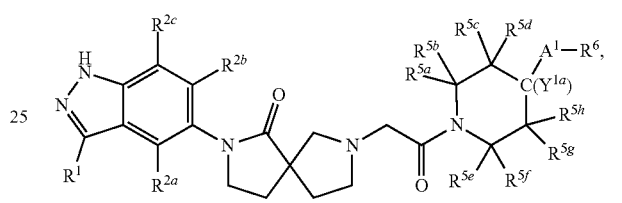

(If)


(Ig)

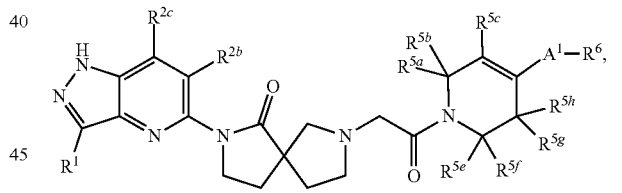

(Ih)

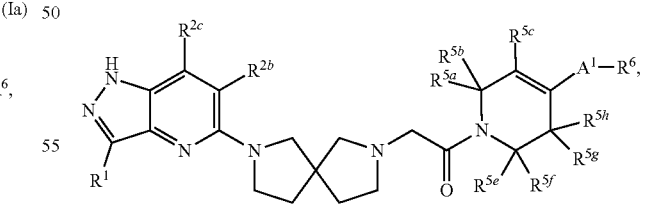

(Ii)

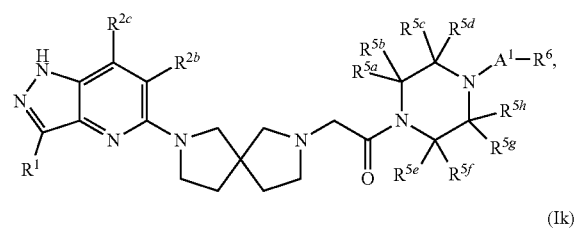
(Ij)
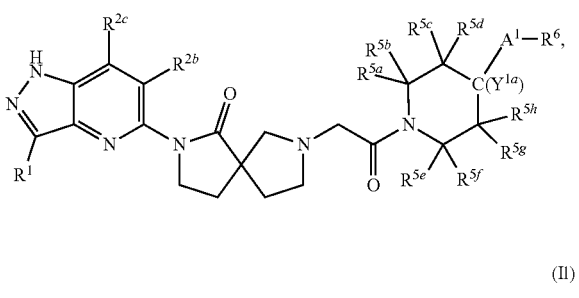
(Ik)
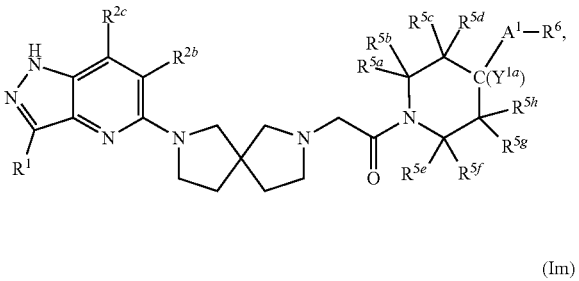
(Il)
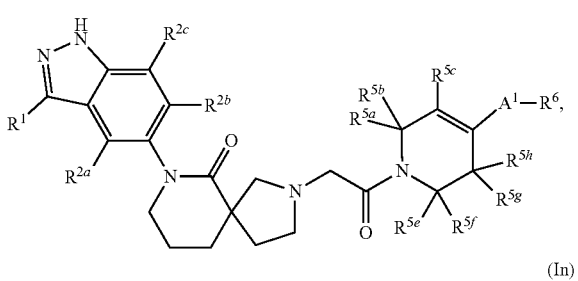
(Im)
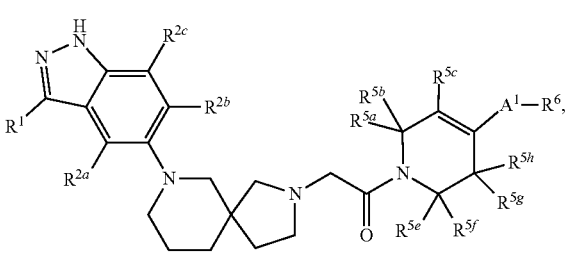
(In)
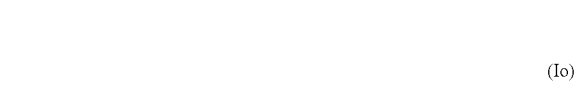
(Io)
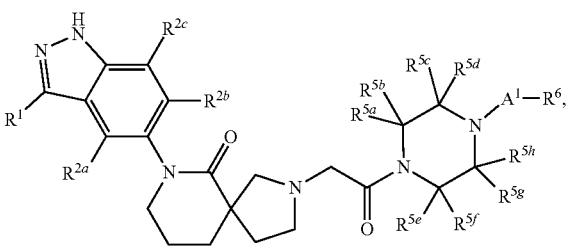
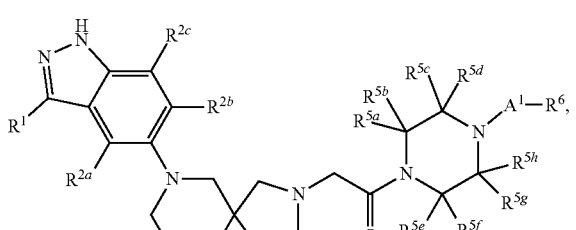
(Ip)
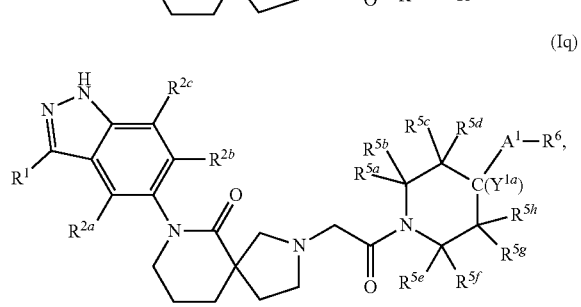
(Iq)

(Ir)
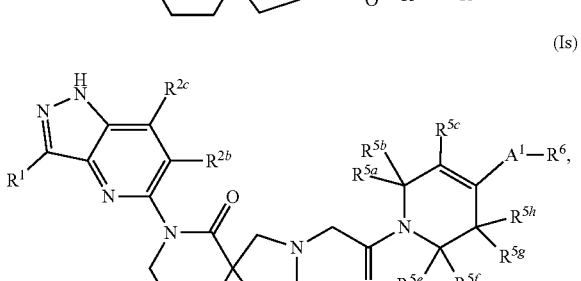
(Is)
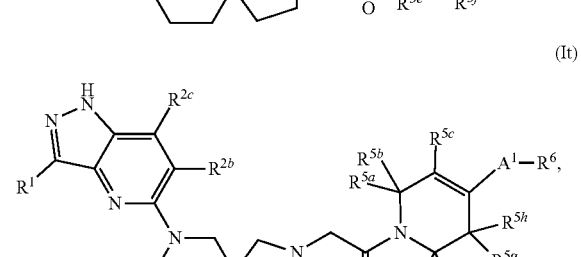
(It)
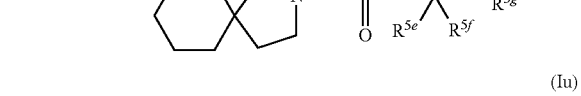
(Iu)
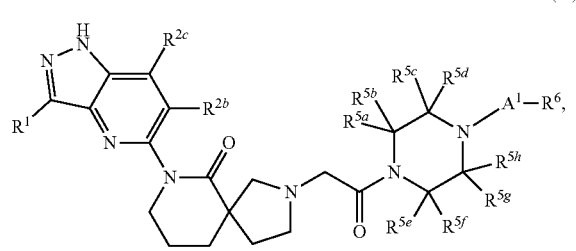

-continued
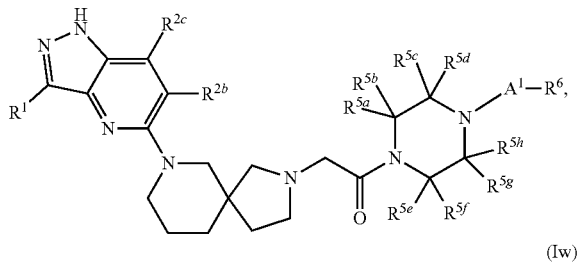
(Iv)
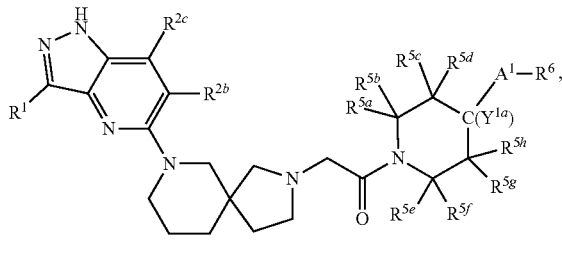
(Ix)
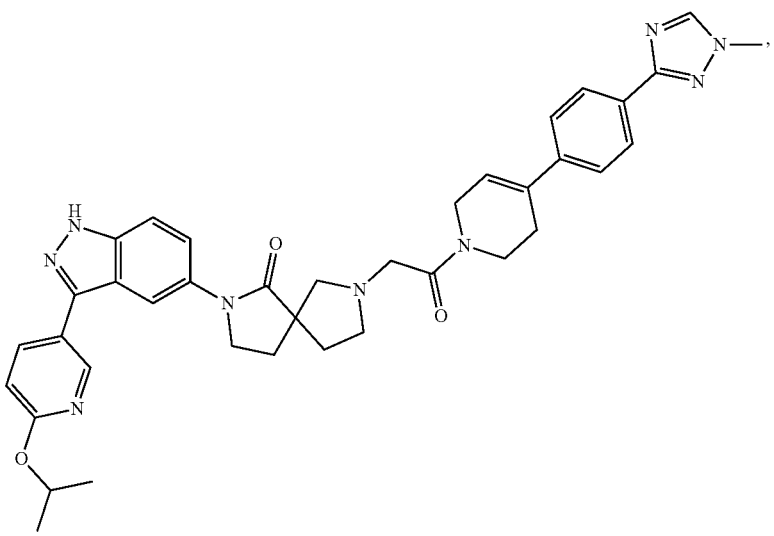
(Iw)
and
or a pharmaceutically acceptable salt of the foregoing.
Examples of compounds of Formula (I) include, but are not limited to, the following:
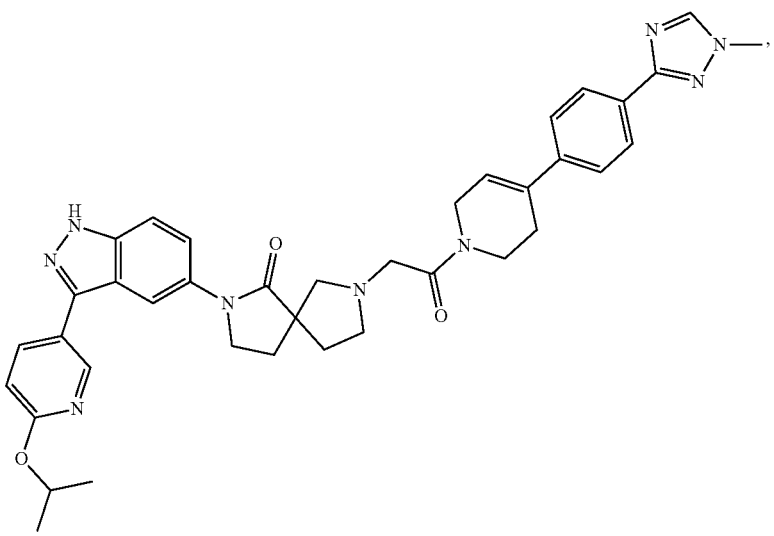
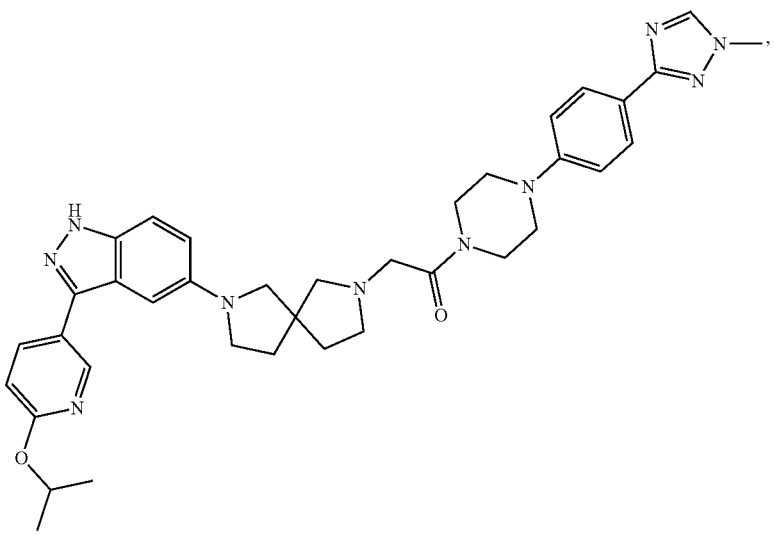

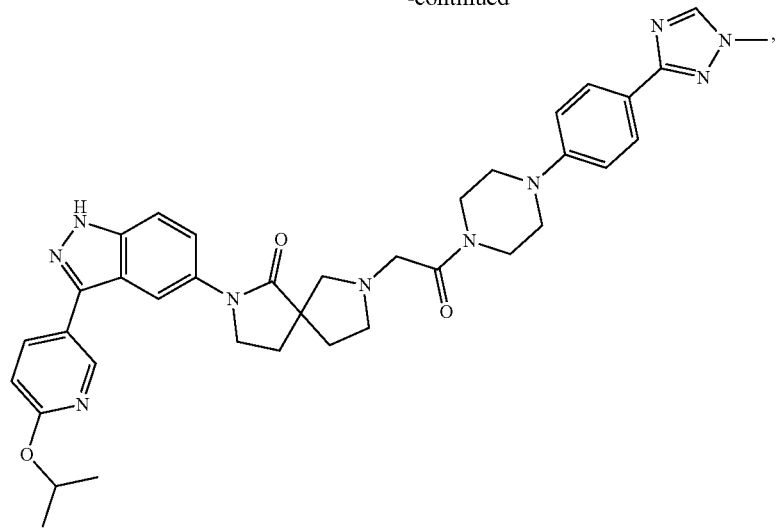
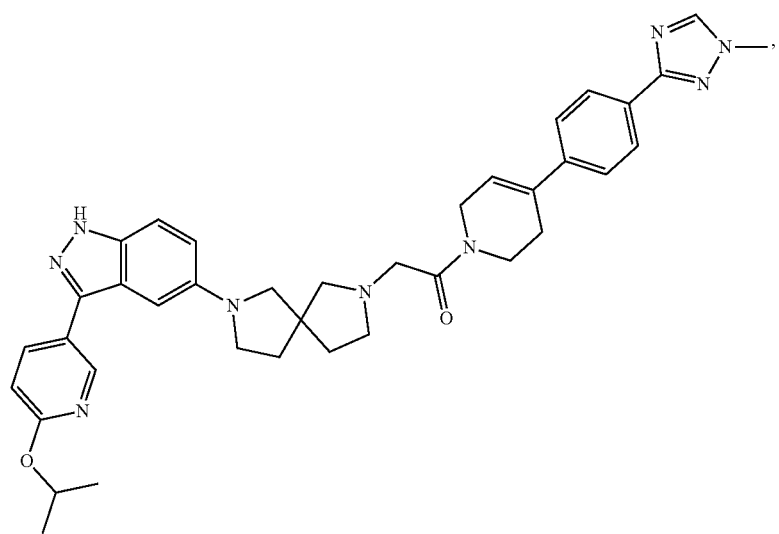
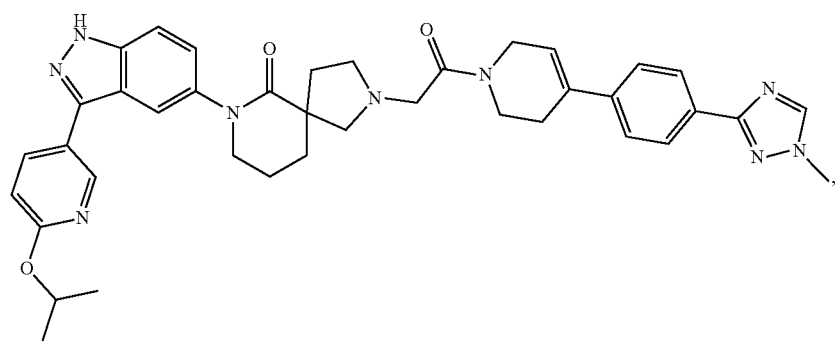

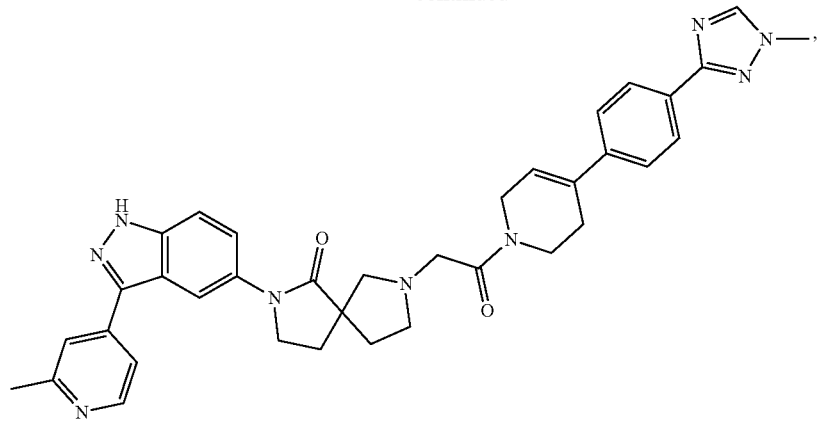
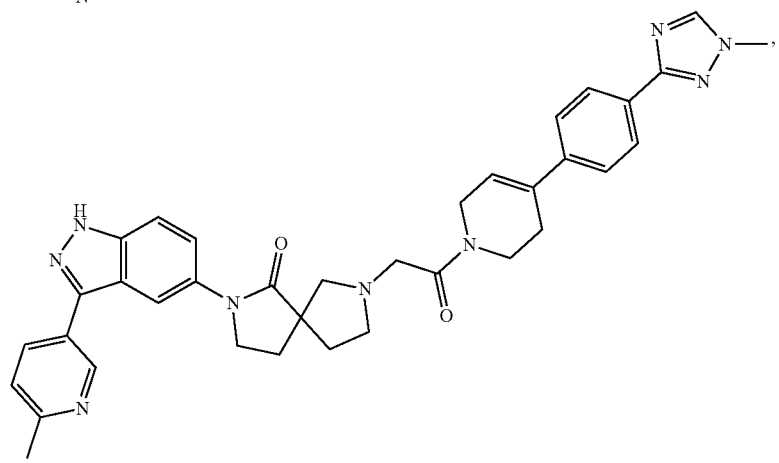
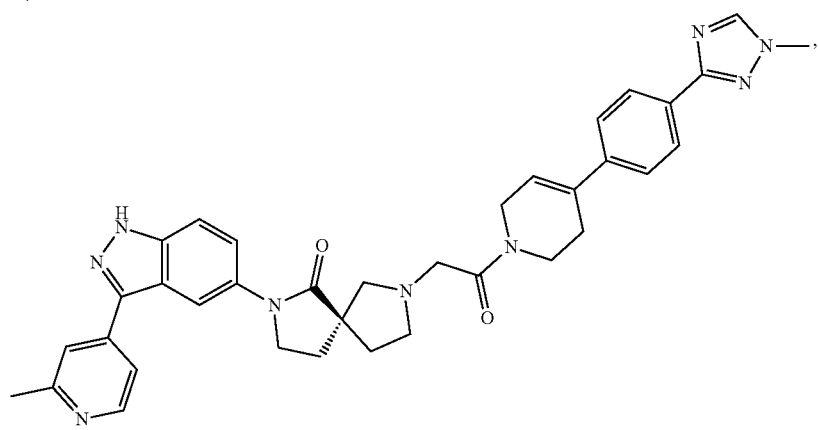
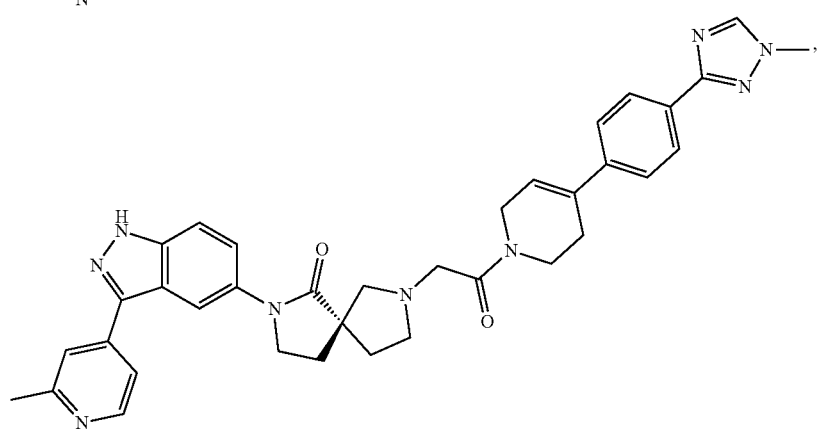

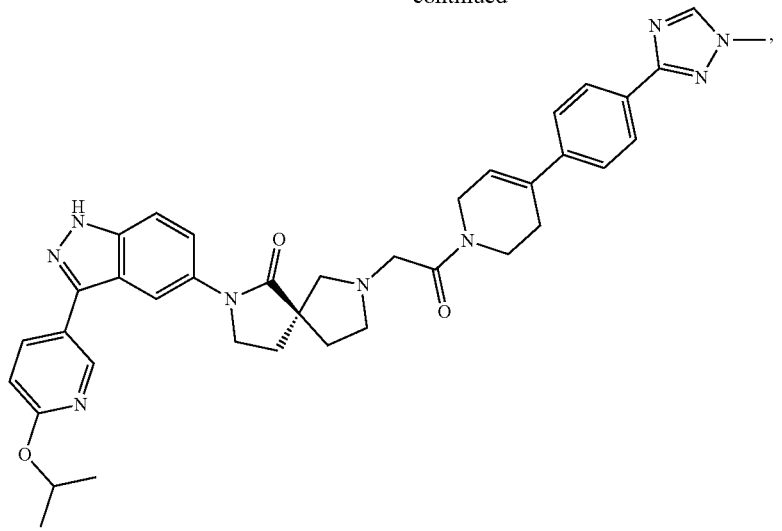
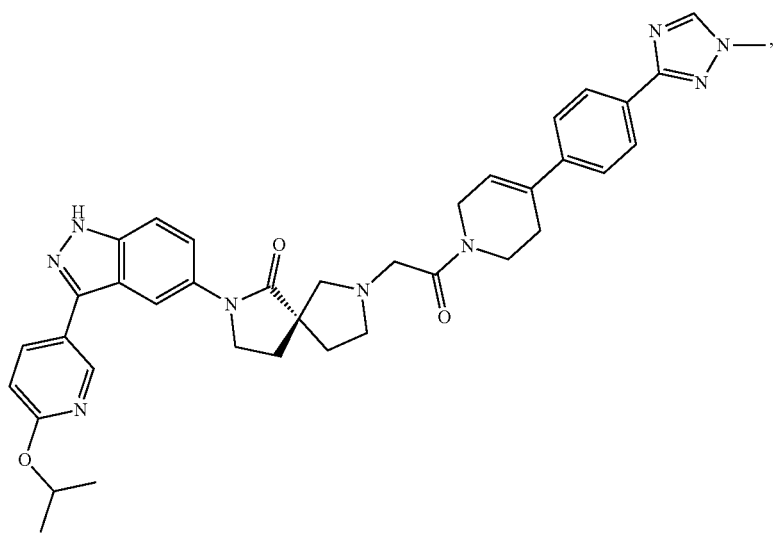
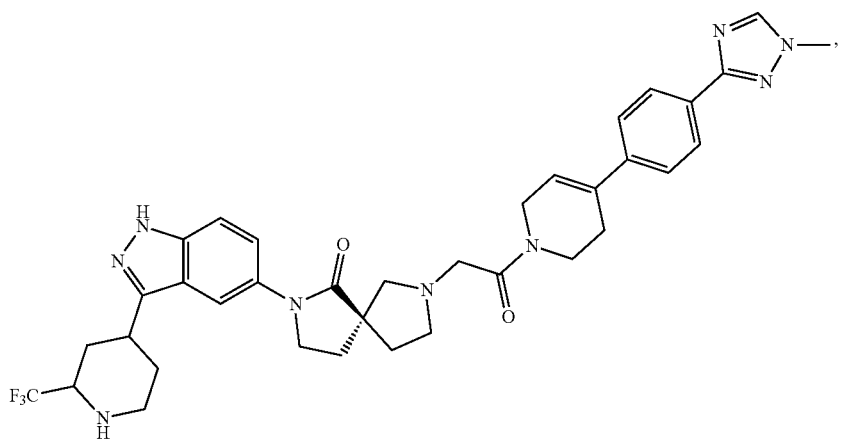

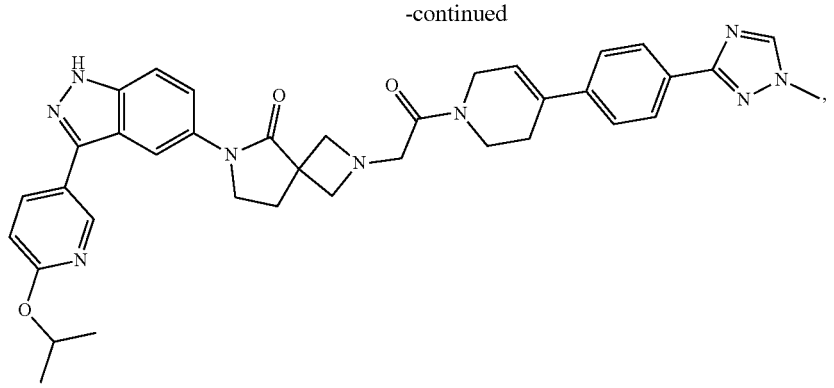
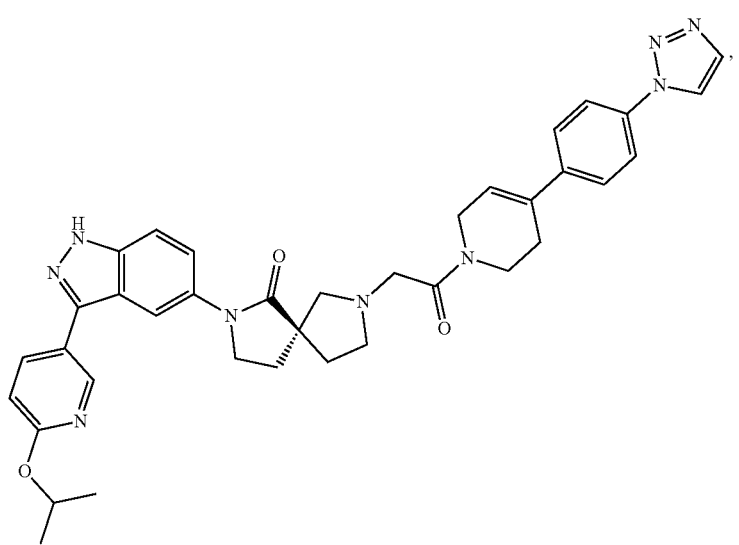
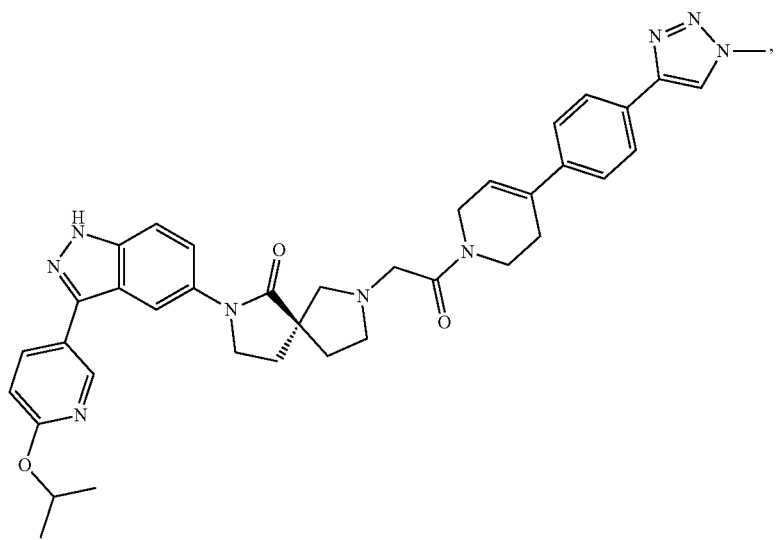

-continued
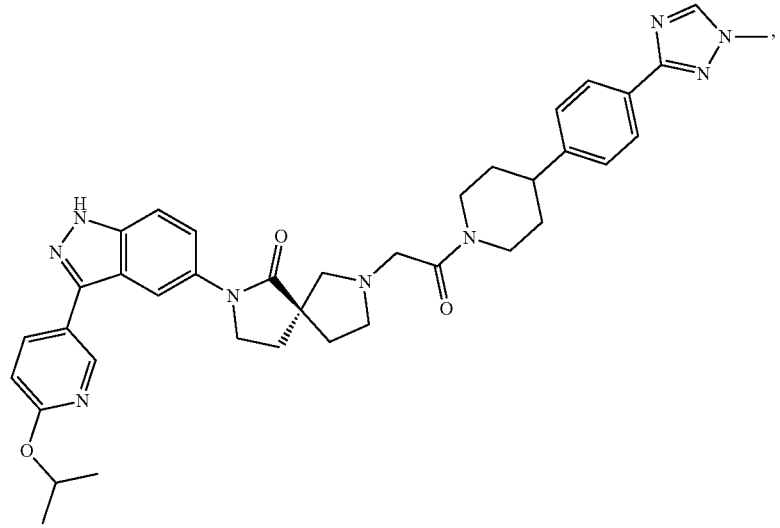
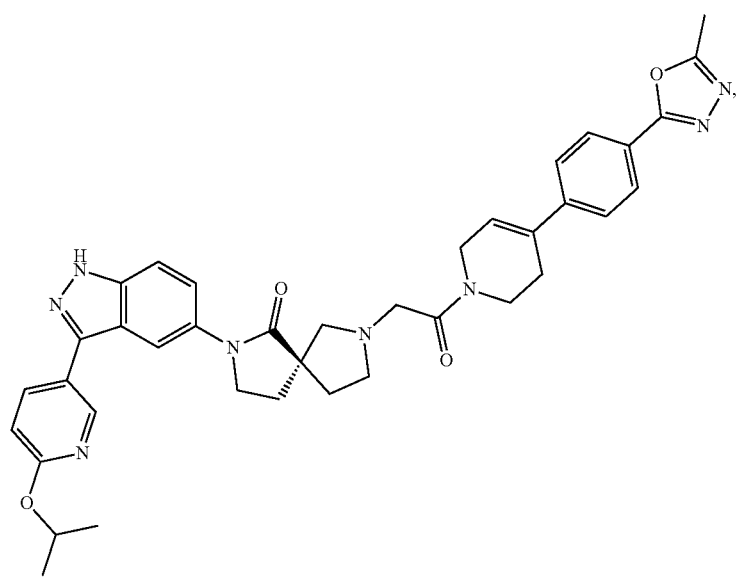

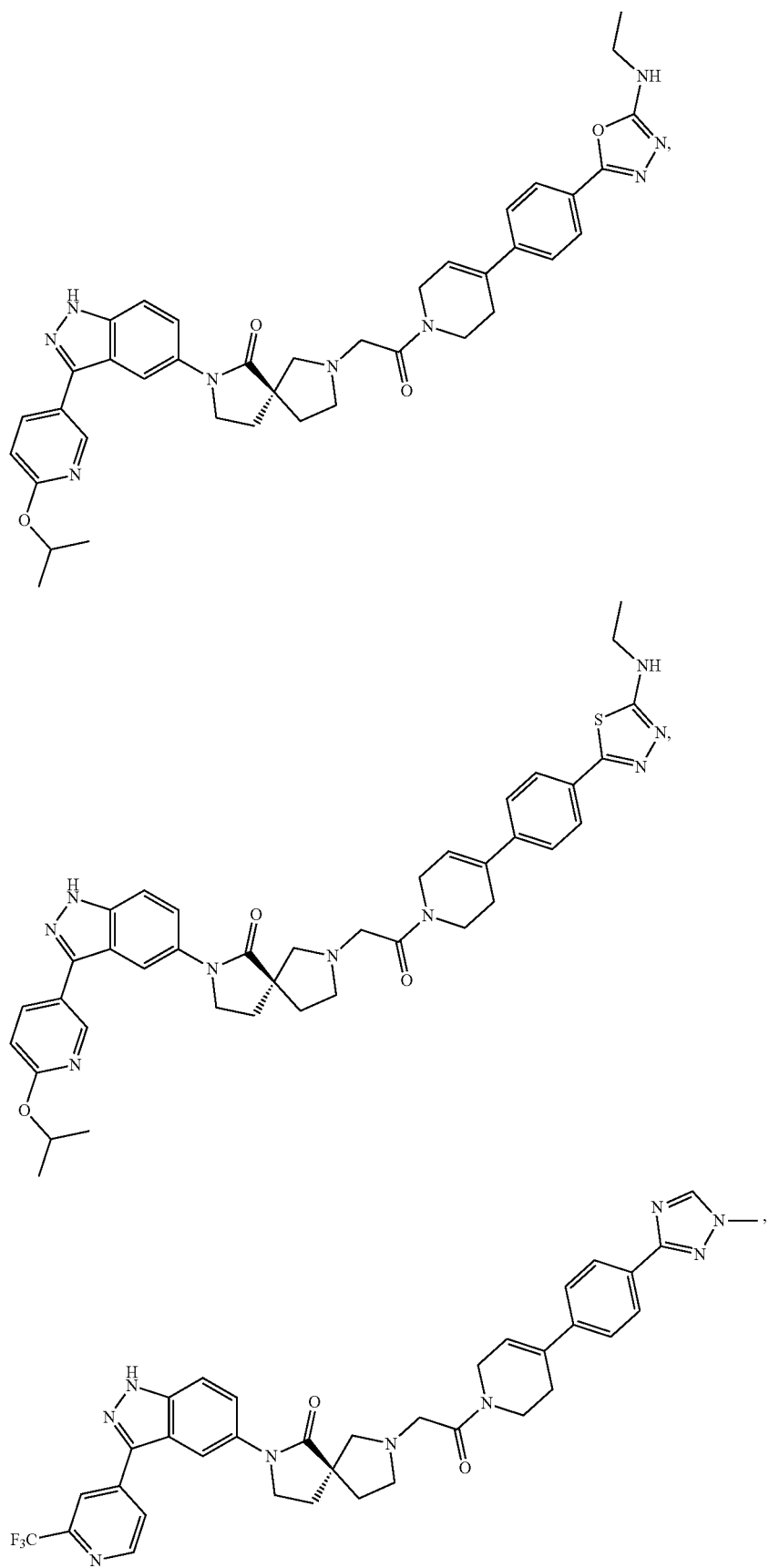 [SMILES: CCNc1nnc(-c2ccc(C3=CCN(C(=O)CN4CC[C@]5(CCN(c6ccc7[nH]nc(-c8ccc(OC(C)C)nc8)c7c6)C5=O)C4)CC3)cc2)o1 ; CCNc1nnc(-c2ccc(C3=CCN(C(=O)CN4CC[C@]5(CCN(c6ccc7[nH]nc(-c8ccc(OC(C)C)nc8)c7c6)C5=O)C4)CC3)cc2)s1 ; Cn1cnc(-c2ccc(C3=CCN(C(=O)CN4CC[C@]5(CCN(c6ccc7[nH]nc(-c8ccnc(C(F)(F)F)c8)c7c6)C5=O)C4)CC3)cc2)n1]

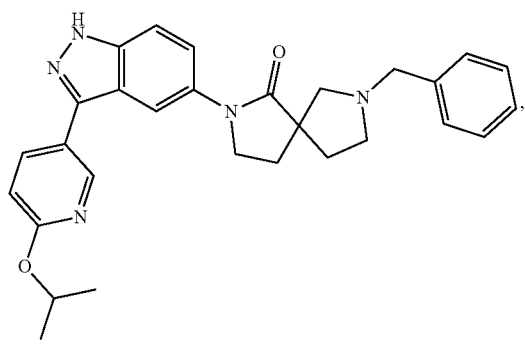
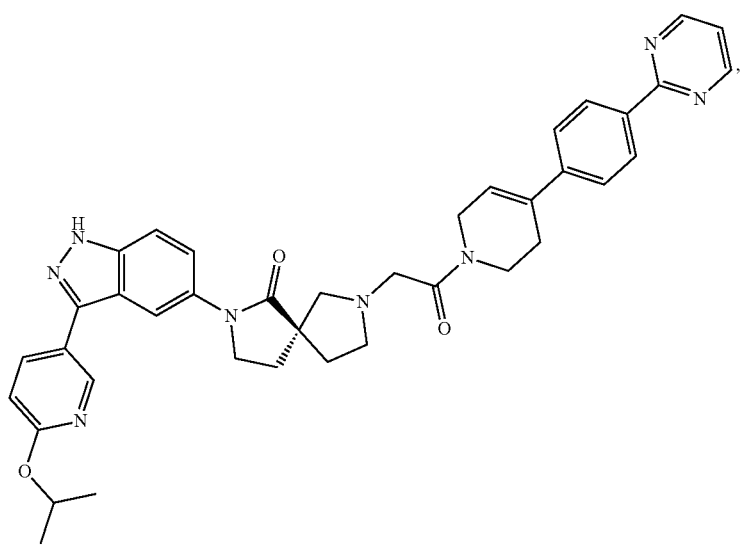
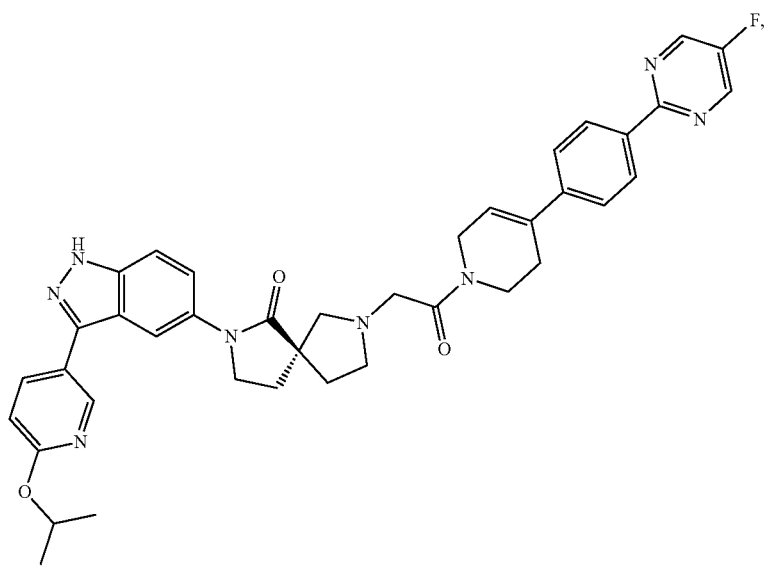

-continued
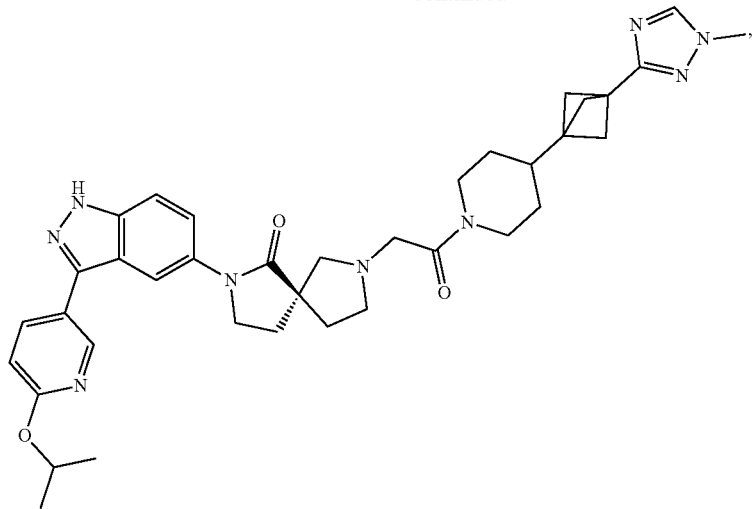
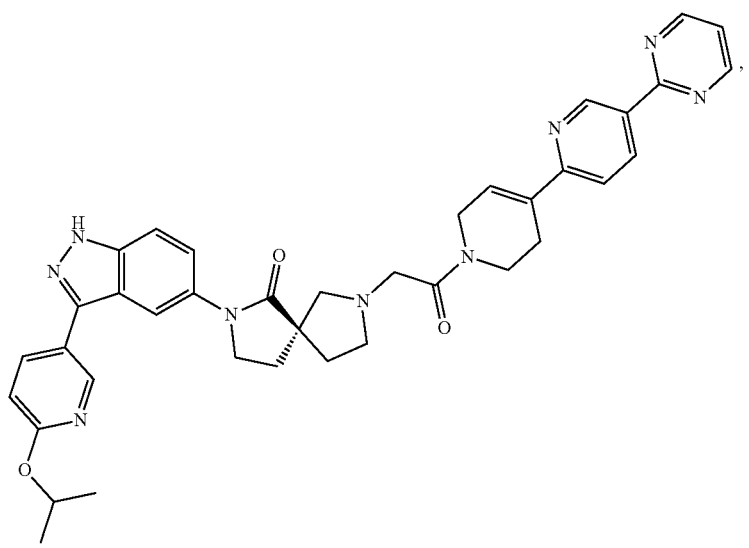
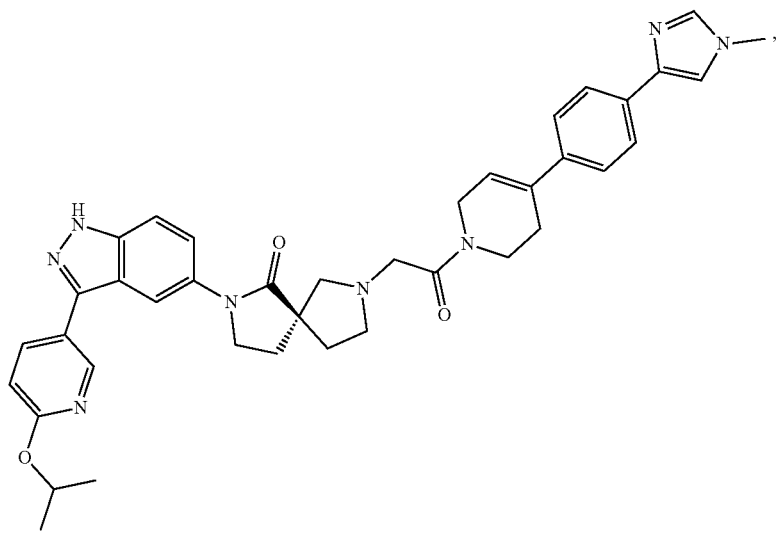

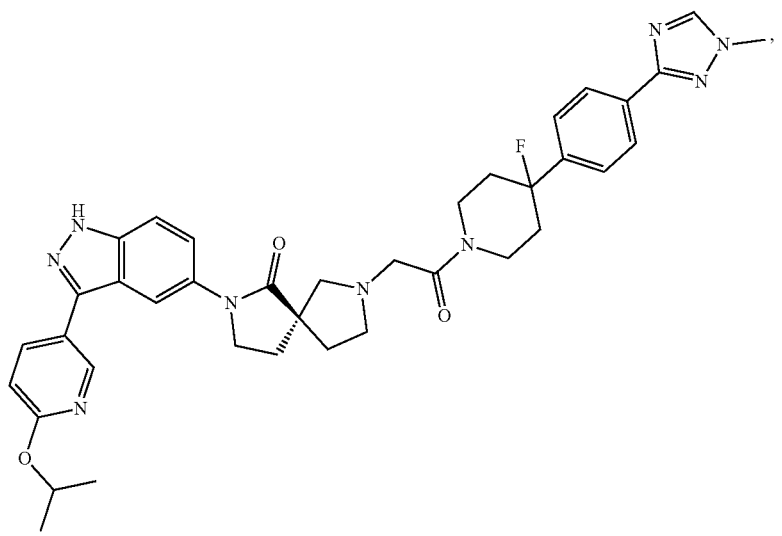
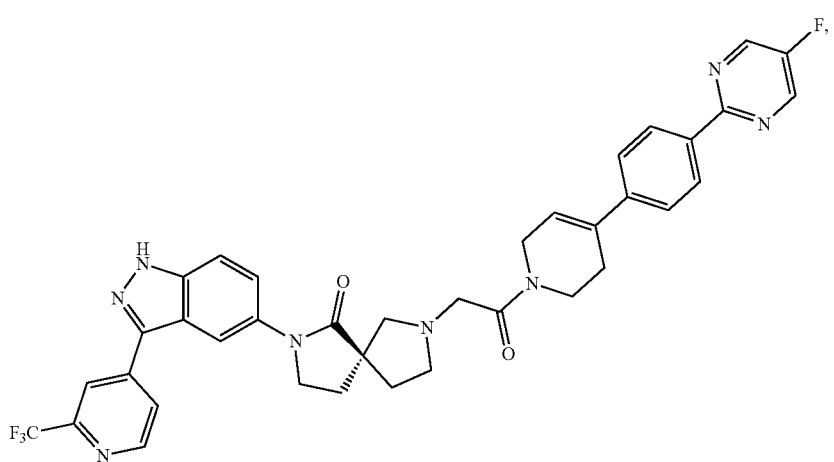
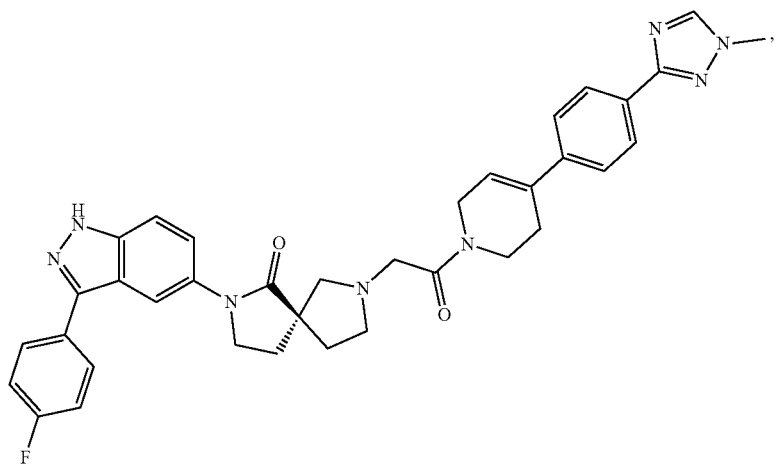

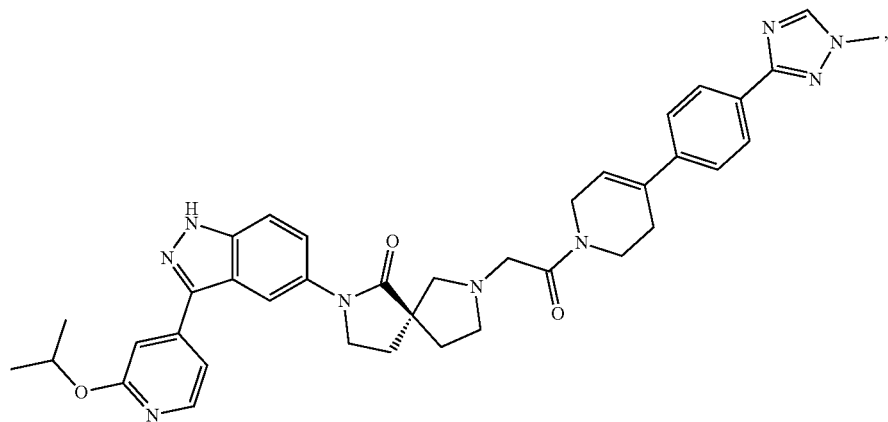
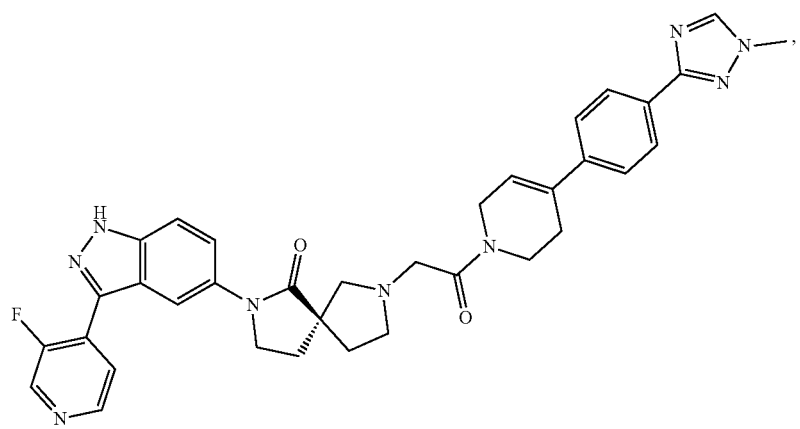
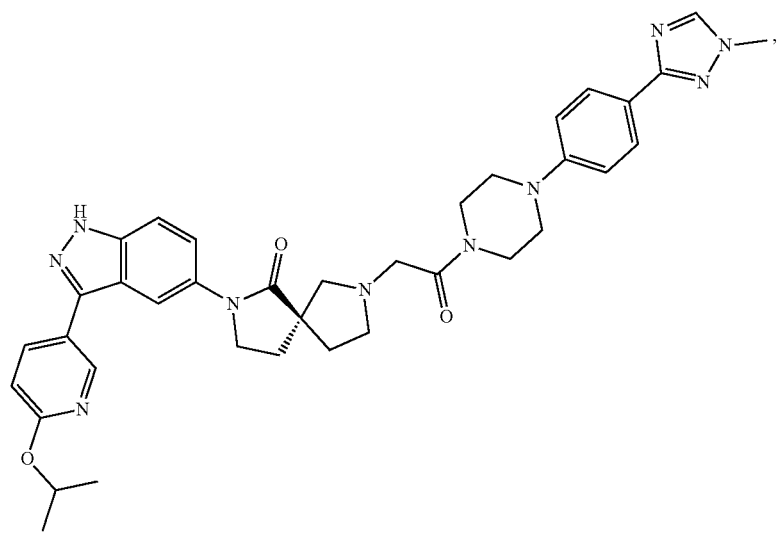

-continued
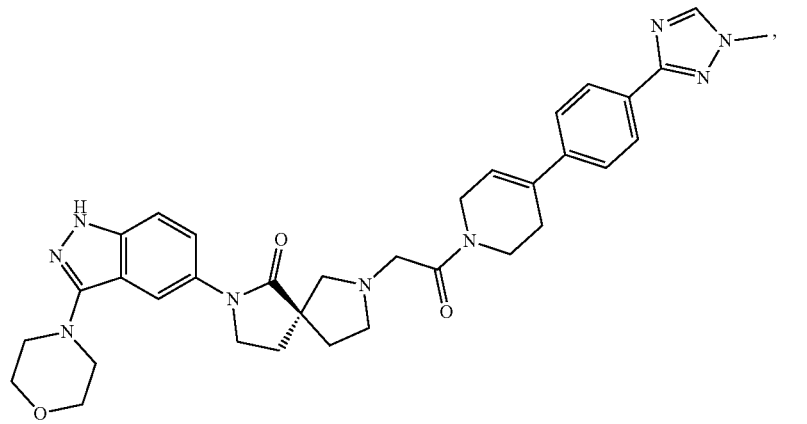
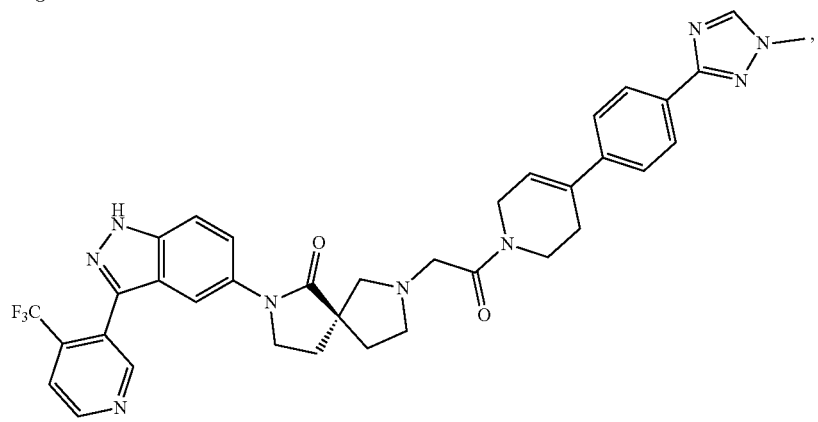
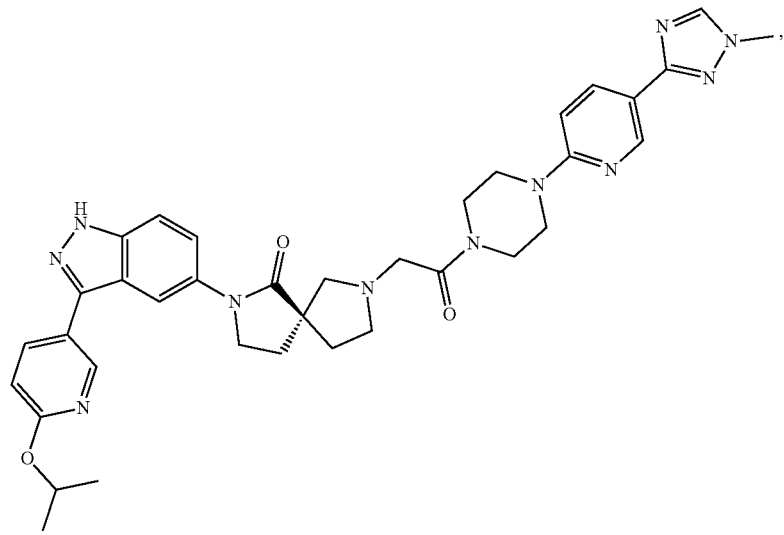
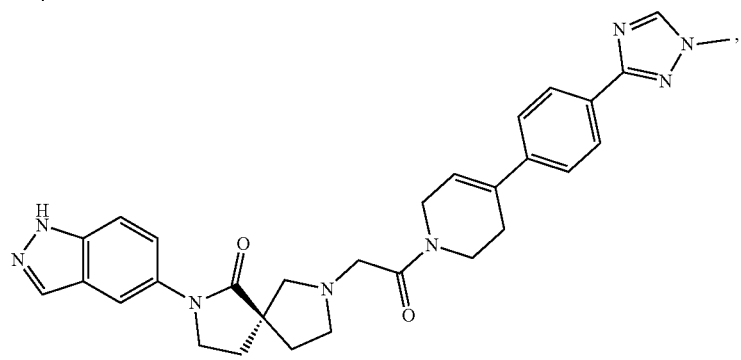

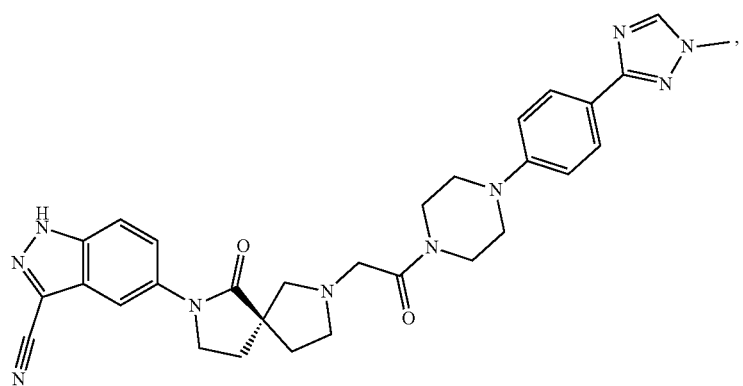
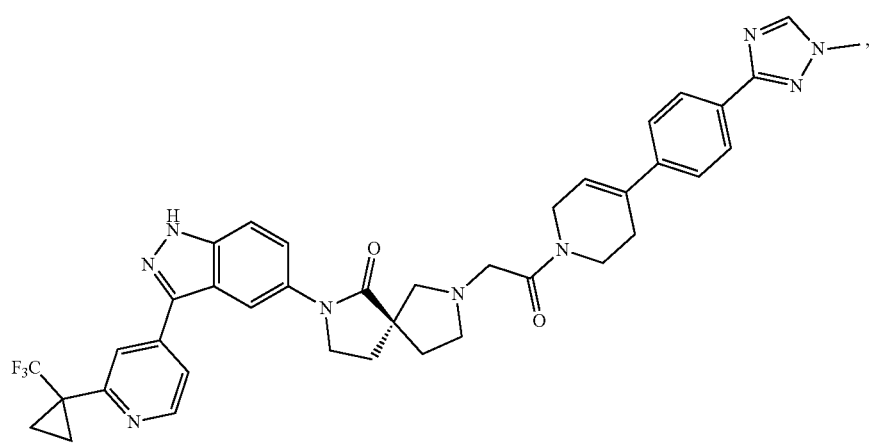
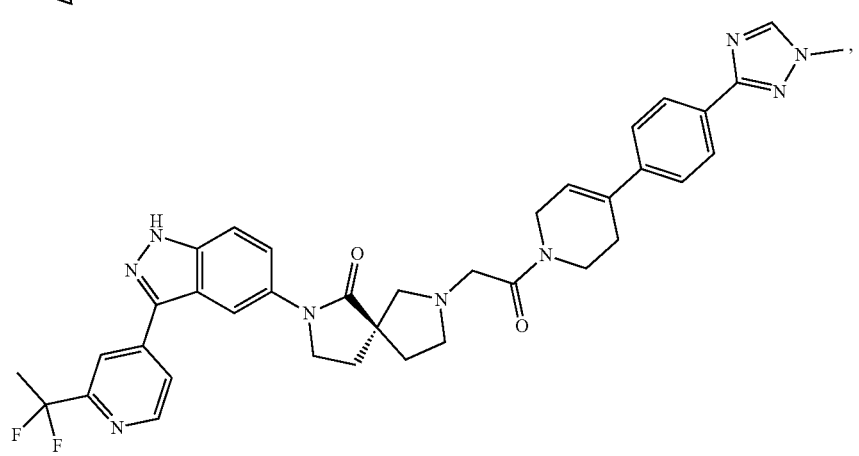
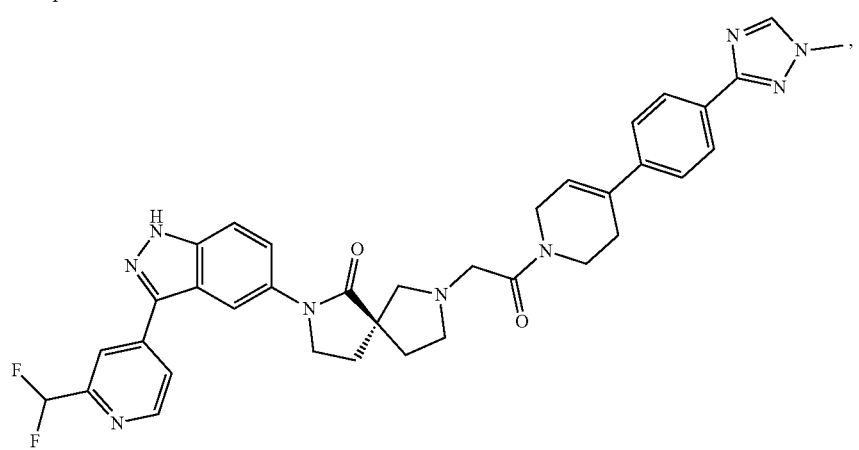

-continued
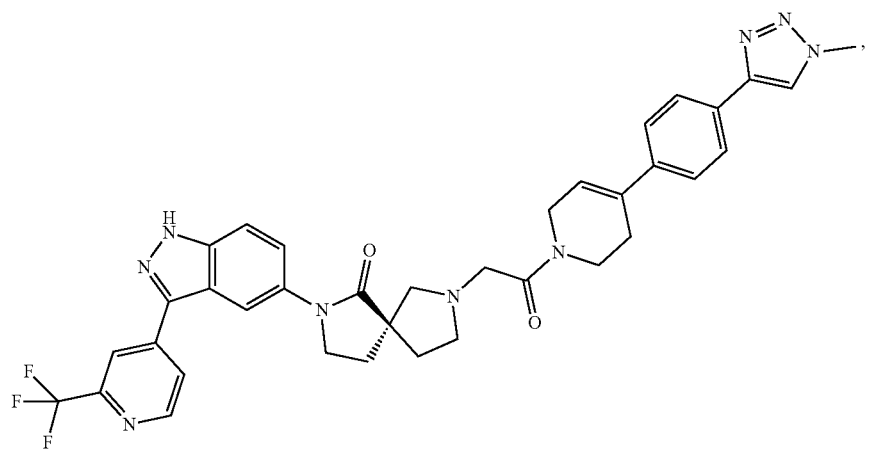
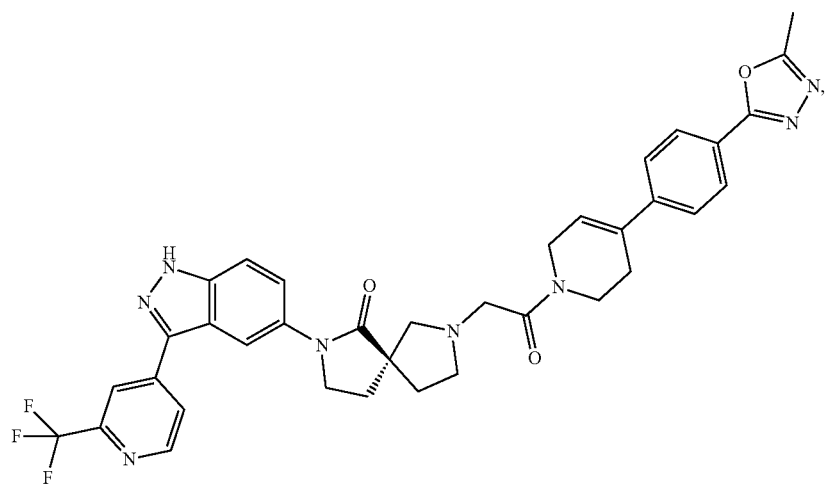
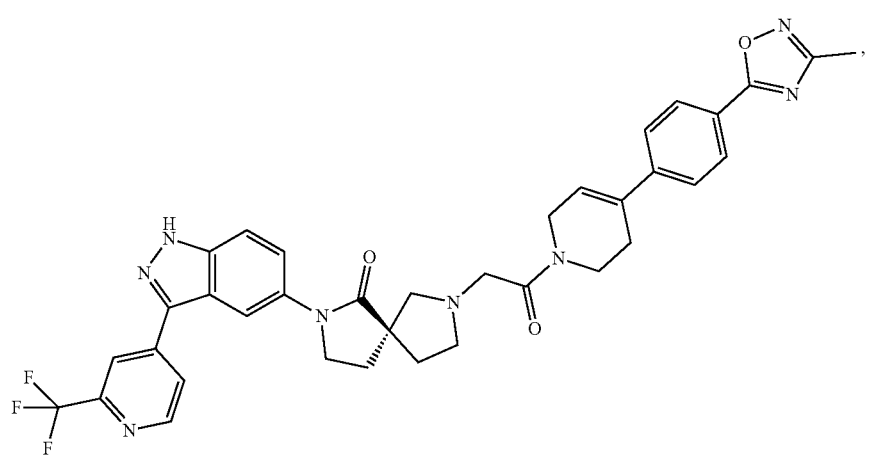

-continued
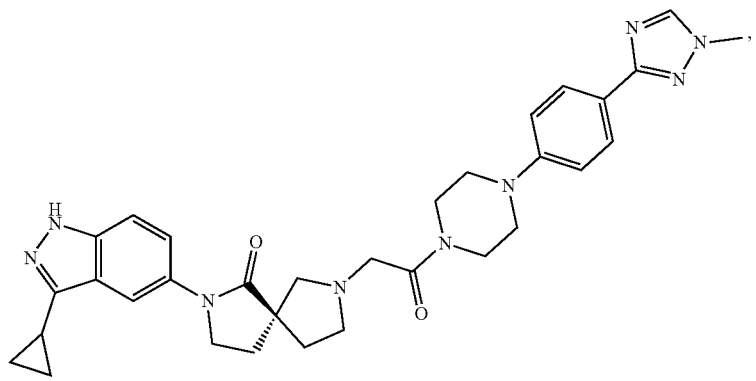
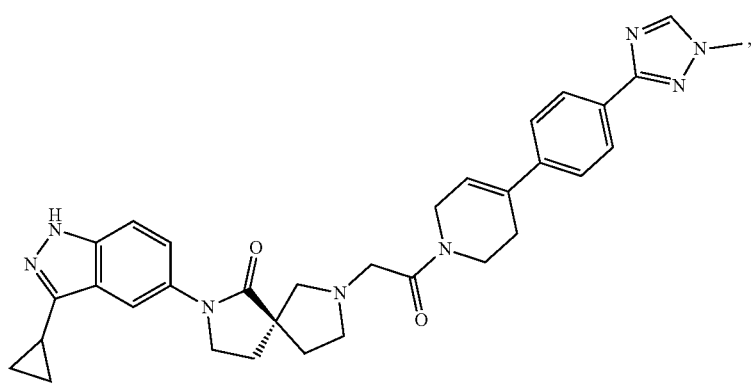
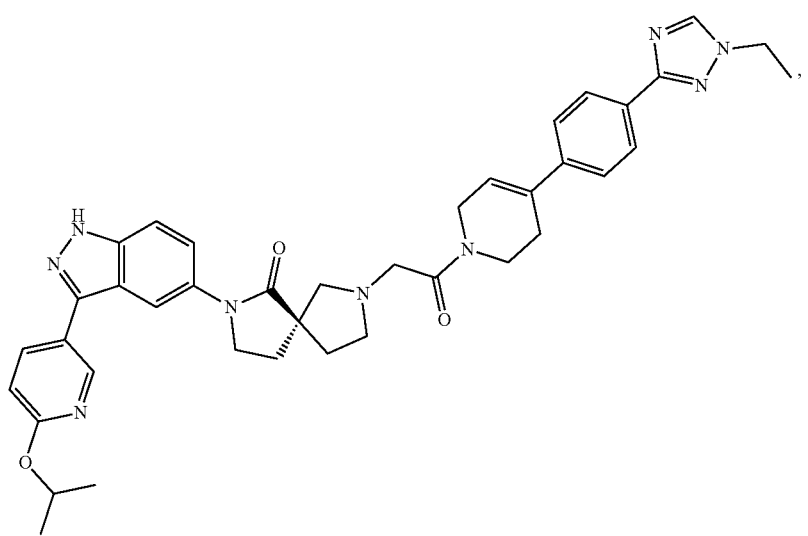

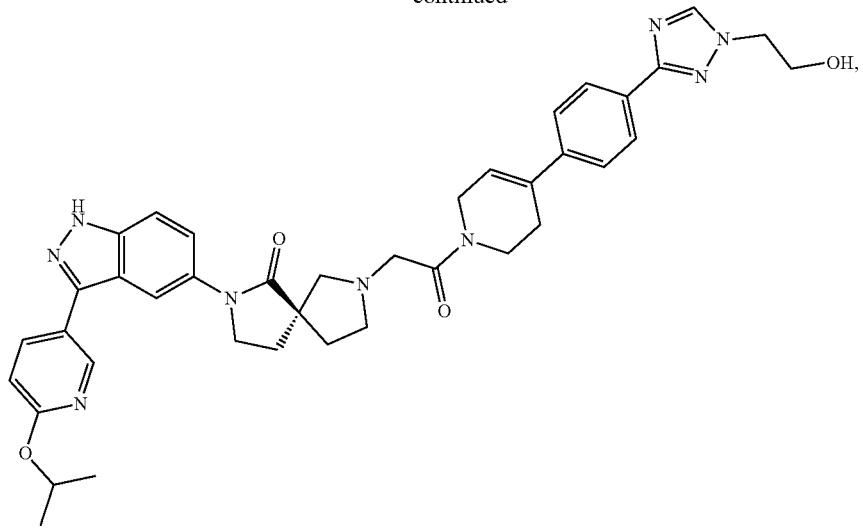
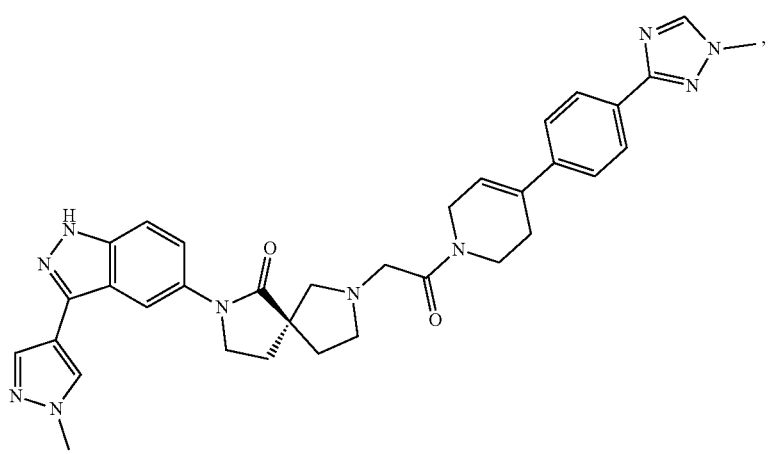
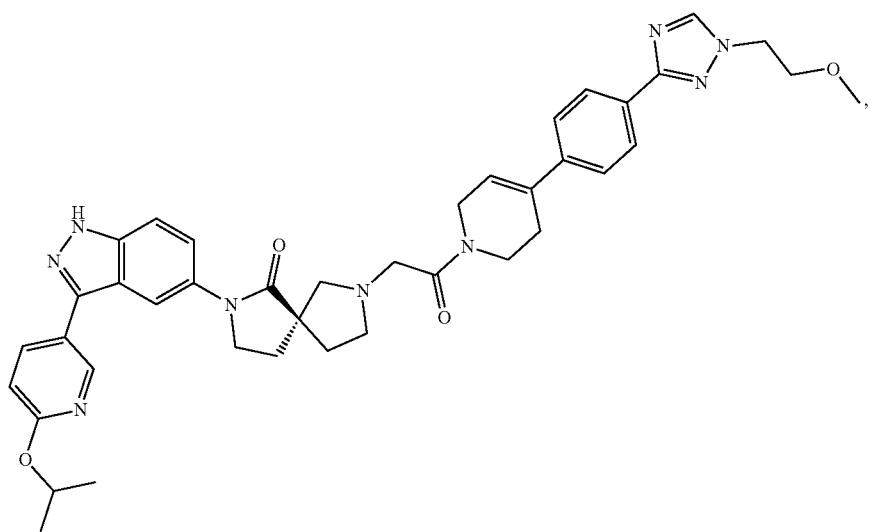

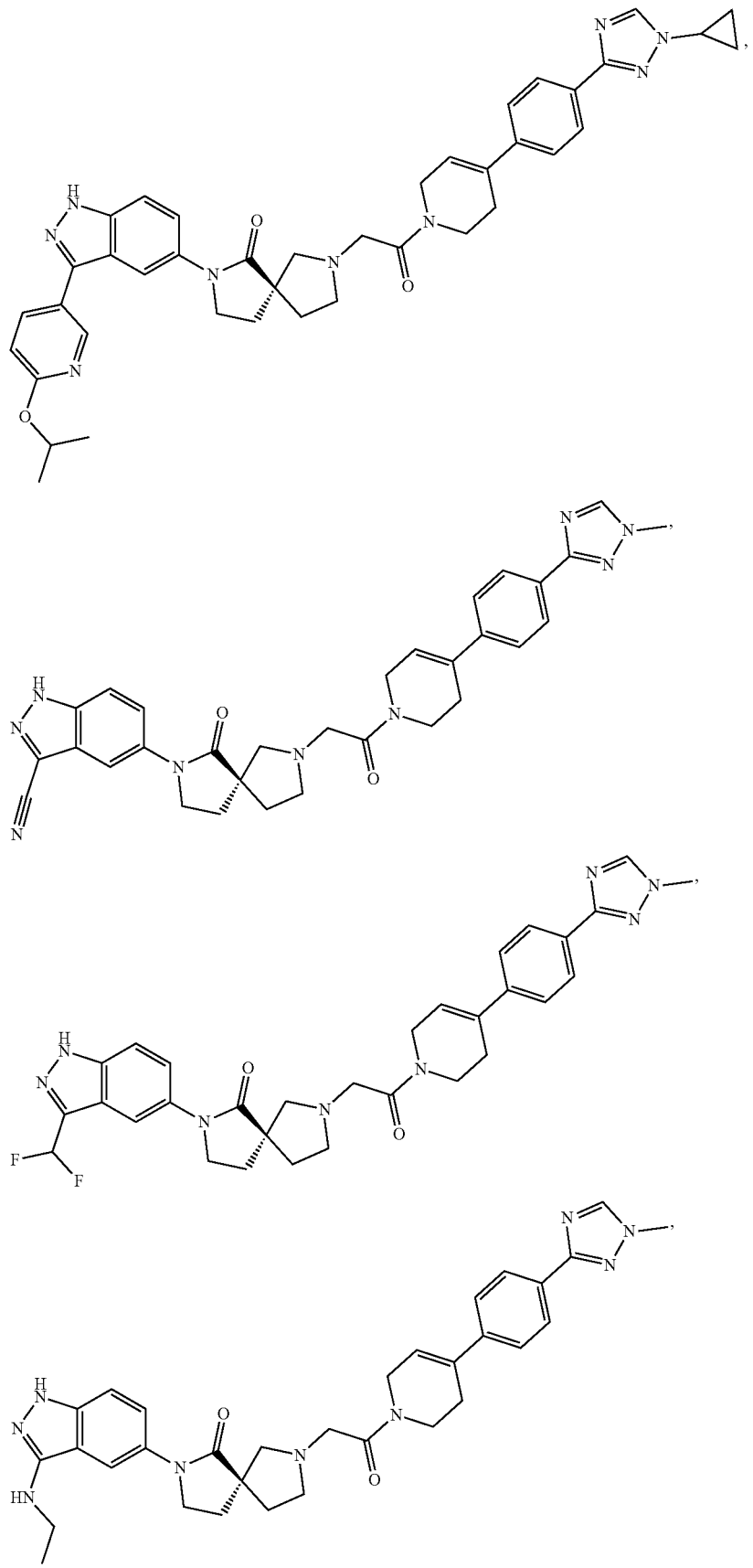

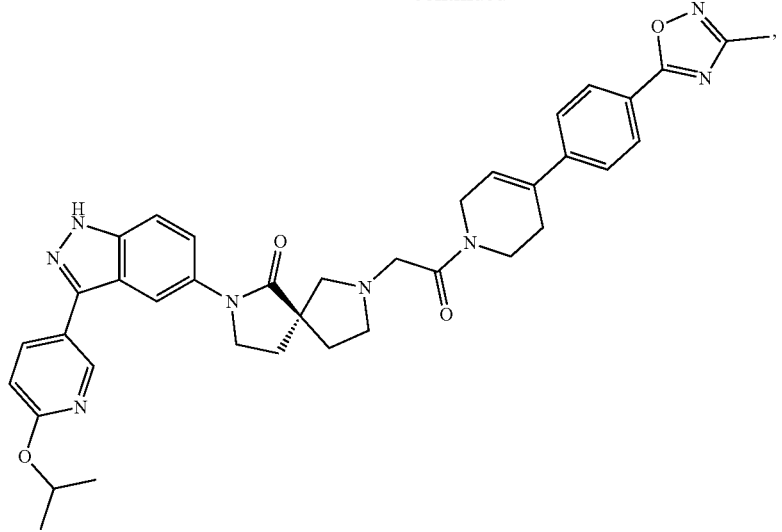
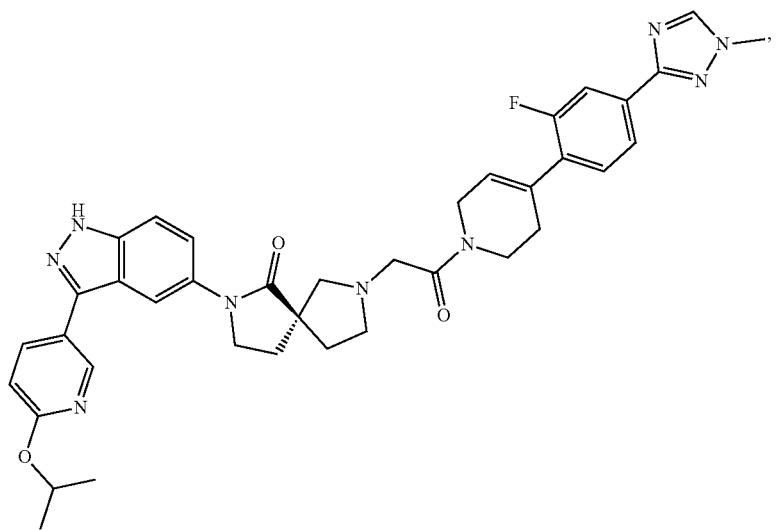
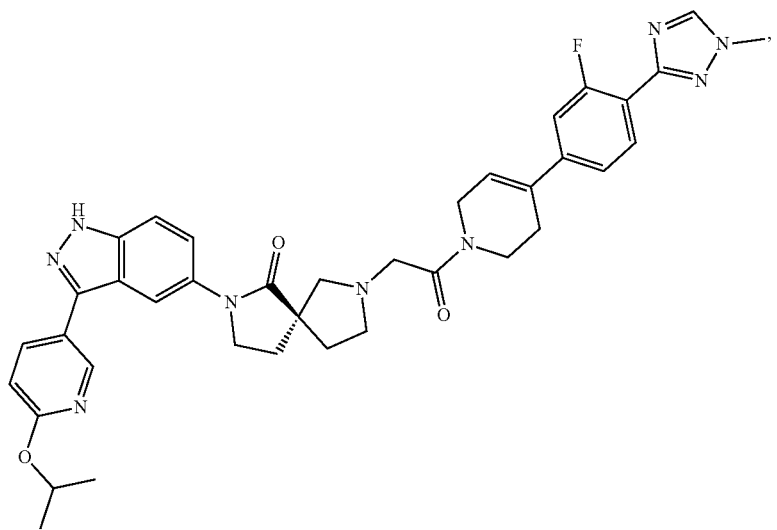

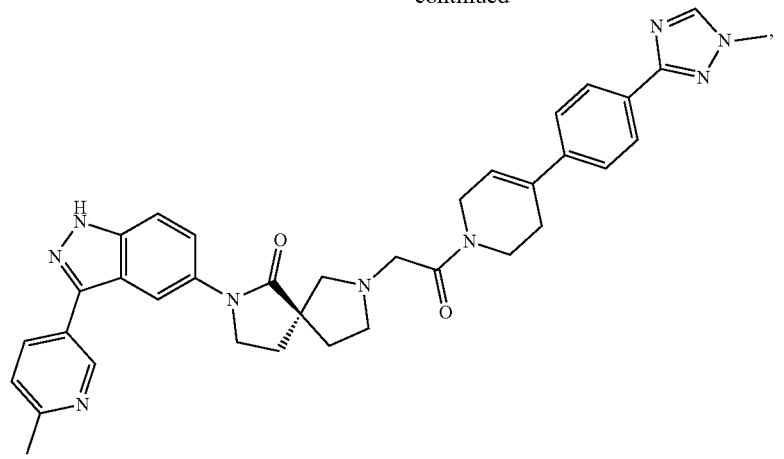
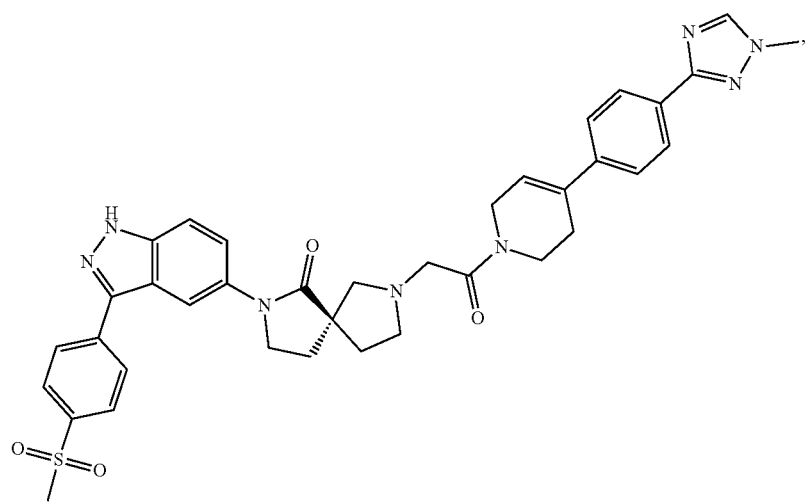
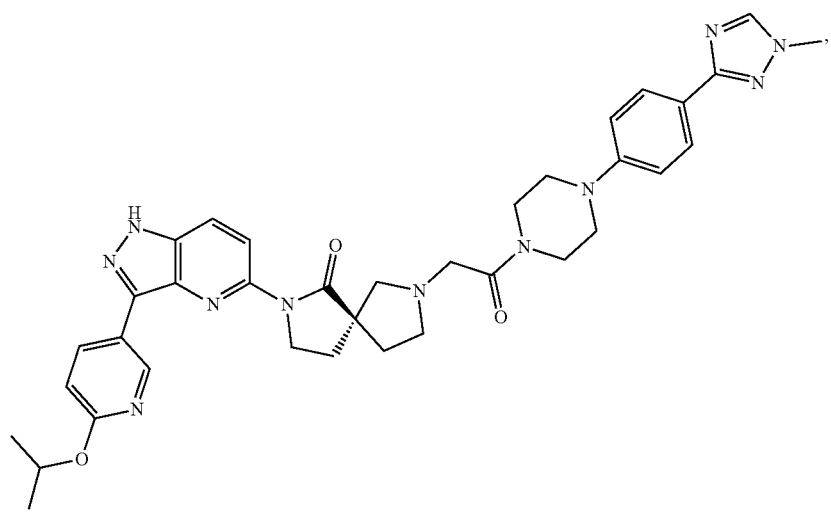

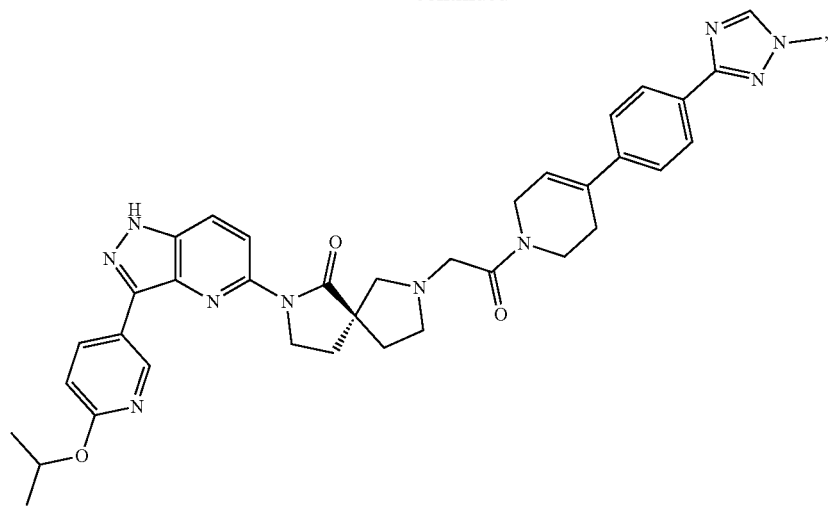
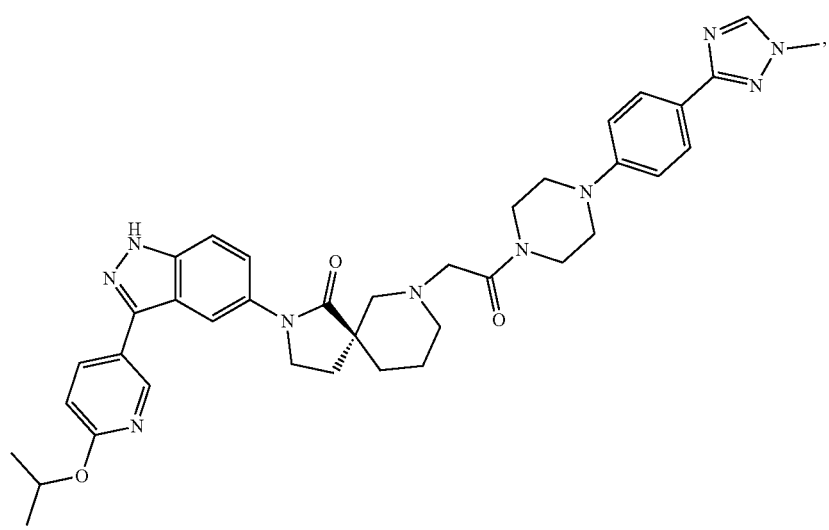
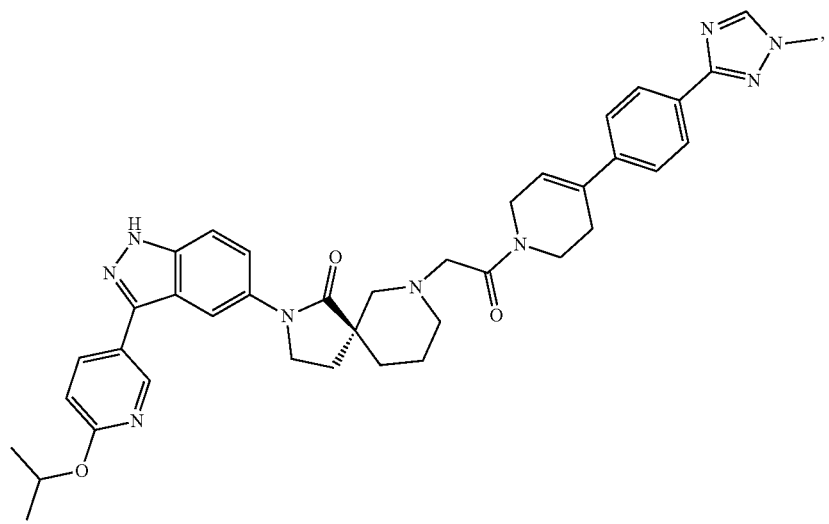

-continued
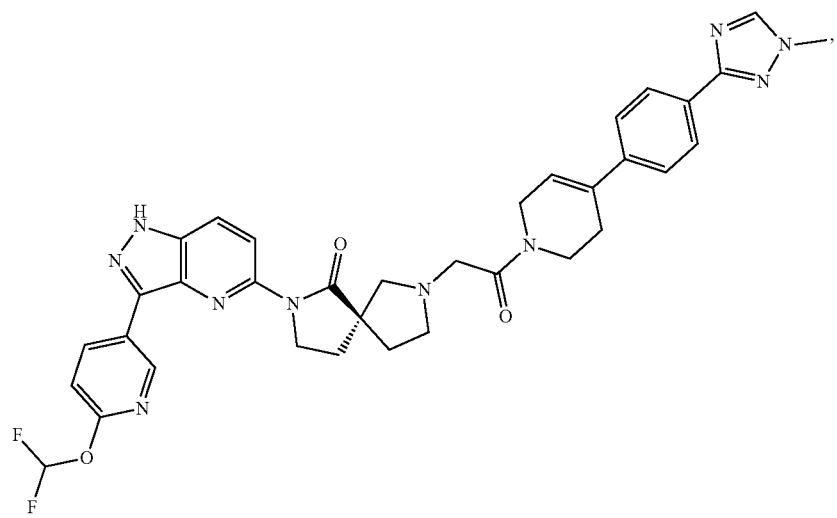
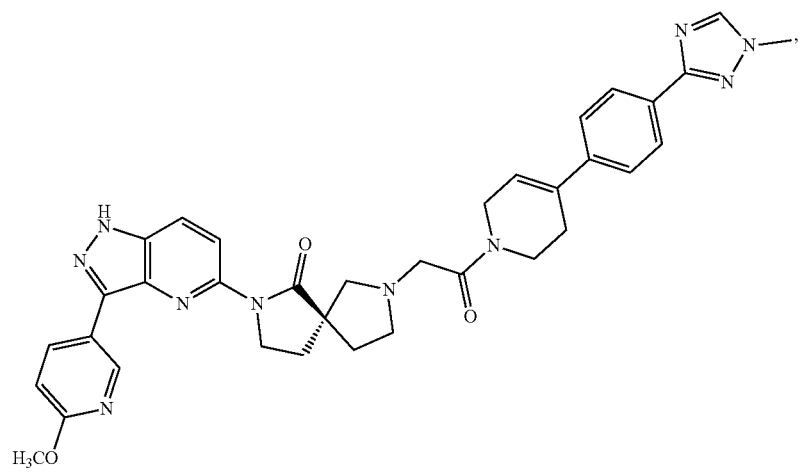
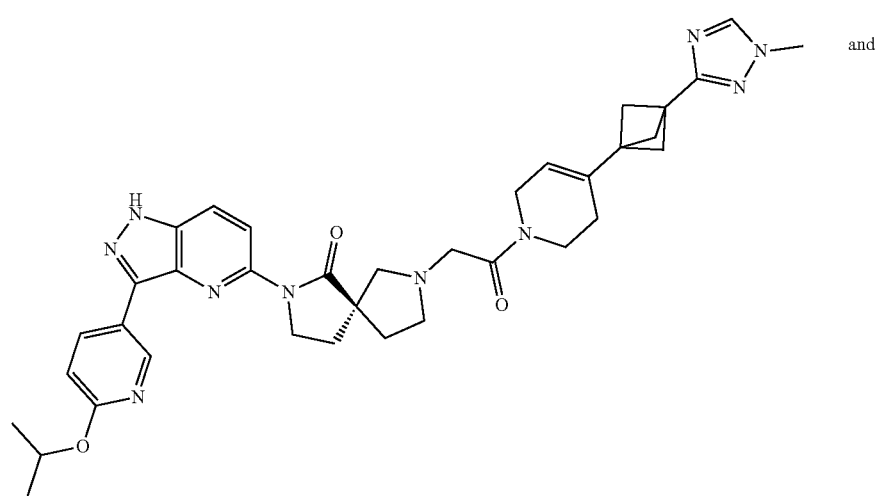
and

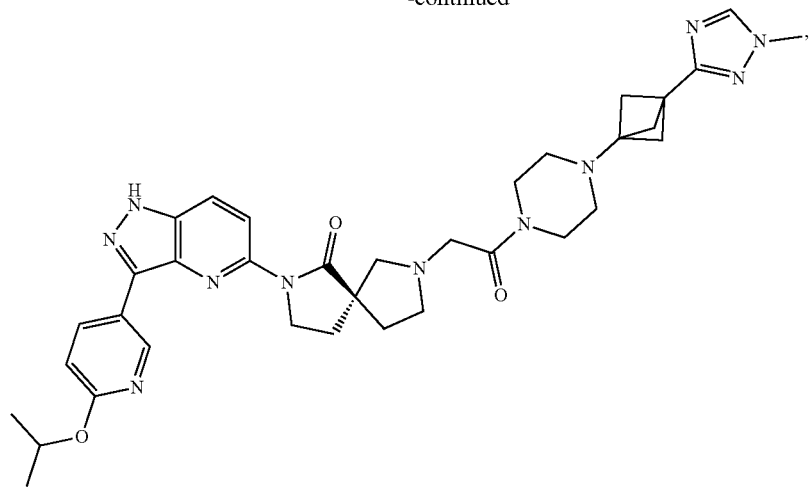

or a pharmaceutically acceptable salt of the foregoing.

Further examples of compounds of Formula (I) include:

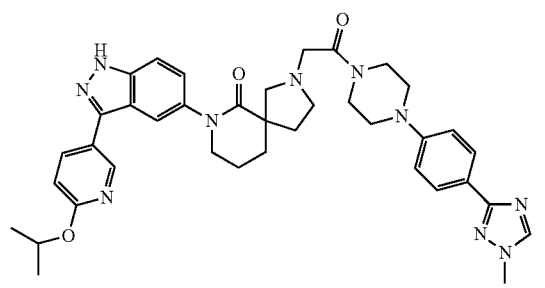

and

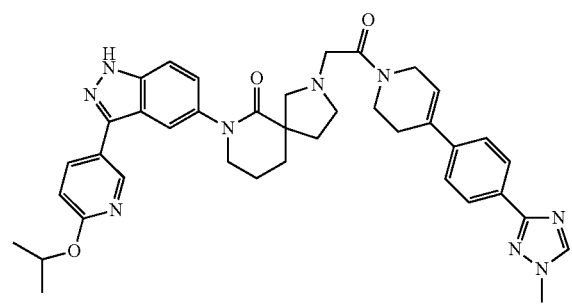

or a pharmaceutically acceptable salt of the foregoing.

Examples of compounds that include a bicyclo[1.1.1] pentyl moiety, but are not limited to, the following:

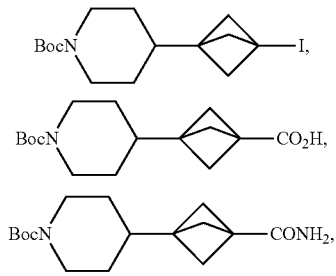

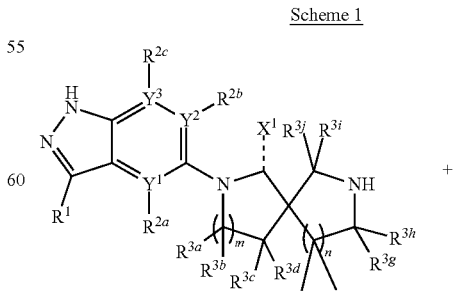

or a pharmaceutically acceptable salt of the foregoing.

Synthesis

Compounds of Formula (I), and those described herein may be prepared in various ways. Some compounds of Formula (I) can be obtained commercially and/or prepared utilizing known synthetic procedures. General synthetic routes to the compounds of Formula (I), and some examples of starting materials used to synthesize the compounds of Formula (I) are shown and described herein in Schemes 1-12. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

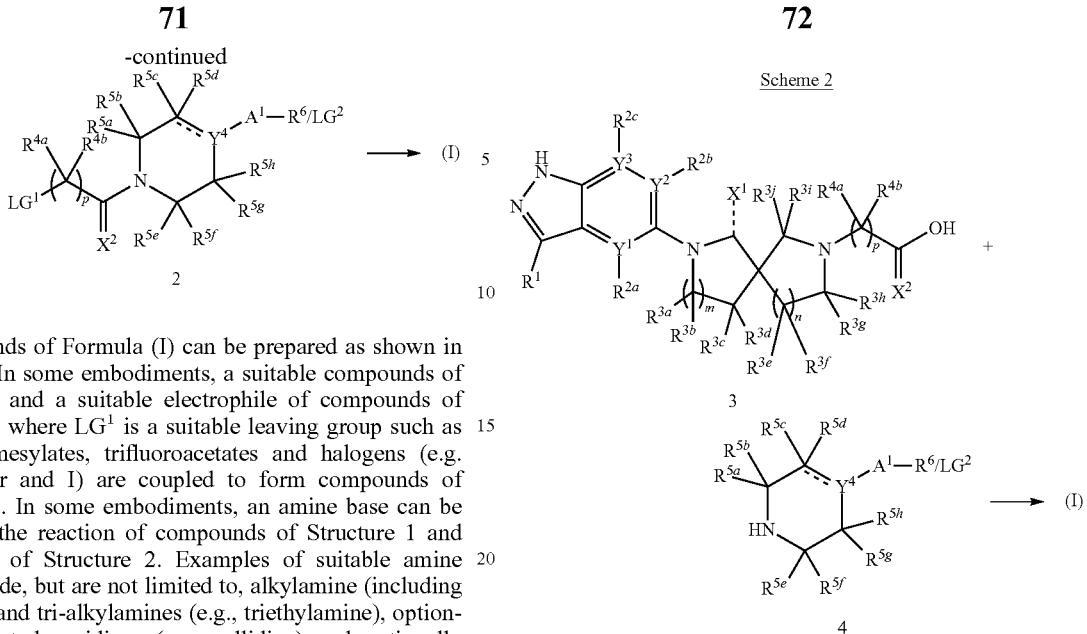

Compounds of Formula (I) can be prepared as shown in Scheme 1. In some embodiments, a suitable compounds of Structure 1 and a suitable electrophile of compounds of Structure 2, where $LG^1$ is a suitable leaving group such as tosylates, mesylates, trifluoroacetates and halogens (e.g. $LG^1$=Cl, Br and I) are coupled to form compounds of Formula (I). In some embodiments, an amine base can be utilized in the reaction of compounds of Structure 1 and compounds of Structure 2. Examples of suitable amine bases, include, but are not limited to, alkylamine (including mono-, di- and tri-alkylamines (e.g., triethylamine), optionally substituted pyridines (e.g. collidine) and optionally substituted imidazoles (e.g., N-methylimidazole). In some embodiments, compounds of Structure 1 and compounds of Structure 2 can be coupled in the presence of a suitable amine base in a solvent with optional heating. In some embodiments, the solvent can be N,N-dimethylformamide.

In some embodiments, $R^6$ is attached to $A^1$ after the reaction between compounds of Structure 1 and compounds of Structure 2, wherein compounds of Structure 2 includes $LG^2$. In some embodiments, $A^1$ can be attached to an optionally substituted heterocyclyl, such as an optionally substituted 1,3,4-oxadiazol-2(3H)-one. In some embodiments, the aryl or the heteroaryl ring(s) can be attached to $A^1$ by a Pd-mediated cross coupling reactions. Examples of suitable Pd-mediated cross coupling reactions are Suzuki, Buchwald and/or Ullmann cross coupling reactions.

Another method for obtaining compounds of Formula (I) are provided in Scheme 2. Compounds of Structure 3 and compounds of Structure 4 can be coupled with a suitable coupling agent in a suitable solvent. A non-limiting list of suitable coupling agents include: 1-[bis(dimethylamino)methylene]-1H-1,2,3-triazolo[4,5-b]pyridinium 3-oxide hexafluorophosphate (HATU), N,N,N',N'-tetramethyl-O-(1H-benzotriazol-1-yl)uronium hexafluorophosphate, O-(Benzotriazol-1-yl)-N,N,N',N'-tetramethyluronium hexafluorophosphate (HBTU) and any such amide coupling agent known to those skilled in the art. In some embodiments, a suitable solvent can be N,N-dimethylformamide. If desired, the reaction can be carried out with heating.

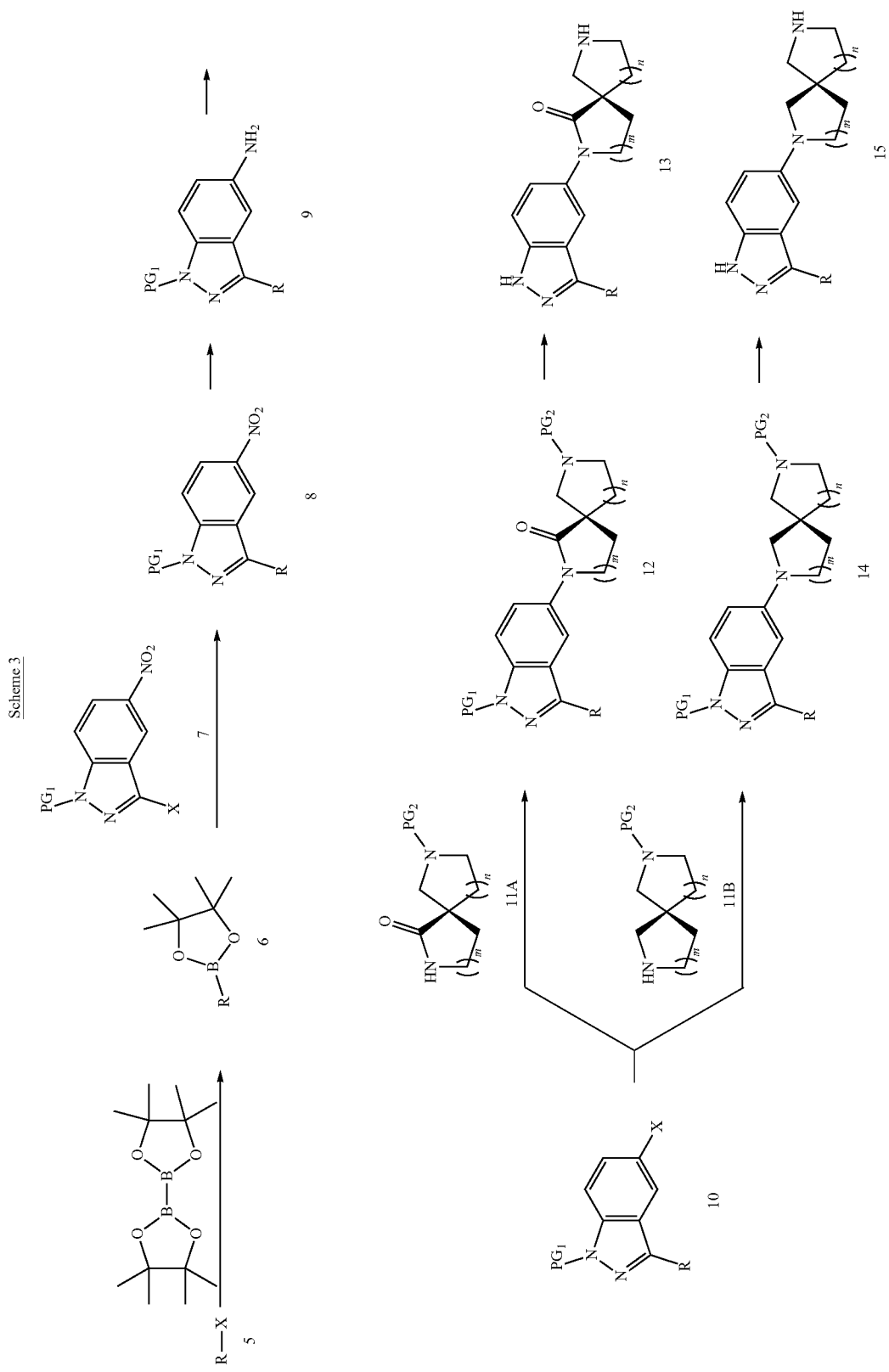

Compounds of Structures 13 and 15 can be prepared as outlined in Scheme 3. In some embodiments, halide compounds of Structure 5 where X can be Br or I are reacted with a boron reagent in the presence of a palladium catalyst and a base in a suitable solvent with optional heating. A suitable example of a boron reagent is bis(pinacolato)diboron, a suitable example of a palladium catalyst is [1,1'-bis(diphenylphosphino)ferrocene] dichloropalladium(II) complex, and an example of a suitable solvent is dichloromethane. In some embodiments, a suitable base can be potassium acetate and a suitable solvent can be 1,4-dioxane. In some embodiments, halide compounds of Structure 5, bis(pinacolato)diboron, [1,1'-bis(diphenylphosphino)ferrocene]dichloropalladium(II) complex with dichloromethane, potassium acetate can be reacted in 1,4-dioxane with optional heating. In some embodiments, compounds of Structure 6 and compounds of Structure 7 (PG=protecting group such as trityl) are reacted under Suzuki cross coupling condition using a suitable palladium catalyst and a base in a suitable solvent to prepare compounds of Structure 8. An example of a suitable palladium catalyst is [1,1'-bis(diphenylphosphino) ferrocene]dichloropalladium(II) complex, an example of a suitable solvent is dichloromethane and an example of a suitable base is potassium carbonate. In some embodiments, the solvent can be a mixture of 1,2-dimethoxyethane and water. If desired, the reaction can be conducted with optional heating. In some embodiments, compounds of Structure 8 can be hydrogenated using a palladium catalyst in a suitable solvent such as methanol, ethanol or a mixture of methanol and toluene. In some embodiments, aryl amine compounds of Structure 9 can be converted to aryl halides of Structure 10 where X can be Br or I using a Sandmeyer reaction. In some embodiments, compounds of Structure 9 can be reacted with sodium nitrite, hydrobromic acid in the presence of copper (I) bromide catalyst to prepare compounds of Structure 10 where X is Br. In some embodiments, compounds of Structure 9 can be reacted with sodium nitrite, hydrochloric acid, sodium iodide in the presence of copper (I) iodide to prepare compounds of Structure 10 where X is I. In some embodiments, aryl halides of compounds of Structure 10 where X is I and amides of Structure 11A (PG$_2$=Boc or Cbz) can be coupled under Ullmann coupling conditions. In some embodiments, compounds of Structure 10 and amide of Structure 11A (PG$_2$=Boc or Cbz) can be reacted in the presence of copper (I) iodide in a suitable solvent (e.g. dimethylsulfoxide) in the presence of a suitable base (such as potassium phosphate) with optimal heating. In some embodiments, compounds of Structure 10 (X=Br or I) and amide of Structure 11A (PG$_2$=Boc or Cbz) can be reacted under Buchwald cross coupling conditions using a suitable palladium catalyst and a suitable solvent with optional heating to prepare compounds of Structure 12. In some embodiment, when PG$_1$ is trityl and PG$_2$ is Boc, both PG$_1$ and PG$_2$ protecting groups can be removed with an acid (such as trifluoroacetic acid) in a suitable solvent (such as dichloromethane). In some embodiments, when PG$_2$ is Cbz, the Cbz group can be removed under hydrogenation condition catalyzed by palladium on carbon in a suitable solvent (for example, methanol) followed by the removal of PG$_1$ under acidic condition to prepare compounds of Structure 13.

In other embodiments, compounds of Structure 10 and amines of Structure 11B can be reacted under Buchwald cross coupling conditions using a suitable palladium catalyst and a suitable solvent with optional heating to prepare compounds of Structure 14. In some embodiment, protecting groups PG$_1$ and PG$_2$ of compounds of Structure 14 can be removed using similar conditions for preparing compounds of Structure 13.

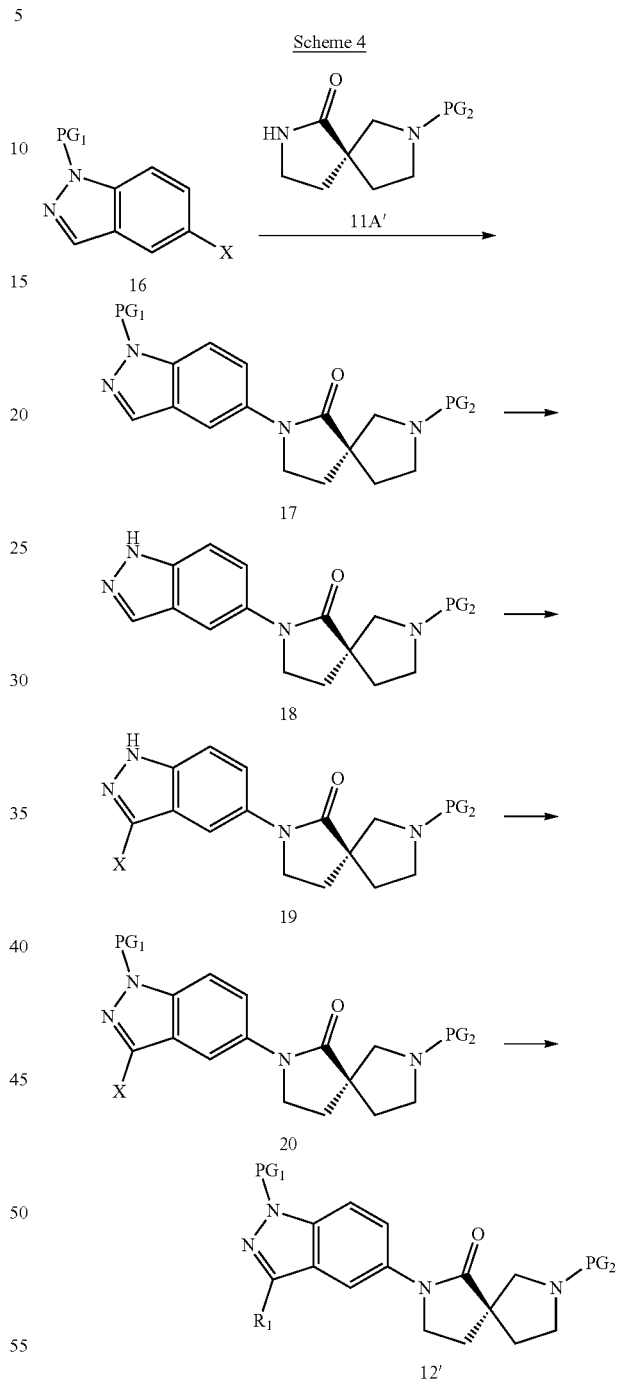

Scheme 4

Compounds of Structure 12' are prepared as outlined in Scheme 4. In some embodiments, aryl halides of compounds of Structure 16 (PG$_1$=trityl and X=I) and amide of Structure 11A' (PG$_2$=Boc or Cbz) can be coupled under Ullmann coupling conditions. In some embodiments, compounds of Structure 16 and amide of Structure 11A' (PG$_2$=Boc or Cbz) can be reacted with catalytic copper (I) iodide in the presence of a suitable base (such as potassium phosphate) in a suitable solvent (for example, dimethylsulfoxide) at elevated temperature (such as 100° C.). In some embodiments, compounds of Structure 16 where X is Br and amide of Structure 11A' can be coupled under Buchwald coupling conditions using a suitable palladium catalyst and a suitable base in a suitable solvent. In some embodiments, compounds of Structure 17 where $PG_1$=trityl and $PG_2$=Cbz can be selectively deprotected under acidic conditions. In some embodiments, compounds of Structure 17 can be deprotected with trifluoroacetic acid in a suitable solvent (such as dichloromethane) at ambient temperature to prepare compounds of Structure 18.

In some embodiments, compounds of Structure 18 can be reacted with an electrophilic halide reagent to prepare compounds of Structure 19 where X is Br or I. In some embodiments, compounds of Structure 18 can be reacted with iodine in the presence of a base (such as potassium hydroxide) in a suitable solvent (such as N,N-dimethylformamide) with an optional heating. In some embodiments, compounds of Structure 18 can be reacted with NBS in the presence of a suitable base in a suitable solvent (such as dichloromethane) to prepare compounds of Structure 19. In some embodiments, compounds of Structure 19 can be reacted with trityl chloride in the presence of a base (such as potassium carbonate) in a suitable solvent(s) (such as acetonitrile) with optional heating to prepare compounds of Structure 20. In some embodiments, compounds of Structure 20 can be reacted with boronic esters of compounds of Structure 6 or boronic acids under Suzuki cross coupling conditions to prepare compounds of Structure 12'. In some embodiments, the palladium catalyst can be [1,1'-bis(diphenylphosphino) ferrocene]dichloropalladium (II) complex with dichloromethane and cesium carbonate as the base. In some embodiments, the solvent can be a mixture of 1,2-dimethoxyethane and water, and the reaction can be conducted with optional heating.

Scheme 5
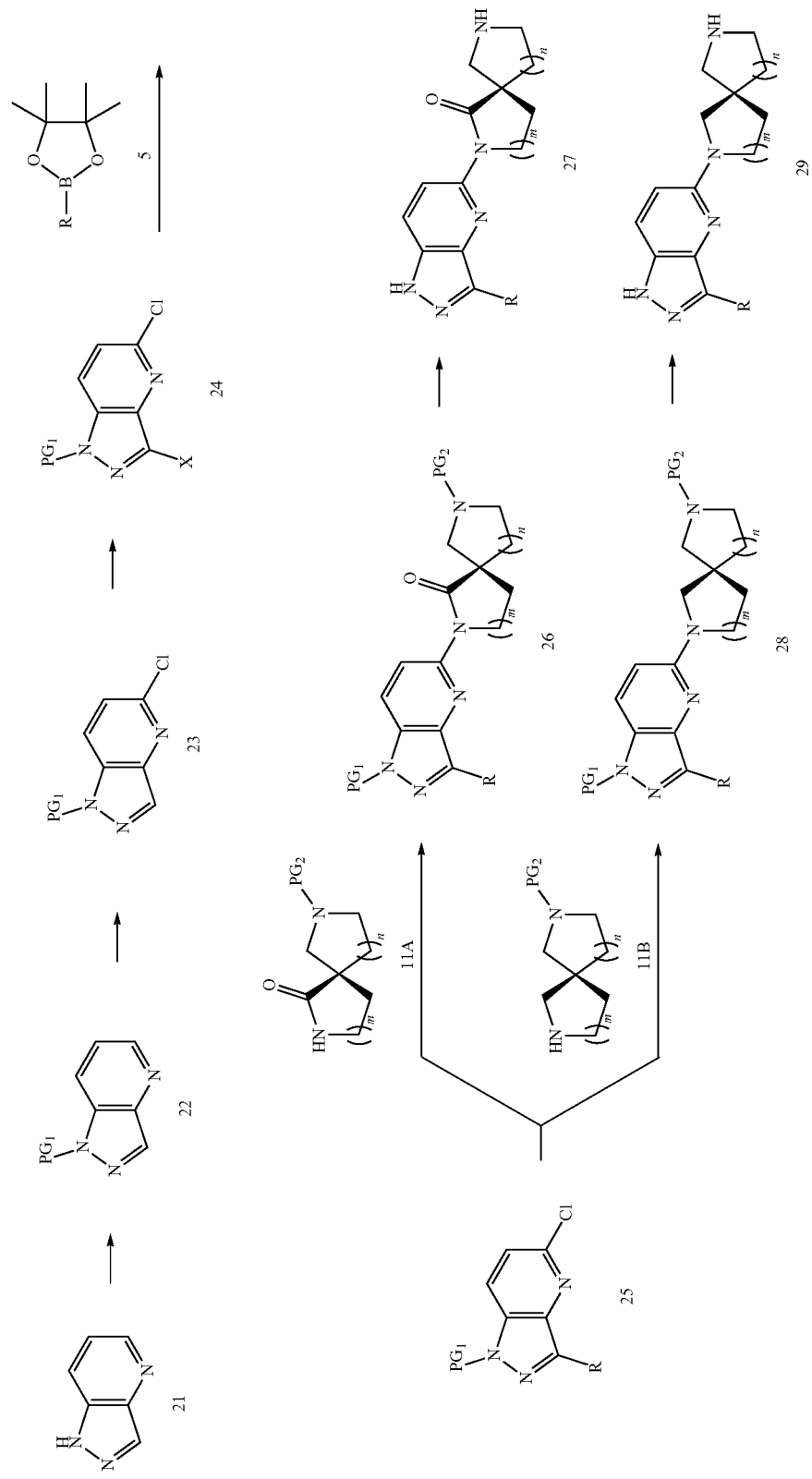

Compounds of Structures 27 and 29 can be prepared as shown in Scheme 5. A compound of Structure 21 can be protected with a suitable protecting group (PG$_1$). In some embodiments, compound of Structure 21 can be reacted with trityl chloride in the presence of a suitable base (such as potassium carbonate) in a suitable solvent (such as acetonitrile) with optional heating. In some embodiments, compound of Structure 22 can be reacted with mCPBA followed by POCl$_3$ and PCl$_5$ to prepare compound of Structure 23. In some embodiments, compound of Structure 23 can be reacted with an electrophilic halogen reagent to prepare compound of Structure 24 where X is Br or I. In some embodiments, compound of Structure 18 can be reacted with iodine in the presence of potassium hydroxide in a suitable solvent to prepare compound of Structure 24 where X is I, or compound of Structure 23 can be reacted with NBS in a suitable solvent (such as dichloromethane) with optional heating to prepare compound of Structure 24 where X is Br. In some embodiments, compounds of Structures 5 and compounds of Structure 24 can be reacted under Suzuki cross coupling conditions using a suitable palladium catalyst and a base in a suitable solvent to prepare compounds of Structure 25. An example of a suitable palladium catalyst is [1,1'-bis(diphenylphosphino) ferrocene]dichloropalladium (II) complex, an example of a suitable solvent is dichloromethane and an example of a suitable base is potassium carbonate. In some embodiments, the solvent can be a mixture of 1,2-dimethoxyethane and water, and the reaction can be conducted with optional heating. In some embodiments, compounds of Structure 25 and compounds of Structures 11A or 11B (PG$_2$=Boc or Cbz) can be reacted under Buchwald cross coupling conditions using a suitable palladium catalyst and a suitable solvent with optional heating to prepare compounds of Structures 26 or 28. In some embodiment, when PG$_2$ is Boc, the Boc group can be removed with trifluoroacetic acid in a suitable solvent (such as dichloromethane). In some embodiments, when PG$_2$ is Cbz, Cbz group can be removed under hydrogenation condition catalyzed by palladium on carbon in a suitable solvent (such as methanol) followed by removal of PG$_1$ under acidic condition to prepare compounds of Structures 27 or 29.

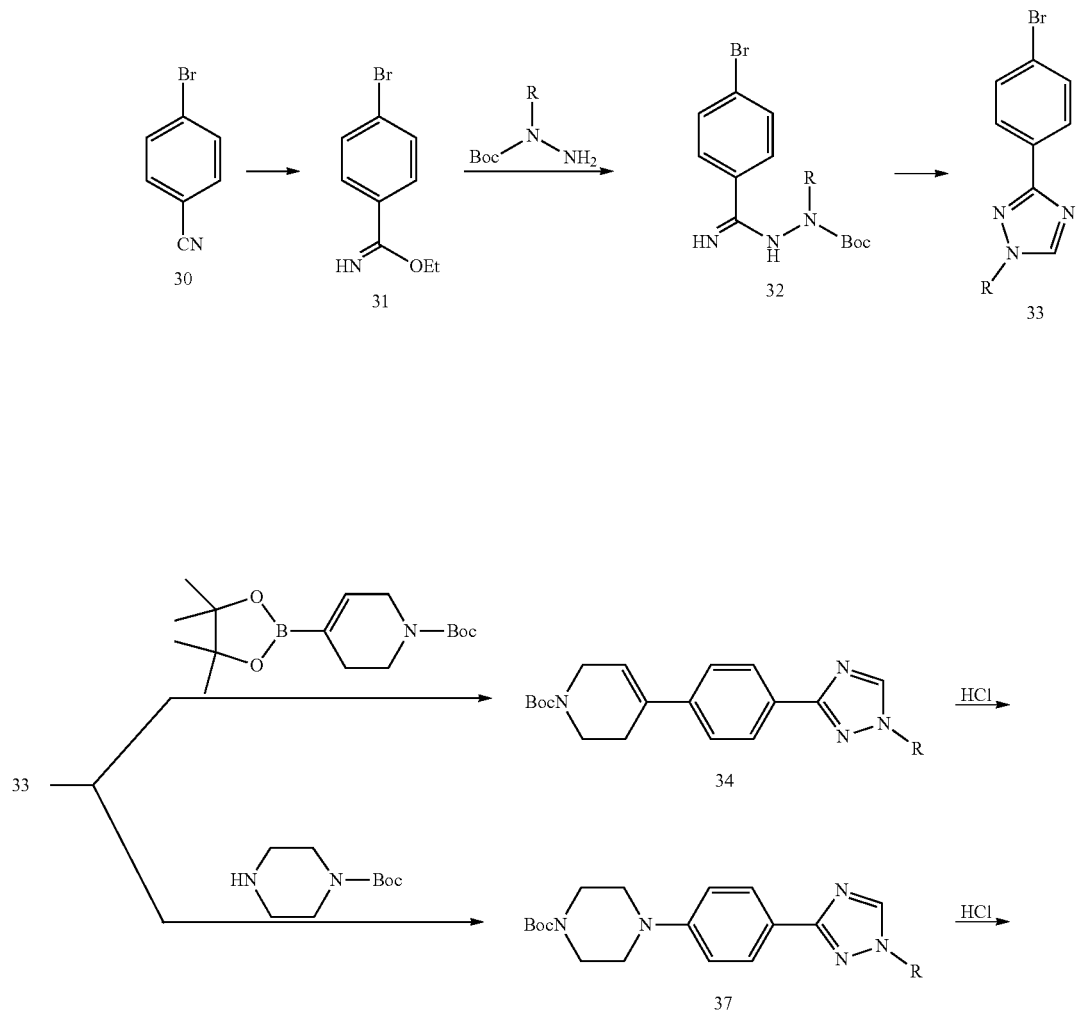

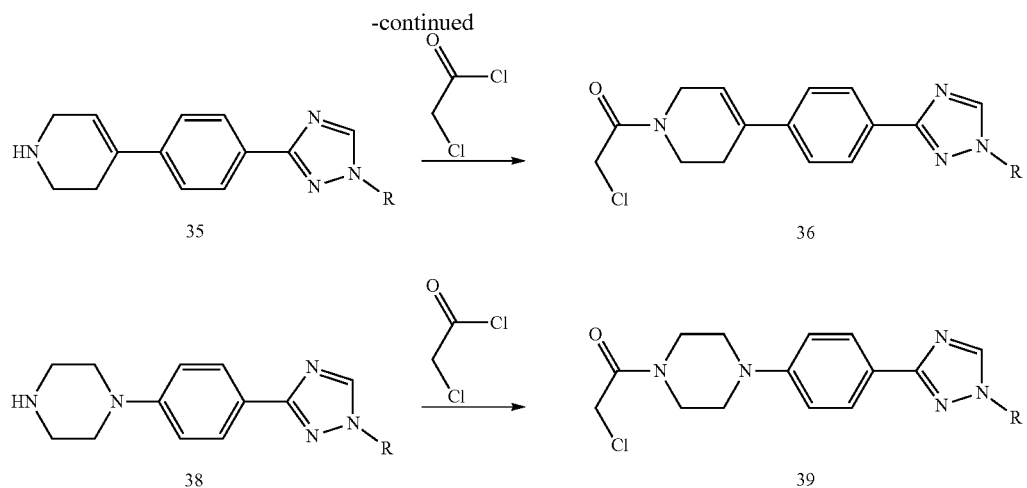

In some embodiments, compounds of Structures 36 and 39 can be prepared as outlined in Scheme 6. In some embodiments, compound of Structure 30 can be reacted with hydrochloric acid gas in an alcohol (such as ethanol) to prepare compound of Structure 31. In some embodiments, compound 31 can be reacted with a substituted hydrazine in an alcoholic solvent (such as methanol) in the presence of a base (such as sodium bicarbonate) to prepare compounds of Structure 32. In some embodiments, compounds of Structure 32 can be cyclized to form a triazole ring in the presence of formic acid to prepare compounds of Structure 33. In some embodiments, compounds of Structure 33 can be reacted under Suzuki cross coupling conditions using a suitable palladium catalyst (for example, palladium catalyst is [1,1'-bis(diphenylphosphino) ferrocene]dichloropalladium (II) complex) and a base (for example, potassium carbonate) in a suitable solvent (such as dichloromethane) to prepare compounds of Structure 34. In some embodiments, the solvent can be a mixture of 1,2-dimethoxyethane and water, and the reaction can be conducted with optional heating. In some embodiments, compounds of Structure 33 can be reacted under Buchwald cross coupling conditions using a suitable palladium catalyst and a suitable solvent with optional heating to prepare compounds of Structure 37. In some embodiments, compounds of Structures 34 or 37 can be reacted with an acid (such as hydrochloric acid) in a suitable solvent (such as 1,4-dioxane) to prepare compounds of Structures 35 or 38. In some embodiments, compounds of Structures 35 or 38 can be reacted with chloroacetyl chloride or chloroacetic anhydride in the presence of a suitable base (such as triethylamine) in a suitable solvent (such as dichloromethane) to prepare compounds of Structures 36 and 39 where R is an alkyl or optionally substituted alkyl, cycloalkyl or optionally substituted cycloalkyl.

Scheme 7

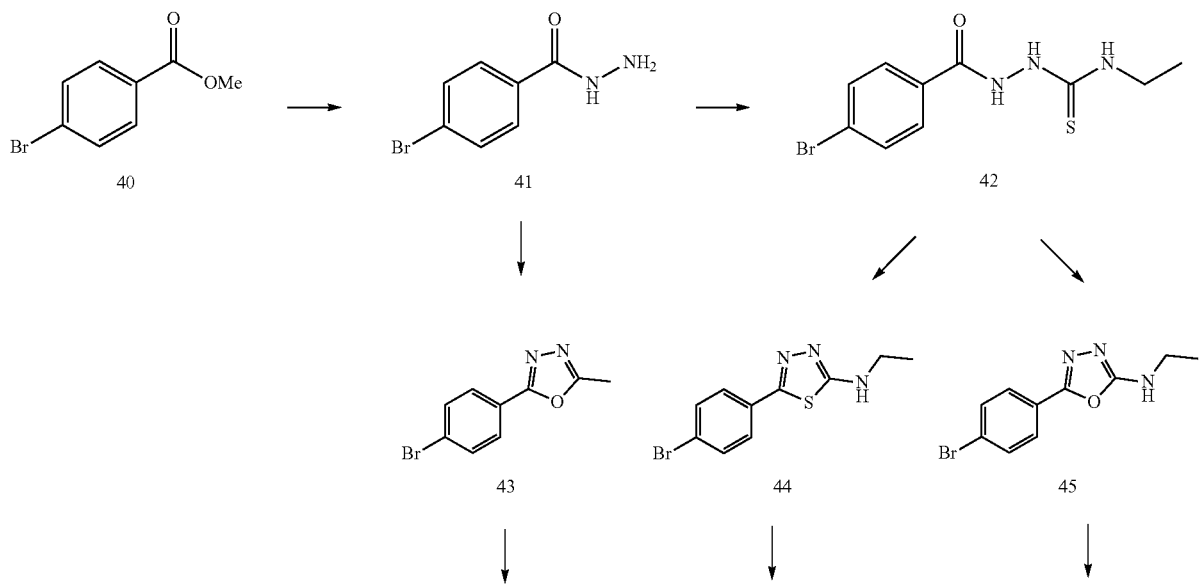

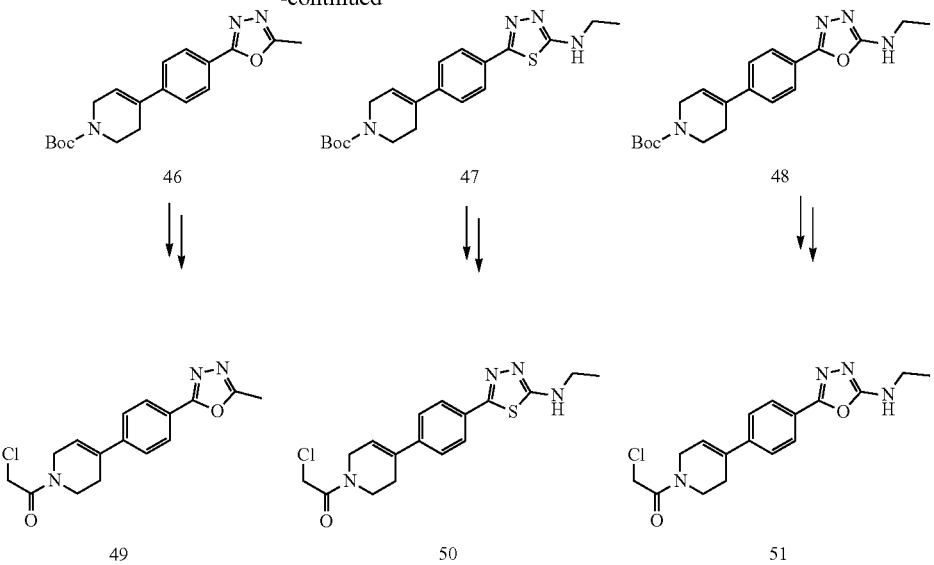

Compounds of Structures 49, 50 and 51 can be prepared as provided in Scheme 7. In some embodiments, compound of Structure 40 can be reacted with hydrazine hydrate in a suitable solvent (such as methanol) with optional heating to prepare compound of Structure 41. In some embodiments, compound of Structure 41 can be reacted with 1,1,1-triethoxyethane, ammonium chloride in suitable solvent (such as ethanol) with optional heating to prepare compound of Structure 43. In other embodiments, compound of Structure 41 can be reacted with ethyl isothiocyanate in the presence of a base (such as trimethylamine) in a suitable solvent (such as tetrahydrofuran) to prepare compound of Structure 42. In some embodiments, compound of Structure 42 can be reacted with tosyl chloride in the presence of a base (such as trimethylamine) in a suitable solvent to prepare compound of Structure 44. Alternatively, compound of Structure 42 can be reacted with EDC in a suitable solvent (such as dimethyl sulfoxide) with optional heating to prepare compound of Structure 45. In some embodiments, compounds of Structures 43, 44 and 45 can be reacted under Suzuki cross coupling conditions to prepare compound of Structures 46, 47 and 48. In some embodiments, compounds of Structures 43, 44 and 45 can be coupled with boronic ester (such as tert-butyl 4-(4,4,5,5-tetramethyl-1,3,2-dioxaborolan-2-yl)-3,6-dihydropyridine-1(2H)-carboxylate) in the presence of a palladium catalyst (such as [1,1'-bis(diphenylphosphino)ferrocene]dichloropalladium(II) complex) with dichloromethane and a base (such as potassium carbonate) in a mixture of solvents (such as 1,2-dimethoxyethane and water) with optional heating. In some embodiments, compounds of Structures 46, 47 and 48 can be deprotected using an acid (such as hydrochloric acid) in a solvent (such as 1,4-dioxane). In some embodiments, compounds of Structures 49, 50 and 51 can be prepared using similar procedures for preparing compounds of Structures 36 and 39 using chloroacetyl chloride or chloroacetic anhydride in the presence of a suitable base (such as triethylamine) in a suitable solvent (such as dichloromethane).

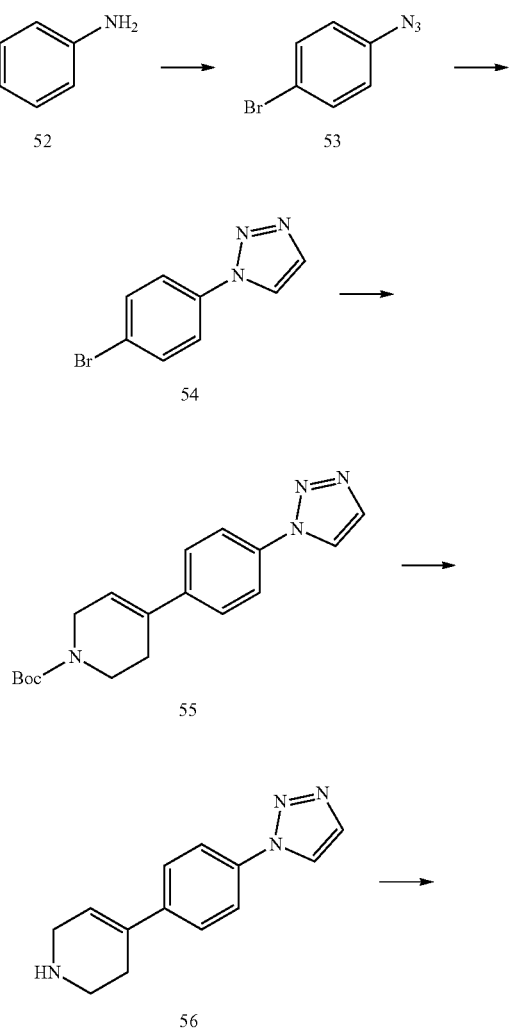

Scheme 8

87

-continued

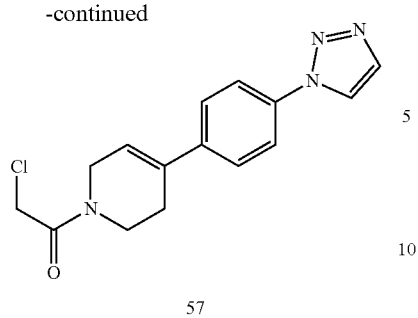

57

Compound of Structure 57 can be prepared as shown in Scheme 8. In some embodiments, compound of Structure 52 can be reacted with sodium nitrite, hydrochloride followed by sodium azide to prepare compound of Structure 53. In some embodiments, compound of Structure 53 can be reacted with trimethylsilyl acetylene, sodium ascorbate, copper (II) sulfate in a suitable solvent (such as a mixture of t-butyl alcohol and water) with optional heating to prepare compound of Structure 54. In some embodiments, compound of Structure 54 can be converted to compound of Structure 57 using procedures similar to those for preparing compounds of Structures 36 and 39 as outlined in Scheme 6.

Scheme 9

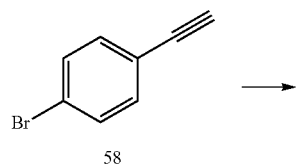

58

88

-continued

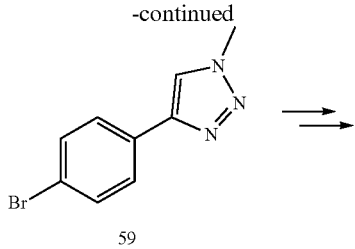

59

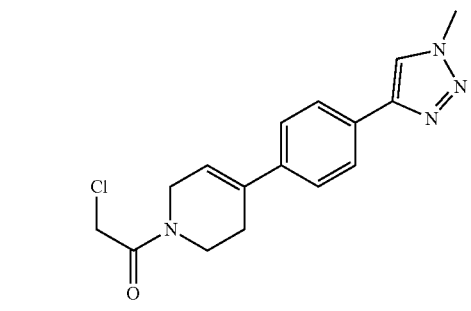

60

Compound of Structure 60 can be prepared as outlined in Scheme 9. In some embodiments, compound of Structure 58 can be reacted with sodium azide, sodium ascorbate, iodomethane in the presence of copper (I) iodide in water with optional heating to prepare compound of Structure 59. In some embodiments, compound of Structure 59 can be converted to compound of Structure 60 using procedures similar to those for preparing compounds of Structures 36 and 39 as outlined in Scheme 6.

Scheme 10

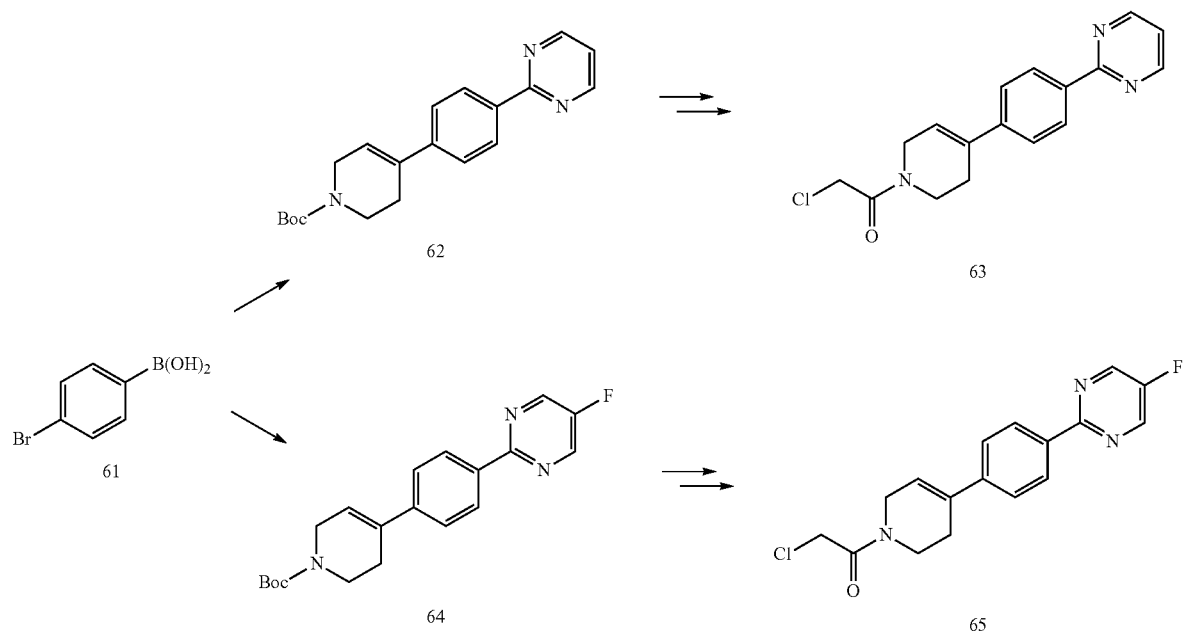

Compounds of Structures 63 and 65 can be prepared using procedures outlined in Scheme 10. In some embodiments, compound of structure 61 can be coupled with 2-bromopyrimidine and tert-butyl 4-(4,4,5,5-tetramethyl-1,3,2-dioxaborolan-2-yl)-3,6-dihydropyridine-1(2H)-carboxylate in the presence of a palladium catalyst (such as [1,1'-bis(diphenylphosphino) ferrocene]dichloropalladium(II) complex) with dichloromethane and a base (such as cesium carbonate) in a mixture of solvents (such as 1,2-dimethoxyethane and water) with optional heating to prepare compound of Structure 62. In some embodiments, compound of Structures 62 can be deprotected using an acid (such as hydrochloric acid) in a solvent (such as 1,4-dioxane). In some embodiments, deprotected compound of Structure 62 can be converted to compound of Structure 63 using methods similar to those for preparing compounds of Structures 36 and 39 using chloroacetyl chloride or chloroacetic anhydride in the presence of a suitable base (such as triethylamine) in a suitable solvent (such as dichloromethane). In some embodiments, compound of Structure 65 can be prepared using methods similar to those for preparing compound of Structure 63.

Scheme 11

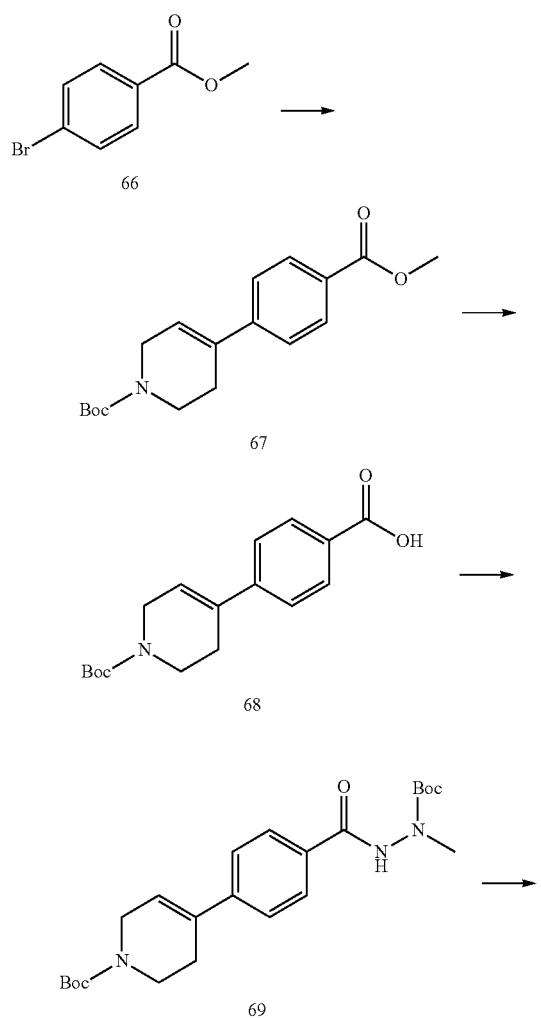

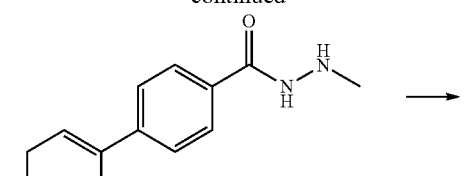

70

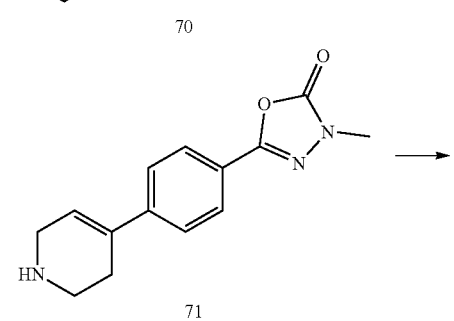

71

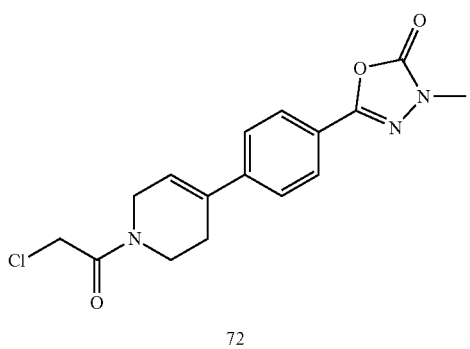

72

Compounds of Structures 72 can be prepared as outlined in Scheme 11. In some embodiments, compound of Structure 67 can be prepared using Suzuki cross coupling conditions. In some embodiments, compound of structure 66 can be coupled with tert-butyl 4-(4,4,5,5-tetramethyl-1,3,2-dioxaborolan-2-yl)-3,6-dihydropyridine-1(2H)-carboxylate in the presence of palladium catalyst (such as bistriphenylphosphinepalladium(II) dichloride) and a base (such as cesium carbonate) in a mixture of solvents (such as 1,2-dimethoxyethane and water) with optional heating to prepare compound of Structure 67. In some embodiments, compound of Structure 67 can be reacted with lithium hydroxide in a suitable solvent (such as tetrahydrofuran and water) to prepare compound of Structure 68. In some embodiments, compound of Structure 68 can be reacted with 1,1'-carbonyldiimidazole followed by tert-butyl 1-methylhydrazine-1-carboxylate in a suitable solvent (such as N,N-dimethylformamide) with optional heating to prepare compound of Structure 69. In some embodiments, compound of Structure 69 can be reacted with hydrochloric acid in a suitable solvent (such as 1,4-dioxane). In some embodiments, compound of Structure 70 can be treated with a suitable reagent (such as bis(trichloromethyl) carbonate) and a base (such as trimethylamine) in a suitable solvent (such as dichloromethane) to prepare compound of Structure 71.

In some embodiments, compound of 71 can be converted to compound of Structure 72 using methods similar to those for preparing compound of Structure 36 and 39 as outlined in Scheme 6.

Scheme 12

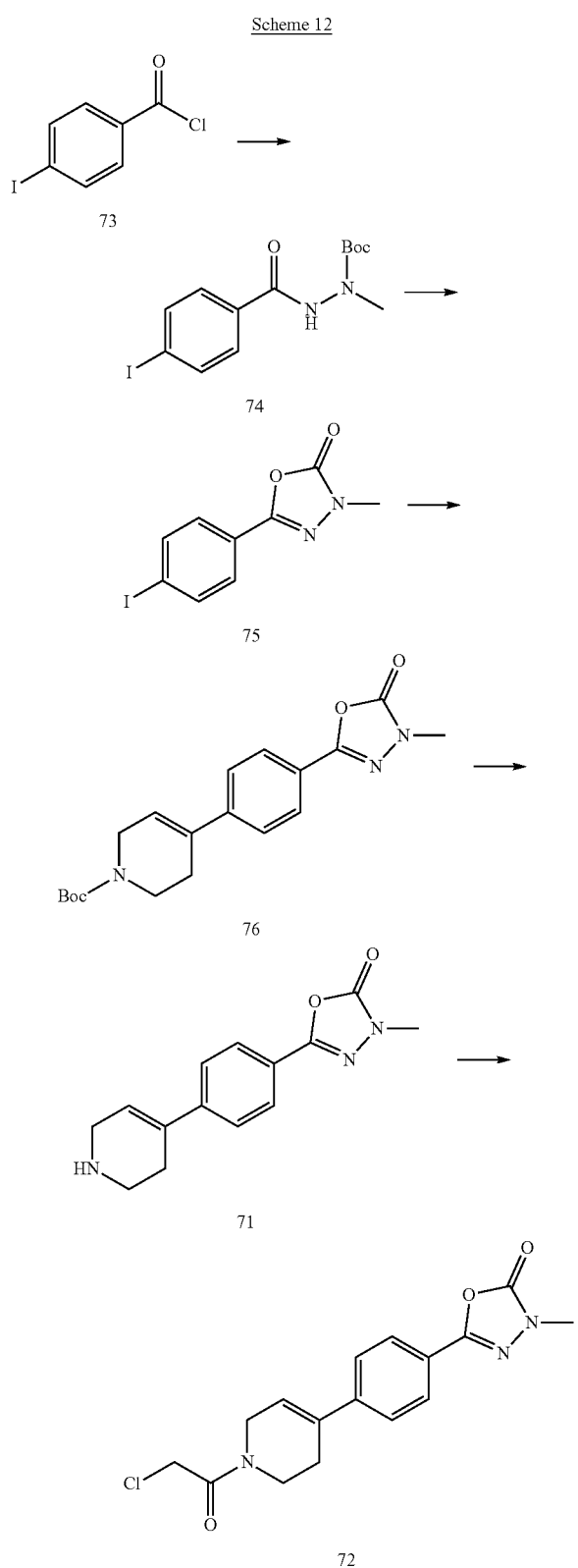

Alternatively, compounds of Structures 71 and 72 can be prepared as outlined in Scheme 12. In some embodiments, compound of Structure 73 can be reacted with tert-butyl 1-methylhydrazine-1-carboxylate in a suitable solvent (such as tetrahydrofuran) and in the presence of a suitable base (such as triethylamine) to prepare a compound of Structure 74. In some embodiments, compound of Structure 74 can be reacted with a suitable reagent (such as 4-nitrophenylchloroformate) in a suitable solvent (such as dichloromethane) in the presence of a suitable base (such as triethylamine) to prepare compound of Structure 75. In some embodiments, compound of Structure 75 can be prepared using Suzuki cross coupling conditions. In some embodiments, compound of structure 75 can be coupled with tert-butyl 4-(4,4,5,5-tetramethyl-1,3,2-dioxaborolan-2-yl)-3,6-dihydropyridine-1(2H)-carboxylate in the presence of palladium catalyst (such as bistriphenylphosphinepalladium (II) dichloride) and a base (such as cesium carbonate) in a mixture of solvents (such as 1,2-dimethoxyethane and water) with optional heating to prepare compound of Structure 76. In some embodiments, compound of Structure 76 can be converted to compound of Structure 72 as outlined in Scheme 6. Throughout the specification, groups and substituents thereof are chosen by one skilled in the field to provide stable moieties and/or compounds.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, pulmonary, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory infection may be desirable.

As described herein, compounds of Formula (I), or a pharmaceutically acceptable salt thereof, can be administered by a variety of methods. In some of the methods described herein, administration can be by injection, infusion and/or intravenous administration over the course of 1 minute, 5 minutes, 10 minutes, 30 minutes, 1 hour, 2 hours, 6 hours, 12 hours, 24 hours or longer, or any intermediate time. Other methods described herein can include oral, intravenous and/or intraperitoneal administration to a subject in need thereof, for example, to a subject to treat a cancer described herein responsive to an ERK inhibitor.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer that can include contacting a malignant growth or a tumor, wherein the malignant growth or tumor is due to a cancer described herein.

Some embodiments described herein relate to a method for inhibiting the activity of ERK1 and/or ERK2 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a sample that includes a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of ERK1 and/or ERK2. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of ERK1 and/or ERK2.

Some embodiments described herein relate to a method for ameliorating or treating a cancer described herein that can include inhibiting the activity of ERK1 and/or ERK2 using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of ERK1 and/or ERK2. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of ERK1 and/or ERK2.

Examples of suitable cancers include, but are not limited to: lung cancer (e.g., lung adenocarcinoma and non-small cell lung cancer, see Adjei, A. A., "The role of mitogen-activated ERK-kinase inhibitors in lung cancer therapy" Clin. Lung. Cancer (2005) 7(3):221-223 and Roberts et al., "Targeting the Raf-MEK-ERK mitogen-activated protein kinase cascade for the treatment of cancer" Oncogene (2007) 26(22):3291-3310), pancreatic cancers (e.g., pancreatic carcinoma such as, for example, exocrine pancreatic carcinoma, see Hayes, et al., "Long-Term ERK Inhibition in KRAS-Mutant Pancreatic Cancer Is Associated with MYC Degradation and Senescence-like Growth Suppression" Cancer Cell (2016) 29(1):75-89 and Morris et al., "Discovery of a novel ERK inhibitor with activity in models of acquired resistance to BRAF and MEK inhibitors" Cancer Discov (2013) 3(7):742-750), colon cancers (e.g., colorectal carcinomas, such as, for example, colon adenocarcinoma and colon adenoma, see Fang et al., "The MAPK signalling pathways and colorectal cancer" Lancet Oncol (2005) 6(5): 322-327), myeloid leukemias (for example, acute myelogenous leukemia (AML), CML, and CMML, see Steelman et al., "Roles of the Ras/Raf/MEK/ERK pathway in leukemia therapy" Leukemia (2011) 25(7):1080-1094), thyroid cancer, myelodysplastic syndrome (MDS), bladder carcinoma (see Noguchi et al., "Replacement treatment with microRNA-143 and -145 induces synergistic inhibition of the growth of human bladder cancer cells by regulating PI3K/Akt and MAPK signaling pathways" Cancer Lett (2013) 328(2):353-361), epidermal carcinoma (see Khavari et al., "Ras/Erk MAPK signaling in epidermal homeostasis and neoplasia" Cell Cycle (2007) 6(23)2928-2931), melanoma (see Morris et al., "Discovery of a novel ERK inhibitor with activity in models of acquired resistance to BRAF and MEK inhibitors" Cancer Discov (2013) 3(7):742-750), breast cancer (see Maiello et al., "EGFR and MEK Blockade in Triple Negative Breast Cancer Cells" J Cell Biochem (2015) 116(12):2778-2785), prostate cancer (see Rodriguez-Berriguete et al., "Relationship between IL-6/ERK and NF-κB: a study in normal and pathological human prostate gland" Eur Cytokine Netw (2010) 21(4):251-250), head and neck cancers (e.g., squamous cell cancer of the head and neck, see Jimenez et al., "Mechanisms of Invasion in Head and Neck Cancer" Arch Pathol Lab Med (2015) 139(11):1334-1348), ovarian cancer (see Sheppard et al., "Synergistic inhibition of ovarian cancer cell growth by combining selective PI3K/mTOR and RAS/ERK pathway inhibitors" Eur J Cancer (2013) 49(18):3936-3944), brain cancers (e.g., gliomas, such as glioma blastoma multiforme, see Chen et al., "Glioma cell proliferation controlled by ERK activity-dependent surface expression of PDGFRA" PLoS One (2014) 9(1)e87281), cancers of mesenchymal origin (e.g., fibrosarcomas and rhabdomyosarcomas, see Buonata et al., "ERK1/2 blockade prevents epithelial-mesenchymal transition in lung cancer cells and promotes their sensitivity to EGFR inhibition" Cancer Res (2014) 74(1):309-319), sarcomas (see Serrano et al., "RAS/MAPK pathway hyperactivation determines poor prognosis in undifferentiated pleomorphic sarcomas" Cancer (2016) 122(1):99-107), tetracarcinomas (see Chambers et al., "Self-renewal of teratocarcinoma and embryonic stem cells" Oncogene (2004) 23(43):7150-7160), neuroblastomas (see Vieira et al., "LGR5 regulates pro-survival MEK/ERK and proliferative Wnt/β-catenin signalling in neuroblastoma" Oncotarget (2015) 6(37):40053-40067), kidney carcinomas (see Chen et al., "Expression and prognostic role of MEKK3 and pERK in patients with renal clear cell carcinoma" Asian Pac J Cancer Prev (2015) 16(6):2495-2499), hepatomas (see Huang et al., "Apelin-13 induces autophagy in hepatoma HepG2 cells through ERK1/2 signaling pathway-dependent upregulation of Beclin1" Oncol Lett (2016) 11(2):1051-1056), non-Hodgkin's lymphoma (see Carlo-Stella et al., "Sorafenib inhibits lymphoma xenografts by targeting MAPK/ERK and AKT pathways in tumor and vascular cells" PLoS One (2013) 8(4):e61603), multiple myeloma (see Jin et al., "USO1 promotes tumor progression via activating Erk pathway in multiple myeloma cells" Biomed Pharmacother (2016) 78:264-271), anaplastic thyroid carcinoma (see Milosevic et al., "Targeting RAS-MAPK-ERK and PI3K-AKT-mTOR signal transduction pathways to chemosensitize anaplastic thyroid carcinoma" Transl Res (2014) 164(5):411-423) and neurofibromatosis (NF-1) (see Wang et al., "ERK inhibition rescues defects in fate specification of Nf1-deficient neural progenitors and brain abnormalities" Cell (2012) 150(4):816-830).

The compound(s) of Formula (I) or a pharmaceutically acceptable salt thereof, that can be used can be any of the embodiments described in the paragraph after the header "Compounds" and "Formula (I)" to the penultimate paragraph before the header "Synthesis".

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance, and may positively affect one or more symptoms or aspects of the disease while having effects on other aspects of the disease or on unrelated systems that may be considered undesirable.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to treat, alleviate or ameliorate one or more symptoms or conditions of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an ERK inhibitor is the amount which results in the reduction in ERK (ERKI and/or ERK2) activity and/or phosphorylation. The reduction in ERK activity are known to those skilled in the art and can be determined by the analysis of pharmacodynamic markers such as phosphorylated RSKI,2 and phosphorylated ERKI,2 and/or or gene expression profile (mRNA).

The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a cancer, are known to those skilled in the art. Example of suitable indicators include, but are not limited to, the reduction, alleviation or disappearance of one or more symptoms caused by the cancer, the reduction of tumor size, the elimination of the tumor, and/or long-term disease stabilization (growth arrest) of the tumor.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

Benzyl 6-oxo-2,7-diazaspiro[4.4]nonane-2-carboxylate

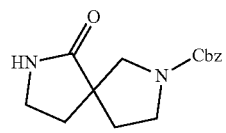

To a stirred solution of 2,7-diazaspiro[4.4]nonan-1-one (4.5 g, 25.48 mmol) in mixture of 1,4-dioxane (50 mL) and water (50 mL) was added sodium bicarbonate (4.28 g, 50.96 mmol), followed by benzyl chloroformate (5.46 mL, 38.22 mmol) and stirred at room temperature (rt) for 16 h. The mixture was poured into water (50 mL) and extracted with ethyl acetate (3×100 mL). The combined organic layers were washed with water (2×50 mL) and brine (50 mL), dried over sodium sulfate and concentrated. The residue was purified by silica-gel (100-200 mesh, 2-3% methanol in dichloromethane) to afford benzyl 6-oxo-2,7-diazaspiro[4.4]nonane-2-carboxylate (4.5 g, 16.42 mmol, 65%) as an off-white solid. LCMS: 275.3 [M+H]$^+$.

Intermediate 1A

Benzyl (R)-6-oxo-2,7-diazaspiro[4.4]nonane-2-carboxylate

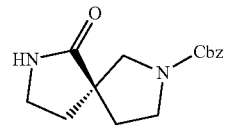 [SMILES: O=C(OCc1ccccc1)N1CC[C@]2(CCNC2=O)C1]

Racemic benzyl 6-oxo-2,7-diazaspiro[4.4]nonane-2-carboxylate (Intermediate 1) (2.89 g) was subjected to chiral SFC separation (Chiralpak AD-H (250×4.6) mm, 5u, 100% methanol) to afford benzyl (R)-6-oxo-2,7-diazaspiro[4.4]nonane-2-carboxylate (1.25 g) as the first eluted peak (RT=2.4 min) with 99.8% ee. $^1$H NMR (400 MHz, CDCl$_3$) δ 7.42-7.27 (m, 5H), 5.87 (br s, 1H), 5.14 (d, J=2.4 Hz, 2H), 3.78-3.57 (m, 2H), 3.51-3.42 (m, 1H), 3.41-3.32 (m, 3H), 2.33-2.01 (m, 3H), 1.89-1.68 (m, 1H). LCMS: 275.09 [M+H]$^+$.

Intermediate 1B

Benzyl (S)-6-oxo-2,7-diazaspiro[4.4]nonane-2-carboxylate

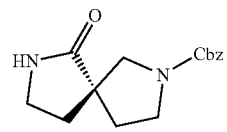 [SMILES: O=C(OCc1ccccc1)N1CC[C@@]2(CCNC2=O)C1]

Racemic benzyl 6-oxo-2,7-diazaspiro[4.4]nonane-2-carboxylate (Intermediate 1) (2.89 g) was subjected to chiral SFC separation (Chiralpak AD-H (250×4.6) mm, 5u, 100% methanol) to afford benzyl (S)-6-oxo-2,7-diazaspiro[4.4]nonane-2-carboxylate (1.25 g) as the second eluted peak (RT=6.18 min) with 99.0% ee. $^1$H NMR (400 MHz, CDCl$_3$) δ 7.48-7.23 (m, 5H), 5.81 (br s, 1H), 5.14 (d, J=2.4 Hz, 2H), 3.81-3.58 (m, 2H), 3.52-3.41 (m, 1H), 3.41-3.32 (m, 3H), 2.33-2.01 (m, 3H), 1.89-1.68 (m, 1H). LCMS: 275.09 [M+H]+.

Intermediate 2

5-Iodo-3-(6-isopropoxypyridin-3-yl)-1-trityl-1H-indazole

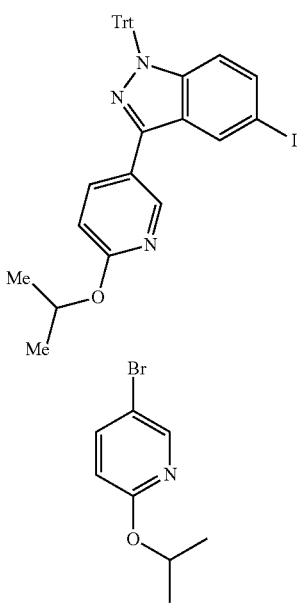

Step 1: 5-Bromo-2-isopropoxypyridine

2-Iodopropane (64.3 mL, 646.6 mmol) was added dropwise to a solution of 5-bromopyridin-2-ol (75 g, 431.1 mmol) and potassium carbonate (178.7 g, 1293 mmol) in DMF (750 mL). The mixture was stirred at rt for 16 h. The reaction progress was monitored by TLC. After completion of the reaction, the mixture was poured into water and extracted with diethyl ether. The organic layer was washed with water. The combined organic extracts were dried over anhydrous sodium sulfate, filtered and concentrated under vacuum to afford crude 5-bromo-2-isopropoxypyridine (60 g, 64%) as a light yellow solid. The crude product was directly used for next step without further purification. $^1$H NMR (400 MHz, CDCl$_3$) δ 8.16 (d, 1H), 7.60 (dd, 1H), 5.59 (d, 1H), 5.24-5.20 (m, 1H), 1.33 (d, 6H). LCMS: 216.1 [M+H]+.

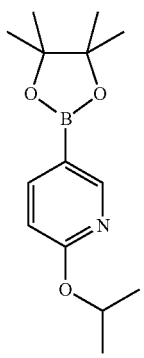 [SMILES: CC(C)Oc1ccc(B2OC(C)(C)C(C)(C)O2)cn1]

Step 2: 2-Isopropoxy-5-(4,4,5,5-tetramethyl-1,3,2-dioxaborolan-2-yl)pyridine PdCl$_2$ (dppf).CH$_2$Cl$_2$ was added to a mixture of 5-bromo-2-isopropoxypyridine (60 g, 277.6 mmol) potassium acetate (81.8 g, 833.02 mmol) and bis(pinacolato)diboron (77.54 g, 305.36 mmol) in 1,4-dioxane (600 mL). The mixture was stirred at 80° C. for 16 h. The reaction progress was monitored by TLC. After completion of the reaction, the reaction was quenched by the addition of water. The solution was extracted with ethyl acetate, and the combined organic layers were concentrated. The crude product was purified by column chromatography on silica gel (100-200 mesh) elution started with 1-10% ethyl acetate in petroleum ether (PE) to afford 2-isopropoxy-5-(4,4,5,5-tetramethyl-1,3,2-dioxaborolan-2-yl)pyridine (55 g, 75%) as a yellow solid. $^1$H NMR (400 MHz, CDCl$_3$) δ 8.5 (d, 1H), 7.89 (dd, 1H), 6.64 (d, 1H), 5.38-5.29 (m, 1H), 1.34-1.32 (m, 18H).

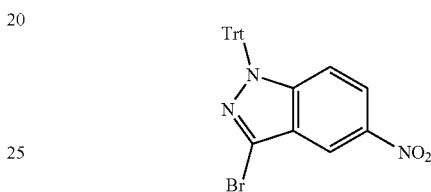

Step 3: 3-Bromo-5-nitro-1-trityl-1H-indazole

Trityl chloride (155.4 g, 557.8 mmol) was added to a solution of 3-bromo-5-nitro-1H-indazole (150 g, 619.8 mmol) and potassium carbonate (411.1 g, 2975 mmol) in CH$_3$CN (3 L). The mixture was stirred at rt for 16 h. The reaction progress was monitored by TLC. After completion of the reaction, the mixture was diluted with DCM (1.5 L). The mixture was washed with water. The combined organic extracts were dried over anhydrous sodium sulfate, filtered and concentrated under vacuum to afford the crude product. The crude was purified by washing with methanol to afford 3-Bromo-5-nitro-1-trityl-1H-indazole (150 g, 50%) as a light yellow solid. $^1$H NMR (400 MHz, CDCl$_3$) δ 8.5 (d, 1H), 7.88 (dd, 1H), 7.33-7.27 (m, 9H), 7.20-7.16 (m, 6H), 6.42 (d, 1H).

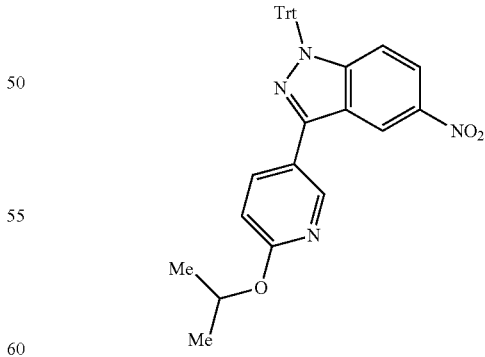

Step 4: 3-(6-Isopropoxypyridin-3-yl)-5-nitro-1-trityl-1H-indazole

PdCl$_2$(dppf).DCM (17.06 g, 20.90 mmol) was added to a solution of 2-isopropoxy-5-(4,4,5,5-tetramethyl-1,3,2-dioxaborolan-2-yl)pyridine, 3-bromo-5-nitro-1-trityl-1H-indazole and potassium carbonate (144.4 g, 1045 mmol) in a mixture of DME (550 mL) and water (100 mL). The mixture was stirred at 80° C. for 16 h. The reaction progress was monitored by TLC. After completion of the reaction, the reaction was quenched by the addition of water. The resulting solution was extracted with ethyl acetate. Combined organic layers were concentrated to afford crude product that was purified by column chromatography on silica gel (100-200 mesh) elution started with 5-15% ethyl acetate in PE to afford 3-(6-isopropoxypyridin-3-yl)-5-nitro-1-trityl-1H-indazole (60 g, 53%) as a pink solid. $^1$H NMR (400 MHz, CDCl$_3$) δ 8.92 (d, 1H), 8.73 (d, 1H), 8.05 (dd, 1H), 7.88 (dd, 1H), 7.31-7.30 (m, 9H), 7.22-7.20 (m, 6H), 6.80 (d, 1H), 6.49 (d, 1H), 5.40-5.34 (m, 1H), 1.40 (d, 6H). LCMS: 541.6 [M+H]$^+$.

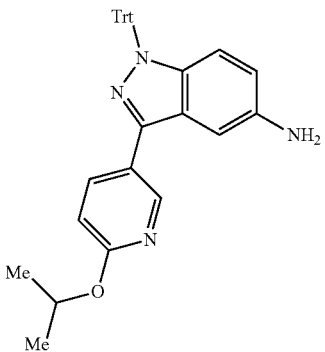

Step 5: 3-(6-Isopropoxypyridin-3-yl)-1-trityl-1H-indazol-5-amine

A solution of 3-(6-isopropoxypyridin-3-yl)-5-nitro-1-trityl-1H-indazole (45 g, 83.2 mmol) in a mixture of toluene (250 mL) and methanol (250 mL) was added 10% palladium on carbon (11.25 g), and the mixture was hydrogenated at rt for 16 h. The reaction progress was monitored by TLC. After completion of the reaction, the mixture was filtered through a Celite bed and washed with methanol. The filtrate was concentrated under vacuum to afford 35 g of crude product that was re-crystallized from methanol to afford 3-(6-Isopropoxypyridin-3-yl)-1-trityl-1H-indazol-5-amine (28 g, 66%) as a pink solid. $^1$H NMR (400 MHz, CDCl$_3$) δ 8.66 (d, 1H), 8.00 (d, 1H), 7.26-7.25 (m, 15h), 7.15 (s, 1H), 6.72 (d, 1H), 6.47 (d, 1H), 6.26 (d, 1H), 5.34-5.31 (m, 1H), 3.55 (s, 2H), 1.36 (d, 6H). LCMS: 511.29 [M+H]$^+$.

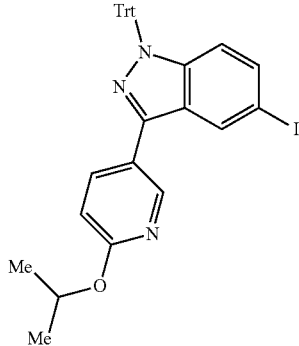

Step 6: 5-Iodo-3-(6-isopropoxypyridin-3-yl)-1-trityl-1H-indazole

A mixture of 3-(6-isopropoxypyridin-3-yl)-1-trityl-1H-indazol-5-amine (1.02 g, 2.0 mmol) in concentrated HCl (3.0 mL) and water (9.0 mL) was cooled to −10° C. to 0° C., and NaNO$_2$ (0.36 g, 5.21 mmol) was added. The mixture was stirred until the starting material consumed. The mixture was then added dropwise to the mixture of NaI (2.0 g, 13.34 mmol) and CuI (220 mg, 1.15 mmol) in water (30 mL). This mixture stirred at RT for 15 h. After completion of the reaction, the mixture was extracted with DCM (3×50 mL). The combined organic layers were dried over Mg$_2$SO$_4$, filtered, concentrated and purified by flash chromatography on silica gel (0-30% ethyl acetate in hexane) to afford 5-Iodo-3-(6-isopropoxypyridin-3-yl)-1-trityl-1H-indazole (800 mg, 65%). $^1$H NMR (500 MHz, CDCl$_3$): δ 8.70 (s, 1H), 8.33 (d, J=7.8 Hz, 1H), 7.23-7.31 (m, 16H), 6.77 (d, J=7.8 Hz, 1H), 6.50 (d, 1H), 6.23 (d, J=7.8 Hz, 1H), 5.32 (m, 1H), 1.42 (d, J=7.2 Hz, 6H).

Intermediate 3

2-(3-(6-isopropoxypyridin-3-yl)-1H-indazol-5-yl)-2,7-diazaspiro[4.4]nonane

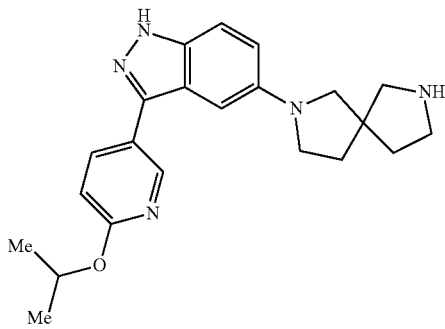

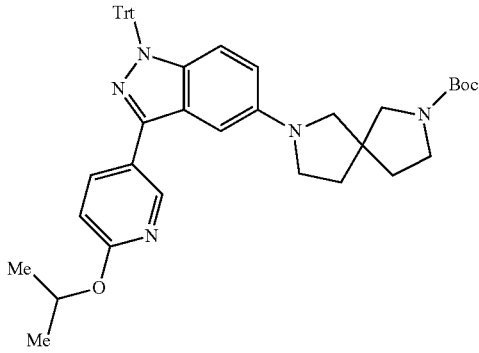

Step 1: tert-Butyl 7-(3-(6-isopropoxypyridin-3-yl)-1-trityl-1H-indazol-5-yl)-2,7-diazaspiro[4.4]nonane-2-carboxylate A flame-dried resealable Schlenk tube was charged with 5-iodo-3-(6-isopropoxypyridin-3-yl)-1-trityl-1H-indazole (Intermediate 2) (1.0 g, 1.608 mmol), tert-butyl 2,7-diazaspiro[4.4]nonane-2-carboxylate (436 mg, 1.93 mmol), Pd(OAc)₂ (36 mg, 0.16 mmol), Xantphos (183 mg, 0.32 mmol) and Cs₂CO₃ (587 mg, 4.2 mmol) in dioxane (5.0 mL). The tube was flushed with argon and sealed. The mixture was heated at 100° C. and stirred for 17 h. The mixture was allowed to cool to rt, and then diluted with dichloromethane (10 mL), filtered and concentrated in vacuo. The crude material was purified by flash chromatography on silica gel (0-20% ethyl acetate in hexane) to afford tert-butyl 7-(3-(6-isopropoxypyridin-3-yl)-1-trityl-1H-indazol-5-yl)-2,7-diazaspiro[4.4]nonane-2-carboxylate (574 mg, 49%). ¹H NMR (500 MHz, CDCl₃): δ 8.72 (s, 1H), 8.11 (d, J=7.8 Hz, 1H), 7.23-7.37 (m, 17H), 6.80 (d, J=7.8 Hz, 1H), 6.34 (d, J=7.8 Hz, 1H), 5.36 (m, 1H), 3.29-3.47 (m, 8H), 1.91-1.95 (m, 4H), 1.46 (s, 9H), 1.39 (d, J=7.2 Hz, 6H).

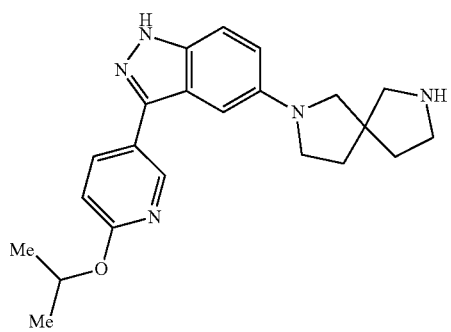 [SMILES: CC(C)Oc1ccc(-c2n[nH]c3ccc(N4CCC5(CCNC5)C4)cc23)cn1]

Step 2: 2-(3-(6-isopropoxypyridin-3-yl)-1H-indazol-5-yl)-2,7-diazaspiro[4.4]nonane A solution of tert-butyl 7-(3-(6-isopropoxypyridin-3-yl)-1-trityl-1H-indazol-5-yl)-2,7-diazaspiro[4.4]nonane-2-carboxylate (0.165 g, 0.229 mmol) in DCM (1.019 mL) was treated with TFA (0.340 mL) and water (0.170 mL). The solution was allowed to stir at rt overnight followed by treatment with additional TFA (1.02 mL). After 6 h, the solution was cooled to 0° C. and quenched with sat. aq. NaHCO₃ and then further diluted with ethyl acetate. The aqueous layer was extracted with ethyl acetate (4×15 mL). The combined organics were dried (Na₂SO₄) and concentrated to afford the crude product which was further purified by silica gel column (0-10% methanol (contains 7N NH₃)/DCM) to provide the product (61.6 mg, 71%) as a grey solid. ¹H NMR (400 MHz, DMSO-d₆) δ 12.86 (br s, 1H), 8.70 (d, J=2.45 Hz, 1H), 8.20 (dd, J=8.68, 2.45 Hz, 1H), 7.43 (d, J=9.05 Hz, 1H), 6.83-6.92 (m, 2H), 6.77-6.83 (m, 1H), 5.32 (quin, J=6.14 Hz, 1H), 3.34-3.42 (m, 2H), 3.11-3.30 (m, 3H), 2.83-3.00 (m, 2H), 2.65-2.77 (m, 2H), 1.86-2.02 (m, 2H), 1.63-1.85 (m, 2H), 1.33 (d, J=6.11 Hz, 6H). LCMS: 378.2 [M+H]⁺.

Intermediate 4

2-(3-(6-isopropoxypyridin-3-yl)-1H-indazol-5-yl)-2,7-diazaspiro[4.4]nonan-1-one

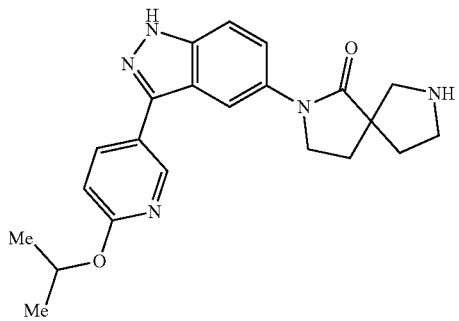

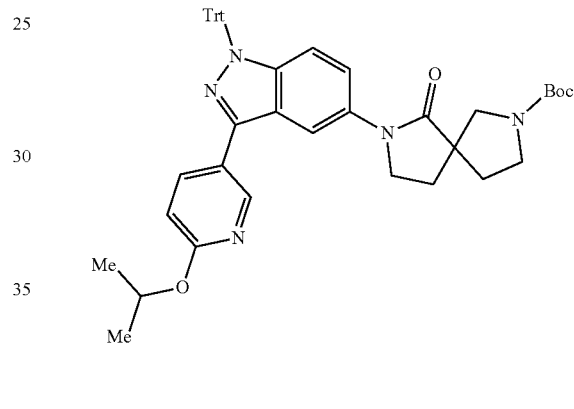

Step 1: tert-Butyl 7-(3-(6-isopropoxypyridin-3-yl)-1-trityl-1H-indazol-5-yl)-6-oxo-2,7-diazaspiro[4.4]nonane-2-carboxylate A flame-dried resealable Schlenk tube was charged with 5-iodo-3-(6-isopropoxypyridin-3-yl)-1-trityl-1H-indazole (Intermediate 2) (1.0 g, 1.608 mmol), tert-butyl 6-oxo-2,7-diazaspiro[4.4]nonane-2-carboxylate (463 mg, 1.93 mmol), CuI (31 mg, 0.10 mmol), CsF (610 mg, 4.2 mmol) and N¹,N²-dimethylethane-1,2-diamine (28 mg, 0.32 mmol) in anhydrous ACN (5.0 mL). The tube was then flushed with argon and sealed. The mixture was heated at 100° C. and stirred for 15 h. The mixture was allowed to cool to rt, diluted with dichloromethane (10 mL), filtered, and concentrated in vacuo. The crude material was purified by flash chromatography on silica gel and eluted with 0-20% ethyl acetate in DCM to yield the tert-butyl 7-(3-(6-isopropoxypyridin-3-yl)-1-trityl-1H-indazol-5-yl)-6-oxo-2,7-diazaspiro[4.4]nonane-2-carboxylate (460 mg, 39%). LCMS: 734.3 [M+H]⁺.

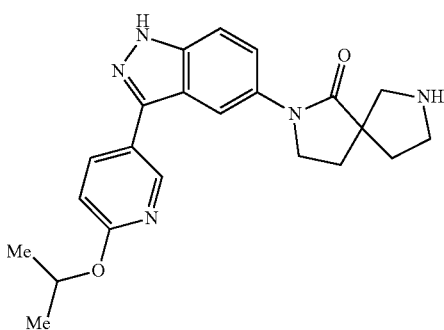 [SMILES: CC(C)Oc1ccc(-c2n[nH]c3ccc(N4CCC5(CCNC5)C4=O)cc23)cn1]

Step 2: 2-(3-(6-isopropoxypyridin-3-yl)-1H-indazol-5-yl)-2,7-diazaspiro[4.4]nonan-1-one The title compound was prepared following a procedure described for Intermediate 3, using tert-Butyl 7-(3-(6-isopropoxypyridin-3-yl)-1-trityl-1H-indazol-5-yl)-6-oxo-2,7-diazaspiro[4.4]nonane-2-carboxylate in Step 2. $^1$H NMR (400 MHz, DMSO-d$_6$) δ 13.25 (s, 1H), 8.73 (d, J=2.4 Hz, 1H), 8.22 (dd, J=8.6, 2.5 Hz, 1H), 8.16 (d, J=1.9 Hz, 1H), 7.79 (dd, J=9.0, 1.9 Hz, 1H), 7.59 (d, J=9.0 Hz, 1H), 6.90 (d, J=8.6 Hz, 1H), 5.33 (sep, J=6.2 Hz, 1H), 3.94-3.86 (m, 2H), 2.92-2.81 (m, 4H), 2.16-2.10 (m, 1H), 2.05-1.99 (m, 2H), 1.75-1.69 (m, 1H), 1.34 (d, J=6.2 Hz, 6H). LCMS: 392.2 [M+H$^+$].

Intermediate 5

(S)-2-(3-(6-isopropoxypyridin-3-yl)-1-trityl-1H-indazol-5-yl)-2,7-diazaspiro[4.4]nonan-1-one

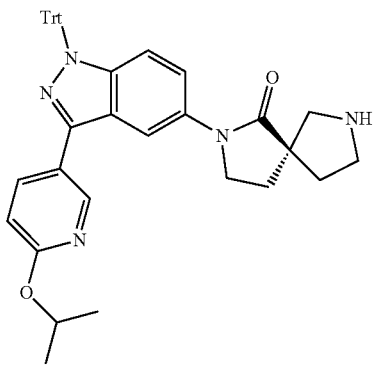

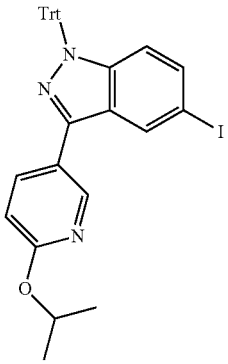

Step 1: 5-Iodo-3-(6-isopropoxypyridin-3-yl)-1-trityl-1H-indazole

To a stirred solution of 3-(6-isopropoxypyridin-3-yl)-1-trityl-1H-indazol-5-amine (1.2 g, 2.35 mmol) in conc. HCl (6 mL) and water (12 mL) was cooled to −10° C. to 0° C., and sodium nitrite (0.422 g, 6.11 mmol) was added. The mixture was stirred until the starting material consumed as monitored by TLC. The mixture was then added dropwise to the mixture of sodium iodide (2.35 g, 15.68 mmol) and copper (I) iodide (257 mg, 1.35 mmol) in water (12 mL). The mixture was stirred at rt for 15 h. After completion of the reaction, water (15 mL) was added to the mixture. The mixture was then extracted with ethyl acetate (3×50 mL). The combined organic layers were washed with water (15 mL) and brine (15 mL), dried over sodium sulfate and concentrated. The residue was purified by column chromatography (100-200 silica) using 3% ethyl acetate in hexane as eluent to afford 5-iodo-3-(6-isopropoxypyridin-3-yl)-1-trityl-1H-indazole (850 mg, 1.36 mmol, 58% yield) as an off white solid. $^1$H NMR (400 MHz, CDCl$_3$) δ 8.66 (d, J=2.0 Hz, 1H), 8.30 (d, J=1.0 Hz, 1H), 8.08-7.91 (m, 1H), 7.30-7.25 (m, 8H), 7.24-7.18 (m, 7H), 6.75 (d, J=8.8 Hz, 1H), 6.21 (d, J=8.8 Hz, 1H), 5.49-5.22 (m, 1H), 1.38 (d, J=6.4 Hz, 6H). LCMS: 622.2 [M+H]$^+$.

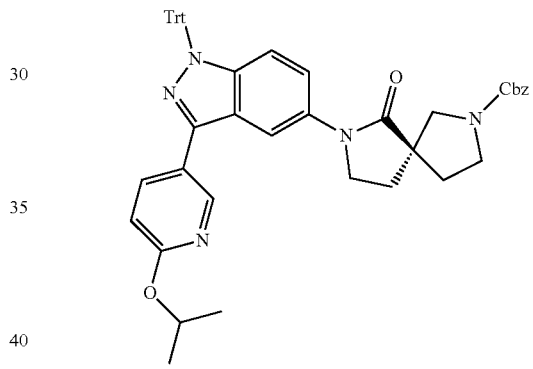

Step 2: Benzyl (R)-7-(3-(6-isopropoxypyridin-3-yl)-1-trityl-1H-indazol-5-yl)-6-oxo-2,7-diazaspiro[4.4]nonane-2-carboxylate To a stirred and degassed solution of 5-iodo-3-(6-isopropoxypyridin-3-yl)-1-trityl-1H-indazole (500 mg, 0.805 mmol) and benzyl (R)-6-oxo-2,7-diazaspiro[4.4]nonane-2-carboxylate (Intermediate 1A) (0.220 mg, 0.805 mmol) in dry dimethyl sulfoxide (10 mL) was added copper (I) iodide (2.62 g, 18.98 mmol) followed by potassium phosphate (341 mg, 1.61 mmol). The solution was degassed for 30 mins and then heated to 100° C. for 36 h. The mixture was cooled to rt, and water (10 mL) was added. The mixture was extracted with ethyl acetate (3×50 mL). The organic layers were washed with water (10 mL) and brine (10 mL), dried over sodium sulfate, filtered and concentrated. The residue was purified by column chromatography (100-200 silica) using 30% ethyl acetate in hexane as eluent to afford benzyl (R)-7-(3-(6-isopropoxypyridin-3-yl)-1-trityl-1H-indazol-5-yl)-6-oxo-2,7-diazaspiro[4.4]nonane-2-carboxylate (250 mg, 0.325 mmol, 40% yield). $^1$H NMR (300 MHz, DMSO-d$_6$) δ 8.66 (br d, J=2.2 Hz, 1H), 8.24 (s, 1H), 8.06 (dd, J=2.2, 8.4 Hz, 1H), 7.45-7.27 (m, 15H), 7.24-7.17 (m, 6H), 6.89 (d, J=8.4 Hz, 1H), 6.44 (d, J=9.2 Hz, 1H), 5.31 (td, J=6.1, 12.4

Hz, 1H), 5.08 (br d, J=2.6 Hz, 2H), 3.88 (br t, J=6.2 Hz, 2H), 3.64-3.33 (m, 4H), 2.20-2.02 (m, 3H), 1.97 (br d, J=12.1 Hz, 1H), 1.32 (d, J=6.2 Hz, 6H). LCMS: 768.3 [M+H]⁺.

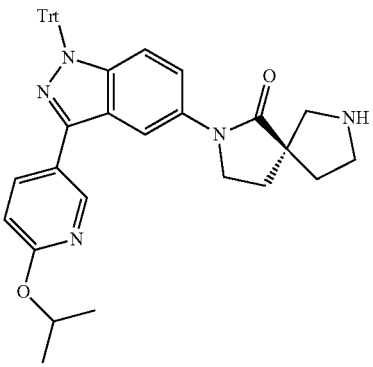

Step 3: (S)-2-(3-(6-isopropoxypyridin-3-yl)-1-trityl-1H-indazol-5-yl)-2,7-diazaspiro[4.4]nonan-1-one A solution of benzyl (R)-7-(3-(6-isopropoxypyridin-3-yl)-1-trityl-1H-indazol-5-yl)-6-oxo-2,7-diazaspiro[4.4]nonane-2-carboxylate (1 g, 1.302 mmol) in toluene (6.51 mL) and methanol (6.51 mL) was added aq. HCl (6.51 mL, 13.02 mmol). The solution was degassed with nitrogen/vacuum cycles (3×). Pd/C (0.139 g, 0.130 mmol) was added in one portion, and the round-bottom flask was furnished with a hydrogen balloon. The mixture was stirred at 25° C. for 2 days. Upon completion, the mixture was filtered through Celite and washed with methanol. The solvents were removed to afford (S)-2-(3-(6-isopropoxypyridin-3-yl)-1-trityl-1H-indazol-5-yl)-2,7-diazaspiro[4.4]nonan-1-one hydrochloride (1.1 g, 1.736 mmol, 133% yield) as a pale yellow foam. ¹H NMR (400 MHz, DMSO-d₆) δ 8.66 (s, 1H), 8.25 (s, 1H), 8.07 (d, 1H), 7.44 (d, 1H), 7.37-7.33 (m, 9H), 7.30-7.23 (m, 6H), 6.88 (d, 1H), 6.42 (d, 1H), 5.3-5.25 (m, 1H), 3.83-3.81 (m, 2H), 3.18 (s, 1H), 2.88-2.79 (m, 4H), 2.20-1.97 (m, 3H), 1.70-1.60 (m, 1H), 1.33 (d, 6H). LCMS: 634.30 [M+H]⁺.

Intermediate 6

(R)-2-(3-(6-isopropoxypyridin-3-yl)-1-trityl-1H-indazol-5-yl)-2,7-diazaspiro[4.4]nonan-1-one

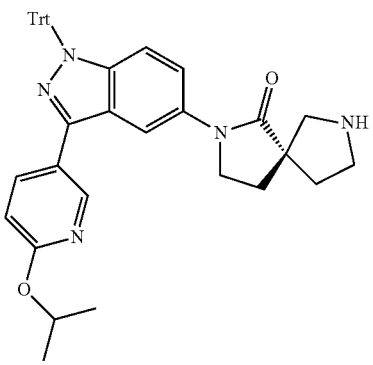

Step 1: Benzyl (S)-7-(3-(6-isopropoxypyridin-3-yl)-1-trityl-1H-indazol-5-yl)-6-oxo-2,7-diazaspiro[4.4]nonane-2-carboxylate

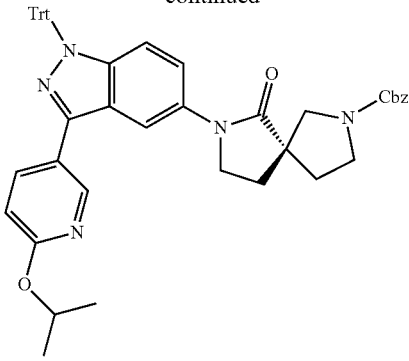

The title compound was prepared following procedures described for Intermediate 5, using 5-iodo-3-(6-isopropoxypyridin-3-yl)-1-trityl-1H-indazole and Intermediate 1B in Step 2. ¹H NMR (300 MHz, DMSO-d₆) 8.66 (d, J=1.8 Hz, 1H), 8.24 (s, 1H), 8.06 (dd, J=2.2, 8.4 Hz, 1H), 7.45-7.27 (m, 15H), 7.25-7.18 (m, 6H), 6.89 (d, J=8.8 Hz, 1H), 6.44 (d, J=9.2 Hz, 1H), 5.31 (td, J=6.2, 12.5 Hz, 1H), 5.08 (br d, J=2.6 Hz, 2H), 3.88 (br t, J=6.4 Hz, 2H), 3.64-3.35 (m, 4H), 2.23-1.83 (m, 4H), 1.32 (d, J=5.9 Hz, 6H). LCMS: 768.3 [M+H]⁺.

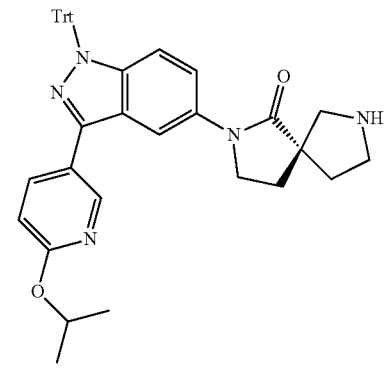

Step 2: (R)-2-(3-(6-isopropoxypyridin-3-yl)-1-trityl-1H-indazol-5-yl)-2,7-diazaspiro[4.4]nonan-1-one The title compound was prepared following the procedure described for Intermediate 5, using benzyl (S)-7-(3-(6-isopropoxypyridin-3-yl)-1-trityl-1H-indazol-5-yl)-6-oxo-2,7-diazaspiro[4.4]nonane-2-carboxylate in Step 3. LCMS: 634.30 [M+H]⁺.

Intermediate 7

Benzyl (R)-7-(3-iodo-1-trityl-1H-indazol-5-yl)-6-oxo-2,7-diazaspiro[4.4]nonane-2-carboxylate

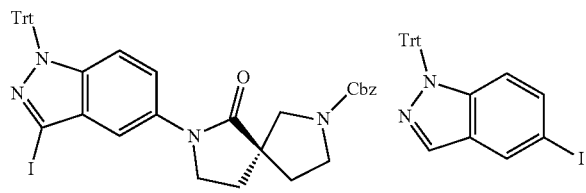

Step 1: 5-Iodo-1-trityl-1H-indazole

To a stirred solution of 5-iodo-1H-indazole (20 g, 81.95 mmol) in acetonitrile (200 mL) at 0° C.-5° C., was added potassium carbonate (56.62 g, 409.7 mmol), followed by trityl chloride (79.96 g, 286.82 mmol). The mixture was heated to 70° C. for 4 h. After completion of the reaction, water (300 mL) was added. The mixture was extracted with ethyl acetate (3×500 mL). The combined organic layers were washed with water (300 mL) and brine (300 mL), dried over sodium sulfate, filtered and concentrated. The residue was purified by column chromatography (100-200 silica) using 100% hexane as eluent to afford 5-iodo-1-trityl-1H-indazole (30.0 g, 61.72 mmol, 75% yield) as an off yellow solid. $^1$H NMR (300 MHz, CDCl$_3$) δ 7.99 (s, 1H), 7.81 (s, 1H), 7.55-7.41 (m, 2H), 7.39-7.27 (m, 9H), 7.21-7.10 (m, 6H).

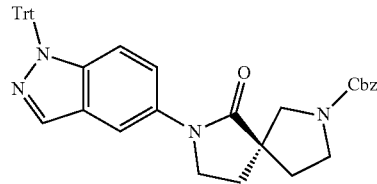

Step 2: Benzyl (R)-6-oxo-7-(1-trityl-1H-indazol-5-yl)-2,7-diazaspiro[4.4]nonane-2-carboxylate To a stirred and degassed solution of 5-iodo-1-trityl-1H-indazole (17.73 g, 36.49 mmol), benzyl (R)-6-oxo-2,7-diazaspiro[4.4]nonane-2-carboxylate (Intermediate 1A) (10.0 g, 36.49 mmol) in dry dimethyl sulfoxide (200 mL) was added copper (I) iodide (0.694 g, 3.64 mmol) followed by potassium phosphate (15.49 g, 72.98 mmol). The solution was degassed for 30 mins and then heated to 100° C. for 36 h. The mixture was cooled to rt, water (10 mL) was added. The mixture was extracted with ethyl acetate (3×50 mL). The organic layers were washed with water (10 mL) and brine (10 mL), dried over sodium sulfate, filtered and concentrated. The residue was purified by column chromatography (100-200 silica) using 50% ethyl acetate in hexane as eluent to afford benzyl (R)-6-oxo-7-(1-trityl-1H-indazol-5-yl)-2,7-diazaspiro[4.4]nonane-2-carboxylate (18.0 g, 28.48 mmol, 78% yield). $^1$H NMR (300 MHz, DMSO-d$_6$) δ 8.02 (s, 1H), 7.78-7.69 (m, 2H), 7.67-7.59 (m, 1H), 7.45-7.27 (m, 14H), 7.08 (dd, J=2.9, 7.0 Hz, 6H), 5.09 (s, 2H), 3.83 (br t, J=6.8 Hz, 2H), 3.68-3.35 (m, 4H), 2.15 (br t, J=6.8 Hz, 2H), 2.04-1.88 (m, 2H). LCMS: 632.9 [M+H]$^+$.

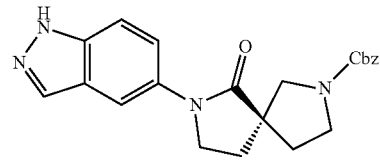 [SMILES: O=C(OCc1ccccc1)N1CC[C@]2(CCN(c3ccc4[nH]ncc4c3)C2=O)C1]

Step 3: Benzyl (R)-7-(1H-indazol-5-yl)-6-oxo-2,7-diazaspiro[4.4]nonane-2-carboxylate To a (R)-benzyl 6-oxo-7-(1-trityl-1H-indazol-5-yl)-2,7-diazaspiro[4.4]nonane-2-carboxylate (18.0 g, 28.48 mmol) in dichloromethane (150 mL) at 0° C.-5° C., was added trifluoroacetic acid (70 mL). The mixture was stirred RT 4 h. The reaction was quenched with aqueous sodium bicarbonate solution and extracted with ethyl acetate (3×250 mL). The combined organic layers were washed with brine (2×250 mL), dried and concentrated to afford a solid. The solid was further washed with ether (100 mL) and dried to afford benzyl (R)-7-(1H-indazol-5-yl)-6-oxo-2,7-diazaspiro[4.4]nonane-2-carboxylate (9.0 g, 23.07 mmol, 81% yield) as an off white solid. $^1$H NMR (300 MHz, DMSO-d$_6$) δ 13.06 (br s, 1H), 8.06 (s, 1H), 7.88 (s, 1H), 7.76 (br d, J=9.2 Hz, 1H), 7.54 (d, J=8.8 Hz, 1H), 7.40-7.29 (m, 5H), 5.09 (s, 2H), 3.88 (br t, J=6.8 Hz, 2H), 3.61-3.38 (m, 4H), 2.22-1.94 (m, 4H). LCMS: 391.2 [M+H]$^+$.

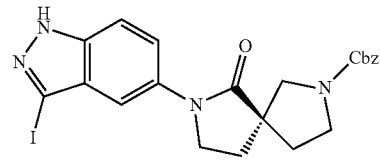 [SMILES: O=C(OCc1ccccc1)N1CC[C@]2(CCN(c3ccc4[nH]nc(I)c4c3)C2=O)C1]

Step 4: Benzyl (R)-7-(3-iodo-1H-indazol-5-yl)-6-oxo-2,7-diazaspiro[4.4]nonane-2-carboxylate To a stirred solution of benzyl (R)-7-(1H-indazol-5-yl)-6-oxo-2,7-diazaspiro[4.4]nonane-2-carboxylate (9.0 g, 23.07 mmol) in N,N-dimethylformamide (150 mL), at 0° C.-5° C., was added potassium hydroxide (4.78 g, 85.35 mmol) followed by iodine (11.6 g, 46.14 mmol). The mixture was heated to 70° C. for 2 h. After completion of the reaction, water (150 mL) was added. The mixture was extracted with ethyl acetate (3×150 mL). The combined organic layers were washed with water (150 mL) and brine (150 mL), dried over sodium sulfate, filtered and concentrated. The residue was purified by column chromatography (100-200 silica) using 50% ethyl acetate in hexane as eluent to afford benzyl (R)-7-(3-iodo-1H-indazol-5-yl)-6-oxo-2,7-diazaspiro[4.4]nonane-2-carboxylate (9.0 g, 17.44 mmol, 75% yield) as an off yellow solid. $^1$H NMR (400 MHz, DMSO-d$_6$) δ 13.56 (br s, 1H), 7.77 (br d, J=8.8 Hz, 1H), 7.65 (s, 1H), 7.57 (d, J=8.8 Hz, 1H), 7.40-7.30 (m, 5H), 5.09 (br d, J=2.4 Hz, 2H), 3.92 (br t, J=6.8 Hz, 2H), 3.64-3.40 (m, 4H), 2.21-2.09 (m, 3H), 2.03-1.94 (m, 1H). LCMS: 516.6 [M+H]$^+$.

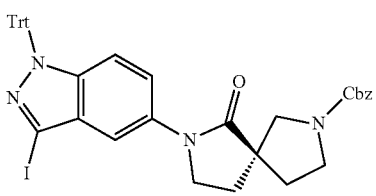

Step 5: Benzyl (R)-7-(3-iodo-1-trityl-1H-indazol-5-yl)-6-oxo-2,7-diazaspiro[4.4]nonane-2-carboxylate To a stirred solution of benzyl (R)-7-(3-iodo-1H-indazol-5-yl)-6-oxo-2,7-diazaspiro[4.4]nonane-2-carboxylate (9.0 g, 17.44 mmol) in acetonitrile (150 mL) cooled to 0° C.-5° C., was added potassium carbonate (12.05 g, 87.2 mmol) followed by trityl chloride (18.68 g, 67.04 mmol). The mixture was heated to 70° C. for 4 h. After completion of the reaction, water (150 mL) was added. The mixture was extracted with ethyl acetate (3×150 mL). The combined organic layers were washed with water (150 mL) and brine (150 mL), dried over sodium sulfate, filtered and concentrated. The residue was purified by column chromatography (100-200 silica) using 50% ethyl acetate in hexane as eluent to afford benzyl (R)-7-(3-iodo-1-trityl-1H-indazol-5-yl)-6-oxo-2,7-diazaspiro[4.4]nonane-2-carboxylate (6.0 g, 8.70 mmol, 50% yield) as an off white solid. $^1$H NMR (400 MHz, DMSO-$d_6$) δ 7.74 (s, 1H), 7.41-7.29 (m, 15H), 7.15 (br d, J=6.8 Hz, 6H), 6.36 (d, J=9.3 Hz, 1H), 5.08 (br d, J=3.9 Hz, 2H), 3.84 (br t, J=6.4 Hz, 2H), 3.56-3.37 (m, 4H), 2.15-2.04 (m, 3H), 1.99-1.90 (m, 1H); $[α]^{25}_{589}$=−13.2° (C=0.5, DCM). LCMS: 759.25 [M+H]$^+$.

Intermediate 8

(S)-2-(3-(4-Fluorophenyl)-1-trityl-1H-indazol-5-yl)-2,7-diazaspiro[4.4]nonan-1-one

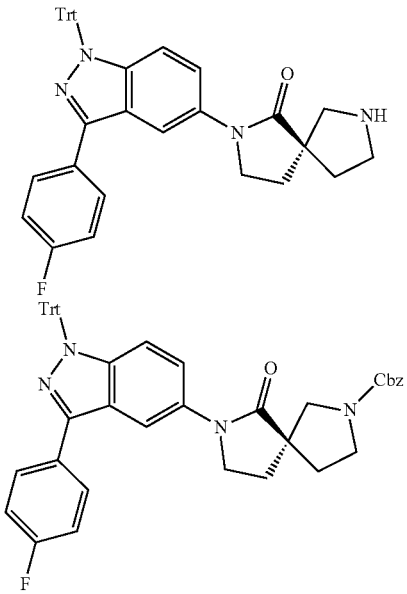

Step 1: Benzyl (R)-7-(3-(4-fluorophenyl)-1-trityl-1H-indazol-5-yl)-6-oxo-2,7-diazaspiro[4.4]nonane-2-carboxylate To a stirred and degassed solution of benzyl (R)-7-(3-iodo-1-trityl-1H-indazol-5-yl)-6-oxo-2,7-diazaspiro[4.4]nonane-2-carboxylate (Intermediate 7) (1.8 g, 2.37 mmol) and 2-(4-fluorophenyl)-4,4,5,5-tetramethyl-1,3,2-dioxaborolane (0.398 g, 2.84 mmol) in ethanol:toluene:water (1:1:1 60 mL), was added potassium carbonate (1.63 g, 11.85 mmol). The solution was degassed for 10 mins. [1,1'-bis (diphenylphosphino)ferrocene] dichloropalladium (II) DCM complex (0.273 g, 0.237 mmol) was added, and degassing was continued for 10 mins, followed by refluxing for 3 h. The mixture was cooled to rt and filtered through a Celite pad. To the filtrate was added cold water. The mixture was extracted with ethyl acetate (3×70 mL). The combined organic layers were washed with water (50 mL) and brine (50 mL), dried over sodium sulfate and concentrated. The residue was purified by column chromatography (100-200 silica) using 50% ethyl acetate in hexanes as eluent to afford benzyl (R)-7-(3-(4-fluorophenyl)-1-trityl-1H-indazol-5-yl)-6-oxo-2,7-diazaspiro[4.4]nonane-2-carboxylate (1.5 g, 2.06 mmol, 87% yield). $^1$H NMR (400 MHz, DMSO-$d_6$) δ 8.25 (d, J=1.5 Hz, 1H), 7.87 (br dd, J=5.9, 8.3 Hz, 2H), 7.42-7.28 (m, 17H), 7.22 (br d, J=7.3 Hz, 6H), 6.45 (d, J=9.3 Hz, 1H), 5.08 (br d, J=3.9 Hz, 2H), 3.87 (br t, J=6.4 Hz, 2H), 3.58-3.37 (m, 4H), 2.16-2.04 (m, 3H), 1.98-1.88 (m, 1H). $[α]^{25}_{589}$=−14.4° (C=0.5, DCM). LCMS: 727.29 [M+H]$^+$.

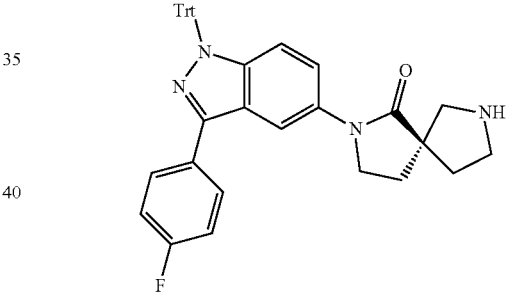

Step 2: (S)-2-(3-(4-Fluorophenyl)-1-trityl-1H-indazol-5-yl)-2,7-diazaspiro[4.4]nonan-1-one A solution of (R)-benzyl 7-(3-(4-fluorophenyl)-1-trityl-1H-indazol-5-yl)-6-oxo-2,7-diazaspiro[4.4]nonane-2-carboxylate (0.5 g, 0.688 mmol) in toluene (3.44 mL) and methanol (3.44 mL) was added HCl (1.720 mL, 3.44 mmol). The solution was degassed with nitrogen/vacuum cycles (3×). Pd/C (0.073 g, 0.069 mmol) was added, and the round bottom flask was furnished with a hydrogen balloon. The mixture was stirred at 25° C. for overnight. Upon completion, the mixture was filtered through Celite and washed with methanol. The solvents were removed to afford (S)-2-(3-(4-fluorophenyl)-1-trityl-1H-indazol-5-yl)-2,7-diazaspiro[4.4]nonan-1-one hydrochloride (0.46 g, 0.776 mmol, 113% yield) salt as a pale yellow foam. This material was used without a further purification. $^1$H NMR (400 MHz, DMSO-$d_6$) δ 9.60 (s, 1H), 9.30 (s, 1H), 8.29 (s, 1H), 7.89-7.85 (m, 2H), 7.40-7.30 (m, 11H), 7.23-7.21 (m, 6H), 6.47 (d, 2H), 3.90-3.86 (m, 2H), 3.37-3.26 (m, 4H), 2.16-2.05 (m, 4H). LCMS: 593.30 [M+H]$^+$.

Intermediate 9

(S)-2-(3-(2-(trifluoromethyl)pyridin-4-yl)-1-trityl-1H-indazol-5-yl)-2,7-diazaspiro[4.4]nonan-1-one

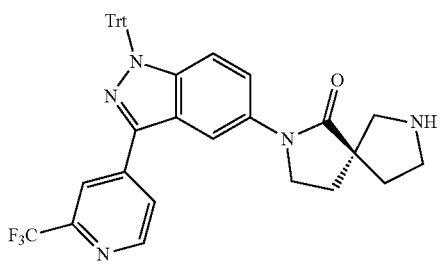

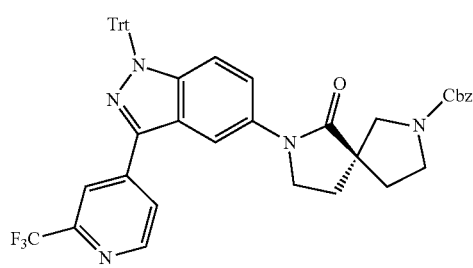

Step 1: Benzyl (R)-6-oxo-7-(3-(2-(trifluoromethyl)pyridin-4-yl)-1-trityl-1H-indazol-5-yl)-2,7-diazaspiro[4.4]nonane-2-carboxylate To a stirred and degassed solution of (R)-benzyl 7-(3-iodo-1-trityl-1H-indazol-5-yl)-6-oxo-2,7-diazaspiro[4.4]nonane-2-carboxylate (Intermediate 7) (1.88 g, 2.489 mmol) and 4-(4,4,5,5-tetramethyl-1,3,2-dioxaborolan-2-yl)-2-(trifluoromethyl)pyridine in ethanol:toluene:water (1:1:1 60 mL), was added potassium carbonate (2.14 g, 15.55 mmol). The solution was degassed for 10 mins. Tetrakis(triphenylphosphine) palladium (0) (0.360 g, 6.311 mmol) was added, and the solution was degassing for an additional 10 mins, followed by refluxing for 3 h. The mixture was cooled to rt and filtered through a Celite pad. To the filtrate was added cold water, and the mixture was extracted with ethyl acetate (3×70 mL). The combined organic layers were washed with water (50 mL) and brine (50 mL), dried over sodium sulfate and concentrated. The crude compound was purified by grace column chromatography (87% acetonitrile in 0.1% aqueous formic acid) to afford (R)-benzyl 6-oxo-7-(3-(2-(trifluoromethyl)pyridin-4-yl)-1-trityl-1H-indazol-5-yl)-2,7-diazaspiro[4.4]nonane-2-carboxylate (1.1 g, 1.41 mmol, 45% yield). $^1$H NMR (300 MHz, DMSO-$d_6$) δ 8.89 (d, J=5.1 Hz, 1H), 8.39 (s, 1H), 8.24-8.12 (m, 2H), 7.52 (br d, J=9.2 Hz, 1H), 7.42-7.28 (m, 14H), 7.19 (dd, J=1.8, 7.7 Hz, 6H), 6.49 (d, J=9.2 Hz, 1H), 5.08 (d, J=3.3 Hz, 1H), 3.92 (br t, J=6.4 Hz, 2H), 3.63-3.37 (m, 4H), 2.20-2.05 (m, 3H), 2.01-1.89 (m, 1H); $[t]^{25}_{589}$=−15.2° (C=0.5, DCM). LCMS: 778.39 [M+H]$^+$.

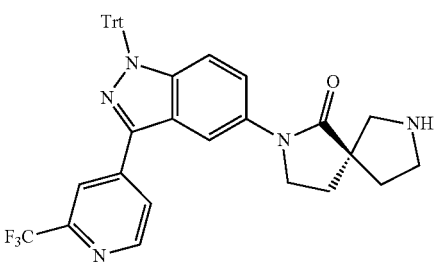

Step 2: (S)-2-(3-(2-(trifluoromethyl)pyridin-4-yl)-1-trityl-1H-indazol-5-yl)-2,7-diazaspiro[4.4]nonan-1-one The title compound was prepared following a procedure for Intermediate 8, using benzyl (R)-6-oxo-7-(3-(2-(trifluoromethyl)pyridin-4-yl)-1-trityl-1H-indazol-5-yl)-2,7-diazaspiro[4.4]nonane-2-carboxylate in Step 3. LCMS: 644.25 [M+H]$^+$.

Intermediate 10

(5S)-2-(3-(2-(trifluoromethyl)piperidin-4-yl)-1H-indazol-5-yl)-2,7-diazaspiro[4.4]nonan-1-one

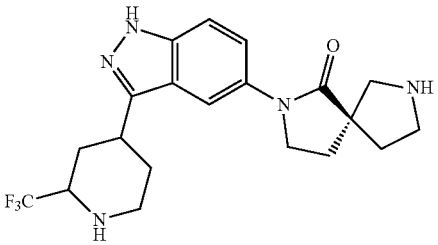 [SMILES: O=C1N(c2ccc3[nH]nc(C4CCNC(C(F)(F)F)C4)c3c2)CC[C@]12CCNC2]

The title compound was prepared following a procedure for Intermediate 9, using benzyl (R)-6-oxo-7-(3-(2-(trifluoromethyl)pyridin-4-yl)-1-trityl-1H-indazol-5-yl)-2,7-diazaspiro[4.4]nonane-2-carboxylate and aq. HCl (10 eq.) in Step 2. LCMS: 408.10 [M+H]$^+$.

Intermediate 11

(S)-2-(7-(3-(6-Isopropoxypyridin-3-yl)-1H-indazol-5-yl)-6-oxo-2,7-diazaspiro[4.4]nonan-2-yl)acetic acid

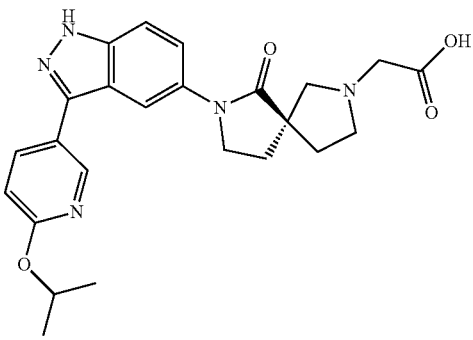 [SMILES: CC(C)Oc1ccc(-c2n[nH]c3ccc(N4CC[C@]5(CCN(CC(=O)O)C5)C4=O)cc23)cn1]

117
-continued

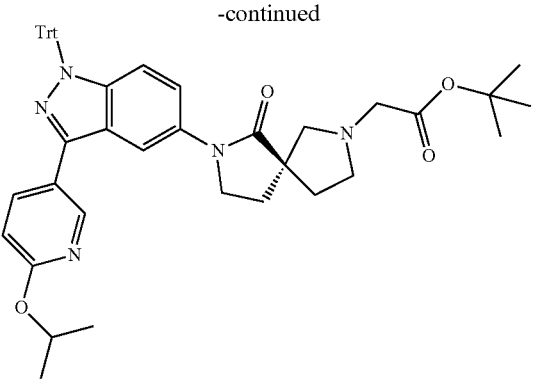

Step 1: tert-butyl (S)-2-(7-(3-(6-isopropoxypyridin-3-yl)-1-trityl-1H-indazol-5-yl)-6-oxo-2,7-diazaspiro[4.4]nonan-2-yl)acetate To a suspension of (S)-2-(3-(6-isopropoxypyridin-3-yl)-1-trityl-1H-indazol-5-yl)-2,7-diazaspiro[4.4]nonan-1-one (0.17 g, 0.268 mmol) in acetonitrile (2.68 mL) at 0° C., neat N,N-diisopropylethylamine (0.140 mL, 0.805 mmol) was added, followed by neat tert-butyl bromoacetate (0.040 mL, 0.268 mmol) via syringe. After the addition was complete, the mixture was stirred at 0° C. for 1 h. The mixture was taken into a separatory funnel, washed with water and brine, dried over sodium sulfate, filtered and concentrated to give the crude material that was purified on a silica gel column eluted with 0-5% MeOH in DCM to afford (S)-tert-butyl 2-(7-(3-(6-isopropoxypyridin-3-yl)-1-trityl-1H-indazol-5-yl)-6-oxo-2,7-diazaspiro[4.4]nonan-2-yl)acetate (0.08 g, 0.107 mmol, 39.9% yield). LCMS: 692.3 [M-tert-Bu+H]$^+$.

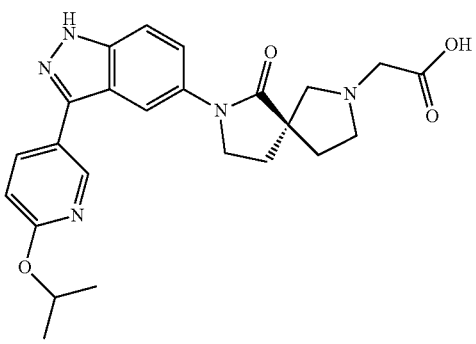

Step 2: (S)-2-(7-(3-(6-Isopropoxypyridin-3-yl)-1H-indazol-5-yl)-6-oxo-2,7-diazaspiro[4.4]nonan-2-yl)acetic acid A suspension of (S)-tert-butyl 2-(7-(3-(6-isopropoxypyridin-3-yl)-1-trityl-1H-indazol-5-yl)-6-oxo-2,7-diazaspiro[4.4]nonan-2-yl)acetate (0.08 g, 0.107 mmol) in a mixture of DCM (0.713 mL), TFA (0.238 mL), and water (0.119 mL) was stirred at 25° C. overnight. Upon completion, the solvents were removed on a rotary evaporator to give the crude product. This crude material was used without a further purification. LCMS: 450.20 [M+H]$^+$.

118

Intermediate 12

7-(3-(6-Isopropoxypyridin-3-yl)-1H-indazol-5-yl)-2,7-diazaspiro[4.5]decan-6-one

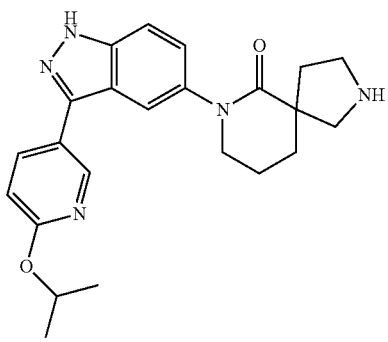 [SMILES: CC(C)Oc1ccc(-c2n[nH]c3ccc(N4CCCC5(CCNC5)C4=O)cc23)cn1]

The title compound was prepared following the procedure described for Intermediate 4, using Intermediate 2 and tert-butyl 6-oxo-2,7-diazaspiro[4.5]decane-2-carboxylate. $^1$H NMR (400 MHz, DMSO-d$_6$) δ 13.33 (s, 1H), 8.90 (br, 1H), 8.76 (s, 1H), 8.25 (dd, 1H), 8.01 (s, 1H), 7.58 (d, 1H), 7.30 (dd, 1H), 6.90 (d, 1H), 5.33-5.30 (m, 1H), 3.69-3.60 (m, 3H), 3.03 (d, 1H), 2.47-2.45 (m, 3H), 1.99-1.93 (m, 5H), 1.33 (d, 6H); LCMS: 406.20 [M+H]$^+$.

Intermediate 13

6-(3-(6-Isopropoxypyridin-3-yl)-1H-indazol-5-yl)-2,6-diazaspiro[3.4]octan-5-one

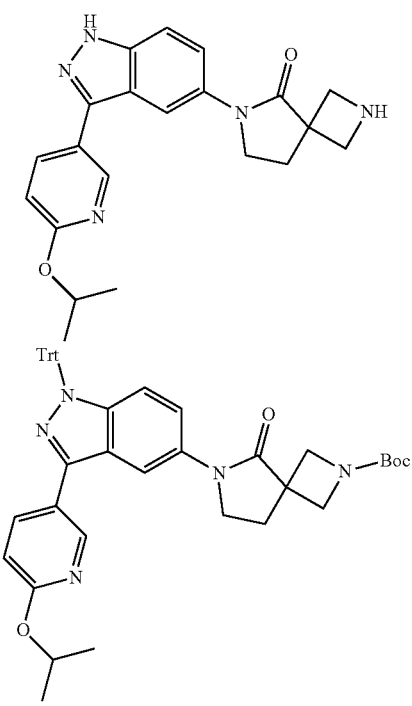

Step 1: tert-butyl 6-(3-(6-isopropoxypyridin-3-yl)-1-trityl-1H-indazol-5-yl)-5-oxo-2,6-diazaspiro[3.4]octane-2-carboxylate A mixture of 5-iodo-3-(6-isopropoxypyridin-3-yl)-1-trityl-1H-indazole (0.687 g, 1.105 mmol), tert-butyl 5-oxo-2,6-diazaspiro[3.4]octane-2-carboxylate (0.25 g, 1.105 mmol), copper(I) iodide (0.042 g, 0.221 mmol), potassium phosphate (0.469 g, 2.210 mmol) in DMSO (2.210 mL) was degassed with vacuum/$N_2$ cycles (3×). The vial was sealed and heated at 110° C. overnight. Upon completion, the mixture was filtered through Celite and washed with ethyl acetate. The filtrate was washed with water and brine, dried over sodium sulfate, filtered and concentrated to give the crude that was purified on a silica gel column eluted with 0-100% EA in hexanes to afford tert-butyl 6-(3-(6-isopropoxypyridin-3-yl)-1-trityl-1H-indazol-5-yl)-5-oxo-2,6-diazaspiro[3.4]octane-2-carboxylate (0.78 g, 1.084 mmol, 98% yield). LCMS: 720.30 [M+H]$^+$.

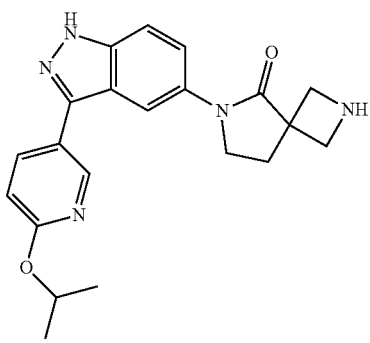 [SMILES: CC(C)Oc1ccc(-c2n[nH]c3ccc(N4CCC5(CNC5)C4=O)cc23)cn1]

Step 2: 6-(3-(6-Isopropoxypyridin-3-yl)-1H-indazol-5-yl)-2,6-diazaspiro[3.4]octan-5-one The title compound was prepared following the procedure described for Intermediate 4, using tert-butyl 6-(3-(6-isopropoxypyridin-3-yl)-1-trityl-1H-indazol-5-yl)-5-oxo-2,6-diazaspiro[3.4]octane-2-carboxylate. LCMS: 378.20 [M+H]$^+$.

Intermediate 14

(S)-2-(3-(3-fluoropyridin-4-yl)-1-trityl-1H-indazol-5-yl)-2,7-diazaspiro[4.4]nonan-1-one

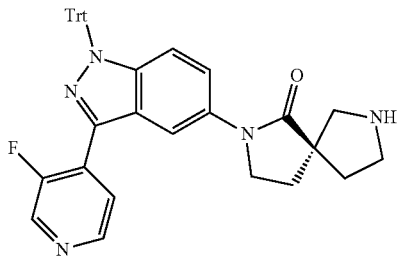

The title compound was prepared following the procedure described for Intermediate 8, using benzyl (R)-7-(3-iodo-1-trityl-1H-indazol-5-yl)-6-oxo-2,7-diazaspiro[4.4]nonane-2-carboxylate (Intermediate 7) and 3-fluoro-4-(4,4,5,5-tetramethyl-1,3,2-dioxaborolan-2-yl)pyridine in Step 1. LCMS: 594.30 [M+H]$^+$.

Intermediate 15

(S)-2-(3-(2-Isopropoxypyridin-4-yl)-1-trityl-1H-indazol-5-yl)-2,7-diazaspiro[4.4]nonan-1-one

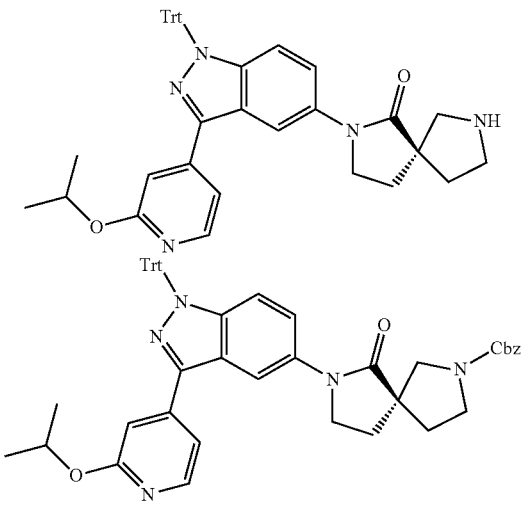

Step 1: Benzyl (R)-7-(3-(2-isopropoxypyridin-4-yl)-1-trityl-1H-indazol-5-yl)-6-oxo-2,7-diazaspiro[4.4]nonane-2-carboxylate A mixture of (R)-benzyl 7-(3-iodo-1-trityl-1H-indazol-5-yl)-6-oxo-2,7-diazaspiro[4.4]nonane-2-carboxylate (Intermediate 7) (0.3 g, 0.395 mmol), 2-isopropoxy-4-(4,4,5,5-tetramethyl-1,3,2-dioxaborolan-2-yl)pyridine (0.104 g, 0.395 mmol), Pd(Ph$_3$P)$_2$Cl$_2$ (0.028 g, 0.040 mmol), and cesium carbonate (0.258 g, 0.791 mmol) in DME (1.797 mL) and water (0.180 mL) was degassed with vacuum/$N_2$ cycles (3×). The mixture was heated at 100° C. for 3 h. Upon completion, the mixture was diluted with water and extracted with ethyl acetate. The organic layer was washed with water and brine, dried over sodium sulfate, filtered and concentrated to give the crude that was purified on silica gel column eluted with 0-100% ethyl acetate in hexanes to afford (R)-benzyl 7-(3-(2-isopropoxypyridin-4-yl)-1-trityl-1H-indazol-5-yl)-6-oxo-2,7-diazaspiro[4.4]nonane-2-carboxylate (0.3 g, 0.391 mmol, 99% yield) as pale yellow foam. LCMS: 768.30 [M+H]$^+$.

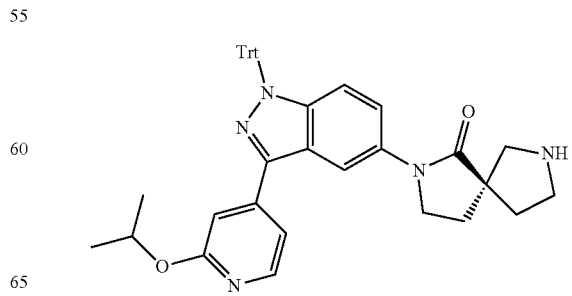

Step 2: (S)-2-(3-(2-Isopropoxypyridin-4-yl)-1-trityl-1H-indazol-5-yl)-2,7-diazaspiro[4.4]nonan-1-one The title compound was prepared following the procedure described for Intermediate 8, using benzyl (R)-7-(3-(2-isopropoxypyridin-4-yl)-1-trityl-1H-indazol-5-yl)-6-oxo-2,7-diazaspiro[4.4]nonane-2-carboxylate in Step 2. LCMS: 634.30 [M+H]$^+$.

Intermediate 16

(S)-2-(3-(3-(Trifluoromethyl)pyridin-4-yl)-1-trityl-1H-indazol-5-yl)-2,7-diazaspiro[4.4]nonan-1-one

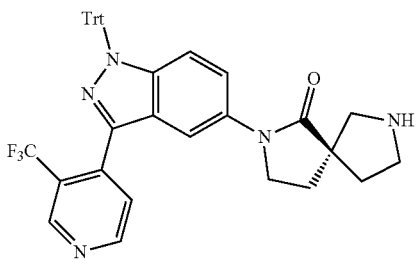

The title compound was prepared following the procedure described for Intermediate 15, using (R)-benzyl 7-(3-iodo-1-trityl-1H-indazol-5-yl)-6-oxo-2,7-diazaspiro[4.4]nonane-2-carboxylate (Intermediate 7) and 4-(4,4,5,5-tetramethyl-1,3,2-dioxaborolan-2-yl)-3-(trifluoromethyl)pyridine in Step 1. LCMS: 644.30 [M+H]$^+$.

Intermediate 17

(S)-2-(3-Morpholino-1-trityl-1H-indazol-5-yl)-2,7-diazaspiro[4.4]nonan-1-one

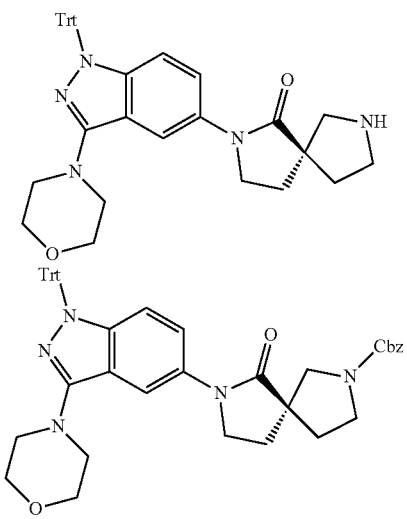

Step 1: Benzyl (R)-7-(3-morpholino-1-trityl-1H-indazol-5-yl)-6-oxo-2,7-diazaspiro[4.4]nonane-2-carboxylate A mixture of (R)-benzyl 7-(3-iodo-1-trityl-1H-indazol-5-yl)-6-oxo-2,7-diazaspiro[4.4]nonane-2-carboxylate (0.5 g, 0.659 mmol), morpholine (0.287 g, 3.30 mmol), diacetoxypalladium (0.015 g, 0.066 mmol), (9,9-dimethyl-9H-xanthene-4,5-diyl)bis(diphenylphosphine) (0.076 g, 0.132 mmol) and cesium carbonate (0.429 g, 1.318 mmol) in dioxane (6.59 mL) was degassed with vacuum/N$_2$ cycles (3×). The mixture was heated at 100° C. overnight. Upon completion, the mixture was cooled rt, diluted with water and extracted with ethyl acetate. The organic layer was washed with brine, dried over sodium sulfate, filtered and concentrated to give the crude that was purified on a silica gel column eluted with 0-100% ethyl acetate/hexanes to afford (R)-benzyl 7-(3-morpholino-1-trityl-1H-indazol-5-yl)-6-oxo-2,7-diazaspiro[4.4]nonane-2-carboxylate (0.25 g, 0.348 mmol, 52.8% yield). $^1$H NMR (400 MHz, DMSO-d$_6$) δ 7.88 (br s, 1H), 7.35 (br d, J=2.9 Hz, 4H), 7.25 (d, J=6.2 Hz, 15H), 7.11 (br d, J=9.5 Hz, 1H), 6.26 (d, J=9.5 Hz, 1H), 5.14 (d, J=3.3 Hz, 2H), 3.89-3.64 (m, 7H), 3.57-3.41 (m, 3H), 3.36-3.26 (m, 3H), 2.30 (br d, J=16.9 Hz, 1H), 2.20-2.07 (m, 2H), 1.86 (br s, 1H), 1.31-1.21 (m, 2H). LCMS: 717.4 [M+H]$^+$.

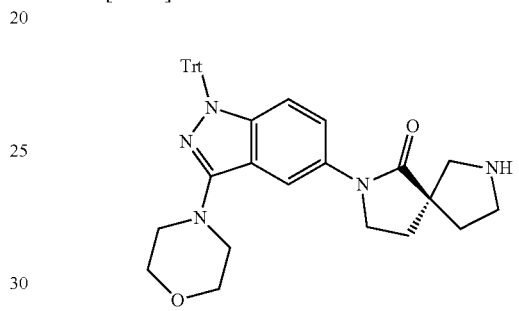

Step 2: (S)-2-(3-Morpholino-1-trityl-1H-indazol-5-yl)-2,7-diazaspiro[4.4]nonan-1-one To a stirred solution of (R)-benzyl 7-(3-morpholino-1-trityl-1H-indazol-5-yl)-6-oxo-2,7-diazaspiro[4.4]nonane-2-carboxylate (0.500 g, 0.697 mmol) in methanol (20 mL) was added 10% wet Pd/C (500 mg). The mixture was stirred at rt under hydrogen atmosphere (20 psi) for 16 h. The mixture was filtered through Celite, and the organic fractions were concentrated to (S)-2-(3-morpholino-1-trityl-1H-indazol-5-yl)-2,7-diazaspiro[4.4]nonan-1-one (0.280 g, 0.514 mmol, 68% yield) as an off white solid. $^1$H NMR (400 MHz, DMSO-d$_6$) δ 9.24 (br s, 1H), 8.09-7.78 (m, 1H), 7.43-7.01 (m, 16H), 6.30 (d, J=9.3 Hz, 1H), 3.94-3.65 (m, 6H), 3.40-3.02 (m, 8H), 2.31-1.89 (m, 4H). LCMS: 584.4 [M+H]$^+$.

Intermediate 18

(S)-2-(3-(2-(1-(Trifluoromethyl)cyclopropyl)pyridin-4-yl)-1-trityl-1H-indazol-5-yl)-2,7-diazaspiro[4.4]nonan-1-one

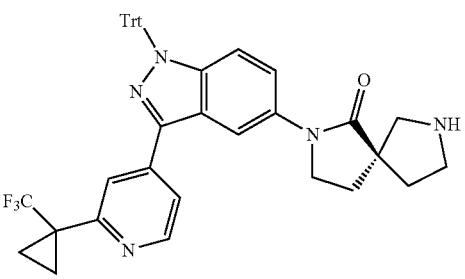

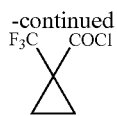

Step 1: 1-(Trifluoromethyl)cyclopropanecarbonyl Chloride

To a stirred solution of 1-(trifluoromethyl)cyclopropanecarboxylic acid (3 g, 19.48 mmol) in DCM (30 mL) at 0° C. was added oxalyl chloride (3.3 mL, 38.96 mmol). The mixture was stirred at rt for 1 h. After completion of the reaction, the mixture was concentrated under inert atmosphere to afford 1-(trifluoromethyl)cyclopropanecarbonyl chloride as a pale yellow gummy solid. The crude material was used for the next step without further purification.

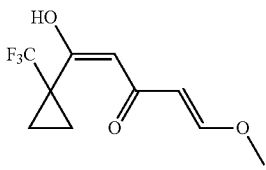 [SMILES: CO/C=C/C(=O)/C=C(/O)C1(C(F)(F)F)CC1]

Step 2: 1-Hydroxy-5-methoxy-1-(1-(trifluoromethyl)cyclopropyl)penta-1,4-dien-3-one To a stirred solution of 4-methoxybut-3-en-2-one (640 mg, 6.39 mmol) in THF (10 mL) was added lithium bis(trimethylsilyl)amide in THF (6.4 mL, 6.39 mmol) at −78° C. dropwise, and the mixture was stirred for 1 h. 1-(Trifluoromethyl)cyclopropanecarbonyl chloride (550 mg, 3.19 mmol) in THF (5 mL) was added at same temperature and stirring was continued at rt for 16 h. After completion of the reaction, aqueous ammonium chloride (20 mL) was added. The mixture was extracted with ethyl acetate (2×10 mL). The combined organic layers were washed with water (15 mL) and brine (10 mL), dried over sodium sulfate and concentrated. The residue was purified by column chromatography (100-200 silica) using 10% ethyl acetate in hexane as eluent to afford 1-hydroxy-5-methoxy-1-(1-(trifluoromethyl)cyclopropyl)penta-1,4-dien-3-one (200 mg, 0.84 mmol, 30% yield) as a pale yellow gummy liquid. $^1$H NMR (300 MHz, CDCl$_3$) δ 5.69 (s, 1H), 5.31 (t, J=4.4 Hz, 1H), 3.53 (s, 3H), 2.86-2.68 (m, 1H), 2.67-2.57 (m, 1H), 1.40-1.27 (m, 4H). LCMS: 237.11 [M+H]$^+$.

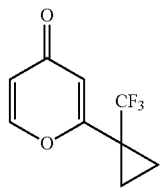

Step 3: 2-(1-(Trifluoromethyl)cyclopropyl)-4H-pyran-4-one

To a stirred solution of 1-hydroxy-5-methoxy-1-(1-(trifluoromethyl)cyclopropyl)penta-1,4-dien-3-one (500 mg, 2.11 mmol) in toluene (5 mL) at 0° C., was added trifluoroacetic acid (0.5 mL). The mixture was allowed to warm to rt with stirring over a period of 6 h. After completion of the reaction, water (20 mL) was added, and the mixture was extracted with ethyl acetate (2×15 mL). The combined organic layers were washed with water (15 mL) and brine (10 mL), dried over sodium sulfate, filtered and concentrated. The residue was purified by column chromatography (100-200 silica) using 50% ethyl acetate in hexane as eluent to afford 2-(1-(trifluoromethyl)cyclopropyl)-4H-pyran-4-one (0.2 g, 0.97 mmol, 46% yield) as pale yellow solid. $^1$H NMR (300 MHz, CDCl$_3$) δ 7.82 (d, J=5.5 Hz, 1H), 6.66 (d, J=1.8 Hz, 1H), 6.52 (dd, J=2.6, 5.9 Hz, 1H), 1.53-1.49 (m, 2H), 1.39-1.33 (m, 2H). LCMS: 204.96 [M+H]$^+$.

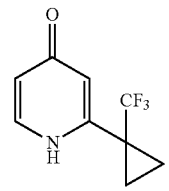

Step 4: 2-(1-(Trifluoromethyl) cyclopropyl) pyridin-4(1H)-one

To 2-(1-(trifluoromethyl)cyclopropyl)-4H-pyran-4-one (0.4 g, 1.96 mmol) was added ammonium hydroxide solution (4 mL). The mixture was stirred at reflux temperature for 3 h. After completion of the reaction, water (5 mL) was added. The mixture was extracted with 2-methyltetrahydrofuran (2×20 mL). The combined organic layers were washed with brine (10 mL), dried over sodium sulfate and concentrated. The residue was purified by GRACE column chromatography using 10% acetonitrile in 0.1% formic acid as eluent to afford 2-(1-(trifluoromethyl)cyclopropyl)pyridin-4 (1H)-one (330 mg, 1.61 mmol, 83% yield) as a pale yellow solid. $^1$H NMR (300 MHz, DMSO-d$_6$) δ 10.73 (br s, 1H), 8.20 (d, J=5.5 Hz, 1H), 6.93 (s, 1H), 6.70 (dd, J=2.2, 5.5 Hz, 1H), 1.34 (s, 4H). LCMS: 203.97 [M+H]$^+$.

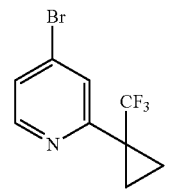 [SMILES: FC(F)(F)C1(c2cc(Br)ccn2)CC1]

Step 5: 4-Bromo-2-(1-(trifluoromethyl)cyclopropyl)pyridine

To 2-(1-(trifluoromethyl)cyclopropyl)pyridin-4(1H)-one (2 g, 9.80 mmol) was added phosphorous oxybromide (4.2 g, 14.7 mmol) at 0° C. and the temperature was to 120° C. over a period of 30 mins. After completion of the reaction, a sat. aq. sodium bicarbonate (50 mL) solution was added, and the mixture was extracted with ethyl acetate (2×30 mL). The combined organic layers were washed with water (30 mL) and brine (30 mL), dried over sodium sulfate and concentrated. The residue was purified by column chromatography (100-200 silica) using 5% ethyl acetate in hexane as eluent to afford 4-bromo-2-(1-(trifluoromethyl)cyclopropyl)pyridine (1.3 g, 4.90 mmol, 50% yield) as a pale yellow gummy liquid. $^1$H NMR (400 MHz, CDCl$_3$) δ 8.34 (d, J=4.9 Hz, 1H), 7.72 (s, 1H), 7.36 (dd, J=1.7, 5.1 Hz, 1H), 1.45-1.41 (m, 4H). LCMS: 265.99 [M+H]$^+$.

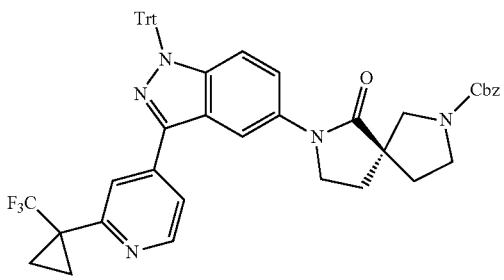

Step 6: (R)-benzyl 6-oxo-7-(3-(2-(1-(trifluoromethyl)cyclopropyl)pyridin-4-yl)-1-trityl-1H-indazol-5-yl)-2,7-diazaspiro[4.4]nonane-2-carboxylate To a stirred and degassed solution of 4-bromo-2-(1-(trifluoromethyl)cyclopropyl)pyridine (0.5 g, 1.88 mmol) and bis(pinacolato)diboron (0.996 g, 3.94 mmol) in 1,4-dioxane (10 mL), was added potassium acetate (0.55 g, 5.64 mmol). The mixture was degassed for 15 mins. To this mixture was added [1,1'-bis(diphenylphosphino)ferrocene]dichloropalladium (II) DCM complex (76 mg, 0.094 mmol). Degassing was continued for 10 mins followed by refluxing for 2 h. After completion of starting material, the mixture was cooled to rt and benzyl (R)-7-(3-iodo-1-trityl-1H-indazol-5-yl)-6-oxo-2,7-diazaspiro[4.4]nonane-2-carboxylate (1.18 g, 1.56 mmol) in ethanol:toluene:water (1:1:1, 60 mL) was added, followed by potassium carbonate (1.32 g, 9.58 mmol). The mixture was degassed for 20 mins. To this mixture was added tetrakis(triphenylphosphine)palladium (0) (110 mg, 0.095 mmol) and degassing was continued for 10 mins followed by heating at 70° C. for 5 h. The mixture was cooled rt and filtered through a Celite pad. To the filtrate was added cold water, and the mixture was extracted with ethyl acetate (3×30 mL). The combined organic layers were washed with water (70 mL) and brine (50 mL), dried over sodium sulfate, filtered and concentrated. The crude compound was purified by GRACE column chromatography using acetonitrile in the presence of 0.1% formic acid as eluent to afford (R)-benzyl 6-oxo-7-(3-(2-(1-(trifluoromethyl)cyclopropyl)pyridin-4-yl)-1-trityl-1H-indazol-5-yl)-2,7-diazaspiro[4.4]nonane-2-carboxylate (330 mg, 0.40 mmol, 22% yield) as an off-white solid. LCMS: 818.45 [M+H]$^+$.

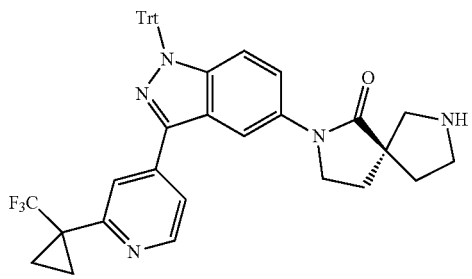

Step 7: (S)-2-(3-(2-(1-(trifluoromethyl)cyclopropyl)pyridin-4-yl)-1-trityl-1H-indazol-5-yl)-2,7-diazaspiro[4.4]nonan-1-one To a stirred solution of (R)-benzyl 6-oxo-7-(3-(2-(1-(trifluoromethyl)cyclopropyl)pyridin-4-yl)-1-trityl-1H-indazol-5-yl)-2,7-diazaspiro[4.4]nonane-2-carboxylate (330 mg, 0.40 mmol in methanol (10 mL) was added 10% Pd/C (100 mg). The mixture was stirred at rt under hydrogen atmosphere (40 psi) for 16 h. The mixture was filtered through Celite and washed with dichloromethane. The organic fraction was concentrated to afford (S)-2-(3-(2-(1-(trifluoromethyl)cyclopropyl)pyridin-4-yl)-1-trityl-1H-indazol-5-yl)-2,7-diazaspiro[4.4]nonan-1-one (150 mg, 0.22 mmol, 55% yield) as a colorless gummy liquid. LCMS: 684.35 [M+H]$^+$.

Intermediate 19

(S)-2-(3-(2-(1,1-Difluoroethyl)pyridin-4-yl)-1-trityl-1H-indazol-5-yl)-2,7-diazaspiro[4.4]nonan-1-one

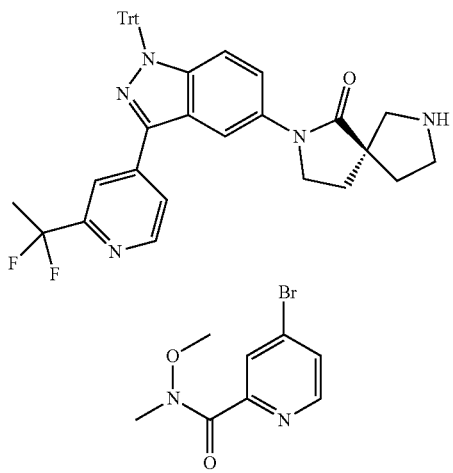

Step 1: 4-Bromo-N-methoxy-N-methylpicolinamide

To a stirred solution of 4-bromopicolinic acid (15 g, 74.25 mmol) in dimethylformamide (150 mL) was added diisopropylethylamine (39.25 mL, 222.7 mmol), HATU (36.63 g, 96.39 mmol) at 10° C. The mixture was stirred at 10° C. for 30 min. N,O-dimethylhydroxylamine hydrochloride (8.68 g, 89.10 mmol) was added, and the mixture was stirred at rt for 16 h. The mixture was poured into water (150 mL) and extracted with ethyl acetate (3×300 mL). The combined organic layers were washed with water (50 mL) and brine (2×100 mL), dried over sodium sulfate, filtered and concentrated. The residue was purified by silica gel column chromatography (100-200 silica) using 30% ethyl acetate in petroleum ether to afford 4-bromo-N-methoxy-N-methylpicolinamide (15.0 g, 61.47 mmol, 83% yield). $^1$H NMR (300 MHz, CDCl$_3$) δ 8.43 (d, J=5.1 Hz, 1H), 7.82 (br s, 1H), 7.53 (dd, J=1.8, 5.1 Hz, 1H), 3.75 (br s, 3H), 3.39 (s, 3H). LCMS: 244.9 [M+H]$^+$.

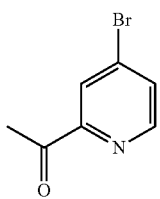

Step 2: 1-(4-Bromopyridin-2-yl)ethanone

A stirred and degassed solution of 4-bromo-N-methoxy-N-methylpicolinamide (11.0 g, 45.08 mmol) in dry tetrahydrofuran (110 mL) was cooled to 0° C.-5° C. Methylmagnesiumbromide (22 mL, 67.62 mmol) was added, and the mixture was stirred at rt for 1 h. The reaction was quenched with aq. ammonium chloride solution (100 mL) and extracted with ethyl acetate (3×250 mL). The combined organic layers were washed with brine (2×100 mL), dried over sodium sulfate, filtered and concentrated. The residue was purified by column chromatography (100-200 silica) using 10% ethyl acetate in hexane as eluent to afford 1-(4-bromopyridin-2-yl)ethanone (5.0 g, 25.12 mmol, 56% yield). $^1$H NMR (400 MHz, CDCl$_3$) δ 8.50 (d, J=5.4 Hz, 1H), 8.20 (d, J=1.5 Hz, 1H), 7.64 (dd, J=2.0, 5.4 Hz, 1H), 2.71 (s, 3H). LCMS: 201.5 [M+2H]$^+$.

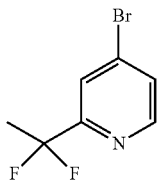

Step 3: 4-Bromo-2-(1,1-difluoroethyl)pyridine

A mixture of 1-(4-bromopyridin-2-yl)ethanone (4.0 g, 20.10 mmol) and diethylaminosulfur trifluoride (13.26 mL, 100.5 mmol) in dichloromethane was stirred at rt 16 h. The reaction was quenched with aq. sodium bicarbonate solution (50 mL) and extracted with ethyl acetate (3×100 mL). The combined organic layers were washed with brine (2×50 mL), dried over sodium sulfate, filtered and concentrated. The residue was purified by column chromatography (100-200 silica) using 5% ethyl acetate in hexane as eluent to afford 4-bromo-2-(1,1-difluoroethyl)pyridine (2.0 g, 9.00 mmol, 45% yield). $^1$H NMR (300 MHz, CDCl$_3$) δ 8.46 (d, J=5.1 Hz, 1H), 7.83 (d, J=1.5 Hz, 1H), 7.57-7.50 (m, 1H), 2.01 (t, J=18.7 Hz, 3H). LCMS: 221.8 [M+H]$^+$.

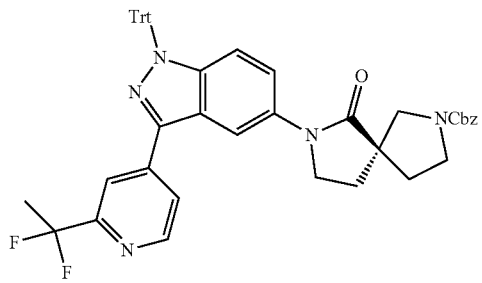

Step 4: (R)-Benzyl 7-(3-(2-(1,1-difluoroethyl)pyridin-4-yl)-1-trityl-1H-indazol-5-yl)-6-oxo-2,7-diazaspiro[4.4]nonane-2-carboxylate To a stirred solution of 4-bromo-2-(1,1-difluoroethyl)pyridine (0.750 g, 3.37 mmol) and bis(pinacolato)diboron (1.709 g, 6.756 mmol) in 1,4-dioxane (10 mL), was added potassium acetate (0.975 g, 10.13 mmol). The solution was degassed for 15 mins. [1,1'-bis (diphenylphosphino)ferrocene]dichloropalladium(II) DCM complex (0.138 g, 0.168 mmol) was added. The mixture was degassed for 10 mins followed by refluxing for 3 h. The mixture was cooled to rt and (R)-benzyl 7-(3-iodo-1-trityl-1H-indazol-5-yl)-6-oxo-2,7-diazaspiro[4.4]nonane-2-carboxylate (2.02 g, 2.66 mmol) (Intermediate 7) in ethanol:toluene:water (1:1:1, 10 mL) was added followed by potassium carbonate (2.23 g, 16.65 mmol). The mixture was degassed for 20 mins. Tetrakis (triphenylphosphine)palladium(0) (0.192 g, 0.05 mmol) was added, and the mixture was degassed for 10 mins followed by refluxing for 3 h. The mixture was cooled to rt and filtered through a Celite pad. To the filtrate was added cold water, and the mixture was extracted with ethyl acetate (3×50 mL). The combined organic layers were washed with water (30 mL) and brine (20 mL), dried over sodium sulfate, filtered and concentrated. The crude compound was purified by column chromatography (100-200 silica) using 50% ethyl acetate in hexane as eluent to afford (R)-benzyl 7-(3-(2-(1,1-difluoroethyl)pyridin-4-yl)-1-trityl-1H-indazol-5-yl)-6-oxo-2,7-diazaspiro[4.4]nonane-2-carboxylate (1.20 g, 1.55 mmol, 60% yield) as an off white solid. $^1$H NMR (300 MHz, DMSO-d$_6$) δ 8.79 (d, J=5.1 Hz, 1H), 8.39 (s, 1H), 8.07-7.99 (m, 2H), 7.49 (br d, J=9.5 Hz, 1H), 7.41-7.29 (m, 15H), 7.23-7.14 (m, 6H), 6.48 (d, J=9.2 Hz, 1H), 5.08 (d, J=2.9 Hz, 2H), 3.90 (br t, J=6.2 Hz, 2H), 3.58-3.39 (m, 4H), 2.18-2.05 (m, 4H), 2.03 (s, 2H), 1.97-1.93 (m, 2H). LCMS: 774.5 [M+H]$^+$.

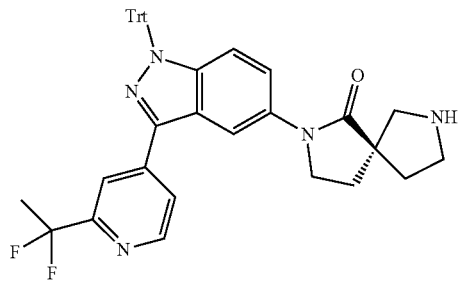

Step 5: (S)-2-(3-(2-(1,1-difluoroethyl)pyridin-4-yl)-1-trityl-1H-indazol-5-yl)-2,7-diazaspiro[4.4]nonan-1-one To a stirred solution of (R)-benzyl 7-(3-(2-(1,1-difluoroethyl)pyridin-4-yl)-1-trityl-1H-indazol-5-yl)-6-oxo-2,7-diazaspiro[4.4]nonane-2-carboxylate (0.350 g, 0.452 mmol) in methanol (10 mL) was added 10% wet Pd/C (350 mg). The mixture was stirred at rt under H$_2$ atmosphere (60 psi) for 16 h. The mixture was filtered through Celite, and the organic fractions were concentrated to afford (S)-2-(3-(2-(1,1-difluoroethyl)pyridin-4-yl)-1-trityl-1H-indazol-5-yl)-2,7-diazaspiro[4.4]nonan-1-one (0.260 g, 8.70 mmol, 90% yield) as an off white solid. $^1$H NMR (300 MHz, DMSO-d$_6$) δ 8.79 (d, J=4.8 Hz, 1H), 8.40 (s, 1H), 8.09-8.00 (m, 2H), 7.49 (br d, J=9.2 Hz, 1H), 7.40-7.28 (m, 9H), 7.24-7.12 (m, 6H), 6.47

(d, J=9.2 Hz, 1H), 4.09 (q, J=5.1 Hz, 2H), 3.84 (br s, 2H), 2.90-2.77 (m, 2H), 2.73 (s, 1H), 2.12-1.92 (m, 7H). LCMS: 640.33 [M+1]⁺.

Intermediate 20

(S)-2-(3-(2-(Difluoromethyl)pyridin-4-yl)-1-trityl-1H-indazol-5-yl)-2,7-diazaspiro[4.4]nonan-1-one

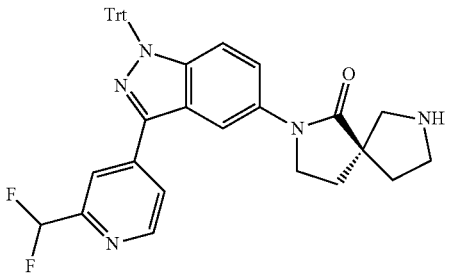

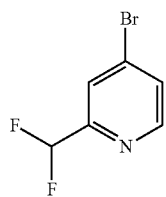

Step 1: 4-Bromo-2-(difluoromethyl)pyridine

To a 4-bromopicolinaldehyde (5.0 g, 26.88 mmol) was added diethylaminosulfur trifluoride (7.03 mL, 53.7 mmol), and the mixture was stirred at rt for 16 h. The reaction was quenched with aq. sodium bicarbonate solution (50 mL) and extracted with ethyl acetate (3×100 mL). The combined organic layers were washed with brine (2×50 mL), dried over sodium sulfate, filtered, concentrated and purified by column chromatography (100-200 silica) using 5% ethyl acetate in hexane as eluent to afford 4-bromo-2-(difluoromethyl)pyridine (3.0 g, 14.492 mmol, 54% yield). ¹H NMR (400 MHz, CDCl₃) δ=8.48 (d, J=4.9 Hz, 1H), 7.82 (d, J=1.5 Hz, 1H), 7.66-7.50 (m, 1H), 6.60 (t, 1H). LCMS: 207.9 [M+H]⁺.

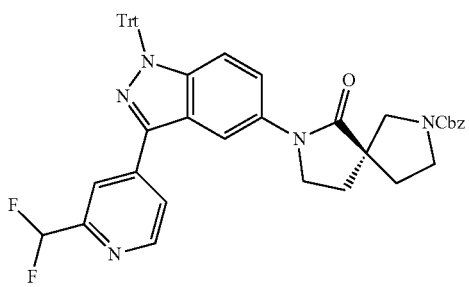

Step 2: (R)-benzyl 7-(3-(2-(difluoromethyl)pyridin-4-yl)-1-trityl-1H-indazol-5-yl)-6-oxo-2,7-diazaspiro[4.4]nonane-2-carboxylate To a stirred solution of 4-bromo-2-(difluoromethyl)pyridine (0.520 g, 2.51 mmol) and bis(pinacolato)diboron (1.270 g, 5.02 mmol) in 1,4-dioxane (15 mL), was added potassium acetate (0.740 g, 7.53 mmol). The solution was degassed for 15 mins. [1,1'-bis(diphenylphosphino)ferrocene]dichloropalladium (II) DCM complex (0.102 g, 0.125 mmol) was added. The mixture was degassed for 10 mins followed by refluxing for 3 h. The mixture was cooled to rt and (R)-benzyl 7-(3-iodo-1-trityl-1H-indazol-5-yl)-6-oxo-2,7-diazaspiro[4.4]nonane-2-carboxylate (Intermediate 7) (1.523 g, 2.009 mmol) in ethanol:toluene:water (1:1:1, 15 mL) was added followed by potassium carbonate (1.733 g, 12.56 mmol). The solution was degassed for 20 mins. Tetrakis(triphenylphosphine)palladium(0) (0.145 g, 0.125 mmol) was added. The mixture was degassed for 10 mins followed by refluxing for 3 h. The mixture was cooled to rt and filtered through a Celite pad. To the filtrate was added cold water, and the mixture was extracted with ethyl acetate (3×50 mL). The combined organic layers were washed with water (30 mL) and brine (20 mL), dried over sodium sulfate, filtered and concentrated. The crude compound was purified by column chromatography (100-200 silica) using 50% ethyl acetate in hexane as eluent to afford (R)-benzyl 7-(3-(2-(difluoromethyl)pyridin-4-yl)-1-trityl-1H-indazol-5-yl)-6-oxo-2,7-diazaspiro[4.4]nonane-2-carboxylate (0.500 g, 0.658 mmol, 33% yield) as an off white solid. ¹H NMR (400 MHz, DMSO-d₆) δ 8.81 (d, J=5.1 Hz, 1H), 8.37 (d, J=1.5 Hz, 1H), 8.09-8.00 (m, 2H), 7.50 (br d, J=9.5 Hz, 1H), 7.43-7.27 (m, 14H), 7.20 (dd, J=1.8, 7.7 Hz, 7H), 6.49 (d, J=9.2 Hz, 1H), 5.08 (d, J=3.3 Hz, 2H), 3.91 (br t, J=6.4 Hz, 2H), 3.66-3.36 (m, 4H), 2.22-2.03 (m, 3H), 1.97 (br d, J=4.8 Hz, 1H). LCMS: 260.44 [M+H]⁺.

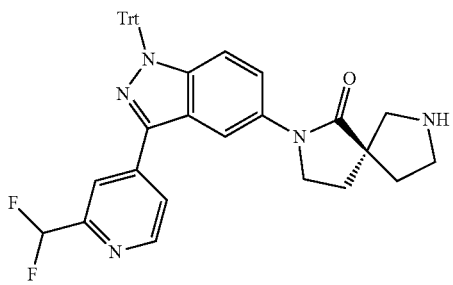

Step 3: (S)-2-(3-(2-(Difluoromethyl)pyridin-4-yl)-1-trityl-1H-indazol-5-yl)-2,7-diazaspiro[4.4]nonan-1-one To a stirred solution of (R)-benzyl 7-(3-(2-(difluoromethyl)pyridin-4-yl)-1-trityl-1H-indazol-5-yl)-6-oxo-2,7-diazaspiro[4.4]nonane-2-carboxylate (0.350 g, 0.461 mmol) in methanol (10 mL) was added wet Pd/C (350 mg). The mixture was stirred at rt under H₂ atmosphere (20 psi) for 16 h. The mixture was filtered through Celite, and the organic fractions were concentrated to give (S)-2-(3-(2-(difluoromethyl)pyridin-4-yl)-1-trityl-1H-indazol-5-yl)-2,7-diazaspiro[4.4]nonan-1-one (0.260 g, 0.48 mmol, 90% yield) as an off white solid. LCMS: 626.55 [M+H]⁺.

Intermediate 21

(S)-2-(3-(2-Methylpyridin-4-yl)-1-trityl-1H-indazol-5-yl)-2,7-diazaspiro[4.4]nonan-1-one

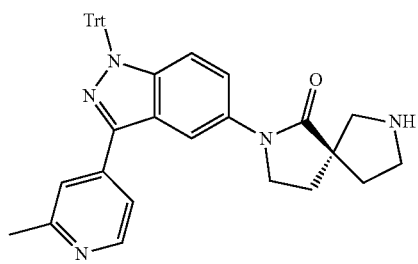

Step 1: 5-Iodo-3-(2-methylpyridin-4-yl)-1-trityl-1H-indazole

The compound was prepared following the procedure described for Intermediate 2 using 3-bromo-5-nitro-1-trityl-1H-indazole and (2-methylpyridin-4-yl)boronic acid in Step 4. LCMS: 578.10 [M+H]$^+$.

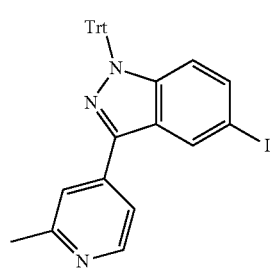

Step 2: (S)-2-(3-(2-Methylpyridin-4-yl)-1-trityl-1H-indazol-5-yl)-2,7-diazaspiro[4.4]nonan-1-one The compound was prepared following the procedure described for Intermediate 5 using 5-iodo-3-(2-methylpyridin-4-yl)-1-trityl-1H-indazole and benzyl (R)-6-oxo-2,7-diazaspiro[4.4]nonane-2-carboxylate (Intermediate 1A) in Step 2. LCMS: 590.30 [M+H]$^+$.

Intermediate 22

(R)-2-(3-(2-Methylpyridin-4-yl)-1-trityl-1H-indazol-5-yl)-2,7-diazaspiro[4.4]nonan-1-one

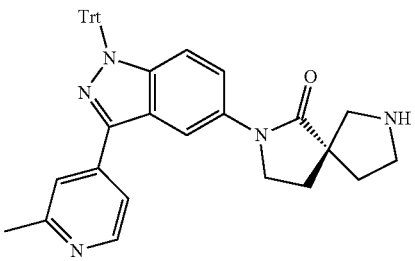

The compound was prepared following the procedure described for Intermediate 21 using 5-iodo-3-(2-methylpyridin-4-yl)-1-trityl-1H-indazole and benzyl (S)-6-oxo-2,7-diazaspiro[4.4]nonane-2-carboxylate (Intermediate 1B) in Step 2. LCMS: 590.30 [M+H]$^+$.

Intermediate 23

2-(3-(2-Methylpyridin-4-yl)-1-trityl-1H-indazol-5-yl)-2,7-diazaspiro[4.4]nonan-1-one

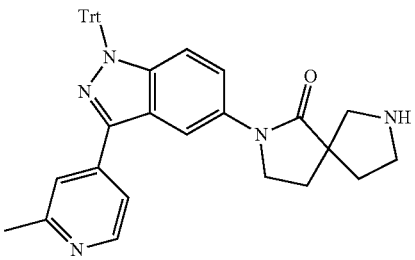

The compound was prepared following the procedure described for Intermediate 21 using 5-iodo-3-(2-methylpyridin-4-yl)-1-trityl-1H-indazole and benzyl 6-oxo-2,7-diazaspiro[4.4]nonane-2-carboxylate (Intermediate 1) in Step 2. LCMS: 590.30 [M+H]$^+$.

Intermediate 24

2-(3-(6-Methylpyridin-3-yl)-1-trityl-1H-indazol-5-yl)-2,7-diazaspiro[4.4]nonan-1-one

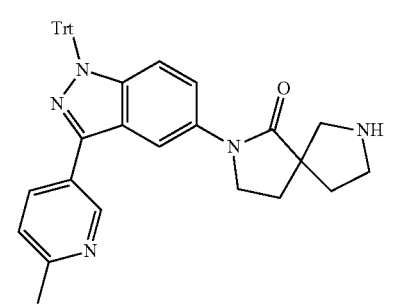

The compound was prepared following the procedure described for Intermediate 21 using 3-bromo-5-nitro-1-trityl-1H-indazole, (6-methylpyridin-3-yl)boronic acid and benzyl 6-oxo-2,7-diazaspiro[4.4]nonane-2-carboxylate (Intermediate 1A). LCMS: 590.3 [M+H]$^+$.

Intermediate 25

(S)-2-(3-(1-Methyl-1H-pyrazol-4-yl)-1-trityl-1H-indazol-5-yl)-2,7-diazaspiro[4.4]nonan-1-one

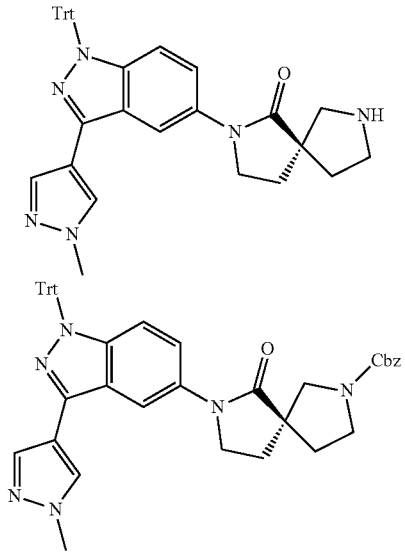

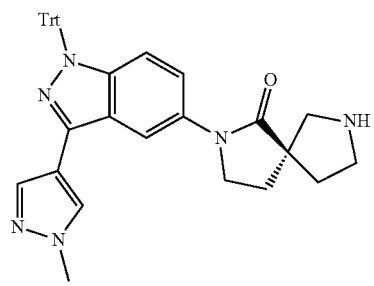

Step 2: (S)-2-(3-(1-Methyl-1H-pyrazol-4-yl)-1-trityl-1H-indazol-5-yl)-2,7-diazaspiro[4.4]nonan-1-one To a stirred solution of (R)-benzyl 7-(3-(1-methyl-1H-pyrazol-4-yl)-1-trityl-1H-indazol-5-yl)-6-oxo-2,7-diazaspiro[4.4]nonane-2-carboxylate (400 mg, 0.56 mmol) in methanol (10 mL) was added 10% Pd/C (400 mg). The mixture was stirred at rt under H$_2$ atmosphere (30 psi) for 2 h. The mixture was filtered through Celite and washed with dichloromethane, and the organic fraction was concentrated. The crude compound was purified by combi-flash column chromatography by using 18% of methanol in dichloromethane to afford (S)-2-(3-(1-methyl-1H-pyrazol-4-yl)-1-trityl-1H-indazol-5-yl)-2,7-diazaspiro[4.4]nonan-1-one (210 mg, 0.36 mmol, 65% yield) as a colorless gummy liquid. LCMS: 579.44 [M+H]$^+$.

Intermediate 26

(S)-2-(3-Cyclopropyl-1H-indazol-5-yl)-2,7-diazaspiro[4.4]nonan-1-one

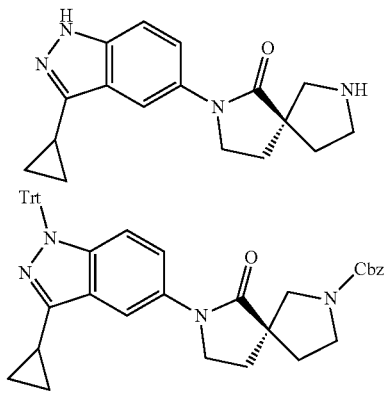

Step 1: Benzyl (R)-7-(3-cyclopropyl-1-trityl-1H-indazol-5-yl)-6-oxo-2,7-diazaspiro[4.4]nonane-2-carboxylate Step 1: (R)-Benzyl 7-(3-(1-methyl-1H-pyrazol-4-yl)-1-trityl-1H-indazol-5-yl)-6-oxo-2,7-diazaspiro[4.4]nonane-2-carboxylate To a stirred and degassed solution of (R)-benzyl 7-(3-iodo-1-trityl-1H-indazol-5-yl)-6-oxo-2,7-diazaspiro[4.4]nonane-2-carboxylate (Intermediate 7) (500 mg, 0.66 mmol) in ethanol:toluene:water (1:1:1, 15 mL) was added potassium carbonate (455 mg, 3.29 mmol) and 1-methyl-4-(4,4,5,5-tetramethyl-1,3,2-dioxaborolan-2-yl)-1H-pyrazole (192 mg, 0.92 mmol). The mixture was degassed for 20 mins. Tetrakis(triphenylphosphine)palladium(0) (38 mg, 0.033 mmol) was added. The mixture was degassed for 10 mins followed by refluxing for 1 6 h. After consumption of starting material, the mixture was cooled to rt and filtered through a Celite pad. To the filtrate was added cold water, and the mixture was extracted with ethyl acetate (3×20 mL). The combined organic layers were washed with water (30 mL) and brine (20 mL), dried over sodium sulfate, filtered and concentrated. The crude compound was purified by combi-flash column chromatography by using 50% of ethyl acetate in hexane to afford (R)-benzyl 7-(3-(1-methyl-1H-pyrazol-4-yl)-1-trityl-1H-indazol-5-yl)-6-oxo-2,7-diazaspiro[4.4]nonane-2-carboxylate (300 mg, 0.42 mmol, 65% yield) as off-white solid. $^1$H NMR (400 MHz, DMSO-d$_6$) δ 8.18 (s, 1H), 8.04 (s, 1H), 7.83 (s, 1H), 7.43 (br d, J=9.3 Hz, 1H), 7.39-7.26 (m, 13H), 7.20 (br d, J=7.3 Hz, 6H), 6.34 (d, J=9.3 Hz, 1H), 5.08 (br d, J=4.4 Hz, 2H), 4.03 (q, J=6.8 Hz, 2H), 3.95-3.84 (m, 5H), 3.64-3.41 (m, 3), 2.18-2.05 (m, 3H), 2.01-1.89 (m, 1H). LCMS: 713.57 [M+H]$^+$.

To a stirred and degassed solution of (R)-benzyl 7-(3-iodo-1-trityl-1H-indazol-5-yl)-6-oxo-2,7-diazaspiro[4.4]nonane-2-carboxylate (Intermediate 7) (500 mg, 0.65 mmol) in mixture of toluene:water (30:10 mL) was added potassium cyclopropyltrifluoroborate (0.125 g, 0.84 mmol), di(1-adamantyl)-n-butylphosphine (7 mg, 0.02 mmol) and cesium carbonate (0.636 g, 1.95 mmol). The mixture was degassed for 30 mins. Palladium(II) acetate (13 mg, 0.02 mmol) was added. The mixture was degassed for 10 mins in sealed tube and then stirred at 100° C. for 16 h. After complete consumption of starting material as determined by LCMS, the mixture was cooled to rt. The mixture was filtered through a Celite pad. To the filtrate was added cold water, and the mixture was extracted with ethyl acetate (3×20 mL). The combined organic layers were washed with water (30 mL) and brine (20 mL), dried over sodium sulfate, filtered and concentrated. The crude compound was purified by combi-flash column chromatography by using 30% of ethyl acetate in hexane to afford the title compound (250 mg, 0.37 mmol, 56% yield) as an off-white solid. $^1$H NMR (300 MHz, DMSO-$d_6$) δ 7.96 (s, 1H), 7.43-7.25 (m, 15H), 7.19-7.13 (m, 6H), 6.26 (d, J=9.2 Hz, 1H), 5.08 (d, J=2.6 Hz, 2H), 3.82 (br t, J=6.8 Hz, 2H), 3.64-3.39 (m, 4H), 2.31-2.17 (m, 2H), 2.11 (br t, J=7.0 Hz, 2H), 1.95 (m, 1H), 0.99-0.91 (m, 2H), 0.85-0.78 (m, 2H). LCMS: 673.14 [M+H]$^+$.

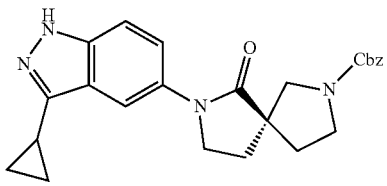 [SMILES: O=C(OCc1ccccc1)N1CC[C@]2(CCN(c3ccc4[nH]nc(C5CC5)c4c3)C2=O)C1]

Step 2: Benzyl (R)-7-(3-cyclopropyl-1H-indazol-5-yl)-6-oxo-2,7-diazaspiro[4.4]nonane-2-carboxylate To a stirred solution of (R)-benzyl 7-(3-cyclopropyl-1-trityl-1H-indazol-5-yl)-6-oxo-2,7-diazaspiro[4.4]nonane-2-carboxylate (350 mg, 0.52 mmol) in dichloromethane (10 mL) was added trifluoroacetic acid (1 mL). The mixture was stirred at rt for 5 h. The reaction was quenched with aq. sodium bicarbonate solution and extracted with ethyl acetate (3×10 mL). The combined organic layers were washed with brine (2×10 mL), dried and concentrated to afford (R)-benzyl 7-(3-cyclopropyl-1H-indazol-5-yl)-6-oxo-2,7-diazaspiro[4.4]nonane-2-carboxylate (200 mg, 0.46 mmol, 90% yield) as an off-white solid. LCMS: 431.33 [M+H]$^+$.

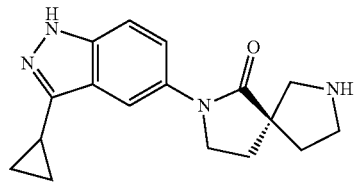 [SMILES: O=C1N(c2ccc3[nH]nc(C4CC4)c3c2)CC[C@]12CCNC2]

Step 3: (S)-2-(3-Cyclopropyl-1H-indazol-5-yl)-2,7-diazaspiro[4.4]nonan-1-one

To a stirred solution of (R)-benzyl 7-(3-cyclopropyl-1H-indazol-5-yl)-6-oxo-2,7-diazaspiro[4.4]nonane-2-carboxylate (300 mg, 0.43 mmol) in methanol (10 mL) was added 10% Pd/C (300 mg). The mixture was stirred at rt under H$_2$ atmosphere (30 psi) for 2 h. The mixture was filtered through Celite and washed with dichloromethane. The organic fraction was concentrated to afford the title compound (150 mg, 0.50 mmol, 75% yield) as a colorless gummy liquid. LCMS: 297.19 [M+H]$^+$.

Intermediate 27

(S)-5-(1-Oxo-2,7-diazaspiro[4.4]nonan-2-yl)-1-trityl-1H-indazole-3-carbonitrile

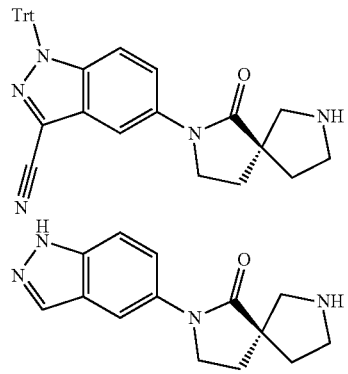

Step 1: (S)-2-(1H-indazol-5-yl)-2,7-diazaspiro[4.4]nonan-1-one

To a stirred and degassed solution of (R)-benzyl 7-(1H-indazol-5-yl)-6-oxo-2,7-diazaspiro[4.4]nonane-2-carboxylate (2.0 g, 5.128 mmol) in methanol (100 mL) was added 10% Pd/C (500 mg) at rt. The mixture was stirred at rt under H$_2$ atmosphere (30 psi) for 4 h. The mixture was filtered through a Celite pad and washed with methanol. The organic fractions was concentrated to afford (S)-2-(1H-indazol-5-yl)-2,7-diazaspiro[4.4]nonan-1-one (1.1 g, 4.296 mmol, 84% yield). $^1$H NMR (300 MHz, DMSO-$d_6$) δ 8.05 (s, 1H), 7.86 (d, J=1.5 Hz, 1H), 7.77 (dd, J=9.3 Hz, 2.4 Hz, 1H), 7.53 (d, 1H), 4.10 (br s, 1H), 3.83 (t, J=6.6 Hz, 2H), 3.16 (s, 1H), 2.93-2.81 (m, 3H), 2.19-2.15 (m, 3H), 1.76-1.70 (m, 1H). LCMS: 257.17 [M+H]$^+$.

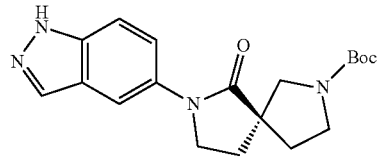

Step 2: (R)-tert-butyl 7-(1H-indazol-5-yl)-6-oxo-2,7-diazaspiro[4.4]nonane-2-carboxylate To a solution of (S)-2-(1H-indazol-5-yl)-2,7-diazaspiro[4.4]nonan-1-one (1.1 g, 4.296 mmol) in THF:H$_2$O (1:1, 20 mL) were added NaHCO$_3$ (1.08 g, 12.890 mmol) followed by Boc$_2$O (0.79 mL, 3.437 mmol) at rt for 4 h. The mixture was diluted with water (100 mL) and extracted with ethyl acetate (2×250 mL). The organic layer was dried over Na$_2$SO$_4$, filtered and concentrated. The crude was purified by column chromatography using 50% ethyl acetate/petroleum ether as an eluent to afford (R)-tert-butyl 7-(1H-indazol-5-yl)-6-oxo-2,7-diazaspiro[4.4]nonane-2-carboxylate (1.0 g, 2.808 mmol, 63% yield) as an off white solid. $^1$H NMR (300 MHz, CDCl$_3$) δ 10.15 (br s, 1H), 8.06 (s, 1H), 7.84-7.79 (m, 2H), 7.50 (d, J=9.0 Hz, 1H), 3.89 (t, J=6.6 Hz, 2H), 3.73-3.64 (m, 2H), 3.52-3.38 (m, 2H), 2.37-2.20 (m, 3H), 1.91-1.85 (m, 1H), 1.47 (s, 9H). LCMS: 357.28 [M+H]+.

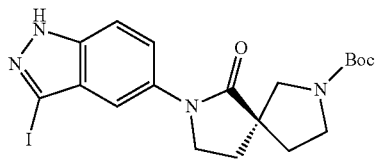

Step 3: (R)-tert-butyl 7-(3-iodo-1H-indazol-5-yl)-6-oxo-2,7-diazaspiro[4.4]nonane-2-carboxylate To a stirred solution of (R)-tert-butyl 7-(1H-indazol-5-yl)-6-oxo-2,7-diazaspiro[4.4]nonane-2-carboxylate (1.0 g, 2.808 mmol) in DMF (20 mL) was added $K_2CO_3$ (1.5 g, 11.235 mmol) followed by $I_2$ (0.78 g, 3.089 mmol) at 0° C. The mixture was stirred at rt for 3 h. The reaction was quenched with a solution of sodium thiosulphate (100 mL) and extracted with ethyl acetate (3×100 mL). The combined organic layers were washed with brine (100 mL), dried over sodium sulfate, filtered and concentrated under reduced pressure. The crude was purified by column chromatography using 50% ethyl acetate in hexane as an eluent to afford (R)-tert-butyl 7-(3-iodo-1H-indazol-5-yl)-6-oxo-2,7-diazaspiro[4.4]nonane-2-carboxylate (1.0 g, 2.074 mmol, 74% yield) as an off white solid. $^1$H NMR (400 MHz, DMSO-$d_6$) δ 13.51 (s, 1H), 7.95 (s, 1H), 7.77 (dd, J=9.6 Hz, 2 Hz, 1H), 7.65 (s, 1H), 7.57 (d, J=8.8 Hz, 1H), 3.93-3.89 (m, 2H), 3.54-3.43 (m, 2H), 3.35-3.26 (m, 2H), 2.16-2.03 (m, 2H), 1.95-1.93 (m, 2H). LCMS: 483.04 [M+H]+.

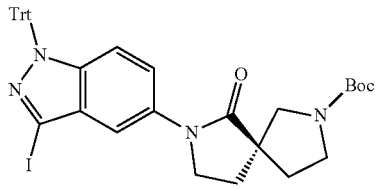

Step 4: (R)-tert-butyl 7-(3-iodo-1-trityl-1H-indazol-5-yl)-6-oxo-2,7-diazaspiro[4.4]nonane-2-carboxylate To a stirred solution of (R)-tert-butyl 7-(3-iodo-1H-indazol-5-yl)-6-oxo-2,7-diazaspiro[4.4]nonane-2-carboxylate (1.0 g, 2.074 mmol) in acetonitrile (10 mL) were added $K_2CO_3$ (1.4 g, 10.373 mmol), TBAI (0.038 g, 0.103 mmol) and trityl chloride (00.635 g, 2.282 mmol) at rt. The mixture was stirred at 75° C. for 4 h. The mixture was diluted with water (50 mL) and extracted with ethyl acetate (3×100 mL). The combined organic layers were washed with brine (100 mL), dried over sodium sulfate, filtered and concentrated under reduced pressure. The crude was purified by column chromatography using 30% ethyl acetate in hexane as an eluent to afford (R)-tert-butyl 7-(3-iodo-1-trityl-1H-indazol-5-yl)-6-oxo-2,7-diazaspiro[4.4]nonane-2-carboxylate (900 mg, 124.309 mmol, 60% yield) as an off white solid. $^1$H NMR (300 MHz, DMSO-$d_6$) δ 7.74 (d, J=1.8 Hz, 1H), 7.43-7.31 (m, 10H), 7.16-7.13 (m, 6H), 6.37 (d, J=9.3 Hz, 1H), 3.83 (t, J=6.9 Hz, 2H), 3.46-3.28 (m, 4H), 2.11-2.07 (m, 3H), 1.84-1.96 (m, 1H), 1.40 (s, 9H). LCMS: 669.23 [M-$^t$Bu+H]+.

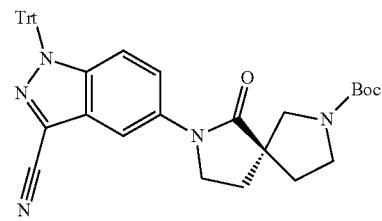

Step 5: (R)-tert-butyl 7-(3-cyano-1-trityl-1H-indazol-5-yl)-6-oxo-2,7-diazaspiro[4.4]nonane-2-carboxylate To a stirred and degassed solution of (R)-tert-butyl 7-(3-iodo-1-trityl-1H-indazol-5-yl)-6-oxo-2,7-diazaspiro[4.4]nonane-2-carboxylate (0.31 g, 428.176 mmol) in DMF (15 mL) were added $Zn(CN)_2$, Zn powder and $Pd(PPh_3)_4$ at rt. The mixture was stirred at 100° C. for 16 h. The mixture was diluted with water (50 mL) and extracted with ethyl acetate (3×100 mL). The combined organic layers were washed with brine (100 mL), dried over sodium sulfate, filtered, and concentrated under reduced pressure. The crude was purified by column chromatography using 20% ethyl acetate/petroleum ether as an eluent to afford (R)-tert-butyl 7-(3-cyano-1-trityl-1H-indazol-5-yl)-6-oxo-2,7-diazaspiro[4.4]nonane-2-carboxylate (150 mg, 288.924 mmol, 56% yield) as off white solid. $^1$H NMR (300 MHz, DMSO-$d_6$) δ 7.77-7.11 (m, 2H), 7.30-7.28 (m, 9H), 7.13-7.10 (m, 1H), 6.47 (d, J=9 Hz), 3.85 (t, J=6.9 Hz, 2H), 3.70-3.58 (m, 2H), 3.47-3.33 (m, 2H), 2.35-2.10 (m, 3H), 1.88-1.80 (m, 1H), 1.46 (s, 9H). LCMS: 568.38 [M-$^t$Bu+H]+.

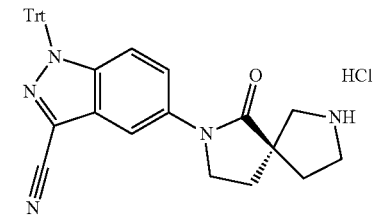

Step 6: (S)-5-(1-oxo-2,7-diazaspiro[4.4]nonan-2-yl)-1-trityl-1H-indazole-3-carbonitrile hydrochloride To a solution of (R)-tert-butyl 7-(3-cyano-1-trityl-1H-indazol-5-yl)-6-oxo-2,7-diazaspiro[4.4]nonane-2-carboxylate (150 mg, 288.92 mmol) in 1,4-dioxane (5 mL) was added 4.0 M HCl: 1,4-dioxane (3 mL) at rt. The mixture was stirred at rt for 2 h. After completion of the reaction, the solvent was evaporated and triturated with $Et_2O$ (5 mL) to afford (S)-5-(1-oxo-2,7-diazaspiro[4.4]nonan-2-yl)-1-trityl-1H-indazole-3-carbonitrile hydrochloride (0.125 g, 0.223 mmol, 93% yield) as an off white solid. $^1$H NMR (400 MHz, DMSO-$d_6$) δ 9.20 (br s, 1H), 9.08 (br s, 1H), 8.145 (d, J=1.5 Hz, 1H), 7.59 (dd, J=9.3 Hz, 1.5 Hz, 1H), 7.39-7.27 (m, 9H), 7.18-7.11 (m, 6H), 6.56 (d, 9.6 Hz, 1H), 3.92-3.86 (m, 2H), 3.36-3.25 (m, 4H), 2.25-2.02 (m, 4H).

Intermediate 28

(S)-2-(3-(Ethylamino)-1-trityl-1H-indazol-5-yl)-2,7-diazaspiro[4.4]nonan-1-one

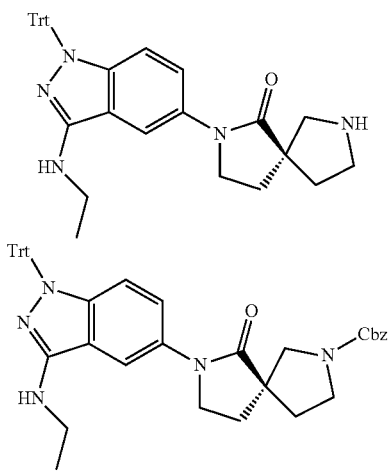

Step 1: (R)-benzyl 7-(3-(ethylamino)-1-trityl-1H-indazol-5-yl)-6-oxo-2,7-diazaspiro[4.4]nonane-2-carboxylate To a stirred and degassed solution of (R)-benzyl 7-(3-iodo-1-trityl-1H-indazol-5-yl)-6-oxo-2,7-diazaspiro[4.4]nonane-2-carboxylate (850 mg, 1.12 mmol) in DMSO (15 mL) was added potassium carbonate (774 mg, 5.60 mmol), L-proline (38 mg, 0.36 mmol), CuI (21 mg, 0.12 mmol) and ethanamine hydrochloride (300 mg, 2.24 mmol). The mixture was degassed for 20 mins in a sealed tube and stirred at 80° C. for 16 h. After consumption of starting material, the mixture was cooled to rt and filtered through a Celite pad. To the filtrate was added cold water, and the mixture was extracted with ethyl acetate (3×20 mL). The combined organic layers were washed with water (30 mL) and brine (20 mL), dried over sodium sulfate, filtered and concentrated. The crude compound was purified by combi-flash column chromatography by using 50% of ethyl acetate in hexane to afford (R)-benzyl 7-(3-(ethylamino)-1-trityl-1H-indazol-5-yl)-6-oxo-2,7-diazaspiro[4.4]nonane-2-carboxylate (400 mg, 0.60 mmol, 53% yield) as an off-white solid. $^1$H NMR (300 MHz, DMSO-d$_6$) δ 7.85 (br s, 1H), 7.41-7.17 (m, 21H), 6.20 (d, J=9.5 Hz, 1H), 6.08 (br s, 1H), 5.07 (d, J=2.6 Hz, 2H), 3.75 (br t, J=6.6 Hz, 2H), 3.64-3.34 (m, 4H), 3.20-3.05 (m, 2H), 2.11 (br t, J=6.8 Hz, 2H), 2.04-1.86 (m, 2H), 1.11 (t, J=7.1 Hz, 3H). LCMS: 676.49 [M+H]$^+$.

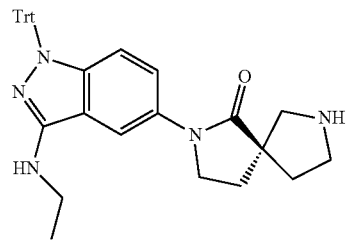

Step 2: (S)-2-(3-(Ethylamino)-1-trityl-1H-indazol-5-yl)-2,7-diazaspiro[4.4]nonan-1-one To a stirred solution of (R)-benzyl 7-(3-(ethylamino)-1-trityl-1H-indazol-5-yl)-6-oxo-2,7-diazaspiro[4.4]nonane-2-carboxylate (250 mg, 0.26 mmol in methanol (5 mL) was added 10% Pd/C (250 mg). The mixture was stirred rt under H$_2$ atmosphere (30 psi) for 2 h. The mixture was filtered through Celite and washed with dichloromethane. The organic fraction was concentrated. The crude compound was purified by combi-flash column chromatography by using 18% of methanol in dichloromethane to afford (S)-2-(3-(ethylamino)-1-trityl-1H-indazol-5-yl)-2,7-diazaspiro[4.4]nonan-1-one (150 mg, 0.27 mmol, 75% yield) as an off-white solid. $^1$H NMR (300 MHz, DMSO-d$_6$) δ 7.83 (d, J=1.5 Hz, 1H), 7.39-7.16 (m, 16H), 6.21 (d, J=9.2 Hz, 1H), 6.08 (t, J=5.3 Hz, 1H), 3.73 (br t, J=6.8 Hz, 2H), 3.20-2.97 (m, 6H), 2.19-1.95 (m, 4H), 1.92-1.77 (m, 1H), 1.11 (t, J=7.2 Hz, 3H). LCMS: 542.43 [M+H]$^+$.

Intermediate 29

(S)-2-(3-(Difluoromethyl)-1-trityl-1H-indazol-5-yl)-2,7-diazaspiro[4.4]nonan-1-one

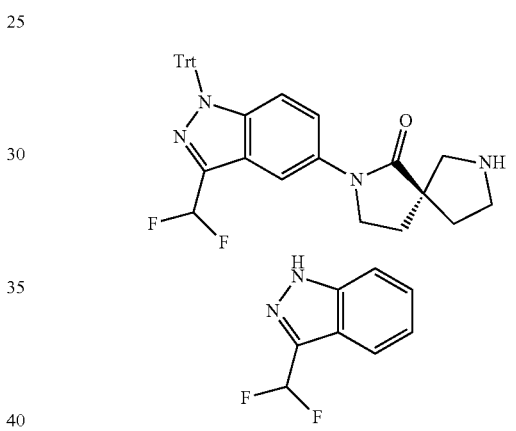

Step 1: 3-(Difluoromethyl)-1H-indazole

DAST (6.6 g, 0.041 mol) was added to 1H-indazole-3-carbaldehyde (3.0 g, 0.020 mol) at 0° C., and the mixture was stirred for 5 h at rt. The reaction was quenched carefully with sat. aq. NaHCO$_3$, and the mixture was extracted with EtOAc (3×300 mL). The combined organic layers were washed with brine (200 mL), dried over Na$_2$SO$_4$ and concentrated under reduced pressure. The residue was purified by flash column chromatography (100-200 silica gel mesh) to afford 3-(difluoromethyl)-1H-indazole (1.37 g, yield 40%) as an off white solid. $^1$H NMR (400 MHz, CDCl$_3$) δ 10.2 (bs, 1H), 7.96 (d, J=11.6 Hz, 1H), 7.53 (d, J=8.4 Hz, 1H), 7.46 (t, J=8.4 Hz, 1H), 7.28 (t, J=8.4 Hz, 1H), 7.00 (bt, J=54.4 Hz, 1H). LCMS: 168.99 [M+H]$^+$.

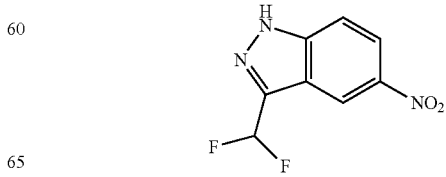

Step 2: 3-(Difluoromethyl)-5-nitro-1H-indazole

To a stirred solution of 3-(difluoromethyl)-1H-indazole (1.3 g, 0.0077 mol) in sulphuric acid (4 mL) at 0° C. was added a mixture of H₂SO₄:HNO₃ (1:1, 3.6 mL). The mixture was stirred for 30 mins at 0° C. The mixture was diluted with water and extracted with EtOAc (3×250 mL). The combined organic layers were washed with brine (300 mL), dried over Na₂SO₄ and concentrated under reduced pressure. The residue was purified by flash column chromatography (100-200 silica gel mesh) to afford 3-(difluoromethyl)-5-nitro-1H-indazole (0.96 g, yield 58%) as an off white solid. ¹H NMR (400 MHz, CDCl₃) δ 8.94 (d, J=2.0 Hz, 1H), 8.38 (dd, J=9.2, 2.4 Hz, 1H), 7.64 (d, J=9.2 Hz, 1H), 7.40-7.30 (m, 1H), 7.02 (bt, J=53.6 Hz, 1H). LCMS: 212.12 [M–H]⁺.

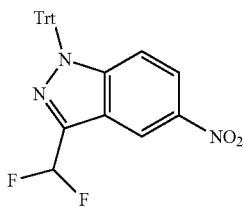

Step 3: 3-(Difluoromethyl)-5-nitro-1-trityl-1H-indazole

To a stirred solution of 3-(difluoromethyl)-5-nitro-1H-indazole (1.2 g, 0.0056 mol) in acetonitrile (30 mL) was added solid K₂CO₃ (2.30 g, 0.0168 mol) and (chloromethanetriyl)tribenzene (2.33 g, 0.0084 mol). The mixture was stirred for 5 h at rt. The mixture was diluted with water and extracted with EtOAc (2×250 mL). The combined organic layers were dried over Na₂SO₄ and concentrated under reduced pressure. The residue was purified by flash column chromatography (100-200 silica gel mesh) to afford 3-(difluoromethyl)-5-nitro-1-trityl-1H-indazole (1.65 g, yield 65%) as an off white solid. ¹H NMR (400 MHz, CDCl₃) δ 8.87 (d, J=1.2 Hz, 1H), 7.89 (dd, J=9.6, 2.0 Hz, 1H), 7.35-7.25 (m, 15H), 6.91 (bt, J=54.0 Hz, 1H), 6.51 (d, J=9.2 Hz, 1H).

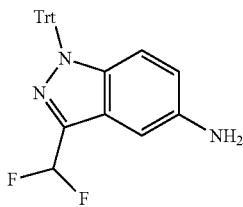

Step 4: 3-(Difluoromethyl)-1-trityl-1H-indazol-5-amine

To a solution of 3-(difluoromethyl)-5-nitro-1-trityl-1H-indazole (1.6 g, 0.0035 mol) in methanol (20 mL) under H₂ was added 10% Pd/C (0.8 g), and the mixture stirred for 16 h at rt. The mixture was filtered through a Celite bed and concentrated under reduced pressure. The obtained crude was used for the next step without any further purification to get 3-(difluoromethyl)-1-trityl-1H-indazol-5-amine (1.2 g, yield 80%). ¹H NMR (300 MHz, DMSO-d₆) δ 7.40-7.25 (m, 9H), 7.15-7.10 (m, 7H), 6.82 (d, J=1.2 Hz, 1H), 6.49 (dd, J=9.0, 2.1 Hz, 1H), 6.15 (d, J=9.0 Hz, 1H), 5.04 (s, 2H). LCMS: 426.31 [M+H]⁺.

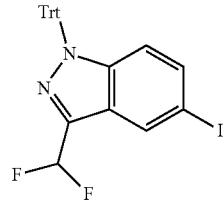

Step 5: 3-(Difluoromethyl)-5-iodo-1-trityl-1H-indazole

To a stirred solution of 3-(difluoromethyl)-1-trityl-1H-indazol-5-amine (1.2 g, 0.0028 mol) in THF (20 mL), was added isoamyl nitrite (0.99 g, 0.0084 mol), CuI (0.53 g, 0.0028) and CH₂I₂ (3.73 g, 014 mol). The mixture was heated to 75° C. for 30 mins. The mixture was diluted with water (100 mL) and extracted with EtOAc (2×250 mL). The combined organic layers were dried over Na₂SO₄ and concentrated under reduced pressure. The residue was purified by flash column chromatography (100-200 silica gel mesh) to afford 3-(difluoromethyl)-5-iodo-1-trityl-1H-indazole (700 mg, yield 46%) as an off white solid. ¹H NMR (300 MHz, CDCl₃) δ 8.27 (s, 1H), 7.44 (d, J=7.8 Hz, 1H), 7.32-7.21 (m, 9H), 7.20-7.10 (m, 6H), 6.85 (bt, J=54.0 Hz, 1H), 6.20 (d, J=9.3 Hz, 1H).

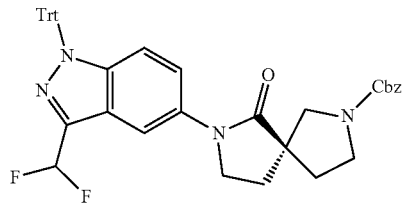

Step 6: (R)-benzyl 7-(3-(difluoromethyl)-1-trityl-1H-indazol-5-yl)-6-oxo-2,7-diazaspiro[4.4]nonane-2-carboxylate To a stirred and degassed solution of 3-(difluoromethyl)-5-iodo-1-trityl-1H-indazole (700 mg, 1.305 mmol), (R)-benzyl 6-oxo-2,7-diazaspiro[4.4]nonane-2-carboxylate (357 mg, 1.305 mmol) in dry DMSO (15 mL) was added copper (I) iodide (24.7 mg, 0.1305 mmol) followed by potassium phosphate (553 mg, 2.610 mmol). The mixture was degassed for 30 mins and heat to 100° C. for 36 h. The mixture was cooled to rt. Water (100 mL) was added, and then extracted with ethyl acetate (3×350 mL). The organic layers were washed with water (150 mL) and brine (150 mL), dried over sodium sulphate and concentrated. The residue was purified by column chromatography (100-200 silica) using 70% ethyl acetate in hexane as eluent to afford (R)-benzyl 7-(3-(difluoromethyl)-1-trityl-1H-indazol-5-yl)-6-oxo-2,7-diazaspiro[4.4]nonane-2-carboxylate (580 mg, 65% yield) as a pale yellow solid. ¹H NMR (300 MHz, CDCl₃) δ 7.78 (s, 1H), 7.62 (d, J=9.2 Hz, 1H), 7.40-7.10 (m, 20H), 6.87 (br t, J=54.3 Hz, 1H), 6.41 (d, J=9.3 Hz, 1H), 5.13 (s, 2H), 3.90-3.65 (m, 4H), 3.55-3.40 (m, 2H), 2.40-2.10 (m, 4H). LCMS: 683.42 [M+H]⁺.

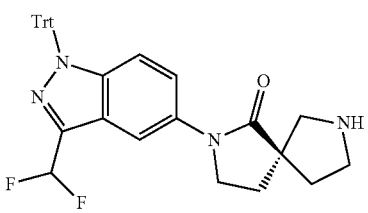

Step 7: (S)-2-(3-(Difluoromethyl)-1-trityl-1H-indazol-5-yl)-2,7-diazaspiro[4.4]nonan-1-one To a stirred solution of (R)-benzyl 7-(3-(difluoromethyl)-1-trityl-1H-indazol-5-yl)-6-oxo-2,7-diazaspiro[4.4]nonane-2-carboxylate (400 mg, 0.586 mmol) in methanol (10 mL) under H₂, was added 10% Pd/C (400 mg). The mixture was stirred at rt for 3 h. The mixture was filtered through a Celite bed and washed with 10% MeOH:DCM. The combined organic layer was concentrated on rotary evaporator to afford crude (S)-2-(3-(difluoromethyl)-1-trityl-1H-indazol-5-yl)-2,7-diazaspiro[4.4]nonan-1-one (200 mg, 62% yield). This material was used for the next step without any further purification. ¹H NMR (300 MHz, DMSO-d₆) δ 8.12 (s, 1H), 7.45 (dd, J=9.3, 2.4 Hz, 1H), 7.40-7.28 (m, 10H), 7.16-7.10 (m, 6H), 6.45 (d, J=9.3 Hz, 1H), 3.78 (t, J=7.2 Hz, 2H), 2.92-2.78 (m, 4H), 2.15-1.93 (m, 3H), 1.74-1.67 (m, 1H). LCMS: 549.41 [M+H]⁺.

Intermediate 30

4-(4-(1-Methyl-1H-1,2,4-triazol-3-yl)phenyl)-1,2,3,6-tetrahydropyridine dihydrochloride

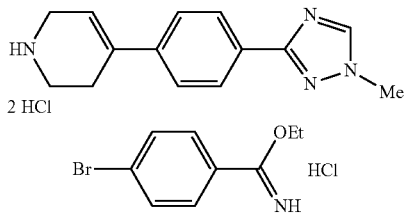

Step 1: Ethyl 4-bromobenzimidate Hydrochloride

To a stirred solution of 4-bromobenzonitrile (40 g, 222 mmol) suspended in absolute ethanol (800 mL) at 0° C. HCl gas (generated from NaCl and H₂SO₄) was bubbled initially vigorously for 1 h and then slowly for 5 h. The solution was allowed to stir overnight at rt. The solvent was concentrated The solid obtained was washed with ether (300 mL) and dried to afford ethyl 4-bromobenzimidate hydrochloride (40 g, 573 mmol, 68% yield) as an off white solid. ¹H NMR (300 MHz, CDCl₃) δ=12.71 (br s, 1H), 12.01 (br s, 1H), 8.28 (d, J=8.8 Hz, 2H), 7.72 (d, J=8.4 Hz, 2H), 4.94 (q, J=6.9 Hz, 2H), 1.80-1.49 (m, 3H). LCMS: 228.11 (M+H)⁺.

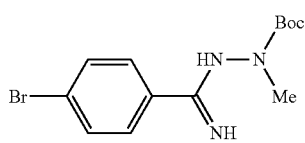

Step 2: tert-Butyl 2-((4-bromophenyl)(imino)methyl)-1-methylhydrazine-1-carboxylate To a solution of ethyl 4-bromobenzimidate hydrochloride (35 g, 132.5 mmol) in pyridine (350 mL) was added t-butyl 1-methylhydrazinecarboxylate (23.73 mL, 159.0 mmol) at rt, and the mixture was stirred for 16 h. The solvent was concentrated under reduced pressure. The obtained gummy liquid was triturated with diethyl ether (200 mL) to afford a solid which was filtered, further washed diethyl ether (100 mL) and dried to afford tert-butyl 2-((4-bromophenyl)(imino)methyl)-1-methylhydrazinecarboxylate hydrochloride (35 g, 106.3 mmol, 79% yield). ¹H NMR (300 MHz, CDCl₃): δ 7.62 (d, 2H), 7.58 (d, 2H), 5.10 (s, 2H), 3.10 (s, 3H), 1.45 (s, 9H). LCMS: 328.17 [M+H]⁺.

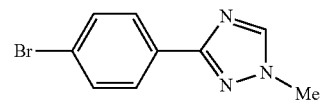 [SMILES: Cn1cnc(-c2ccc(Br)cc2)n1]

Step 3:
3-(4-Bromophenyl)-1-methyl-1H-1,2,4-triazole

To a tert-butyl 2-((4-bromophenyl)(imino)methyl)-1-methylhydrazinecarboxylate hydrochloride (50 g, 8.79 mmol) was added formic acid (750 mL) at rt and then refluxed for 16 h. The mixture was concentrated, and the residue was treated with sat. aq. sodium bicarbonate solution. The mixture was extracted with ethyl acetate (3×800 mL). The combined organic layers were washed with brine (2×150 mL), dried and concentrated to give a solid. The solid was washed with ether (300 mL) and dried to afford 3-(4-bromophenyl)-1-methyl-1H-1,2,4-triazole (22 g, 92.4 mmol, 77% yield) as an off white solid. ¹H NMR (300 MHz, CDCl₃): δ 8.05 (s, 1H), 7.96 (d, 2H), 7.56 (d, 2H), 3.64 (s, 3H). LCMS: 238.05 [M+H]⁺.

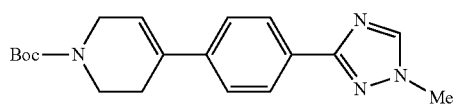 [SMILES: Cn1cnc(-c2ccc(C3=CCN(C(=O)OC(C)(C)C)CC3)cc2)n1]

Step 4: tert-butyl 4-(4-(1-methyl-1H-1,2,4-triazol-3-yl)phenyl)-3,6-dihydropyridine-1(2H)-carboxylate To a stirred and degassed solution of 3-(4-bromophenyl)-1-methyl-1H-1,2,4-triazole (22 g, 92.43 mmol) and tert-butyl 4-(4,4,5,5-tetramethyl-1,3,2-dioxaborolan-2-yl)-5,6-dihydropyridine-1(2H)-carboxylate (31.41 g, 101.68 mmol) in 1,2-dimethoxy ethane:water (5:1, 240 mL) was added potassium carbonate (38.26 g, 277.2 mmol). The mixture was degassed for 10 mins. [1,1'-bis(diphenylphosphino)ferrocene]dichloropalladium(II) DCM complex (3.77 g, 4.62 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×500 mL). The combined organic layers were washed with water (2×100 mL) and brine (1×100 mL), dried over sodium sulfate, filtered and concentrated. The residue was purified by column chromatography (100-200 silica) using 3% methanol in dichloromethane as eluent to afford tert-butyl 4-(4-(1-methyl-1H-1,2,4-triazol-3-yl)phenyl)-5,6-dihydropyridine-1(2H)-carboxylate (20 g, 58.65 mmol, 63% yield). ¹H NMR (300 MHz, CDCl₃): δ 8.06-8.04 (m, 3H), 7.45 (d, 2H), 6.12 (s, 1H), 4.09 (s, 2H), 3.97 (s, 3H), 3.65 (t, 2H), 2.56 (br, 2H), 1.49 (s, 9H). LCMS: 341.27 [M+H]⁺.

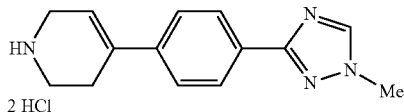 [SMILES: Cn1cnc(-c2ccc(C3=CCNCC3)cc2)n1]

2 HCl

Step 5: 4-(4-(1-Methyl-1H-1,2,4-triazol-3-yl)phenyl)-1,2,3,6-tetrahydropyridine

To tert-butyl 4-(4-(1-methyl-1H-1,2,4-triazol-3-yl)phenyl)-5,6-dihydropyridine-1(2H)-carboxylate (20 g, 58.65 mmol) in 1,4-dioxane (100 mL) was added 4M HCl:1,4-dioxane (300 mL), and the mixture was stirred at rt for 2 h. The mixture was concentrated and triturated with diethyl ether (300 mL) to afford 4-(4-(1-methyl-1H-1,2,4-triazol-3-yl)phenyl)-1,2,3,6-tetrahydropyridine hydrochloride (15.5 g, 56.15 mmol, 96% yield) as an off white solid. The crude was used for the next step without purification. ¹H NMR (300 MHz, DMSO-d₆) δ 9.48 (br s, 2H), 8.65 (br s, 1H), 8.00 (d, J=8.5 Hz, 2H), 7.59 (d, J=8.5 Hz, 2H), 6.29 (br s, 1H), 3.94 (s, 3H), 3.75 (br s, 2H), 3.30 (br s, 2H), 2.73 (br s, 2H). LCMS: 241.34 [M+H]⁺.

Intermediate 31

2-Chloro-1-(4-(4-(1-methyl-1H-1,2,4-triazol-3-yl)phenyl)-3,6-dihydropyridin-1(2H)-yl)ethan-1-one

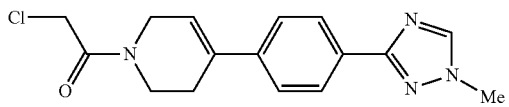

To a stirred solution of 4-(4-(1-methyl-1H-1,2,4-triazol-3-yl)phenyl)-1,2,3,6-tetrahydropyridine hydrochloride (38 g, 137.68 mmol) in dichloromethane (1520 mL) was added triethylamine (191.26 mL, 826.08. mmol) followed by chloroacetyl chloride (683 mL, 413.08 mmol) at 0° C. The mixture was stirred at 0° C. for 1 h. The mixture was diluted with water (1000 mL) and extracted with dichloromethane (3×1000 mL). The combined organic layers were washed with brine (500 mL), dried over sodium sulfate and concentrated under reduced pressure. The compound was triturated in DMSO:H₂O (1:100, 2.5 L), to afford 2-chloro-1-(4-(4-(1-methyl-1H-1,2,4-triazol-3-yl)phenyl)-5,6-dihydropyridin-1(2H)-yl)ethanone (24.3 g, 76.65 mmol, 55% yield) as a pale brown solid. ¹H NMR (300 MHz, DMSO-d₆) δ 8.51 (s, 1H), 7.97 (d, J=8.4 Hz, 2H), 7.55 (dd, J=4.8, 8.1 Hz, 2H), 6.28 (br s, 1H), 4.46 (d, J=7.7 Hz, 2H), 4.25-4.10 (m, 2H), 3.92 (s, 3H), 3.77-3.62 (m, 2H), 2.67-2.58 (m, 2H). LCMS: 317.12 [M+H]⁺.

Intermediate 32

2-Chloro-1-(4-(4-(1-methyl-1H-1,2,4-triazol-3-yl)phenyl)piperazin-1-yl)ethan-1-one

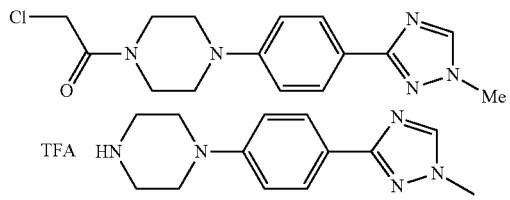

Step 1: 1-(4-(1-Methyl-1H-1,2,4-triazol-3-yl)phenyl)piperazine trifluroacetic acid salt To a solution of tert-butyl 4-(4-(1-methyl-1H-1,2,4-triazol-3-yl)phenyl)piperazine-1-carboxylate (1.5 g, 4.37 mmol) in DCM (10 mL), was added TFA (5 mL). The mixture was stirred for 6 h. The solvents were removed under reduced pressure to afford a crude material that was used for the next step without a further purification.

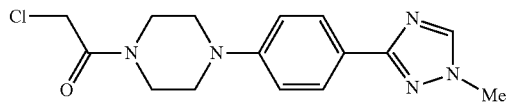

Step 2: 2-Chloro-1-(4-(4-(1-methyl-1H-1,2,4-triazol-3-yl)phenyl)piperazin-1-yl)ethan-1-one 1-(4-(1-Methyl-1H-1,2,4-triazol-3-yl)phenyl)piperazine trifluroacetic acid salt was dissolved discovered in DCM (10 mL) and followed by the addition of Et₃N (3.0 mL, 21.52 mmol). Chloroacetic anhydride (600 mg, 3.50 mmol) was added at rt, and the mixture was stirred overnight. After completion of the reaction, the mixture was poured into water and extracted with DCM. The organic layer was dried over Mg₂SO₄, filtered, concentrated, and purified by flash chromatography on silica gel column eluted with 0-20% ethyl acetate in DCM to give 2-chloro-1-(4-(4-(1-methyl-1H-1,2,4-triazol-3-yl)phenyl)piperazin-1-yl)ethan-1-one (706 mg, 51%). ¹H NMR (500 MHz, CDCl₃) δ 8.04 (s, 1H), 8.00 (d, J=7.8 Hz, 2H), 6.96 (d, J=7.8 Hz, 2H), 4.12 (s, 2H), 3.95 (s, 3H), 3.87 (t, J=7.2 Hz, 2H), 3.70 (t, J=7.2 Hz, 2H), 3.30 (t, J=7.2 Hz, 2H), 3.27 (t, J=7.2 Hz, 2H).

Intermediate 33

2-Chloro-1-(4-(4-(1-methyl-1H-1,2,4-triazol-3-yl)phenyl)piperidin-1-yl)ethanone

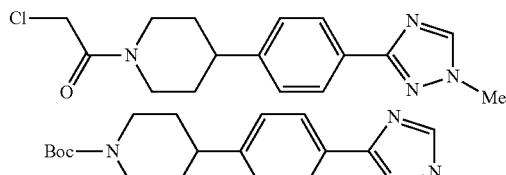

Step 1: tert-Butyl 4-(4-(1-methyl-1H-1,2,4-triazol-3-yl)phenyl)piperidine-1-carboxylate To a solution of tert-butyl 4-(4-(1-methyl-1H-1,2,4-triazol-3-yl)phenyl)-5,6-dihydropyridine-1(2H)-carboxylate (2.5 g, 7.35 mmol) in methanol (100 mL) was added 10% wet Pd/C (1 g). The mixture was hydrogenated for 8 h. The mixture was then passed through Celite, and the filtrate was concentrated to afford tert-butyl 4-(4-(1-methyl-1H-1,2,4-triazol-3-yl)phenyl)piperidine-1-carboxylate (2 g, 5.84 mmol, 80% yield). $^1$H NMR (300 MHz, DMSO-$d_6$) δ 8.48 (s, 1H), 7.91 (d, J=8.1 Hz, 2H), 7.32 (d, J=8.1 Hz, 2H), 4.08 (br d, J=11.0 Hz, 2H), 3.90 (s, 3H), 2.93-2.57 (m, 3H), 1.77 (br d, J=12.8 Hz, 2H), 1.60-1.31 (m, 2H), 1.30 (s, 9H). LCMS: 287.16 [M-tert-Butyl+Hl]$^+$.

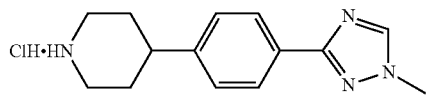

Step 2: 4-(4-(1-Methyl-1H-1,2,4-triazol-3-yl)phenyl)piperidine hydrochloride To a stirred solution of tert-butyl 4-(4-(1-methyl-1H-1,2,4-triazol-3-yl)phenyl)piperidine-1-carboxylate (2 g, 5.84 mmol) in 1,4-dioxane (50 mL) was added a solution 4M HCl in 1,4-dioxane (100 mL). The mixture was stirred at rt for 2 h. The mixture was concentrated and triturated with diethyl ether (50 mL) to afford 4-(4-(1-methyl-1H-1,2,4-triazol-3-yl)phenyl)piperidine hydrochloride (1.6 g, 5.74 mmol, 99% yield) as an off white solid. The crude was used in the next step without further purification.

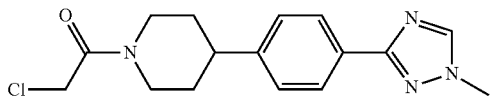 [SMILES: Cn1cnc(-c2ccc(C3CCN(C(=O)CCl)CC3)cc2)n1]

Step 3: 2-Chloro-1-(4-(4-(1-methyl-1H-1,2,4-triazol-3-yl)phenyl)piperidin-1-yl)ethanone To a stirred solution of 4-(4-(1-methyl-1H-1,2,4-triazol-3-yl)phenyl)piperidine hydrochloride (1.6 g, 5.74 mmol) in dichloromethane (40 mL) was added triethylamine (4.83 mL, 34.47 mmol) followed by chloroacetyl chloride (1.37 mL, 17.23 mmol) at 0° C. The mixture was stirred at 0° C. for 1 h. The mixture was diluted with water (70 mL) and extracted with dichloromethane (3×50 mL). The combined organic layers were washed with brine (30 mL), dried over sodium sulfate and concentrated under reduced pressure. The residue was purified by silica-gel (100-200 mesh) column using 5% methanol in dichloromethane to afford 2-chloro-1-(4-(4-(1-methyl-1H-1,2,4-triazol-3-yl)phenyl)piperidin-1-yl)ethanone (940 mg, 2.95 mmol, 52% yield) as an off white solid. $^1$H NMR (400 MHz, DMSO-$d_6$) δ 8.49 (s, 1H), 7.92 (d, J=8.3 Hz, 2H), 7.33 (d, J=8.3 Hz, 2H), 4.49 (br d, J=13.2 Hz, 1H), 4.41 (s, 2H), 3.99-3.89 (m, 4H), 3.18 (br t, J=12.0 Hz, 1H), 2.88-2.80 (m, 1H), 2.71 (br t, J=12.0 Hz, 1H), 1.84 (br d, J=12.7 Hz, 2H), 1.72-1.60 (m, 1H), 1.57-1.41 (m, 1H). LCMS: 319.08 [M+H]$^+$.

Intermediate 34

2-Chloro-1-(4-(4-(5-(ethylamino)-1,3,4-thiadiazol-2-yl)phenyl)-5,6-dihydropyridin-1(2H)-yl)ethanone

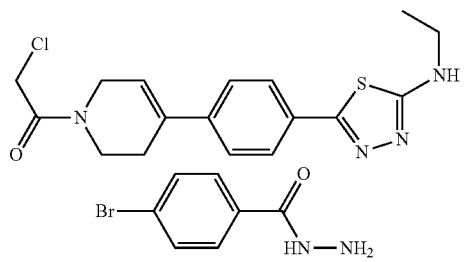

Step 1: 4-Bromobenzohydrazide

To a stirred solution of methyl 4-bromobenzoate (10 g, 46.51 mmol) in methanol (200 mL) was added hydrazine hydrate (23.2 g, 465.1 mmol) at rt. The mixture was then refluxed for 16 h. The mixture was concentrated, diluted with water (70 mL) and extracted with ethyl acetate (3×70 mL). The combined organic layers were washed with brine (30 mL), dried over sodium sulfate, filtered and concentrated under reduced pressure. The residue was triturated with diethyl ether (30 mL) to afford 4-bromobenzohydrazide (8 g, 37.38 mmol, 80% yield) as an off white solid. $^1$H NMR (300 MHz, DMSO-$d_6$) δ 7.68-7.53 (m, 4H), 7.38 (br s, 1H), 4.10 (br s, 2H). LCMS: 216.89 [M+2H]$^+$.

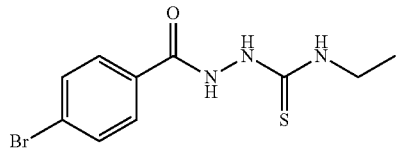 [SMILES: CCNC(=S)NNC(=O)c1ccc(Br)cc1]

Step 2: 2-(4-Bromobenzoyl)-N-ethylhydrazinecarbothioamide

To a stirred solution of 4-bromobenzohydrazide (7 g, 32.55 mmol) in THF (200 mL) was added triethylamine (3.28 g, 32.55 mmol) followed by ethylisothiocyanate (3.39 g, 1.2 mmol). The mixture was stirred at rt for 16 h. reaction mixture was concentrated and triturated with diethyl ether (50 mL) to afford 2-(4-bromobenzoyl)-N-ethylhydrazinecarbothioamide (9 g, 29.9 mmol, 92% yield) as an off white solid. $^1$H NMR (300 MHz, DMSO-$d_6$) δ 10.39 (s, 1H), 9.26 (s, 1H), 8.12 (br t, J=5.1 Hz, 1H), 7.85 (d, J=5.1 Hz, 2H), 7.72 (d, J=5.1 Hz, 2H), 3.44 (q, J=6.8 Hz, 2H), 1.06 (t, J=7.2 Hz, 3H). LCMS: 304.2 [M+2H]$^+$.

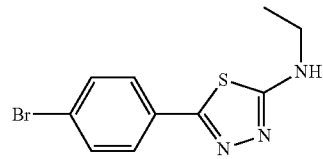

Step 3: 5-(4-Bromophenyl)-N-ethyl-1,3,4-thiadiazol-2-amine

To a stirred solution of 2-(4-bromobenzoyl)-N-ethylhydrazinecarbothioamide (9 g, 29.9 mmol) in N-methyl-2-pyrrolidone (220 mL) was added p-toluenesulfonyl chloride (8.55 g, 44.8 mmol), followed by triethylamine (9.05 g, 89.7 mmol). The mixture was stirred at rt for 2 h. The mixture was poured in to ice-water (70 mL), and the solid was filtered to afford 5-(4-bromophenyl)-N-ethyl-1,3,4-thiadiazol-2-amine (6.5 g, 22.96 mmol, 77% yield) as an off white solid. $^1$H NMR (300 MHz, DMSO-$d_6$) δ 7.99 (t, J=5.1 Hz, 1H), 7.76-7.62 (m, 4H), 3.40-3.29 (m, 2H), 1.20 (br t, J=6.9 Hz, 3H). LCMS: 284.15 [M+H]$^+$.

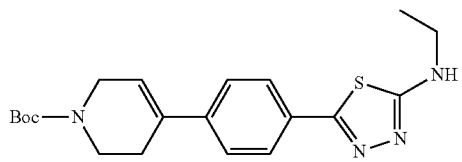 [SMILES: Cl ; CCNc1nnc(-c2ccc(C3=CCNCC3)cc2)s1]

Step 4: tert-Butyl 4-(4-(5-(ethylamino)-1,3,4-thiadiazol-2-yl)phenyl)-5,6-dihydropyridine-1(2H)-carboxylate To a stirred and degassed solution of 5-(4-bromophenyl)-N-ethyl-1,3,4-thiadiazol-2-amine (3 g, 10.63 mmol), tert-butyl 4-(4,4,5,5-tetramethyl-1,3,2-dioxaborolan-2-yl)-5,6-dihydropyridine-1(2H)-carboxylate (3.61 g, 11.70 mmol) in 1,2-dimethoxy ethane:water (5:1, 200 mL) was added potassium carbonate (4.4 g, 31.89 mmol). The mixture was degassed for 10 mins. [1,1'-bis(diphenylphosphino)ferrocene]dichloropalladium(II) DCM complex (868 mg, 1.063 mmol) was added. The mixture was degassed for 10 mins and then refluxed for 16 h. The mixture was cooled to rt and filtered through a Celite pad. To the filtrate was added cold water, and the mixture was extracted with ethyl acetate (3×70 mL). The organic layers were washed with water (50 mL) and brine (50 mL), dried over sodium sulfate and concentrated. The residue was purified by column chromatography (100-200 silica) using 50% ethyl acetate in hexanes as eluent to afford tert-butyl 4-(4-(5-(ethylamino)-1,3,4-thiadiazol-2-yl)phenyl)-5,6-dihydropyridine-1(2H)-carboxylate (3 g, 7.77 mmol, 73% yield). $^1$H NMR (300 MHz, DMSO-$d_6$) δ 7.77 (d, J=8.4 Hz, 2H), 7.42 (d, J=8.4 Hz, 2H), 6.12 (br s, 1H), 5.13 (br s, 1H), 4.10 (br s, 2H), 3.65 (t, J=5.8 Hz, 2H), 3.50-3.40 (m, 2H), 2.54 (br s, 2H), 1.50 (s, 9H), 1.34 (t, J=7.0 Hz, 3H). LCMS: 387.38 [M+H]$^+$.

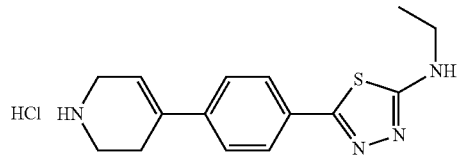

Step 5: N-Ethyl-5-(4-(1,2,3,6-tetrahydropyridin-4-yl)phenyl)-1,3,4-thiadiazol-2-amine hydrochloride To a stirred solution of tert-butyl 4-(4-(5-(ethylamino)-1,3,4-thiadiazol-2-yl)phenyl)-5,6-dihydropyridine-1(2H)-carboxylate (3 g, 7.77 mmol) in methanol (100 mL) was added a solution 4M HCl in 1,4-dioxane (100 mL). The mixture was stirred at rt for 2 h. The mixture was concentrated and triturated with diethylether (30 mL) to afford N-ethyl-5-(4-(1,2,3,6-tetrahydropyridin-4-yl)phenyl)-1,3,4-thiadiazol-2-amine (2.5 g, 7.75 mmol, 99% yield) as an off white solid. $^1$H NMR (300 MHz, DMSO-$d_6$) δ 9.17 (br s, 2H), 8.36 (br s, 1H), 7.77 (d, J=8.4 Hz, 2H), 7.60 (d, J=8.4 Hz, 2H), 6.32 (br s, 1H), 3.77 (br s, 2H), 3.42-3.27 (m, 4H), 2.67-2.56 (m, 2H), 1.21 (t, J=7.0 Hz, 3H). LCMS: 287.32 [M+H]$^+$.

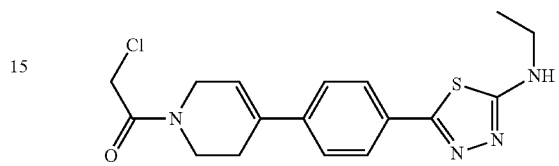

Step 6: 2-Chloro-1-(4-(4-(5-(ethylamino)-1,3,4-thiadiazol-2-yl)phenyl)-5,6-dihydropyridin-1(2H)-yl)ethanone To a stirred solution of N-ethyl-5-(4-(1,2,3,6-tetrahydropyridin-4-yl)phenyl)-1,3,4-thiadiazol-2-amine (2.5 g, 7.75 mmol) in DCM (100 mL) was added triethylamine (6.26 mL, 46.51 mmol) followed by chloro acetylchloride (1.85 mL, 23.25 mmol) at 0° C. The mixture was stirred at 0° C. for 1 h. The mixture was diluted with water (70 mL) and extracted with DCM (3×50 mL). The combined organic layers were washed with brine (30 mL), dried over sodium sulfate, filtered and concentrated under reduced pressure. The residue was purified by silica-gel (100-200 mesh) column using 5% methanol in DCM to afford 2-chloro-1-(4-(4-(5-(ethylamino)-1,3,4-thiadiazol-2-yl)phenyl)-5,6-dihydropyridin-1(2H)-yl)ethanone (850 mg, 2.348 mmol, 30% yield) as a white solid. $^1$H NMR (300 MHz, DMSO-$d_6$) δ 7.95 (br s, 1H), 7.73 (br d, J=7.7 Hz, 2H), 7.54 (br d, J=7.0 Hz, 2H), 6.30 (br s, 1H), 4.47 (br d, J=7.3 Hz, 2H), 4.18 (br d, J=19.1 Hz, 2H), 3.68 (br s, 2H), 3.35-3.33 (m, 2H), 2.61 (br s, 2H), 1.20 (br t, J=7.0 Hz, 3H). LCMS: 363.32 [M+H]$^+$.

Intermediate 35

2-Chloro-1-(4-(4-(5-(ethylamino)-1,3,4-oxadiazol-2-yl)phenyl)-5,6-dihydropyridin-1(2H)-yl)ethanone

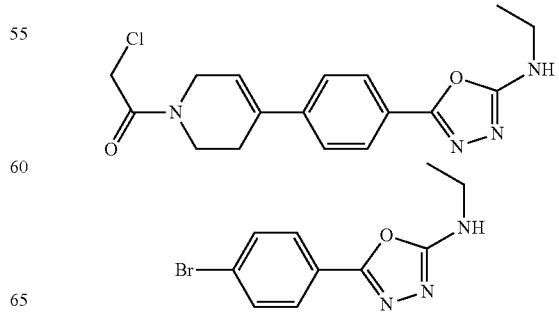

Step 1: 5-(4-Bromophenyl)-N-ethyl-1,3,4-oxadiazol-2-amine

To a stirred solution of 2-(4-bromobenzoyl)-N-ethylhydrazinecarbothioamide (6 g, 19.93 mmol) in DMSO (60 mL) was added EDC.HCl (3.71 g, 23.92 mmol). The mixture was stirred at 60° C. for 2 h. The mixture was diluted with water (70 mL) and extracted with ethyl acetate (3×50 mL). The combined organic layers were washed with brine (30 mL), dried over sodium sulfate, filtered and concentrated under reduced pressure. The residue was purified by silica-gel (100-200 mesh) column using 50% ethyl acetate in petroleum ether to afford 5-(4-bromophenyl)-N-ethyl-1,3,4-oxadiazol-2-amine (3 g, 11.23 mmol, 56% yield) as an off white solid. $^1$H NMR (300 MHz, DMSO-$d_6$) δ 7.77 (d, J=8.8 Hz, 2H), 7.59 (d, J=8.8 Hz, 2H), 4.66 (br s, 1H), 3.50 (m, 2H), 1.32 (t, J=7.2 Hz, 3H). LCMS: 268.14 [M+H]$^+$.

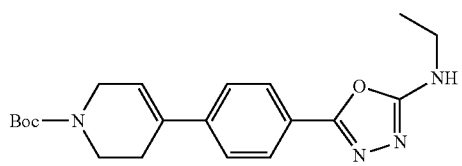

Step 2: tert-butyl 4-(4-(5-(ethylamino)-1,3,4-oxadiazol-2-yl)phenyl)-5,6-dihydropyridine-1(2H)-carboxylate To a stirred and degassed solution of 5-(4-bromophenyl)-N-ethyl-1,3,4-oxadiazol-2-amine (3 g, 11.23 mmol), tert-butyl 4-(4,4,5,5-tetramethyl-1,3,2-dioxaborolan-2-yl)-5,6-dihydropyridine-1(2H)-carboxylate (2.85 g, 12.35 mmol) in 1,2-dimethoxy ethane:water (5:1, 300 mL) was added potassium carbonate (3.47 g, 33.69 mmol). The mixture was degassed for 10 mins. [1,1'-bis(diphenylphosphino)ferrocene]dichloropalladium(II) DCM complex (458 mg, 0.63 mmol) was added. The mixture was degassed for 20 mins and then refluxed for 16 h. The mixture was cooled to rt and filtered through a Celite pad. To the filtrate was added cold water, and the mixture was extracted with ethyl acetate (3×70 mL). The combined organic layers were washed with water (50 mL) and brine (50 mL), dried over sodium sulfate and concentrated. The residue was purified by column chromatography (100-200 silica) using 50% ethyl acetate in hexanes as eluent to afford tert-butyl 4-(4-(5-(ethylamino)-1,3,4-oxadiazol-2-yl)phenyl)-5,6-dihydropyridine-1(2H)-carboxylate (3 g, 8.08 mmol, 72% yield). $^1$H NMR (300 MHz, DMSO-$d_6$) δ 7.81-7.71 (m, 3H), 7.59 (d, J=8.7 Hz, 2H), 6.30 (br s, 1H), 4.03 (br s, 2H), 3.55 (t, J=5.4 Hz, 2H), 3.38-3.20 (m, 4H), 1.43 (br s, 9H), 1.18 (t, J=7.5 Hz, 3H). LCMS: 371.19 [M+H]$^+$.

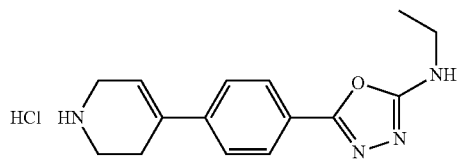

Step 3: N-Ethyl-5-(4-(1,2,3,6-tetrahydropyridin-4-yl)phenyl)-1,3,4-oxadiazol-2-amine hydrochloride To a stirred solution of tert-butyl 4-(4-(5-(ethylamino)-1,3,4-oxadiazol-2-yl)phenyl)-5,6-dihydropyridine-1(2H)-carboxylate (2.8 g, 7.56 mmol) in methanol (100 mL) was added 4M HCl:1,4-dioxane (100 mL). The mixture was stirred at rt for 2 h. The mixture was concentrated and triturated with diethyl ether (30 mL) to afford N-ethyl-5-(4-(1,2,3,6-tetrahydropyridin-4-yl)phenyl)-1,3,4-oxadiazol-2-amine (2.3 g, 7.51 mmol, 99% yield) as an off white solid. $^1$H NMR (300 MHz, DMSO-$d_6$) δ 9.18 (br s, 2H), 7.913 (br s, 1H), 7.81 (d, J=8.8 Hz, 2H), 7.65 (d, J=8.2 Hz, 2H), 6.34 (br s, 1H), 3.77 (br s, 2H), 3.40-3.24 (m, 4H), 2.72 (br s, 2H), 1.19 (t, J=7.2 Hz, 3H). LCMS: 271.31 [M+H]$^+$.

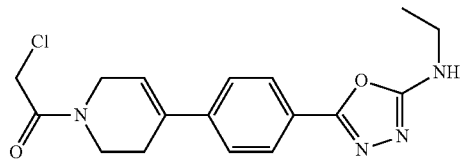 [SMILES: CCNc1nnc(-c2ccc(C3=CCN(C(=O)CCl)CC3)cc2)s1]

Step 4: 2-Chloro-1-(4-(4-(5-(ethylamino)-1,3,4-oxadiazol-2-yl)phenyl)-5,6-dihydropyridin-1(2H)-yl)ethanone To a stirred solution of N-ethyl-5-(4-(1,2,3,6-tetrahydropyridin-4-yl)phenyl)-1,3,4-oxadiazol-2-amine (2.3 g, 7.5 mmol) in dichloromethane (50 mL) was added triethylamine (6.31 mL, 45.02 mmol) followed by chloroacetyl chloride (1.789 mL, 22.5 mmol) at 0° C. The mixture was stirred at 0° C. for 1 h. The mixture was diluted with water (70 mL) and extracted with dichloromethane (3×50 mL). The combined organic layers were washed with brine (30 mL), dried over sodium sulfate and concentrated under reduced pressure. The residue was purified by silica-gel (100-200 mesh) column using 5% methanol in dichloromethane to afford 2-chloro-1-(4-(4-(5-(ethylamino)-1,3,4-oxadiazol-2-yl)phenyl)-5,6-dihydropyridin-1(2H)-yl)ethanone (1.5 g, 4.33 mmol, 63% yield) as a pale yellow solid. $^1$H NMR (300 MHz, DMSO-$d_6$) δ 7.81-7.74 (m, 3H), 7.65-7.56 (m, 2H), 6.34 (br s, 1H), 4.47 (d, J=7.7 Hz, 2H), 4.25-4.11 (m, 2H), 3.74-3.63 (m, 2H), 3.31-3.20 (m, 2H), 2.62 (br s, 2H), 1.18 (t, J=7.2 Hz, 3H). LCMS: 346.95 [M+H]$^+$.

Intermediate 36

2-Chloro-1-(4-(4-(5-methyl-1,3,4-oxadiazol-2-yl)phenyl)-5,6-dihydropyridin-1(2H)-yl)ethanone

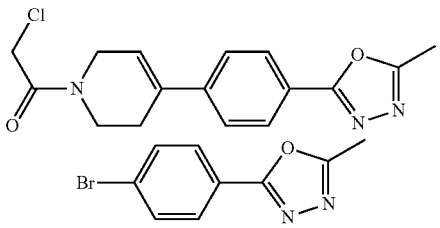

Step 1: 2-(4-Bromophenyl)-5-methyl-1,3,4-oxadiazole

To a stirred solution of 4-bromobenzohydrazide (8 g, 37.2 mmol) in ethanol (150 mL) was added ammonium chloride (5.97 g, 111.6 mmol) followed by triethylorthoacetate (8.28 mL, 40.93 mmol). The mixture was refluxed for 40 h. The mixture was concentrated, diluted with water (70 mL) and extracted with ethyl acetate (3×100 mL). The combined organic layers were washed with brine (30 mL), dried over sodium sulfate, filtered and concentrated under reduced pressure. The residue was purified by silica-gel (100-200 mesh) column using 25% ethyl acetate in petroleum ether to afford 2-(4-bromophenyl)-5-methyl-1,3,4-oxadiazole (4.8 g, 20.16 mmol, 54% yield) as an off white solid. $^1$H NMR (300 MHz, DMSO-$d_6$) δ 7.90 (d, J=8.4 Hz, 2H), 7.65 (m, J=8.4 Hz, 2H), 2.61 (s, 3H). LCMS: 238.94 [M+H]$^+$.

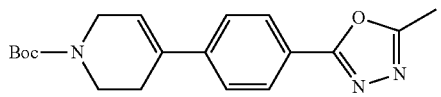

Step 2: tert-Butyl 4-(4-(5-methyl-1,3,4-oxadiazol-2-yl)phenyl)-5,6-dihydropyridine-1(2H)-carboxylate To a stirred and degassed solution of 2-(4-bromophenyl)-5-methyl-1,3,4-oxadiazole (3 g, 12.6 mmol) and tert-butyl 4-(4,4,5,5-tetramethyl-1,3,2-dioxaborolan-2-yl)-5,6-dihydropyridine-1(2H)-carboxylate (2.85 g, 13.86 mmol) in 1,2-dimethoxy ethane:water (5:1, 300 mL), was added potassium carbonate (3.47 g, 37.8 mmol). The mixture was degassed for 10 mins. [1,1'-bis(diphenylphosphino)ferrocene]dichloropalladium(II) DCM complex (342 mg, 0.63 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×70 mL). The combined organic layers were washed with water (50 mL) and brine (50 mL), dried over sodium sulfate, filtered and concentrated. The residue was purified by column chromatography (100-200 silica) using 50% ethyl acetate in hexanes as eluent to afford tert-butyl 4-(4-(5-methyl-1,3,4-oxadiazol-2-yl)phenyl)-5,6-dihydropyridine-1(2H)-carboxylate (3 g, 8.79 mmol, 70% yield). $^1$H NMR (300 MHz, DMSO-$d_6$) δ 7.99 (d, J=8.4 Hz, 2H), 7.50 (d, J=8.4 Hz, 2H), 6.18 (br s, 1H), 4.12 (br d, J=2.7 Hz, 2H), 3.66 (t, J=5.7 Hz, 2H), 2.62 (s, 3H), 2.56 (br s, 2H), 1.50 (s, 9H). LCMS: 342.39 [M+H]$^+$.

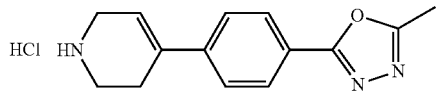

Step 3: 2-Methyl-5-(4-(1,2,3,6-tetrahydropyridin-4-yl)phenyl)-1,3,4-oxadiazole hydrochloride To a stirred solution of tert-butyl 4-(4-(5-methyl-1,3,4-oxadiazol-2-yl)phenyl)-5,6-dihydropyridine-1(2H)-carboxylate (3 g, 8.79 mmol) in methanol (100 mL) was added 4M HCl:1,4-dioxane (100 mL). The mixture was stirred at rt for 2 h. The mixture was concentrated and triturated with diethyl ether (30 mL) to afford 2-methyl-5-(4-(1,2,3,6-tetrahydropyridin-4-yl)phenyl)-1,3,4-oxadiazole hydrochloride (2.3 g, 8.3 mmol, 94% yield) as an off white solid. The crude was used to next step without purification. $^1$H NMR (300 MHz, DMSO-$d_6$) δ 9.20-8.95 (m, 2H), 7.94 (d, J=8.4 Hz, 2H), 7.65 (d, J=8.4 Hz, 2H), 6.38 (br s, 1H), 3.79 (br s, 2H), 3.40-3.27 (m, 2H), 2.72 (br s, 2H), 2.50 (s, 3H).

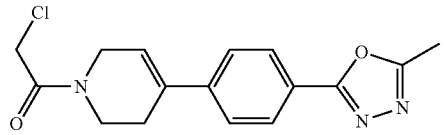 [SMILES: Cc1nnc(-c2ccc(C3=CCN(C(=O)CCl)CC3)cc2)o1]

Step 4: 2-Chloro-1-(4-(4-(5-methyl-1,3,4-oxadiazol-2-yl)phenyl)-5,6-dihydropyridin-1(2H)-yl)ethanone To a stirred solution of 2-methyl-5-(4-(1,2,3,6-tetrahydropyridin-4-yl)phenyl)-1,3,4-oxadiazole hydrochloride (2.3 g, 8.3 mmol) in dichloromethane (100 mL) was added triethylamine (7 mL, 49.8 mmol) followed by chloroacetyl chloride (2 mL, 24.9 mmol) at 0° C. The mixture was stirred at 0° C. for 1 h. The mixture was diluted with water (70 mL) and extracted with dichloromethane (3×50 mL). The combined organic layers were washed with brine (30 mL), dried over sodium sulfate, filtered and concentrated under reduced pressure. The residue was purified by silica-gel (100-200 mesh) column using 5% methanol in dichloromethane to afford 2-chloro-1-(4-(4-(5-methyl-1,3,4-oxadiazol-2-yl)phenyl)-5,6-dihydropyridin-1(2H)-yl)ethanone (800 mg, 2.52 mmol, 30% yield) as an off white solid. $^1$H NMR (300 MHz, DMSO-$d_6$) δ 7.95 (d, J=8.4 Hz, 2H), 7.70-7.65 (m, 2H), 6.39 (br s, 1H), 4.47 (d, J=6 Hz, 2H), 4.27-4.12 (m, 2H), 3.79-3.62 (m, 2H), 2.63-2.58 (m, 5H). LCMS: 317.96 [M+H]$^+$.

Intermediate 37

1-(4-(4-(1H-1,2,3-Triazol-1-yl)phenyl)-5,6-dihydropyridin-1(2H)-yl)-2-chloroethanone

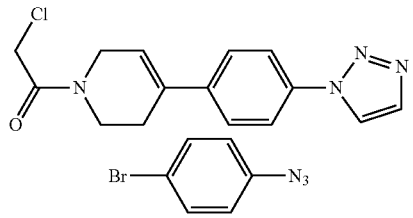

Step 1: 1-Azido-4-bromobenzene

To a stirred solution of 4-bromoaniline (5 g, 29.06 mmol) in 6N HCl (50 mL) was added aqueous NaNO$_2$ (2.17 g, 8 mL, 31.97 mmol) at 0° C. The mixture was stirred at 0° C. for 30 mins. A solution of NaN$_3$ (2.07 g, 31.97 mmol) in H$_2$O (8 mL) was added at 0° C., and the mixture was stirred at rt for 3 h. The mixture was diluted with water (20 mL) and extracted with ethyl acetate (3×100 mL). The combined organic layers were washed with brine (30 mL), dried over sodium sulfate and concentrated under reduced pressure to afford 1-azido-4-bromobenzene (3.5 g, 17.6 mmol, 61% yield) as a gummy liquid. FT-IR=2129 cm$^{-1}$. $^1$H NMR (400 MHz, CDCl$_3$) δ 7.46 (d, J=8.8 Hz, 2H), 6.90 (d, J=8.8 Hz, 2H).

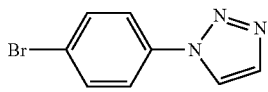

Step 2: 1-(4-Bromophenyl)-1H-1,2,3-triazole

To a stirred solution of 1-azido-4-bromobenzene (3.5 g, 17.6 mmol) in t-butanol:water (1:1, 60 mL) was added trimethylsilyl acetylene (8.67 g, 88.3 mmol) followed by copper (II) sulfate (1.4 g, 8.8 mmol) and sodium ascorbate (1.05 g, 5.28 mmol). The mixture was stirred at 55° C. for 16 h in sealed tube. The mixture was concentrated, diluted with water (70 mL) and extracted with ethyl acetate (3×100 mL). The combined organic layers were washed with brine (30 mL), dried over sodium sulfate, filtered and concentrated under reduced pressure. The residue was purified by silica-gel (100-200 mesh) column using 30% ethyl acetate in petroleum ether to afford 1-(4-bromophenyl)-1H-1,2,3-triazole (1.2 g, 5.357 mmol, 30% yield) as an off white solid. $^1$H NMR (400 MHz, CDCl$_3$) δ 7.98 (s, 1H), 7.87 (s, 1H), 7.70-7.62 (m, 4H). LCMS: 223.96 [M+H]$^+$.

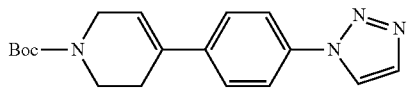

Step 3: tert-Butyl 4-(4-(1H-1,2,3-triazol-1-yl)phenyl)-5,6-dihydropyridine-1(2H)-carboxylate To a stirred and degassed solution of 1-(4-bromophenyl)-1H-1,2,3-triazole (1.2 g, 5.357 mmol) and tert-butyl 4-(4,4,5,5-tetramethyl-1,3,2-dioxaborolan-2-yl)-5,6-dihydropyridine-1(2H)-carboxylate (1.82 g, 5.892 mmol) in 1,2-dimethoxyethane:water (5:1, 60 mL) was added potassium carbonate (2.21 g, 16.07 mmol). The mixture was degassed for 10 mins. [1,1'-bis(diphenylphosphino)ferrocene]dichloropalladium(II) DCM complex (437 mg, 0.535 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×70 mL). The combined organic layers were washed with water (50 mL) and brine (50 mL), dried over sodium sulfate and concentrated. The residue was purified by column chromatography (100-200 silica) using 50% ethyl acetate in hexanes as eluent to afford tert-butyl 4-(4-(1H-1,2,3-triazol-1-yl)phenyl)-5,6-dihydropyridine-1(2H)-carboxylate (1.4 g, 4.29 mmol, 80% yield). $^1$H NMR (400 MHz, CDCl$_3$) δ 7.99 (s, 1H), 7.86 (s, 1H), 7.72 (d, J=8.8 Hz, 2H), 7.53 (d, J=8.8 Hz, 2H), 6.14 (br s, 1H), 4.12 (br d, J=2.4 Hz, 2H), 3.67 (br t, J=5.6 Hz, 2H), 2.56 (br s, 2H), 1.50 (s, 9H). LCMS: 327.11 [M+H]$^+$.

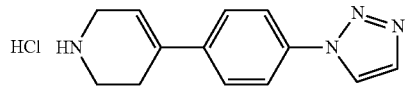

Step 4: 4-(4-(1H-1,2,3-triazol-1-yl)phenyl)-1,2,3,6-tetrahydropyridine hydrochloride To a stirred solution of tert-butyl 4-(4-(1H-1,2,3-triazol-1-yl)phenyl)-5,6-dihydropyridine-1(2H)-carboxylate (1.4 g, 4.29 mmol) in 1,4-dioxane (30 mL) was added 4M HCl:1,4-dioxane (50 mL). The mixture was stirred at rt for 2 h. The mixture was concentrated and triturated with diethyl ether (30 mL) to afford 4-(4-(1H-1,2,3-triazol-1-yl)phenyl)-1,2,3,6-tetrahydropyridine hydrochloride (1.0 g, 3.816 mmol, 90% yield) as an off white solid. $^1$H NMR (300 MHz, DMSO-d$_6$) δ 9.40 (br s, 1H), 8.85 (s, 1H), 7.99 (s, 1H), 8.00-7.90 (m, 3H), 7.72 (d, J=8.8 Hz, 2H), 6.34 (br s, 1H), 3.80 (br s, 2H), 3.35 (br s, 2H), 2.76 (br s, 2H). LCMS: 227.39 [M+H]$^+$.

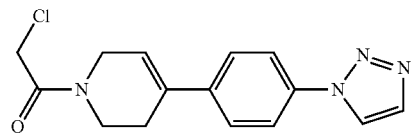 [SMILES: O=C(CCl)N1CC=C(c2ccc(-n3ccnn3)cc2)CC1]

Step 5: 1-(4-(4-(1H-1,2,3-triazol-1-yl)phenyl)-5,6-dihydropyridin-1(2H)-yl)-2-chloroethanone To a stirred solution of 4-(4-(1H-1,2,3-triazol-1-yl)phenyl)-1,2,3,6-tetrahydropyridine hydrochloride (1.0 g, 3.816 mmol) in dichloromethane (25 mL) was added triethylamine (3.2 mL, 22.90 mmol) followed by chloroacetyl chloride (0.91 mL, 11.45 mmol) at 0° C. The mixture was stirred at 0° C. for 1 h. The mixture was diluted with water (50 mL) and extracted with dichloromethane (3×50 mL). The combined organic layers were washed with brine (30 mL), dried over sodium sulfate, filtered and concentrated under reduced pressure. The residue was purified by silica-gel (100-200 mesh) column using 5% methanol in dichloromethane to afford 1-(4-(4-(1H-1,2,3-triazol-1-yl)phenyl)-5,6-dihydropyridin-1(2H)-yl)-2-chloroethanone (800 mg, 2.649 mmol, 70% yield) as a pale brown solid. $^1$H NMR (300 MHz, DMSO-d$_6$) δ 8.85 (s, 1H), 7.98 (d, J=1.1 Hz, 1H), 7.91 (d, J=8.8 Hz, 2H), 7.72-7.63 (m, 2H), 6.36 (br s, 1H), 4.53-4.42 (m, 2H), 4.19 (br d, J=16.5 Hz, 2H), 3.76-3.63 (m, 2H), 2.64-2.55 (m, 2H). LCMS: 303.23 [M+H]$^+$.

Intermediate 38

2-Chloro-1-(4-(4-(1-methyl-1H-1,2,3-triazol-4-yl)phenyl)-5,6-dihydropyridin-1(2H)-yl)ethanone

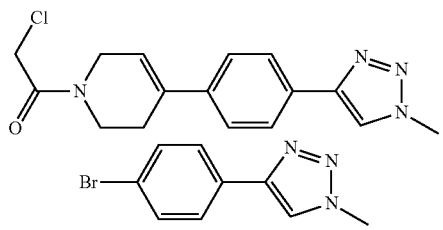

Step 1: 4-(4-Bromophenyl)-1-methyl-1H-1,2,3-triazole

To a stirred solution of 1-bromo-4-ethynylbenzene (2 g, 11.049 mmol) in water (20 mL) was added sodium azide (797.2 mg, 12.26 mmol), iodomethane (0.819 mL, 13.25 mmol) and copper iodide (419 mg, 2.209 mmol) at rt. The mixture was heated to 75° C. for 16 h. The mixture was diluted with water (30 mL) and extracted with ethyl acetate (3×30 mL). The combined organic layers were washed with brine (30 mL), dried over sodium sulfate and concentrated under reduced pressure. The residue was purified by column chromatography (100-200 silica) using 5% ethyl acetate in hexane as eluent to afford 4-(4-bromophenyl)-1-methyl-1H-1,2,3-triazole (800 mg, 3.37 mmol, 30% yield) as an off white solid. $^1$H NMR (300 MHz, DMSO-d$_6$) δ 8.59 (s, 1H), 7.80 (d, J=8.4 Hz, 2H), 7.61 (d, J=8.4 Hz, 2H), 4.09 (m, 3H). LCMS: 238.21 [M+H]$^+$.

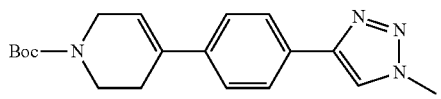

Step 2: tert-butyl 4-(4-(1-methyl-1H-1,2,3-triazol-4-yl)phenyl)-5,6-dihydropyridine-1(2H)-carboxylate To a stirred and degassed solution of 5-(4-bromophenyl)-N-ethyl-1,3,4-thiadiazol-2-amine (1.5 g, 6.32 mmol), tert-butyl 4-(4,4,5,5-tetramethyl-1,3,2-dioxaborolan-2-yl)-5,6-dihydropyridine-1(2H)-carboxylate (2.15 g, 6.96 mmol) in 1,2-dimethoxy ethane:water (5:1, 200 mL) was added potassium carbonate (2.62 g, 18.98 mmol). The mixture degassed for 10 mins. [1,1'-bis(diphenylphosphino)ferrocene]dichloropalladium(II) dichloromethane complex (516 mg, 0.63 mmol) was added. The mixture was degassed for 10 mins followed by refluxing for 16 h. The mixture was cooled to rt and filtered through a Celite pad. The filtrate was added to cold water, and the mixture was extracted with ethyl acetate (3×30 mL). The organic layers were washed with water (30 mL) and brine (30 mL), dried over sodium sulfate, filtered and concentrated. The residue was purified by column chromatography (100-200 silica) using 30% ethyl acetate in hexane as eluent to afford tert-butyl 4-(4-(1-methyl-1H-1,2,3-triazol-4-yl)phenyl)-5,6-dihydropyridine-1(2H)-carboxylate (1.4 g, 4.11 mmol, 65% yield). $^1$H NMR (300 MHz, DMSO-d$_6$) δ 8.51 (s, 1H), 7.80 (d, J=8.4 Hz, 2H), 7.52 (d, J=8.4 Hz, 2H), 6.22 (br s, 1H), 4.12-4.05 (m, 4H), 4.02 (br s, 2H), 3.55 (brt, J=5.7 Hz, 2H), 3.17 (d, J=5.1 Hz, 4H), 1.43 (s, 9H). LCMS: 341.15 [M+H]$^+$.

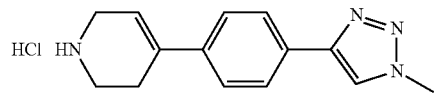 [SMILES: Cl ; Cn1cc(-c2ccc(C3=CCNCC3)cc2)nn1]

Step 3: 4-(4-(1-Methyl-1H-1,2,3-triazol-4-yl)phenyl)-1,2,3,6-tetrahydropyridine hydrochloride To a stirred solution of tert-butyl 4-(4-(5-(ethylamino)-1,3,4-thiadiazol-2-yl)phenyl)-5,6-dihydropyridine-1(2H)-carboxylate (1.4 g, 4.11 mmol) in 1,4-dioxane (30 mL) was added a solution 4M HCl in 1,4-dioxane (20 mL). The mixture was stirred at rt for 2 h. The mixture was concentrated and triturated with diethyl ether (30 mL) to afford 4-(4-(1-methyl-1H-1,2,3-triazol-4-yl)phenyl)-1,2,3,6-tetrahydropyridine hydrochloride (1.09 g, 3.95 mmol, 96% yield). $^1$H NMR (300 MHz, DMSO-d$_6$) δ 8.99 (br s, 1H), 8.55 (s, 1H), 7.85 (d, J=8.4 Hz, 2H), 7.57 (d, J=8.4 Hz, 2H), 6.27 (br s, 1H), 4.09 (s, 3H), 3.78 (br s, 2H), 3.33 (br s, 2H), 2.72 (br s, 2H). LCMS: 241.10 [M+H]$^+$.

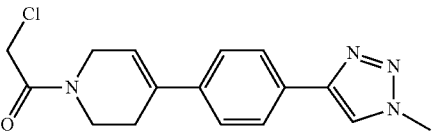 [SMILES: Cn1cc(-c2ccc(C3=CCN(C(=O)CCl)CC3)cc2)nn1]

Step 4: 2-Chloro-1-(4-(4-(1-methyl-1H-1,2,3-triazol-4-yl)phenyl)-5,6-dihydropyridin-1(2H)-yl)ethanone To a stirred solution of 4-(4-(1-methyl-1H-1,2,3-triazol-4-yl)phenyl)-1,2,3,6-tetrahydropyridine hydrochloride (1.2 g, 4.34 mmol) in DCM (40 mL) was added triethylamine (4.2 mL, 30.37 mmol) followed by chloro acetylchloride (1.04 mL, 13.01 mmol) at 0° C. The mixture was stirred at 0° C. for 1 h. The mixture was diluted with water (30 mL) and extracted with DCM (3×25 mL). The combined organic layers were washed with brine (25 mL), dried over sodium sulfate and concentrated under reduced pressure. The residue was purified by silica-gel (100-200 mesh) column using 5% methanol in dichloromethane to afford 2-chloro-1-(4-(4-(1-methyl-1H-1,2,3-triazol-4-yl)phenyl)-5,6-dihydropyridin-1(2H)-yl)ethanone (580 mg, 1.84 mmol, 42% yield) as a white solid. $^1$H NMR (300 MHz, DMSO-d$_6$) δ 8.52 (s, 1H), 7.82 (d, J=8.4 Hz, 2H), 7.53 (br dd, J=4.6, 7.9 Hz, 2H), 6.26 (br s, 1H), 4.50-4.41 (m, 2H), 4.17 (brd, J=17.2 Hz, 2H), 4.09 (s, 3H), 3.83-3.54 (m, 2H), 2.66-2.29 (m, 2H). LCMS: 363.32 [M+H]$^+$.

Intermediate 39

2-Chloro-1-(4-(2-fluoro-4-(1-methyl-1H-1,2,4-triazol-3-yl)phenyl)-3,6-dihydropyridin-1(2H)-yl)ethan-1-one

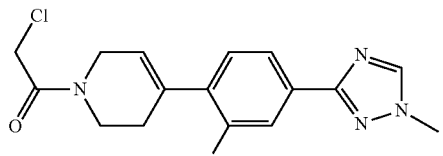

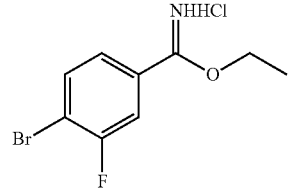

Step 1: Ethyl 4-bromo-3-fluorobenzimidate hydrochloride

To a stirred solution of 4-bromo-3-fluorobenzonitrile (5 g, 25.12 mmol) in absolute ethanol (100 mL) at 0° C. was bubbled HCl gas (generated from NaCl with H$_2$SO$_4$) initially vigorously for 1 h and then slowly for 5 h at 0° C. The mixture was stirred overnight at rt. The solvent was concentrated. The solid was washed with ether (100 mL) and dried to afford ethyl 4-bromo-3-fluorobenzimidate hydrochloride (5 g, 17.79 mmol, 71% yield) as an off white solid. $^1$H NMR (400 MHz, DMSO-$d_6$) δ 12.00 (br s, 2H), 8.18 (br t, J=9.5 Hz, 1H), 8.08-7.98 (m, 1H), 7.90 (br d, J=6.4 Hz, 1H), 4.67-4.55 (m, 2H), 1.47 (t, J=7.1 Hz, 3H).

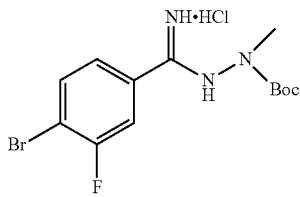

Step 2: tert-butyl 2-((4-bromo-3-fluorophenyl)(imino)methyl)-1-methylhydrazinecarboxylate hydrochloride To a solution of ethyl 4-bromo-3-fluorobenzimidate hydrochloride (5 g, 17.79 mmol) in pyridine (50 mL) was added t-butyl 1-methylhydrazinecarboxylate (3.2 g, 21.34 mmol) at rt. The mixture was stirred for 16 h. The solvent was concentrated under reduced pressure. The obtained gummy liquid was triturated with diethyl ether (50 mL) to afford a solid which was filtered, further washed diethyl ether (50 mL) and dried to afford tert-butyl 2-((4-bromo-3-fluorophenyl)(imino)methyl)-1-methylhydrazinecarboxylate hydrochloride (5 g, 13.12 mmol, 74% yield). $^1$H NMR (300 MHz, DMSO-$d_6$) δ 12.12 (br s, 1H), 10.52-9.66 (m, 2H), 8.08 (dd, J=7.2, 8.3 Hz, 1H), 7.87 (br d, J=8.1 Hz, 1H), 7.59 (br d, J=8.4 Hz, 1H), 3.13 (s, 3H), 1.44 (s, 9H). LCMS: 348 [M+3H]$^+$.

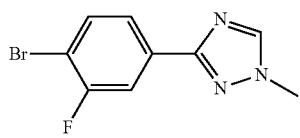

Step 3: 3-(4-Bromo-3-fluorophenyl)-1-methyl-1H-1,2,4-triazole

To tert-butyl 2-((4-bromo-3-fluorophenyl)(imino)methyl)-1-methylhydrazinecarboxylate hydrochloride (5 g, 13.12 mmol) was added formic acid (75 mL) at rt. The mixture was refluxed for 16 h. The mixture was concentrated, and the residue was treated with sat. aq. sodium bicarbonate solution. The mixture was extracted with ethyl acetate (3×150 mL). The combined organic layers were washed with brine (2×50 mL), dried and concentrated to afford 3-(4-bromo-3-fluorophenyl)-1-methyl-1H-1,2,4-triazole (2.5 g, 9.65 mmol, 74% yield) as an off white solid. $^1$H NMR (300 MHz, DMSO-$d_6$) δ 8.57 (s, 1H), 7.83-7.74 (m, 3H), 3.95 (s, 3H). LCMS: 256.15 [M+H]$^+$.

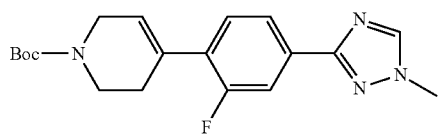

Step 4: tert-butyl 4-(2-fluoro-4-(1-methyl-1H-1,2,4-triazol-3-yl)phenyl)-5,6-dihydropyridine-1(2H)-carboxylate To a stirred and degassed solution of 3-(4-bromo-3-fluorophenyl)-1-methyl-1H-1,2,4-triazole (2 g, 7.84 mmol) and tert-butyl 4-(4,4,5,5-tetramethyl-1,3,2-dioxaborolan-2-yl)-5,6-dihydropyridine-1(2H)-carboxylate (2.66 g, 8.62 mmol) in 1,2-dimethoxy ethane:water (5:1, 60 mL) was added potassium carbonate (3.24 g, 23.52 mmol). The mixture was degassed for 30 mins. [1,1'-bis(diphenylphosphino)ferrocene] dichloropalladium(II) DCM complex (320 mg, 0.392 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×100 mL). The combined organic layers were washed with water (2×50 mL) and brine (1×50 mL), dried over sodium sulfate and concentrated. The residue was purified by column chromatography (100-200 silica) using 50% ethyl acetate in petroleum ether as an eluent to afford tert-butyl 4-(2-fluoro-4-(1-methyl-1H-1,2,4-triazol-3-yl)phenyl)-5,6-dihydropyridine-1(2H)-carboxylate (2 g, 5.58 mmol, 72% yield). $^1$H NMR (400 MHz, CDCl$_3$) δ 8.05 (s, 1H), 7.83 (dd, J=1.5, 8.3 Hz, 1H), 7.77 (dd, J=1.2, 12.0 Hz, 1H), 7.31 (t, J=7.8 Hz, 1H), 6.02 (br s, 1H), 4.09 (br d, J=2.0 Hz, 2H), 3.97 (s, 3H), 3.63 (br t, J=5.6 Hz, 2H), 2.54 (br s, 2H), 1.50 (s, 9H). LCMS: 359.67 [M+H]$^+$.

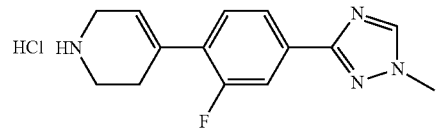 [SMILES: Cl ; Cn1cnc(-c2ccc(C3=CCNCC3)c(F)c2)n1]

Step 5: 4-(2-Fluoro-4-(1-methyl-1H-1,2,4-triazol-3-yl)phenyl)-1,2,3,6-tetrahydropyridine hydrochloride To tert-butyl 4-(2-fluoro-4-(1-methyl-1H-1,2,4-triazol-3-yl)phenyl)-5,6-dihydropyridine-1(2H)-carboxylate (2 g, 5.57 mmol) in 1,4-dioxane (10 mL) was added 4M HCl:1,4-dioxane (15 mL). The mixture was stirred at rt for 2 h. The mixture was concentrated and triturated with diethyl ether (30 mL) to afford 4-(2-fluoro-4-(1-methyl-1H-1,2,4-triazol-3-yl)phenyl)-1,2,3,6-tetrahydropyridine hydrochloride (1.2 g, 4.65 mmol, 86% yield) as an off white solid. $^1$H NMR (300 MHz, DMSO-$d_6$) δ 9.30 (br s, 2H), 8.58 (s, 1H), 7.83 (dd, J=1.2, 8.1 Hz, 1H), 7.71 (dd, J=1.2, 12.5 Hz, 1H), 7.49 (t, J=8.1 Hz, 1H), 6.12 (br s, 1H), 3.93 (s, 3H), 3.77 (br s, 2H), 3.30 (br s, 2H), 2.69 (br s, 2H). LCMS: 259.06 [M+H]$^+$.

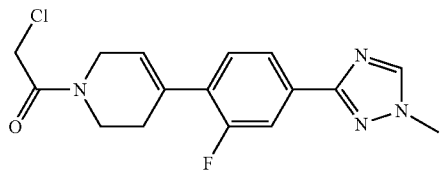 [SMILES: Cn1cnc(-c2ccc(C3=CCN(C(=O)CCl)CC3)c(F)c2)n1]

Step 6: 2-Chloro-1-(4-(2-fluoro-4-(1-methyl-1H-1,2,4-triazol-3-yl)phenyl)-3,6-dihydropyridin-1(2H)-yl)ethan-1-one The compound was prepared following the procedure described for Intermediate 34, using 4-(2-fluoro-4-(1- methyl-1H-1,2,4-triazol-3-yl)phenyl)-1,2,3,6-tetrahydropyridine hydrochloride and chloro acetylchloride. LCMS: 335.10 [M+H]⁺.

Intermediate 40

2-Chloro-1-(4-(3-fluoro-4-(1-methyl-1H-1,2,4-triazol-3-yl)phenyl)-3,6-dihydropyridin-1(2H)-yl)ethan-1-one

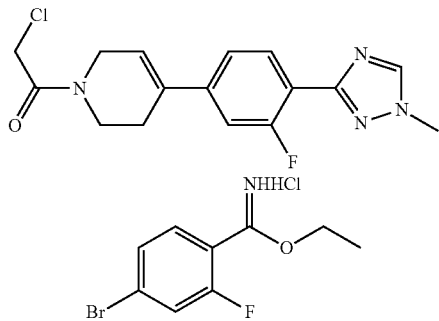

Step 1: Ethyl 4-bromo-2-fluorobenzimidate hydrochloride

To a stirred solution of 4-bromo-2-fluorobenzonitrile (5 g, 25.12 mmol) in absolute ethanol (100 mL) at 0° C. was bubbled HCl gas (generated from NaCl with H₂SO₄) initially vigorously for 1 h and then slowly for 5 h at 0° C. The mixture was stirred overnight at rt. The solvent was concentrated. The solid was washed with ether (100 mL) and dried to afford ethyl 4-bromo-2-fluorobenzimidate hydrochloride (5 g, 17.79 mmol, 71% yield) as an off white solid. ¹H NMR (300 MHz, DMSO-d₆) δ 11.76 (br s, 1H), 7.91 (dd, J=2.1, 10.8 Hz, 1H), 7.86-7.81 (m, 1H), 7.70 (dd, J=1.2, 8.4 Hz, 1H), 4.64 (q, J=6.9 Hz, 2H), 1.43 (t, J=6.9 Hz, 3H).

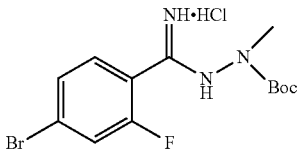

Step 2: tert-Butyl 2-((4-bromo-2-fluorophenyl)(imino)methyl)-1-methylhydrazinecarboxylate hydrochloride To a solution of ethyl 4-bromo-2-fluorobenzimidate hydrochloride (5 g, 17.79 mmol) in pyridine (50 mL) was added t-butyl 1-methylhydrazinecarboxylate (3.2 g, 21.34 mmol) at rt, and the mixture was stirred for 16 h. The solvent was concentrated under reduced pressure. The obtained gummy liquid was triturated with diethyl ether (50 mL) to afford a solid which was filtered, further washed diethyl ether (50 mL) and dried to afford tert-butyl 2-((4-bromo-2-fluorophenyl)(imino)methyl)-1-methylhydrazinecarboxylate hydrochloride (5 g, 13.12 mmol, 74% yield). ¹H NMR (300 MHz, DMSO-d₆) δ 12.25 (br s, 1H), 10.35-10.07 (m, 2H), 7.95 (dd, J=1.5, 8.4 Hz, 1H), 7.75-7.63 (m, 2H), 3.12 (s, 3H), 1.45 (s, 9H). LCMS: 346.10 [M+H]⁺.

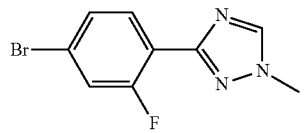

Step 3: 3-(4-Bromo-2-fluorophenyl)-1-methyl-1H-1,2,4-triazole

To a tert-butyl 2-((4-bromo-2-fluorophenyl)(imino)methyl)-1-methylhydrazinecarboxylate hydrochloride (5 g, 13.12 mmol) was added formic acid (75 mL) at rt. The mixture was refluxed for 16 h. The mixture was concentrated. The residue was treated with sat. aq. sodium bicarbonate solution and extracted with ethyl acetate (3×150 mL). The combined organic layers were washed with brine (2×50 mL), dried and concentrated to afford 3-(4-bromo-2-fluorophenyl)-1-methyl-1H-1,2,4-triazole (2.5 g, 9.65 mmol, 74% yield) as an off white solid. ¹H NMR (400 MHz, DMSO-d₆) δ 8.59 (s, 1H), 7.95 (t, J=8.1 Hz, 1H), 7.67 (dd, J=1.7, 10.5 Hz, 1H), 7.53 (dd, J=1.7, 8.6 Hz, 1H), 3.94 (s, 3H). LCMS: 256.15 [M+H]⁺

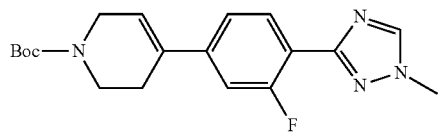 [SMILES: Cn1cnc(-c2ccc(C3=CCN(C(=O)OC(C)(C)C)CC3)cc2F)n1]

Step 4: tert-Butyl 4-(3-fluoro-4-(1-methyl-1H-1,2,4-triazol-3-yl)phenyl)-5,6-dihydropyridine-1(2H)-carboxylate To a stirred and degassed solution of 3-(4-bromo-2-fluorophenyl)-1-methyl-1H-1,2,4-triazole (2 g, 7.84 mmol) and tert-butyl 4-(4,4,5,5-tetramethyl-1,3,2-dioxaborolan-2-yl)-5,6-dihydropyridine-1(2H)-carboxylate (2.66 g, 8.62 mmol) in 1,2-dimethoxy ethane:water (5:1, 60 mL) was added potassium carbonate (3.24 g, 23.52 mmol). The mixture was degassed for 30 mins. [1,1'-bis(diphenylphosphino)ferrocene]dichloropalladium(II) DCM complex (320 mg, 0.392 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×100 mL). The combined organic layers were washed with water (2×50 mL) and brine (1×50 mL), dried over sodium sulfate and concentrated. The residue was purified by column chromatography (100-200 silica) using 50% ethyl acetate in petroleum ether as eluent to afford tert-butyl 4-(3-fluoro-4-(1-methyl-1H-1,2,4-triazol-3-yl)phenyl)-5,6-dihydropyridine-1(2H)-carboxylate (2 g, 5.58 mmol, 72% yield). ¹H NMR (300 MHz, DMSO-d₆) δ 8.10-8.0 (m, 2H), 7.23-7.18 (m, 2H), 6.16 (br s, 1H), 4.09 (br s, 2H), 4.0 (s, 3H), 3.65 (t, J=5.1 Hz, 2H), 2.53 (br s, 2H), 1.49 (s, 9H). LCMS: 359.24 [M+H]⁺.

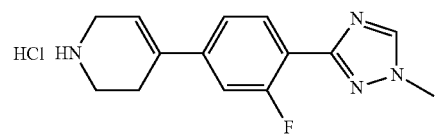 [SMILES: Cl ; Cn1cnc(-c2ccc(C3=CCNCC3)cc2F)n1]

Step 5: 4-(3-Fluoro-4-(1-methyl-1H-1,2,4-triazol-3-yl)phenyl)-1,2,3,6-tetrahydropyridine hydrochloride To tert-butyl 4-(3-fluoro-4-(1-methyl-1H-1,2,4-triazol-3-yl)phenyl)-5,6-dihydropyridine-1(2H)-carboxylate (1 g, 2.79 mmol) in 1,4-dioxane (20 mL) was added 4M HCl:1,4-dioxane (15 mL). The mixture was stirred at rt for 2 h. The mixture was concentrated and triturated with diethyl ether (30 mL) to afford 4-(3-fluoro-4-(1-methyl-1H-1,2,4-triazol-3-yl)phenyl)-1,2,3,6-tetrahydropyridine hydrochloride (700 mg, 2.38 mmol, 85% yield) as a pale yellow solid. $^1$H NMR (400 MHz, DMSO-$d_6$) δ 9.40 (br s, 2H), 8.60 (s, 1H), 8.0 (t, J=7.6 Hz, 1H), 7.46-7.42 (m, 2H), 6.39 (br s, 1H), 3.94 (s, 3H), 3.76 (br s, 2H), 3.30 (br s, 2H), 2.72 (br s, 2H). LCMS: 259.16 [M+H]$^+$.

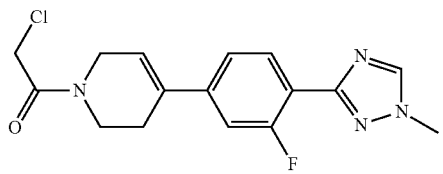 [SMILES: Cn1cnc(-c2ccc(C3=CCN(C(=O)CCl)CC3)cc2F)n1]

Step 6: 2-Chloro-1-(4-(3-fluoro-4-(1-methyl-1H-1,2,4-triazol-3-yl)phenyl)-3,6-dihydropyridin-1(2H)-yl)ethan-1-one The title compounds was prepared following the procedure described for Intermediate 34, using 4-(3-fluoro-4-(1-methyl-1H-1,2,4-triazol-3-yl)phenyl)-1,2,3,6-tetrahydropyridine hydrochloride and chloro acetylchloride. LCMS: 335.10 [M+H]$^+$.

Intermediate 41

2-Chloro-1-(4-(3-fluoro-4-(1-methyl-1H-1,2,4-triazol-3-yl)phenyl)piperazin-1-yl)ethanone

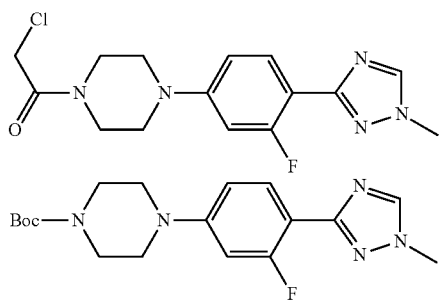

Step 1: tert-Butyl 4-(3-fluoro-4-(1-methyl-1H-1,2,4-triazol-3-yl)phenyl)piperazine-1-carboxylate To a stirred and degassed solution of 3-(4-bromo-2-fluorophenyl)-1-methyl-1H-1,2,4-triazole (2.5 g, 9.803 mmol) and tert-butyl piperazine-1-carboxylate (7.3 g, 39.215 mmol) in toluene (100 mL) was added cesium carbonate (25.55 g, 78.431 mmol) and (2,2'-bis(diphenylphosphino)-1,1'-binaphthyl) (0.610 g, 0.980 mmol). The mixture was degassed for 40 mins. Pd(OAc)$_2$ (0.11 g, 0.490 mmol) was added. The mixture was degassed for 10 mins followed by heating at 100° C. for 16 h. The mixture was cooled to rt. Water was added, and the mixture was extracted with ethyl acetate (3×100 mL). The combined organic layers were washed with water (2×100 mL) and brine (1×100 mL), dried over sodium sulfate, filtered and concentrated. The residue was purified by column chromatography (100-200 silica) using 70% ethyl acetate in petroleum ether as eluent to afford tert-butyl 4-(3-fluoro-4-(1-methyl-1H-1,2,4-triazol-3-yl)phenyl)piperazine-1-carboxylate (1.8 g, 4.986 mmol, 51% yield). $^1$H NMR (300 MHz, CDCl$_3$) δ 8.06 (s, 1H), 7.95 (t, J=8.7 Hz, 1H), 7.27 (d, J=1.2 Hz, 1H), 6.76-6.65 (br s, 1H), 3.98 (s, 3H), 3.59 (t, J=4.5 Hz, 4H), 3.24 (t, J=4.5 Hz, 4H), 1.49 (s, 9H). LCMS: 362.35 [M+H]$^+$.

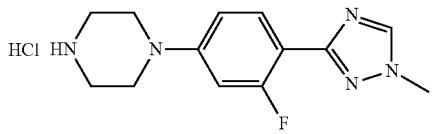

Step 2: 1-(3-Fluoro-4-(1-methyl-1H-1,2,4-triazol-3-yl)phenyl)piperazine hydrochloride To tert-butyl 4-(3-fluoro-4-(1-methyl-1H-1,2,4-triazol-3-yl)phenyl)piperazine-1 carboxylate (1.8 g, 3.61 mmol) in 1,4-dioxane (100 mL) was added 4M HCl: 1,4-dioxane (100 mL). The mixture was stirred at rt for 2 h. The mixture was concentrated and triturated with diethyl ether (100 mL) to afford 1-(3-fluoro-4-(1-methyl-1H-1,2,4-triazol-3-yl)phenyl)piperazine hydrochloride (1.4 g, 96% yield) as an off white solid. The crude was used for the next step without purification. $^1$H NMR (400 MHz, DMSO-$d_6$) δ 9.30 (br s, 2H), 8.58 (s, 1H), 7.84 (t, J=8.8 Hz, 1H), 6.93-6.89 (m, 2H), 3.91 (s, 3H), 3.51 (t, J=5.2 Hz, 4H), 3.19 (br s, 4H). LCMS: 294.10 [M+H]$^+$.

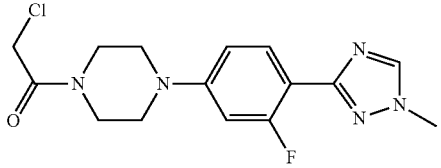 [SMILES: Cn1cnc(-c2ccc(N3CCN(C(=O)CCl)CC3)cc2F)n1]

Step 3: 2-Chloro-1-(4-(3-fluoro-4-(1-methyl-1H-1,2,4-triazol-3-yl)phenyl)piperazin-1-yl)ethanone To a stirred solution of 1-(3-fluoro-4-(1-methyl-1H-1,2,4-triazol-3-yl)phenyl)piperazine hydrochloride (1.4 g, 4.761 mmol) in dichloromethane (100 mL) was added triethylamine (3.9 mL, 28.571 mmol) followed by chloroacetyl chloride (1.1 mL, 14.285 mmol) at 0° C. The mixture was stirred at 0° C. for 1 h. The mixture was diluted with water (100 mL) and extracted with dichloromethane (3×100 mL). The combined organic layers were washed with brine (100 mL), dried over sodium sulfate, filtered and concentrated under reduced pressure. The crude was purified by column chromatography using 5% methanol:DCM as an eluent, and then triturated with 5% methanol:DCM in diethyl ether (1:100, 100 mL), to afford 2-chloro-1-(4-(3-fluoro-4-(1-methyl-1H-1,2,4-triazol-3-yl)phenyl)piperazin-1yl)ethanone (1.2 g, 3.560 mmol, 75% yield) as a pale yellow solid. $^1$H NMR (300 MHz, DMSO-$d_6$) δ 8.47 (s, 1H), 7.81 (t, J=9.0 Hz, 1H), 9.87-6.81 (m, 2H), 4.44 (s, 2H), 3.89 (s, 3H), 3.60 (t, J=4.5 Hz, 4H), 3.28 (t, J=4.5 Hz, 4H). LCMS: 338.22 [M+H]+.

Intermediate 42

2-Chloro-1-(4-(2-fluoro-4-(1-methyl-1H-1,2,4-triazol-3-yl)phenyl)piperazin-1-yl)ethan-1-one

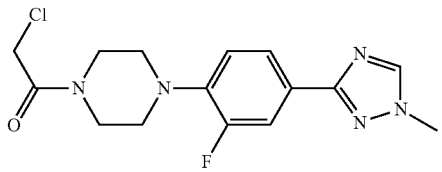

The title compound was prepared following the procedure described for Intermediate 37 using 3-(4-bromo-3-fluorophenyl)-1-methyl-1H-1,2,4-triazole. LCMS: 338.20 [M+H]+.

Intermediate 43

5-(Pyrimidin-2-yl)-1',2',3',6'-tetrahydro-2,4'-bipyridine hydrochloride

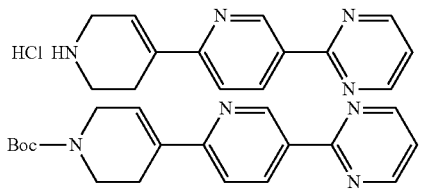

Step 1: tert-butyl 4-(5-(pyrimidin-2-yl)pyridin-2-yl)-5,6-dihydropyridine-1(2H)-carboxylate To a stirred and degassed solution of 6-bromopyridin-3-ylboronic acid (6 g, 29.73 mmol), 2-bromo pyrimidine (4.7 g, 29.73 mmol) in 1,2-dimethoxy ethane:water (9:1, 160 mL) was added cesium carbonate (38.6 g, 118.92 mmol). The mixture was degassed for 10 mins. Bis(triphenylphosphine)palladium(II) dichloride (2.0 g, 2.973 mmol) was added. The mixture was degassed for 10 min and then refluxed for 2 h. Tert-butyl 4-(4,4,5,5-tetramethyl-1,3,2-dioxaborolan-2-yl)-5,6-dihydropyridine-1(2H)-carboxylate (9.1 g, 29.73 mmol) was added. The mixture was degassed for 10 mins and then refluxed for 16 h. The mixture was cooled to rt and filtered through a Celite pad. To the filtrate was added cold water, and the mixture was extracted with ethyl acetate (3×100 mL). The organic layers were washed with water (50 mL) and brine (50 mL), dried over sodium sulfate, filtered and concentrated. The residue was purified by column chromatography (100-200 silica) using 50% ethyl acetate in hexanes as eluent and further purified by Reveleris C-18 reversed phase column using 95% acetonitrile in aqueous formic acid (0.1%) to afford tert-butyl 4-(5-(pyrimidin-2-yl)pyridin-2-yl)-5,6-dihydropyridine-1(2H)-carboxylate (1.04 g, 3.07 mmol, 10% yield). 1H NMR (400 MHz, DMSO-d6) δ 9.47 (d, J=1.5 Hz, 1H), 8.95 (d, J=4.9 Hz, 2H), 8.65 (dd, J=2.0, 8.3 Hz, 1H), 7.73 (d, J=8.3 Hz, 1H), 7.50 (t, J=4.9 Hz, 1H), 6.86 (br s, 1H), 4.09 (br s, 2H), 3.57 (t, J=5.6 Hz, 2H), 2.62 (br d, J=1.5 Hz, 2H), 1.44 (s, 9H). LCMS: 339.17 [M+H]+.

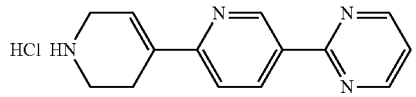 [SMILES: Cl ; C1=C(c2ccc(-c3ncccn3)cn2)CCNC1]

Step 2: 5-(Pyrimidin-2-yl)-1',2',3',6'-tetrahydro-2,4'-bipyridine hydrochloride

The title compound was prepared following the procedure described for Intermediate 37 using tert-butyl 4-(5-(pyrimidin-2-yl)pyridin-2-yl)-5,6-dihydropyridine-1(2H)-carboxylate. LCMS: 239.2 [M+H]+.

Intermediate 44

2-(4-(1,2,3,6-Tetrahydropyridin-4-yl)phenyl)pyrimidine hydrochloride

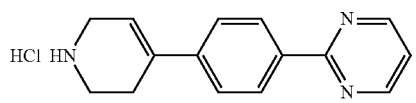

The title compound was prepared following the procedure described for Intermediate 39 using (4-bromophenyl)boronic acid, 2-bromopyrimidine and tert-butyl 4-(4,4,5,5-tetramethyl-1,3,2-dioxaborolan-2-yl)-5,6-dihydropyridine-1(2H)-carboxylate in Step 1. LCMS: 238.2 [M+H]+.

Intermediate 45

5-Fluoro-2-(4-(1,2,3,6-tetrahydropyridin-4-yl)phenyl)pyrimidine hydrochloride

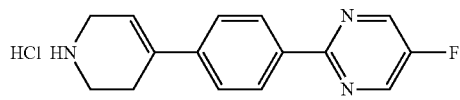

The title compound was prepared following the procedure described for Intermediate 39 using (4-bromophenyl)boronic acid, 2-bromo-5-fluoropyrimidine and tert-butyl 4-(4,4,5,5-tetramethyl-1,3,2-dioxaborolan-2-yl)-5,6-dihydropyridine-1(2H)-carboxylate in Step 1. LCMS: 256.2 [M+H]+.

Intermediate 46

4-(4-(1-Methyl-1H-imidazol-4-yl)phenyl)-1,2,3,6-tetrahydropyridine dihydrochloride

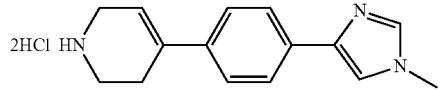

-continued

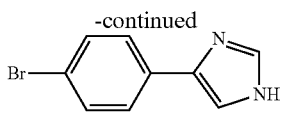

Step 1: 4-(4-Bromophenyl)-1H-imidazole

A mixture of 2-bromo-1-(4-bromophenyl)ethanone (7.0 g, 25.3 mmol) in formamide (28 mL) was heated at 140° C. for 24 h. The mixture was diluted with ethyl acetate (300 mL), washed with aqueous NaHCO$_3$ solution (200 mL) and brine (100 mL), dried over sodium sulfate and concentrated to afford 4-(4-bromophenyl)-1H-imidazole (5 g, 22.52 mmol, 89% yield) as a pale brown solid. $^1$H NMR (400 MHz, CDCl$_3$) δ 7.71 (s, 1H), 7.63 (d, J=8.3 Hz, 2H), 7.50 (d, J=8.8 Hz, 2H), 7.33 (s, 1H). LCMS: 222.78 [M+H]$^+$.

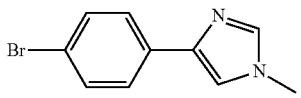

Step 2: 4-(4-Bromophenyl)-1-methyl-1H-imidazole

To a mixture of 4-(4-bromophenyl)-1H-imidazole (2.0 g, 9.0 mmol) and cesium carbonate (2 eq.) in THF (35 mL) at 0° C. was added methyl iodide (2.55 g, 18 mmol). The mixture was stirred at rt for 16 h. The mixture was diluted with ethyl acetate (100 mL), washed with water (80 mL) and brine (50 mL), dried over sodium sulfate, filtered and concentrated to afford 4-(4-bromophenyl)-1-methyl-1H-imidazole (780 mg, 3.30 mmol, 37% yield) as a pale brown solid. $^1$H NMR (400 MHz, CDCl$_3$) δ 7.62 (d, J=8.4 Hz, 2H), 7.51-7.43 (m, 3H), 7.16 (s, 1H), 3.72 (s, 3H). LCMS: 236.78 [M+H]$^+$.

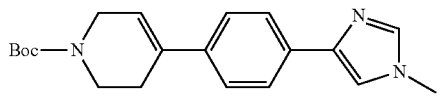

Step 3: tert-butyl 4-(4-(1-methyl-1H-imidazol-4-yl)phenyl)-5,6-dihydropyridine-1(2H)-carboxylate To a stirred and degassed solution of 4-(4-bromophenyl)-1-methyl-1H-imidazole (1.0 g, 6.355 mmol) and tert-butyl 4-(4,4,5,5-tetramethyl-1,3,2-dioxaborolan-2-yl)-5,6-dihydropyridine-1(2H)-carboxylate (2.25 g, 6.991 mmol) in 1,2-dimethoxy ethane:water (5:1, 54 mL) was added potassium carbonate (1.98 g, 19.06 mmol). The mixture was degassed for 10 mins. [1,1'-bis(diphenylphosphino)ferrocene]dichloropalladium(II) DCM complex (517 mg, 0.635 mmol) was added. The mixture was degassed for 10 mins and then heated at 80° C. for 16 h. The mixture was cooled to rt and filtered through a Celite pad. The filtrate was added cold water (50 mL), and the mixture was extracted with ethyl acetate (3×100 mL). The combined organic layers were washed with water (2×50 mL) and brine (1×50 mL), dried over sodium sulfate, filtered and concentrated. The residue was purified by column chromatography (100-200 silica) using 80% ethyl acetate in hexane as eluent to afford tert-butyl 4-(4-(1-methyl-1H-imidazol-4-yl)phenyl)-5,6-dihydropyridine-1(2H)-carboxylate (955 mg, 2.817 mmol, 42% yield). $^1$H NMR (300 MHz, DMSO-d$_6$) δ 7.70 (d, J=8.4 Hz, 2H), 7.62 (s, 1H), 7.59 (s, 1H), 7.41 (d, J=8.4 Hz, 2H), 6.16 (s, 1H), 4.0 (br s, 2H), 3.54 (t, J=5.4 Hz, 2H), 2.47 (br s, 2H), 1.43 (s, 9H). LCMS: 340.23 [M+H]$^+$.

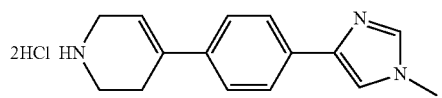 [SMILES: Cn1cnc(-c2ccc(C3=CCNCC3)cc2)c1]

Step 4: 4-(4-(1-methyl-1H-imidazol-4-yl)phenyl)-1,2,3,6-tetrahydropyridine dihydrochloride The title compound was prepared following the procedure described for Intermediate 37 using tert-butyl 4-(4-(1-methyl-1H-imidazol-4-yl)phenyl)-5,6-dihydropyridine-1(2H)-carboxylate. LCMS: 240.2 [M+H]$^+$.

Intermediate 47

4-Fluoro-4-(4-(1-methyl-1H-1,2,4-triazol-3-yl)phenyl)piperidine hydrochloride

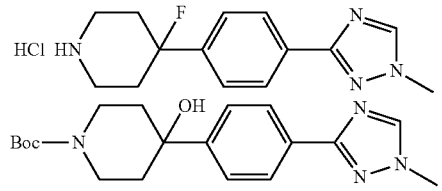

Step 1: tert-butyl 4-hydroxy-4-(4-(1-methyl-1H-1,2,4-triazol-3-yl)phenyl)piperidine-1-carboxylate To a cold (−78° C.) and stirred solution of 3-(4-bromophenyl)-1-methyl-1H-1,2,4-triazole (2.7 g, 11.34 mmol) in THF (60 mL) was added n-butyl lithium (2.5M in hexane, 5.4 mL, 13.61 mmol) dropwise. The mixture was stirred at −78° C. for 1 h. To this a solution of tert-butyl 4-oxopiperidine-1-carboxylate (2.25 g, 11.34 mmol) in THF (30 mL) was added at −78° C. The mixture was stirred at −78° C. for 2 h. The reaction was quenched with aqueous NH$_4$Cl (50 mL) and extracted with ethyl acetate (3×100 mL). The combined organic layers were washed with water (100 mL) and brine (80 mL), dried over sodium sulfate, filtered and concentrated. The residue was purified by column chromatography (100-200 silica) using 40% ethyl acetate in hexane as eluent and further purified by Reveleris C-18 reversed phase column using 65% acetonitrile in aqueous formic acid (0.1%) to afford tert-butyl 4-hydroxy-4-(4-(1-methyl-1H-1,2,4-triazol-3-yl)phenyl)piperidine-1-carboxylate (1.2 g, 3.35 mmol, 29% yield) as an off-white solid. $^1$H NMR (400 MHz, CDCl$_3$) δ 8.15-7.94 (m, 2H), 7.53-7.30 (m, 3H), 4.09 (s, 3H), 3.95 (br d, J=11.7 Hz, 2H), 3.38 (br t, J=11.5 Hz, 2H), 2.36 (s, 1H), 2.33-2.22 (m, 2H), 2.04 (s, 1H), 1.91 (br d, J=13.2 Hz, 2H), 1.48 (s, 9H). LCMS: 358.92 [M+H]$^+$.

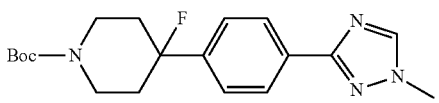

Step 2: tert-butyl 4-fluoro-4-(4-(1-methyl-1H-1,2,4-triazol-3-yl)phenyl)piperidine-1-carboxylate To a stirred solution of tert-butyl 4-hydroxy-4-(4-(1-methyl-1H-1,2,4-triazol-3-yl)phenyl)piperidine-1-carboxylate (1.2 g, 3.33 mmol) in DCM (60 mL) at −78° C., was added DAST (0.7 mL, 4.99 mmol). The mixture was allowed to warm to rt with stirring over a period of 2 h. After completion of the reaction, saturated sodium bicarbonate solution was added. Dichloromethane (3×70 mL) was extracted. The combined organic layers were washed with water (150 mL) and brine (150 mL), dried over sodium sulfate, filtered and concentrated. The residue was purified by column chromatography (100-200 silica) using 15% ethyl acetate in hexane as eluent to afford tert-butyl 4-fluoro-4-(4-(1-methyl-1H-1,2,4-triazol-3-yl)phenyl)piperidine-1-carboxylate (900 mg, 2.50 mmol, 75% yield) as a white solid. $^1$H NMR (400 MHz, CDCl$_3$) δ 8.03 (dd, J=1.7, 8.1 Hz, 2H), 7.49-7.30 (m, 3H), 4.06 (d, J=2.0 Hz, 5H), 3.29 (br t, J=12.0 Hz, 2H), 2.46-2.22 (m, 2H), 2.22-2.09 (m, 2H), 1.49 (s, 9H). LCMS: 382.92 [M+H]$^+$.

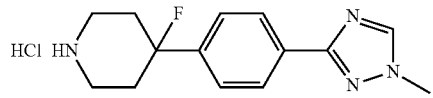

Step 3: 4-Fluoro-4-(4-(1-methyl-1H-1,2,4-triazol-3-yl)phenyl)piperidine hydrochloride To a stirred solution of tert-butyl 4-fluoro-4-(4-(1-methyl-1H-1,2,4-triazol-3-yl)phenyl)piperidine-1-carboxylate (1.0 g, 2.77 mmol) in 1,4-Dioxane (30 mL) was added a solution 4M HCl in 1,4-dioxane (10 mL). The mixture was stirred at rt for 2 h. The mixture was concentrated and triturated with diethylether (30 mL) to afford 4-fluoro-4-(4-(1-methyl-1H-1,2,4-triazol-3-yl)phenyl)piperidine hydrochloride (570 mg, 1.92 mmol, 68% yield) as an off white solid. $^1$H NMR (400 MHz, DMSO-d$_6$) δ 9.23 (br s, 1H), 7.97 (dd, J=1.2, 8.1 Hz, 2H), 7.57-7.36 (m, 3H), 4.03 (d, J=2.0 Hz, 3H), 3.43-3.34 (m, 2H), 3.26-3.14 (m, 2H), 2.64-2.53 (m, 2H), 2.53-2.44 (m, 2H). LCMS: 261.14 [M+H]$^+$.

Intermediate 48

2-Chloro-1-(4-(4-(3-methyl-1,2,4-oxadiazol-5-yl)phenyl)-3,6-dihydropyridin-1(2H)-yl)ethan-1-one

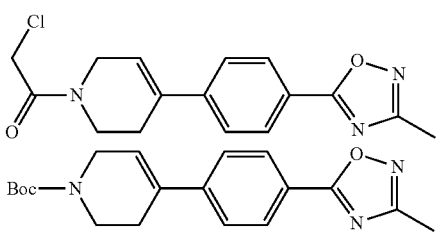

Step 1: tert-Butyl 4-(4-(3-methyl-1,2,4-oxadiazol-5-yl)phenyl)-3,6-dihydropyridine-1(2H)-carboxylate A mixture of 5-(4-bromophenyl)-3-methyl-1,2,4-oxadiazole (0.5 g, 2.091 mmol), tert-butyl 4-(4,4,5,5-tetramethyl-1,3,2-dioxaborolan-2-yl)-5,6-dihydropyridine-1(2H)-carboxylate (0.647 g, 2.091 mmol), Pd(Ph$_3$P)$_2$Cl$_2$ (0.147 g, 0.209 mmol) and cesium carbonate (1.363 g, 4.18 mmol) was degassed with vacuum/nitrogen cycles (3×). This mixture was heated at 100° C. overnight. Upon completion, the mixture was diluted with water and extracted with ethyl acetate. The organics were washed with water and brine, dried over sodium sulfate, filtered and concentrated to give the crude that was purified on silica gel eluted with 0-100% ethyl acetate in hexanes to afford tert-butyl 4-(4-(3-methyl-1,2,4-oxadiazol-5-yl)phenyl)-5,6-dihydropyridine-1(2H)-carboxylate (0.3 g, 0.879 mmol, 42.0% yield). $^1$H NMR (400 MHz, CDCl$_3$) δ 8.10 (d, 2H), 7.55 (d, 2H), 6.22 (br, 1H), 4.15 (br, 2H), 3.69 (s, 2H), 2.58 (br, 2H), 2.49 (s, 3H), 1.49 (s, 9H). LCMS: 342.20 [M+H]$^+$.

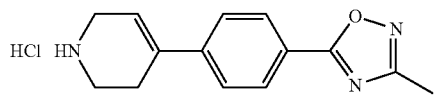

Step 2: 3-Methyl-5-(4-(1,2,3,6-tetrahydropyridin-4-yl)phenyl)-1,2,4-oxadiazole hydrochloride tert-Butyl 4-(4-(3-methyl-1,2,4-oxadiazol-5-yl)phenyl)-5,6-dihydropyridine-1(2H)-carboxylate (0.3 g, 0.879 mmol) was stirred in 4M HCl in dioxane at rt overnight. The mixture was directly concentrated on a rotary evaporator and dried to give 3-methyl-5-(4-(1,2,3,6-tetrahydropyridin-4-yl)phenyl)-1,2,4-oxadiazole hydrochloride (0.16 g, 0.663 mmol, 75% yield). This material was used without a further purification. LCMS: 242.10 [M+H]$^+$.

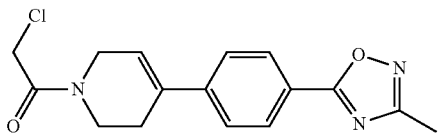

Step 3: 2-Chloro-1-(4-(4-(3-methyl-1,2,4-oxadiazol-5-yl)phenyl)-3,6-dihydropyridin-1(2H)-yl)ethan-1-one To a suspension of 3-methyl-5-(4-(1,2,3,6-tetrahydropyridin-4-yl)phenyl)-1,2,4-oxadiazole hydrochloride (0.16 g, 0.663 mmol) in DCM (6.63 mL) at 0° C. neat triethylamine (0.277 mL, 1.989 mmol) was added. After stirring at 0° C. for 10 mins, solid chloroacetic anhydride (0.113 g, 0.663 mmol) was added in one portion. The mixture was allowed to stir at 0° C. for 1 h. Upon completion, the mixture was diluted with DCM, washed with water and brine, dried over sodium sulfate and concentrated to afford crude 2-chloro-1-(4-(4-(3-methyl-1,2,4-oxadiazol-5-yl)phenyl)-5,6-dihydropyridin-1(2H)-yl)ethanone that was used without a further purification. LCMS: 318.00 [M+H]$^+$.

Intermediate 49

2-Chloro-1-(4-(5-(1-methyl-1H-1,2,4-triazol-3-yl)pyridin-2-yl)piperazin-1-yl)ethan-1-one

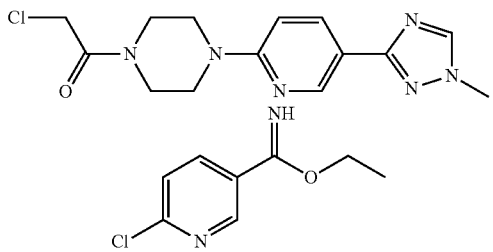

Step 1: Ethyl 6-chloronicotinimidate

To a stirred solution of 6-chloronicotinonitrile (50 g, 362.3 mmol) suspended in absolute ethanol (800 mL) at 0° C. was bubbled HCl gas (generated from NaCl and $H_2SO_4$) initially vigorously for 1 h and then slowly for 5 h. The solution was allowed to stir overnight at rt. The solvent was concentrated. The solid obtained was washed with ether (300 mL) and dried to afford ethyl 6-chloronicotinimidate (50 g, 271 mmol, 75% yield) as an off white solid. $^1$H NMR (300 MHz, CDCl$_3$) δ 8.91 (d, J=2.7 Hz, 1H), 8.31 (d, J=2.4 Hz, 1H), 7.69 (d, J=8.7 Hz, 1H), 4.43-4.26 (m, 2H), 1.32 (s, 3H). LCMS: 185.6 [M+H]$^+$.

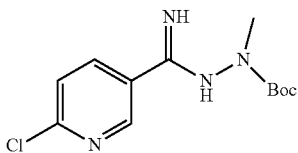 [SMILES: CN(NC(=N)c1ccc(Cl)nc1)C(=O)OC(C)(C)C]

Step 2: tert-Butyl 2-((6-chloropyridin-3-yl)(imino)methyl)-1-methylhydrazinecarboxylate To a solution of ethyl 6-chloronicotinimidate (15 g, 81.5 mmol) in pyridine (150 mL) was added t-butyl 1-methylhydrazinecarboxylate (11.5 mL, 81.5.0 mmol) at rt. The mixture was stirred for 16 h, and the solvent was concentrated under reduced pressure. The obtained gummy liquid was triturated with diethyl ether (200 mL) to afford a solid which was filtered, further washed diethyl ether (100 mL) and dried to afford tert-butyl 2-((6-chloropyridin-3-yl)(imino)methyl)-1-methylhydrazinecarboxylate (14 g, 49.3 mmol, 60% yield). $^1$H NMR (300 MHz, DMSO-d$_6$) δ 12.07 (s, 1H), 10.0-10.01 (m, 1H), 10.02-10.04 (m, 1H), 8.09 (s, 1H), 3.01 (s, 3H), 1.04 (s, 9H). LCMS: 284.03 [M+H]$^+$.

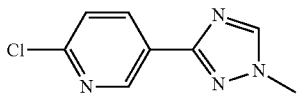

Step 3: 2-Chloro-5-(1-methyl-1H-1,2,4-triazol-3-yl)pyridine

To a tert-butyl 2-((6-chloropyridin-3-yl)(imino)methyl)-1-methylhydrazinecarboxylate (30 g, 105.6 mmol) was added formic acid (350 mL) at rt. The mixture was refluxed for 16 h, and the mixture was concentrated. The residue was treated with saturated aqueous sodium bicarbonate solution and extracted with ethyl acetate (3×500 mL). The combined organic layers were washed with brine (2×150 mL), dried and concentrated to give a solid which was further washed with ether (300 mL) and dried to afford 2-chloro-5-(1-methyl-1H-1,2,4-triazol-3-yl)pyridine (8 g, 41.2 mmol, 41% yield). $^1$H NMR (300 MHz, DMSO-d$_6$) 8.08 (s, 1H), 8.06-8.04 (m, 1H), 8.01-8.02 (m, 1H), 8.09 (s, 1H), 3.72 (s, 3H). LCMS: 194.18 [M+H]$^+$.

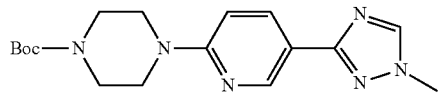

Step 4: tert-Butyl 4-(5-(1-methyl-1H-1,2,4-triazol-3-yl)pyridin-2-yl)piperazine-1-carboxylate A mixture of 2-chloro-5-(1-methyl-1H-1,2,4-triazol-3-yl)pyridine (4 g, 20.61 mmol) and tert-butyl piperazine-1-carboxylate (7.6 g, 41. mmol) in NMP (20 mL) was heated in a sealed tube for 36 h. The mixture was cooled to rt and cold water was added. The mixture was extracted with ethyl acetate (3×500 mL). The combined organic layers were washed with water (2×250 mL) and brine (1×100 mL), dried over sodium sulfate, filtered and concentrated. The residue was purified by column chromatography (100-200 silica) using 2% methanol in dichloromethane as eluent to afford tert-butyl 4-(5-(1-methyl-1H-1,2,4-triazol-3-yl)pyridin-2-yl)piperazine-1-carboxylate (2.8 g, 8.1 mmol, 40% yield). $^1$H NMR (300 MHz, DMSO-d$_6$) δ 8.68 (d, J=1.8 Hz, 1H), 8.40 (s, 1H), 8.05 (dd, J=2.1, Hz, 1H), 6.91 (d, J=9.3 Hz, 1H), 3.86 (s, 3H), 3.54 (d, J=3 Hz, 2H), 3.48 (s, 3H), 3.42 (d, J=5.4 Hz, 2H). LCMS: 344.02 [M+H]$^+$.

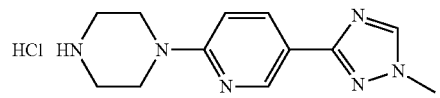

Step 5: 1-(5-(1-methyl-1H-1,2,4-triazol-3-yl)pyridin-2-yl)piperazine hydrochloride To tert-butyl 4-(5-(1-methyl-H-1,2,4-triazol-3-yl)pyridin-2-yl)piperazine-1-carboxylate (1.5 g, 4.36 mmol) in 1,4-dioxane (10 mL) was added 4M HCl:1,4-dioxane (6 mL). The mixture was stirred at rt for 2 h. The mixture was concentrated and triturated with diethyl ether (20 mL) to afford 1-(5-(1-methyl-H-1,2,4-triazol-3-yl)pyridin-2-yl)piperazine hydrochloride (1 g, 3.57 mmol, 83% yield) as an off white solid. The crude was used for the next step without a further purification. $^1$H NMR (300 MHz, DMSO-d$_6$) δ 9.652 (br s, 1H), 8.68 (s, 1H), 8.61 (d, J=2.1, Hz, 1H), 8.32 (dd, J=2.1 Hz, 1H), 7.29 (d, J=9 Hz, 1H), 3.91 (m, 4H), 3.93 (s, 3H), 3.234 (br s, 4H). LCMS: 245.15 [M+H]$^+$.

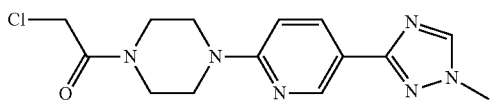

Step 6: 2-Chloro-1-(4-(5-(1-methyl-1H-1,2,4-triazol-3-yl)pyridin-2-yl)piperazin-1-yl)ethanone To a stirred solution of 1-(5-(1-methyl-1H-1,2,4-triazol-3-yl)pyridin-2-yl)piperazine hydrochloride (0.8 g, 3.26 mmol) in dichloromethane (10 mL) was added triethylamine (3 mL, 22.08. mmol) followed by chloroacetyl chloride (3 mL, 9.79 mmol) at 0° C. The mixture was stirred at 0° C. for 1 h. The mixture was diluted with water (50 mL) and extracted with dichloromethane (3×100 mL). The combined organic layers were washed with brine (100 mL), dried over sodium sulphate, filtered and concentrated under reduced pressure. The residue was purified by column chromatography (100-200 silica) using 2% methanol in dichloromethane as eluent to afford 2-chloro-1-(4-(5-(1-methyl-1H-1,2,4-triazol-3-yl)pyridin-2-yl)piperazin-1-yl)ethanone (0.400 g, 1.25 mmol, 43% yield) as an off white solid. $^1$H NMR (300 MHz, DMSO-$d_6$) δ 8.88 (s, 1H), 8.18-8.17 (d, J=1.8, Hz, 1H), 8.09 (s, 1H), 6.73-6.70 (d, J=9 Hz, 1H), 4.13 (s, 4H), 3.96 (s, 3H), 3.77-3.76 (d, 5.1 Hz, 4H), 3.66-3.62 (m, 2H).

Intermediate 50

2-Chloro-1-(4-(4-(1-ethyl-1H-1,2,4-triazol-3-yl)phenyl)-3,6-dihydropyridin-1(2H)-yl)ethan-1-one

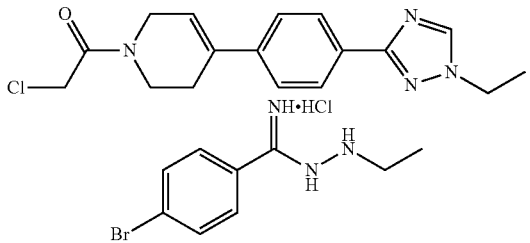

Step 1: 4-Bromo-N'-ethylbenzimidohydrazide Hydrochloride

To a solution of ethyl 4-bromobenzimidate hydrochloride (1 g, 3.82 mmol) in pyridine (15 mL) was added ethyl hydrazine oxalate (687 mg, 4.58 mmol) at rt. The mixture was stirred for 16 h, and solvent was concentrated under reduced pressure to afford a gummy liquid. This gummy material was triturated with diethyl ether (100 mL) to afford a solid which was filtered, further washed diethyl ether (50 mL) and dried to afford 4-bromo-N'-ethylbenzimidohydrazide hydrochloride (0.9 g, 3.24 mmol, 85% yield). LCMS: 244.04 [M+H]$^+$.

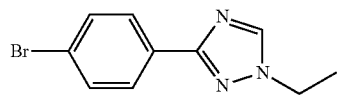

Step 2: 3-(4-Bromophenyl)-1-ethyl-1H-1,2,4-triazole

To a 4-bromo-N'-ethylbenzimidohydrazide hydrochloride (7 g, 29.04 mmol) was added formic acid (70 mL) at rt and refluxed for 16 h. The mixture was concentrated. The residue was treated with saturated aqueous sodium bicarbonate solution and extracted with ethyl acetate (3×100 mL). The combined organic layers were washed with brine (2×50 mL), dried and concentrated to give a solid which was further washed with ether (150 mL) and dried to afford 3-(4-bromophenyl)-1-ethyl-1H-1,2,4-triazole (1.5 g, 5.97 mmol, 23% yield) as an off white solid. $^1$H NMR (400 MHz, CDCl$_3$) δ 8.07 (s, 1H), 8.00-7.95 (m, 2H), 7.60-7.54 (m, 2H), 4.25 (q, J=7.3 Hz, 2H), 1.57 (t, J=7.3 Hz, 3H). LCMS: 252.10 [M+H]$^+$.

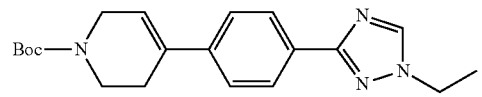

Step 3: tert-Butyl 4-(4-(1-ethyl-1H-1,2,4-triazol-3-yl)phenyl)-5,6-dihydropyridine-1(2H)-carboxylate To a stirred and degassed solution of 3-(4-bromophenyl)-1-methyl-1H-1,2,4-triazole (1 g, 3.91 mmol) and tert-butyl 4-(4,4,5,5-tetramethyl-1,3,2-dioxaborolan-2-yl)-5,6-dihydropyridine-1(2H)-carboxylate (1.35 g, 4.38 mmol) in 1,2-dimethoxy ethane:water (5:1, 60 mL) was added potassium carbonate (1.61 g, 11.73 mmol). The mixture was degassed for 10 mins. [1,1'-bis(diphenylphosphino)ferrocene]dichloropalladium(II) DCM complex (0.16 g, 0.195 mmol) was added. The mixture was degassed for 10 mins followed by refluxing for 16 h. The mixture was cooled to rt and filtered through a Celite pad. To the filtrate was added cold water, and the mixture was extracted with ethyl acetate (3×40 mL). The combined organic layers were washed with water (2×20 mL) and brine (1×20 mL), dried over sodium sulfate, and concentrated. The residue was purified by column chromatography (100-200 silica) using 3% methanol in dichloromethane as eluent to afford tert-butyl 4-(4-(1-ethyl-1H-1,2,4-triazol-3-yl)phenyl)-5,6-dihydropyridine-1(2H)-carboxylate (0.6 g, 1.69 mmol, 43% yield). $^1$H NMR (400 MHz, DMSO-$d_6$) δ 8.55 (s, 1H), 7.96 (d, J=8.3 Hz, 2H), 7.53 (d, J=7.8 Hz, 2H), 6.24 (br s, 1H), 4.24 (q, J=7.2 Hz, 2H), 4.02 (br s, 2H), 3.55 (br t, J=5.6 Hz, 2H), 1.48-1.39 (m, 12H). LCMS: 354.91 [M+H]$^+$.

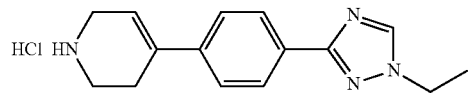 [SMILES: Cl ; CCn1cnc(-c2ccc(C3=CCNCC3)cc2)n1]

Step 4: 4-(4-(1-Ethyl-1H-1,2,4-triazol-3-yl)phenyl)-1,2,3,6-tetrahydropyridine hydrochloride To tert-butyl 4-(4-(1-ethyl-1H-1,2,4-triazol-3-yl)phenyl)-5,6-dihydropyridine-1(2H)-carboxylate (500 mg, 1.41 mmol) in 1,4-dioxane (10 mL) was added 4M HCl: 1,4-dioxane (5 mL). The mixture was stirred at rt for 2 h. The mixture was concentrated and triturated with diethyl ether (50 mL) to afford 4-(4-(1-ethyl-1H-1,2,4-triazol-3-yl)phenyl)-1,2,3,6-tetrahydropyridine hydrochloride (0.3 g, 1.03 mmol, 75% yield) as an off white solid. The crude was used for next step without a further purification. $^1$H NMR (400 MHz, DMSO-d$_6$) δ 8.97 (br s, 2H), 8.58 (s, 1H), 8.00 (d, J=8.3 Hz, 2H), 7.58 (d, J=8.3 Hz, 2H), 6.29 (br s, 1H), 4.25 (q, J=7.3 Hz, 2H), 3.78 (br s, 2H), 3.34 (br s, 2H), 2.72 (br s, 2H), 1.44 (t, J=7.1 Hz, 3H). LCMS: 255.56 [M+H]$^+$.

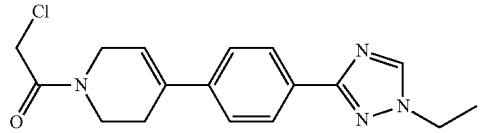 [SMILES: CCn1cnc(-c2ccc(C3=CCN(C(=O)CCl)CC3)cc2)n1]

Step 5: 2-Chloro-1-(4-(4-(1-ethyl-1H-1,2,4-triazol-3-yl)phenyl)-5,6-dihydropyridin-1(2H)-yl)ethanone To a stirred solution of 4-(4-(1-ethyl-1H-1,2,4-triazol-3-yl)phenyl)-1,2,3,6-tetrahydropyridine hydrochloride (0.3 g, 1.03 mmol) in dichloromethane (10 mL) was added triethylamine (0.8 mL, 6.20 mmol) followed by chloroacetyl chloride (0.2 mL, 3.11 mmol) at 0° C. The mixture was stirred at 0° C. for 1 h. The mixture was diluted with water (30 mL) and extracted with dichloromethane (3×20 mL). The combined organic layers were washed with brine (20 mL), dried over sodium sulfate, filtered and concentrated. The residue was purified by column chromatography (100-200 silica) using 5% methanol in dichloromethane as eluent to afford 2-chloro-1-(4-(4-(1-ethyl-1H-1,2,4-triazol-3-yl)phenyl)-5,6-dihydropyridin-1(2H)-yl)ethanone (150 mg, 4.54 mmol, 50% yield) as a pale brown solid. LCMS: 331.34 [M+H]$^+$.

Intermediate 51

2-Chloro-1-(4-(4-(1-(2-hydroxyethyl)-1H-1,2,4-triazol-3-yl)phenyl)-3,6-dihydropyridin-1(2H)-yl)ethan-1-one

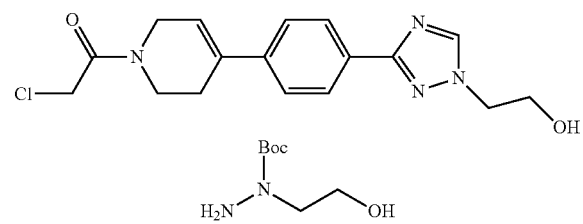

Step 1: tert-Butyl 1-(2-hydroxyethyl)hydrazinecarboxylate

To a solution of 2-hydrazinylethanol (3 g, 39.47 mmol) in ethanol (30 mL) was added di-tert-butyl dicarbonate (7.7 mL, 33.52 mmol) at 0° C. The mixture was stirred at rt for 16 h. The solvent was concentrated under reduced pressure to afford tert-butyl 1-(2-hydroxyethyl)hydrazinecarboxylate (5 g, 28.4 mmol, 72% yield) as an oily liquid. $^1$H NMR (300 MHz, DMSO-d$_6$) δ 4.53 (t, J=5.9 Hz, 1H), 4.39 (s, 2H), 3.53-3.45 (m, 2H), 3.31-3.25 (m, 2H), 1.42-1.37 (m, 9H).

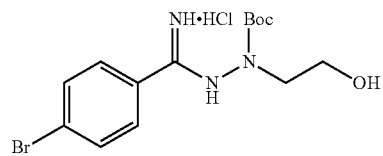

Step 2: tert-butyl 2-((4-bromophenyl)(imino)methyl)-1-(2-hydroxyethyl)hydrazine carboxylate hydrochloride To a solution of ethyl 4-bromobenzimidate hydrochloride (2 g, 7.63 mmol) in pyridine (20 mL) was added tert-butyl 1-(2-hydroxyethyl)hydrazinecarboxylate (1.6 mg, 4.58 mmol) at rt, and the mixture was stirred for 16 h. The solvent was concentrated under reduced pressure. The obtained gummy liquid was triturated with diethyl ether (100 mL) to afford a solid which was filtered, further washed diethyl ether (50 mL) and dried to afford tert-butyl 2-((4-bromophenyl)(imino)methyl)-1-(2-hydroxyethyl)hydrazinecarboxylate hydrochloride (1.3 g, 3.30 mmol, 44% yield) as gummy solid. LCMS: 358.15 [M+H]$^+$.

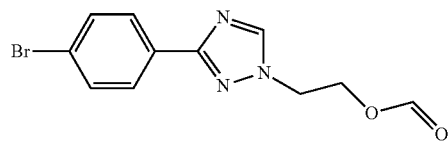 [SMILES: O=COCCn1cnc(-c2ccc(Br)cc2)n1]

Step 3: 2-(3-(4-Bromophenyl)-1H-1,2,4-triazol-1-yl) ethyl formate

To a tert-butyl 2-((4-bromophenyl)(imino)methyl)-1-(2-hydroxyethyl)hydrazinecarboxylate hydrochloride (0.8 g, 2.24 mmol) was added formic acid (8 mL) at rt, and the mixture was refluxed for 16 h. The mixture was concentrated. The residue was treated with saturated aqueous sodium bicarbonate solution and extracted with ethylacetate (3×100 mL). The combined organic layers were washed with brine (2×50 mL), dried and concentrated to afford 2-(3-(4-bromophenyl)-1H-1,2,4-triazol-1-yl)ethyl format as an off white solid. The crude material was used for the next step without a further purification.

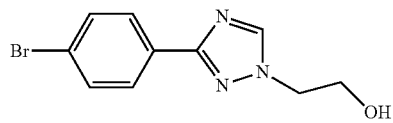 [SMILES: OCCn1cnc(-c2ccc(Br)cc2)n1]

Step 4: 2-(3-(4-Bromophenyl)-1H-1,2,4-triazol-1-yl) ethanol

To a 2-(3-(4-bromophenyl)-1H-1,2,4-triazol-1-yl)ethyl formate (0.6 g, 2.03 mmol) was added 6N HCl (8 mL) at 0° C. The mixture was stirred at rt for 2 h. The mixture was concentrated and the residue was washed with ether (150 mL) and dried to afford 2-(3-(4-bromophenyl)-1H-1,2,4-triazol-1-yl)ethanol (0.4 g, 1.49 mmol, 70% yield) as an off white solid. $^1$H NMR (300 MHz, DMSO-d$_6$) δ 8.52 (s, 1H), 7.92 (d, J=8.8 Hz, 2H), 7.65 (d, J=8.4 Hz, 2H), 4.98 (t, J=5.3 Hz, 1H), 4.24 (t, J=5.3 Hz, 2H), 3.76 (q, J=5.1 Hz, 2H). LCMS: 268.11 [M+H]+.

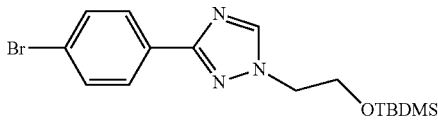 [SMILES: CC(C)(C)[Si](C)(C)OCCn1cnc(-c2ccc(Br)cc2)n1]

Step 5: 3-(4-Bromophenyl)-1-(2-(tert-butyldimethylsilyloxy)ethyl)-1H-1,2,4-triazole To a 2-(3-(4-bromophenyl)-1H-1,2,4-triazol-1-yl)ethanol (2 g, 7.49 mmol) in dichloromethane (20 mL) was added tert-butylchlorodimethylsilane (1.7 g, 11.23 mmol), imidazole (1.3 g, 18.72 mmol) and DMAP (80 mg, 0.74 mmol) at 0° C. The mixture was stirred at rt for 16 h. The reaction was quenched with cold water, and the mixture was extracted with ethyl acetate (3×40 mL). The combined organic layers were washed with water (2×20 mL) and brine (2×20 mL), dried over sodium sulphate, filtered and concentrated. The residue was purified by column chromatography (100-200 silica) using 50% ethyl acetate in hexane as eluent to afford 3-(4-bromophenyl)-1-(2-(tert-butyldimethylsilyloxy)ethyl)-1H-1,2,4-triazole (1.8 g, 4.72 mmol, 64% yield) as an off white solid. LCMS: 382.25 [M+H]+.

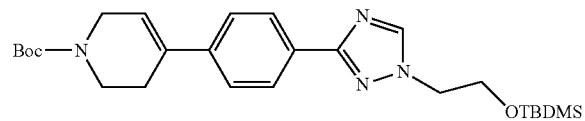 [SMILES: CC(C)(C)OC(=O)N1CC=C(c2ccc(-c3ncn(CCO[Si](C)(C)C(C)(C)C)n3)cc2)CC1]

Step 6: tert-Butyl 4-(4-(1-(2-(tert-butyldimethylsilyloxy)ethyl)-1H-1,2,4-triazol-3-yl)phenyl)-5,6-dihydropyridine-1(2H)-carboxylate To a stirred and degassed solution of 3-(4-bromophenyl)-1-(2-(tert-butyldimethylsilyloxy)ethyl)-1H-1,2,4-triazole (2 g, 5.24 mmol) and tert-butyl 4-(4,4,5,5-tetramethyl-1,3,2-dioxaborolan-2-yl)-5,6-dihydropyridine-1(2H)-carboxylate (1.94 g, 6.29 mmol) in 1,4-dioxane:water (5:1, 60 mL) was added sodium carbonate (2.1 g, 15.72 mmol). The mixture was degassed for 10 mins. [1,1'-bis(diphenylphosphino)ferrocene]dichloropalladium(II) DCM complex (0.213 g, 0.262 mmol) was added. The mixture was degassed for 10 mins followed by refluxing for 4 h. The mixture was cooled to rt and filtered through a Celite pad. To the filtrate was added cold water, and the mixture extracted with ethyl acetate (3×40 mL). The combined organic layers were washed with water (2×20 mL) and brine (2×20 mL), dried over sodium sulphate and concentrated. The residue was purified by column chromatography (100-200 silica) using 4% methanol in dichloromethane as eluent to afford tert-butyl 4-(4-(1-(2-(tert-butyldimethylsilyloxy)ethyl)-1H-1,2,4-triazol-3-yl)phenyl)-5,6-dihydropyridine-1 (2H)-carboxylate (1.5 g, 3.10 mmol, 60% yield) as an off white solid. LCMS: 484.99 [M+H]+.

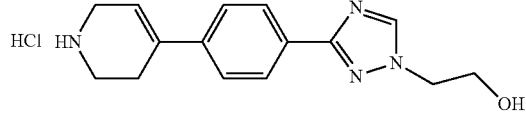 [SMILES: Cl ; OCCn1cnc(-c2ccc(C3=CCNCC3)cc2)n1]

Step 7: 2-(3-(4-(1,2,3,6-Tetrahydropyridin-4-yl)phenyl)-1H-1,2,4-triazol-1-yl)ethanol hydrochloride To tert-butyl 4-(4-(1-(2-(tert-butyldimethylsilyloxy)ethyl)-1H-1,2,4-triazol-3-yl)phenyl)-5,6-dihydropyridine-1 (2H)-carboxylate (1.7 g, 5.55 mmol) in 1,4-dioxane (10 mL) was added 4M HCl:1,4-dioxane (10 mL). The mixture was stirred at rt for 2 h. The mixture was concentrated and triturated with diethyl ether (100 mL) to afford 2-(3-(4-(1,2,3,6-tetrahydropyridin-4-yl)phenyl)-1H-1,2,4-triazol-1-yl)ethanol hydrochloride (0.9 g, 2.94 mmol, 90% yield) as an off white solid. LCMS: 271.18 [M+H]+.

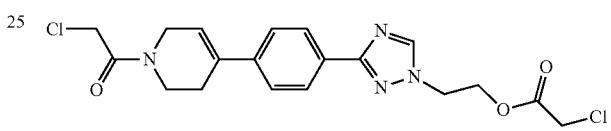

Step 8: 2-(3-(4-(1-(2-Chloroacetyl)-1,2,3,6-tetrahydropyridin-4-yl)phenyl)-1H-1,2,4-triazol-1-yl)ethyl 2-chloroacetate To a stirred solution of 2-(3-(4-(1,2,3,6-tetrahydropyridin-4-yl)phenyl)-1H-1,2,4-triazol-1-yl)ethanol hydrochloride (1 g, 3.26 mmol) in dichloromethane (10 mL) was added triethylamine (2.63 mL, 19.56 mmol) followed by chloroacetyl chloride (0.73 mL, 9.08 mmol) at 0° C. The mixture stirred at 0° C. for 1 h. The mixture was diluted with water (30 mL) and extracted with dichloromethane (3×20 mL). The combined organic layers were washed with brine (30 mL), dried over sodium sulphate, filtered and concentrated. The residue was purified by column chromatography (100-200 silica) using 5% methanol in dichloromethane as eluent to afford 2-(3-(4-(1-(2-chloroacetyl)-1,2,3,6-tetrahydropyridin-4-yl)phenyl)-1H-1,2,4-triazol-1-yl)ethyl 2-chloroacetate (900 mg, 2.13 mmol, 65% yield) as an off-white solid. $^1$H NMR (300 MHz, DMSO-$d_6$) δ 8.60 (s, 1H), 7.98 (d, J=8.4 Hz, 2H), 7.55 (br d, J=8.1 Hz, 2H), 6.29 (br s, 1H), 4.53 (s, 4H), 4.49-4.43 (m, 3H), 4.38 (s, 2H), 4.18 (br d, J=19.1 Hz, 2H), 3.75-3.64 (m, 2H), 2.62 (br s, 1H). LCMS: 423.16 [M+H]+.

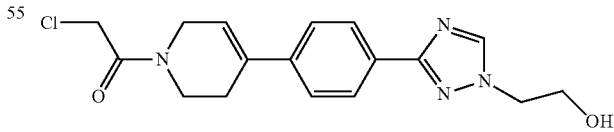

Step 9: 2-Chloro-1-(4-(4-(1-(2-hydroxyethyl)-1H-1,2,4-triazol-3-yl)phenyl)-5,6-dihydropyridin-1(2H)-yl)ethanone To a solution of 2-(3-(4-(1-(2-chloroacetyl)-1,2,3,6-tetrahydropyridin-4-yl)phenyl)-1H-1,2,4-triazol-1-yl)ethyl 2-chloroacetate (0.9 g, 2.13 mmol) in mixture of THF: MeOH:H$_2$O (1:1:1, 15 mL) was added lithium hydroxide (268 mg, 6.40 mmol) at 0° C. The mixture stirred at rt for 2 h. The mixture was diluted with water (30 mL) and extracted with dichloromethane (3×20 mL). The combined organic layers were washed with brine (20 mL), dried over sodium sulphate, filtered and concentrated. The residue was purified by column chromatography (100-200 silica) using 5% methanol in dichloromethane as eluent to afford to 2-chloro-1-(4-(4-(1-(2-hydroxyethyl)-1H-1,2,4-triazol-3-yl) phenyl)-5,6-dihydropyridin-1(2H)-yl)ethanone (0.6 g, 1.73 mmol, 82% yield) as off-white solid. LCMS: 347.22 [M+H]$^+$.

Intermediate 52

2-Chloro-1-(4-(4-(1-(2-methoxyethyl)-1H-1,2,4-triazol-3-yl)phenyl)-3,6-dihydropyridin-1(2H)-yl) ethan-1-one

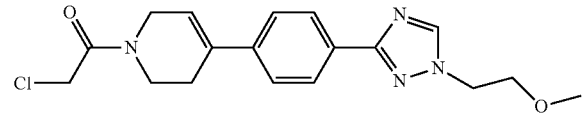 [SMILES: COCCn1cnc(-c2ccc(C3=CCN(C(=O)CCl)CC3)cc2)n1]

To a solution of 2-(3-(4-(1-(2-chloroacetyl)-1,2,3,6-tetrahydropyridin-4-yl)phenyl)-1H-1,2,4-triazol-1-yl)ethyl 2-chloroacetate (0.4 g, 2.17 mmol) in DMF (10 mL) was added sodium hydride (260 mg, 10.83 mmol) and methyl iodide (0.2 mL, 3.25 mmol) at 0° C. The mixture was stirred at rt for 16 h. The mixture was diluted with water (20 mL) and extracted with dichloromethane (2×20 mL). The combined organic layers were washed with brine (20 mL), dried over sodium sulphate, filtered and concentrated. The residue was purified by column chromatography (100-200 silica) using 5% methanol in dichloromethane as eluent to afford to afford 2-chloro-1-(4-(4-(1-(2-methoxyethyl)-1H-1,2,4-triazol-3-yl)phenyl)-5,6-dihydropyridin-1(2H)-yl)ethanone (0.2 g, 0.55 mmol, 50% yield) as a pale green colored solid. $^1$H NMR (300 MHz, DMSO-d$_6$) δ 8.52 (s, 1H), 7.97 (d, J=8.4 Hz, 2H), 7.59-7.50 (m, 2H), 6.29 (br s, 1H), 4.49-4.43 (m, 2H), 4.39 (t, J=5.1 Hz, 2H), 4.18 (br d, J=17.6 Hz, 2H), 3.77-3.66 (m, 4H), 3.25 (s, 3H), 2.62 (br s, 1H). LCMS: 361.34 [M+H]$^+$.

Intermediate 53

2-Chloro-1-(4-(4-(1-cyclopropyl-1H-1,2,4-triazol-3-yl)phenyl)-3,6-dihydropyridin-1(2H)-yl)ethan-1-one

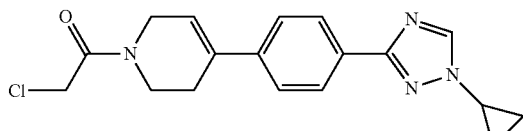

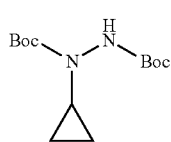

Step 1: Di-tert-butyl 1-cyclopropylhydrazine-1,2-dicarboxylate

To a stirred solution of di-tert-butyl diazene-1,2-dicarboxylate (30 g, 0.131 mol) in DMF (300 mL), was added cyclopropylboronic acid (22.6 g, 0.263 mol) and Cu(OAc)$_2$ (2.38 g, 0.013 mol). The mixture was heated to 85° C. for 5 h. The mixture cooled to rt, diluted with cold water (500 mL) and extracted with EtOAc (2×1000 mL). The combined organic layers were washed with brine (1000 mL), dried over Na$_2$SO$_4$, filtered and concentrated on rotary evaporator. The residue was purified by flash column chromatography (100-200 silica gel mesh) using 10-20% EtOAc/hexane as eluent to afford di-tert-butyl 1-cyclopropyl hydrazine-1,2-dicarboxylate (20 g, yield 57%) as an off white solid. $^1$H NMR (300 MHz, DMSO) δ 8.98 (bs, 0.7H), 8.87 (bs, 0.3H), 2.82-2.74 (m, 1H), 1.39-1.37 (m, 18H) 0.70-0.48 (m, 4H).

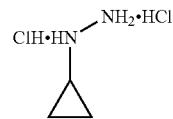

Step 2: Cyclopropylhydrazine dihydrochloride

To a stirred solution of di-tert-butyl 1-cyclopropylhydrazine-1,2-dicarboxylate (20 g, 0.073 mol) in 1,4 dioxane (40 mL) was added 4M HCl in dioxane (200 mL). The mixture was stirred for 16 h at rt. The mixture was directly concentrated on rotary evaporator and triturated with diethyl ether. The obtained crude (10 g, 99% yield) was used for next step without any further purification. $^1$H NMR (400 MHz, DMSO-d$_6$) δ 8.80 (bs, 6H), 2.65-2.59 (m, 1H), 0.61-0.53 (m, 4H).

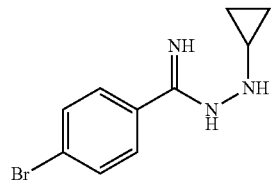 [SMILES: N=C(NNC1CC1)c1ccc(Br)cc1]

Step 3: 4-Bromo-N'-cyclopropylbenzimidohydrazide

To a solution of ethyl 4-bromobenzimidate hydrochloride (5.0 g, 0.022 mol) in pyridine (50 mL) was added cyclopropylhydrazine dihydrochloride (3.8 g, 0.026 mol). The mixture was stirred for 16 h at rt. The solvent was concentrated under reduced pressure to give gummy liquid that was triturated with diethyl ether several times to afford 4-bromo-N'-cyclopropylbenzimidohydrazide. This material was used for the next step without a further purification (4.4 g, crude 80% yield). LCMS: 254.06 [M+H]$^+$.

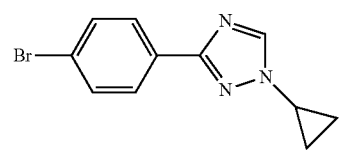

Step 4:
3-(4-Bromophenyl)-1-cyclopropyl-1H-1,2,4-triazole

To a stirred solution of 4-bromo-N'-cyclopropylbenzimidohydrazide (4.4 g, 1.9 mmol) in formic acid (50 mL), heated to reflux for 16 h. The mixture was directly concentrated on rotary evaporator. The residue was dissolved in EtOAc (300 mL) and washed with sat. NaHCO₃ (100 mL). The organic layer was dried over Na₂SO₄ and concentrated. The residue was purified by flash column chromatography (100-200 silica gel mesh) using 50-60% EtOAc/hexane as eluent to afford 3-(4-bromophenyl)-1-cyclopropyl-1H-1,2,4-triazole (250 mg, 5% yield) as an off white solid. ¹H NMR (300 MHz, CDCl₃) δ 8.12 (s, 1H), 7.96 (d, J=9.0 Hz, 2H), 7.56 (d, J=9.0 Hz, 2H), 3.67-3.59 (m, 1H), 1.22-1.12 (m, 4H). LCMS: 264.04 [M+H]⁺.

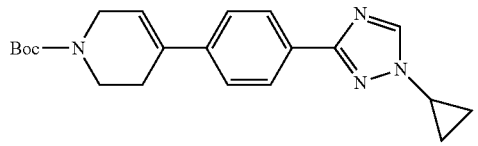 [SMILES: CC(C)(C)OC(=O)N1CC=C(c2ccc(-c3ncn(C4CC4)n3)cc2)CC1]

Step 5: tert-butyl 4-(4-(1-cyclopropyl-1H-1,2,4-triazol-3-yl)phenyl)-5,6-dihydropyridine-1(2H)-carboxylate To a stirred and degassed solution of 3-(4-bromophenyl)-1-cyclopropyl-1H-1,2,4-triazole (230 mg, 0.871 mmol) and tert-butyl 4-(4,4,5,5-tetramethyl-1,3,2-dioxaborolan-2-yl)-5,6-dihydropyridine-1(2H)-carboxylate (322.9 mg, 1.045 mmol) in 1,2-dimethoxy ethane:water (5:1, 6 mL) was added K₂CO₃ (240.3 mg, 1.742 mmol). The mixture was degassed for 10 mins. [1,1'-bis(diphenylphosphino)ferrocene]dichloropalladium (II) DCM complex (71 mg, 0.087 mmol) was added. The mixture was degassed for 10 mins followed by refluxing for 16 h. The mixture was cooled to rt, diluted with cold water (10 mL) and extracted with ethyl acetate (3×40 mL). The combined organic layers were washed with brine (20 mL), dried over sodium sulphate and concentrated. The residue was purified by column chromatography (100-200 silica) using 60-70% EtOAc/Hexane as eluent to afford tert-butyl 4-(4-(1-cyclopropyl-1H-1,2,4-triazol-3-yl)phenyl)-5,6-dihydro pyridine-1(2H)-carboxylate (190 mg, 60% yield). ¹H NMR (300 MHz, CDCl₃) δ 8.12 (s, 1H), 8.05 (d, J=8.4 Hz, 2H), 7.44 (d, J=8.4 Hz, 2H), 6.12 (br s, 1H), 4.09 (d, J=2.4 Hz, 2H), 3.69-3.60 (m, 3H), 2.60-2.52 (m, 2H), 1.49 (s, 9H), 1.29-1.10 (m, 4H). LCMS: 367.3 [M+H]⁺

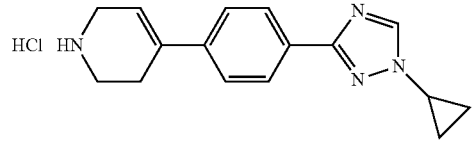 [SMILES: Cl ; C1=C(c2ccc(-c3ncn(C4CC4)n3)cc2)CCNC1]

Step 6: 4-(4-(1-cyclopropyl-1H-1,2,4-triazol-3-yl)phenyl)-1,2,3,6-tetrahydropyridine hydrochloride To a stirred solution of tert-butyl 4-(4-(1-cyclopropyl-1H-1,2,4-triazol-3-yl)phenyl)-5,6-dihydropyridine-1(2H)-carboxylate (220 mg, 0.601 mmol) in 1,4-dioxane (1 mL) was added 4M HCl in 1,4-dioxane (3 mL). The mixture was stirred at rt for 1 h. The mixture was concentrated and triturated with diethyl ether (3 mL) to afford 4-(4-(1-cyclopropyl-1H-1,2,4-triazol-3-yl)phenyl)-1,2,3,6-tetrahydropyridine hydrochloride (170 mg, 94% yield) as a pale yellow solid. ¹H NMR (300 MHz, DMSO-d₆) δ 9.26 (br s, 2H), 8.67 (s, 1H), 7.99 (d, J=8.4 Hz, 2H), 7.58 (d, J=8.4 Hz, 2H), 6.28 (br s, 1H), 3.90-3.70 (m, 3H), 3.31 (br s, 2H), 2.72 (br s, 2H), 1.19-1.02 (m, 4H).

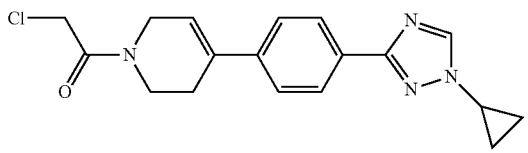 [SMILES: O=C(CCl)N1CC=C(c2ccc(-c3ncn(C4CC4)n3)cc2)CC1]

Step 7: 2-Chloro-1-(4-(4-(1-cyclopropyl-1H-1,2,4-triazol-3-yl)phenyl)-5,6-dihydropyridin-1(2H)-yl)ethanone To a stirred solution of 4-(4-(1-cyclopropyl-1H-1,2,4-triazol-3-yl)phenyl)-1,2,3,6-tetrahydropyridine hydrochloride (170 mg, 0.562 mmol) in dichloromethane (5 mL) at 0° C. was added triethylamine (0.55 mL, 3.934 mmol) followed by chloro acetyl chloride (190 mg, 1.686 mmol). The mixture was stirred at 0° C. for 1 h. The mixture was diluted with water (40 mL) and extracted with dichloromethane (3×60 mL). The combined organic layers were washed with brine (50 mL), dried over sodium sulphate and concentrated under reduced pressure. The residue was purified by flash column chromatography (silica gel 100-200 mesh) using 3% methanol/DCM as eluent to afford 2-chloro-1-(4-(4-(1-cyclopropyl-1H-1,2,4-triazol-3-yl)phenyl)-5,6-dihydropyridin-1(2H)-yl)ethanone (92 mg, 48% yield). ¹H NMR (300 MHz, DMSO-d₆) δ 8.62 (s, 1H), 7.96 (d, J=8.4 Hz, 2H), 7.54 (dd, J=8.4, 4.5 Hz, 2H), 6.28 (br s, 1H), 4.46 (d, J=7.5 Hz, 2H), 4.25-4.13 (m, 2H), 3.85-3.77 (m, 1H), 3.73-3.66 (m, 2H), 2.65-2.50 (m, 2H), 1.18-1.0 (m, 4H). LCMS: 343.2 [M+H]⁺.

Intermediate 54

(S)-2-(3-(6-Methylpyridin-3-yl)-1-trityl-1H-indazol-5-yl)-2,7-diazaspiro[4.4]nonan-1-one

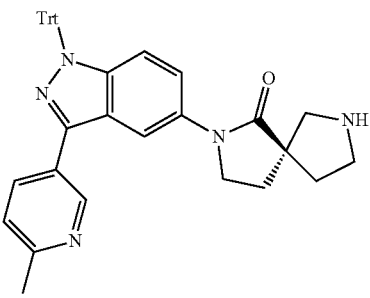

The title compound was prepared following the procedure described for Intermediate 8, using benzyl (R)-7-(3-iodo-1-trityl-1H-indazol-5-yl)-6-oxo-2,7-diazaspiro[4.4]nonane-2- carboxylate (Intermediate 7) and (6-methylpyridin-3-yl)boronic acid in Step 1. LCMS: 590.3 [M+H]+.

Intermediate 55

(S)-2-(3-(4-(Methylsulfonyl)phenyl)-1-trityl-1H-indazol-5-yl)-2,7-diazaspiro[4.4]nonan-1-one

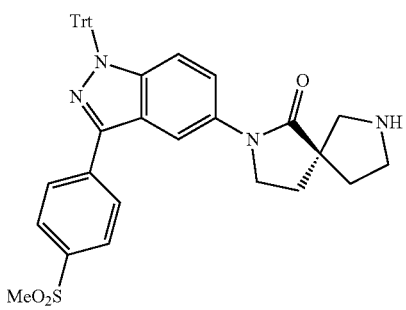

The title compound was prepared following the procedure described for Intermediate 8, using benzyl (R)-7-(3-iodo-1-trityl-1H-indazol-5-yl)-6-oxo-2,7-diazaspiro[4.4]nonane-2-carboxylate (Intermediate 7) and (4-(methylsulfonyl)phenyl)boronic acid in Step 1. LCMS: 653.20 [M+H]+.

General Procedure A: Alkylation of Secondary Amine

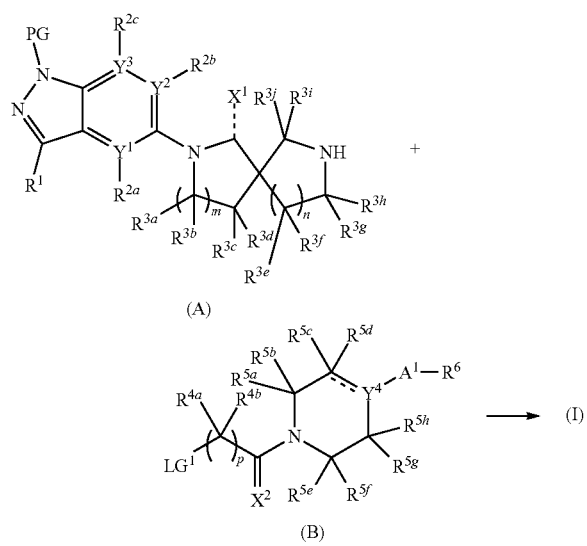

To a solution of corresponding secondary amine (A) (1 eq.) in N,N-dimethylformamide (0.1-0.5 M, initial concentration of secondary amine in DMF varied from 0.1 M to 0.5 M based on solubility) at 25° C., neat N-ethyl-N-isopropylpropan-2-amine (3-6 eq., excess N-ethyl-N-isopropylpropan-2-amine was used or N-ethyl-N-isopropylpropan-2-amine was replaced for trimethylamine) was added followed by an addition of a corresponding alkylating agent (B) (1.0-1.1 eq., preferably 1 eq. of alkylating agent was used in order to minimize over alkylation) in one portion. The mixture was stirred at rt for 6-24 h (if desired, the mixture was heated at 50° C.). Upon completion as determined by LCMS, the mixture was either, 1) concentrated directly on a rotary evaporator to give the crude mixture that was used for the next step without a further purification, or 2) purified on a silica gel column eluted with methanol in dichloromethane or purified on a RP-C18 column eluted with acetonitrile in water in the presence of 0.1% formic acid to afford the desired compound of Formula (I).

General Procedure B: Deprotection of Indazole

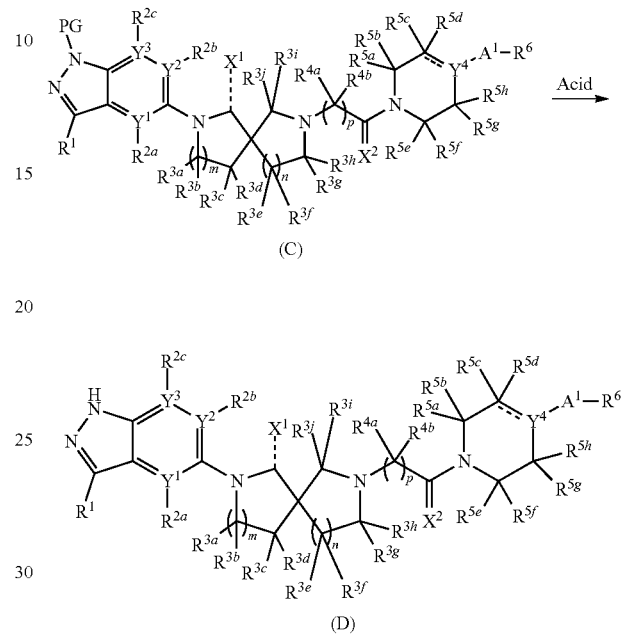

A solution of protected indazole (trityl or THP) (C) (1 eq.) in dichloromethane:trifluoroacetic acid:water (3:1:0.5, 0.05 or 0.5 M, conditions varied based on solubility of staring material and a mixture of dichloromethane/trifluroacetic acid was used in some preparations) was stirred at 25° C. overnight. Upon completion as determined by LCMS, the reaction was quenched with saturated aqueous sodium bicarbonate and extracted with dichloromethane (or extracted with ethyl acetate or ethyl acetate/tetrahydrofuran mixtures). The combined organic layers were dried over sodium sulfate, filtered and concentrated to afford the crude product (D). Crude product (D) was then purified either 1) on a silica gel column eluted with 0-100% (0-10% 7M ammonia in methanol):dichloromethane or 2) purified on a RP-C18 column eluted with 0-100% acetonitrile:water in the presence of 0.1% formic acid to afford the pure compound (D) (when crude material was purified on RP-C18 HPLC column (or C-18 cartridges), compounds were free-based using aqueous saturated aqueous sodium bicarbonate and extracted with either dichloromethane, ethyl acetate or ethyl acetate:THF mixtures).

General Procedure C: Preparation of Hydrochloride Salt

Compound (D) was dissolved in a suitable solvent (0.1-0.5 M, dichloromethane, methanol or i-propyl alcohol, and in some cases, about 10% methanol was added prior to hydrochloric acid addition) and cooled to 0° C. Hydrochloric acid (1-3 eq., 2.0 M in diethyl ether) was added via a syringe. The precipitate was stirred for 5-10 mins at 0° C. Excess solvent(s) and hydrochloric acid were removed using a rotary evaporator at 0° C. The product was dried to afford the corresponding hydrochloric acid salt (equivalence of hydrochloride salt was determined by $^1$H NMR analysis).

Example 1

2-(3-(6-Isopropoxypyridin-3-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

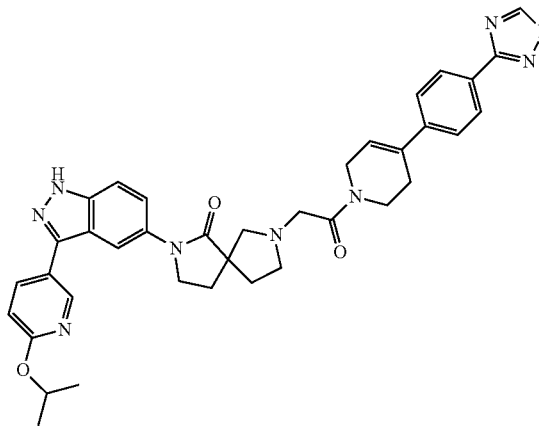

The title compound was prepared following General Procedures A and C using 2-(3-(6-isopropoxypyridin-3-yl)-1H-indazol-5-yl)-2,7-diazaspiro[4.4]nonan-1-one (Intermediate 4) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-$d_6$, 80° C.; HCl salt) δ 13.09 (s, 1H), 10.17 (s, 0.5H), 8.74 (dd, J=2.5, 0.8 Hz, 1H), 8.45 (s, 1H), 8.22 (dd, J=8.6, 2.5 Hz, 1H), 8.18 (s, 1H), 8.00-7.98 (m, 2H), 7.74 (dd, J=9.0, 1.9 Hz, 1H), 7.61 (d, J=9.0 Hz, 1H), 7.55 (d, J=8.3 Hz, 2H), 6.90 (dd, J=8.6, 0.8 Hz, 1H), 6.28 (s, 1H), 5.35 (p, J=6.2 Hz, 1H), 4.21 (s, 2H), 3.93 (s, 6H), 3.74-3.68 (m, 3H), 3.32-3.21 (m, 3H), 2.64-2.57 (m, 3H), 2.33-2.22 (m, 3H), 2.14-2.05 (m, 1H), 1.36 (d, J=6.1 Hz, 6H). LCMS: 672.3 [M+H]$^+$.

Example 2

2-(7-(3-(6-Isopropoxypyridin-3-yl)-1H-indazol-5-yl)-2,7-diazaspiro[4.4]nonan-2-yl)-1-(4-(4-(1-methyl-1H-1,2,4-triazol-3-yl)phenyl)piperazin-1-yl)ethan-1-one

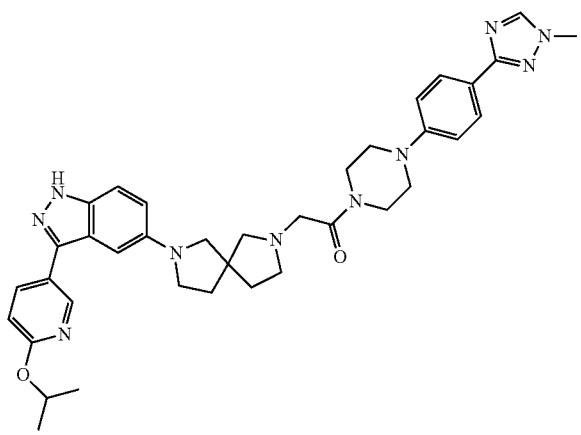 [SMILES: CC(C)Oc1ccc(-c2n[nH]c3ccc(N4CCC5(CCN(CC(=O)N6CCN(c7ccc(-c8ncn(C)n8)cc7)CC6)C5)C4)cc23)cn1]

The title compound was prepared following General Procedure A using 2-(3-(6-isopropoxypyridin-3-yl)-1H-indazol-5-yl)-2,7-diazaspiro[4.4]nonane (Intermediate 3) and 2-chloro-1-(4-(4-(1-methyl-1H-1,2,4-triazol-3-yl)phenyl)piperazin-1-yl)ethan-1-one (Intermediate 32). $^1$H NMR (400 MHz, DMSO-$d_6$) δ 12.83 (s, 1H), 8.70 (d, J=2.32 Hz, 1H), 8.42 (s, 1H), 8.19 (dd, J=8.56, 2.45 Hz, 1H), 7.83 (d, J=8.80 Hz, 2H), 7.40 (d, J=8.93 Hz, 1H), 7.01 (d, J=8.93 Hz, 2H), 6.86 (d, J=9.00 Hz, 2H), 6.80 (s, 1H), 5.26-5.35 (m, 1H), 3.88 (s, 3H), 3.72 (br s, 2H), 3.59 (br s, 2H), 3.31-3.36 (m, 5H), 3.12-3.28 (m, 5H), 2.64-2.74 (m, 2H), 2.53-2.64 (m, 2H), 1.90-2.06 (m, 2H), 1.76-1.89 (m, 2H), 1.32 (d, J=6.11 Hz, 6H). LCMS: 661.40 [M+H]$^+$.

Example 3

2-(3-(6-Isopropoxypyridin-3-yl)-1H-indazol-5-yl)-7-(2-(4-(4-(1-methyl-1H-1,2,4-triazol-3-yl)phenyl)piperazin-1-yl)-2-oxoethyl)-2,7-diazaspiro[4.4]nonan-1-one

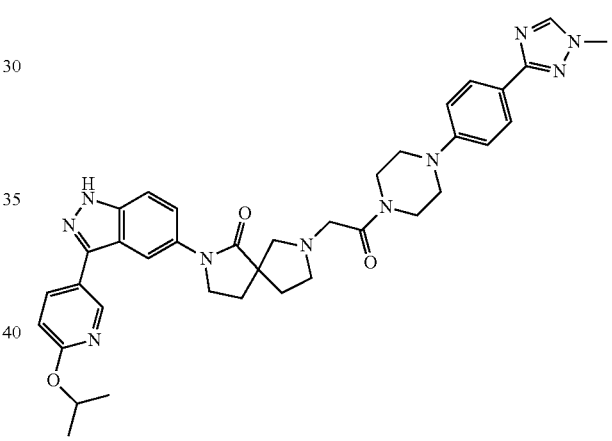

The title compound was prepared following General Procedures A and C using 2-(3-(6-isopropoxypyridin-3-yl)-1H-indazol-5-yl)-2,7-diazaspiro[4.4]nonan-1-one (Intermediate 4) and 2-chloro-1-(4-(4-(1-methyl-1H-1,2,4-triazol-3-yl)phenyl)piperazin-1-yl)ethan-1-one (Intermediate 32). $^1$H NMR (400 MHz, DMSO-$d_6$, 80° C.; HCl salt) δ 13.04 (s, 1H), 8.72 (d, J=2.5 Hz, 1H), 8.35 (s, 1H), 8.20 (dd, J=8.6, 2.5 Hz, 1H), 8.14 (d, J=1.9 Hz, 1H), 7.86-7.84 (m, 2H), 7.74 (dd, J=9.0, 2.0 Hz, 1H), 7.57 (d, J=9.0 Hz, 1H), 7.01-6.97 (m, 2H), 6.88 (d, J=8.5 Hz, 1H), 5.39-5.30 (m, 1H), 3.96-3.87 (m, 4H), 3.69 (br s, 4H), 3.39 (s, 2H), 3.27 (br s, 4H), 3.10-3.09 (2H), 2.97-2.92 (m, 1H), 2.85 (d, J=9.0 Hz, 1H), 2.74 (d, J=9.0 Hz, 1H), 2.63-2.57 (m, 1H), 2.28-2.11 (m, 2H), 1.85-1.79 (m, 1H), 1.36 (d, J=6.1 Hz, 6H). LCMS: 675.3 [M+H]$^+$.

Example 4

2-(7-(3-(6-Isopropoxypyridin-3-yl)-1H-indazol-5-yl)-2,7-diazaspiro[4.4]nonan-2-yl)-1-(4-(4-(1-methyl-1H-1,2,4-triazol-3-yl)phenyl)-3,6-dihydropyridin-1(2H)-yl)ethan-1-one

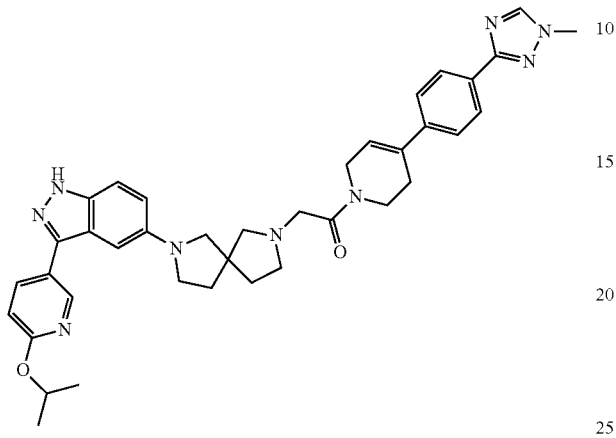

The title compound was prepared following General Procedure A using 2-(3-(6-isopropoxypyridin-3-yl)-1H-indazol-5-yl)-2,7-diazaspiro[4.4]nonane (Intermediate 3) and 2-chloro-1-(4-(4-(1-methyl-1H-1,2,4-triazol-3-yl)phenyl)-3,6-dihydropyridin-1 (2H)-yl)ethan-1-one (Intermediate 31). $^1$H NMR (400 MHz, DMSO-d$_6$, 80° C.) δ 12.63 (s, 1H), 8.70 (d, J=2.20 Hz, 1H), 8.44 (s, 1H), 8.19 (dd, J=8.68, 2.32 Hz, 1H), 7.94-7.99 (m, 2H), 7.52 (d, J=8.31 Hz, 2H), 7.41 (d, J=8.93 Hz, 1H), 6.81-6.93 (m, 3H), 6.26 (br s, 1H), 5.33 (quin, J=6.17 Hz, 1H), 4.09-4.36 (m, 2H), 3.93 (s, 3H), 3.76 (br s, 2H), 3.26-3.43 (m, 6H), 2.59-2.81 (m, 6H), 1.94-2.09 (m, 2H), 1.79-1.94 (m, 2H), 1.34 (d, J=6.12 Hz, 6H). LCMS: 658.40 [M+H]$^+$.

Example 5

7-(3-(6-Isopropoxypyridin-3-yl)-1H-indazol-5-yl)-2-(2-(4-(4-(1-methyl-1H-1,2,4-triazol-3-yl)phenyl)-3,6-dihydropyridin-1 (2H)-yl)-2-oxoethyl)-2,7-diazaspiro[4.5]decan-6-one

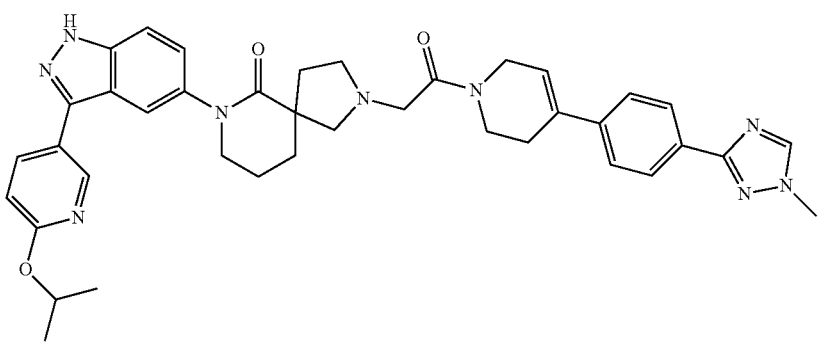 [SMILES: CC(C)Oc1ccc(-c2n[nH]c3ccc(N4CCCC5(CCN(CC(=O)N6CC=C(c7ccc(-c8ncn(C)n8)cc7)CC6)C5)C4=O)cc23)cn1]

The title compound was prepared following General Procedure A using 7-(3-(6-isopropoxypyridin-3-yl)-1H-indazol-5-yl)-2,7-diazaspiro[4.5]decan-6-one (Intermediate 12) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, CDCl$_3$) δ 11.3 (br, 1H), 8.66 (s, 1H), 8.09-8.01 (m, 4H), 7.70 (s, 1H), 7.41-7.39 (m, 2H), 7.13 (t, 1H), 6.77 (d, 1H), 6.10 (d, 1H), 5.36-5.33 (m, 1H), 4.30-4.24 (m, 1H), 3.98 (s, 3H), 3.68-3.66 (m, 6H), 3.10-3.09 (m, 2H), 2.90 (m, 1H), 2.58 (m, 3H), 2.11-2.00 (m, 8H), 1.38 (d, 6H). LCMS: 686.30 [M+H]$^+$.

Example 6

7-(2-(4-(4-(1-Methyl-1H-1,2,4-triazol-3-yl)phenyl)-3,6-dihydropyridin-1(2H)-yl)-2-oxoethyl)-2-(3-(2-methylpyridin-4-yl)-1H-indazol-5-yl)-2,7-diazaspiro[4.4]nonan-1-one

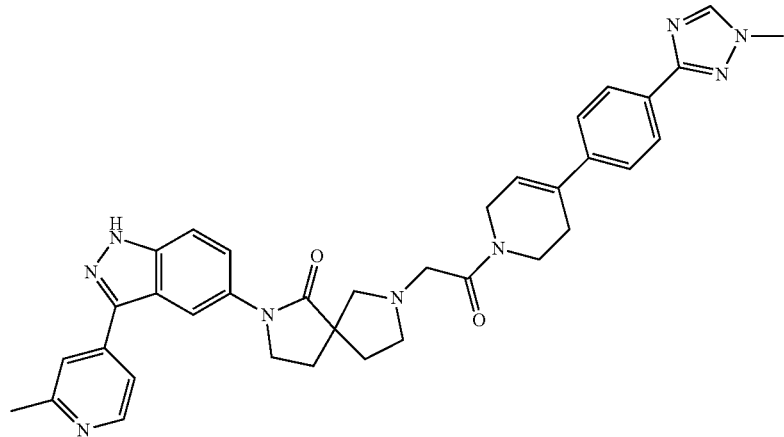

The title compound was prepared following General Procedures A and B using 2-(3-(2-methylpyridin-4-yl)-1-trityl-1H-indazol-5-yl)-2,7-diazaspiro[4.4]nonan-1-one (Intermediate 23) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, CDCl$_3$) δ 11.10 (br, 1H), 8.62 (d, 1H), 8.15-8.04 (m, 4H), 7.75-7.68 (m, 3H), 7.52-7.45 (m, 3H), 6.19 (d, 1H), 4.30-4.27 (m, 2H), 3.99 (s, 3H), 3.89-3.82 (m, 4H), 3.55-3.54 (m, 2H), 3.20-3.10 (m, 2H), 2.91-2.80 (m, 2H), 2.67 (s, 3H), 2.60 (s, br, 1H), 2.40-2.38 (m, 2H), 2.30 (br, 1H), 1.95-1.93 (m, 2H). LCMS: 628.30 [M+H]$^+$.

Example 7

7-(2-(4-(4-(1-Methyl-1H-1,2,4-triazol-3-yl)phenyl)-3,6-dihydropyridin-1(2H)-yl)-2-oxoethyl)-2-(3-(6-methylpyridin-3-yl)-1H-indazol-5-yl)-2,7-diazaspiro[4.4]nonan-1-one

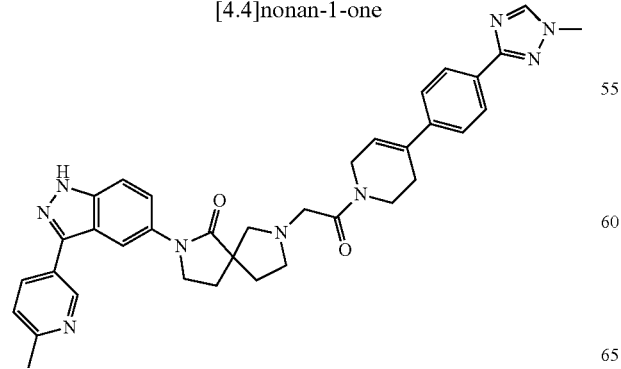

The title compound was prepared following General Procedures A and B using 2-(3-(6-methylpyridin-3-yl)-1-trityl-1H-indazol-5-yl)-2,7-diazaspiro[4.4]nonan-1-one (Intermediate 24) and 2-chloro-1-(4-(4-(1-methyl-1H-1,2,4-triazol-3-yl)phenyl)-3,6-dihydropyridin-1(2H)-yl)ethan-1-one (Intermediate 31). LCMS: 628.30 [M+H]⁺.

Example 8

(S)-7-(2-(4-(4-(1-Methyl-1H-1,2,4-triazol-3-yl)phenyl)-3,6-dihydropyridin-1(2H)-yl)-2-oxoethyl)-2-(3-(2-methylpyridin-4-yl)-1H-indazol-5-yl)-2,7-diazaspiro[4.4]nonan-1-one

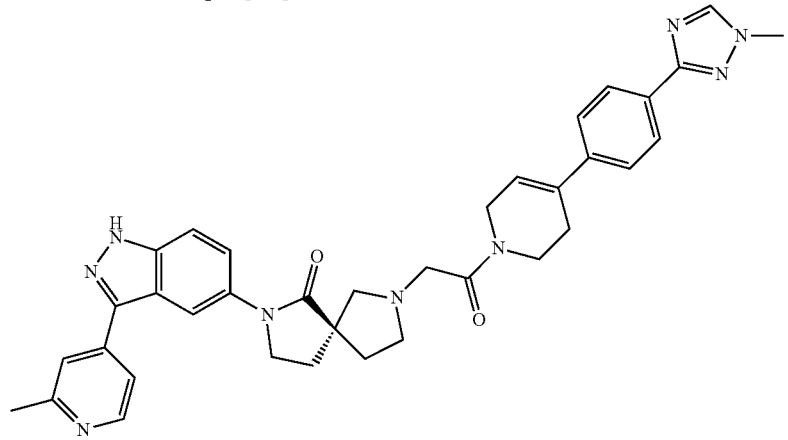

The title compound was prepared following General Procedures A and B using (S)-2-(3-(2-methylpyridin-4-yl)-1-trityl-1H-indazol-5-yl)-2,7-diazaspiro[4.4]nonan-1-one (Intermediate 21) and 2-chloro-1-(4-(4-(1-methyl-1H-1,2,4-triazol-3-yl)phenyl)-3,6-dihydropyridin-1(2H)-yl)ethan-1-one (Intermediate 31). ¹H NMR (400 MHz, CDCl₃) δ 11.10 (br, 1H), 8.62 (d, 1H), 8.15-8.04 (m, 4H), 7.75-7.68 (m, 3H), 7.52-7.45 (m, 3H), 6.19 (d, 1H), 4.30-4.27 (m, 2H), 3.99 (s, 3H), 3.89-3.82 (m, 4H), 3.55-3.54 (m, 2H), 3.20-3.10 (m, 2H), 2.91-2.80 (m, 2H), 2.67 (s, 3H), 2.60 (s, br, 1H), 2.40-2.38 (m, 2H), 2.30 (br, 1H), 1.95-1.93 (m, 2H). LCMS: 628.30 [M+H]⁺.

Example 9

(R)-7-(2-(4-(4-(1-Methyl-1H-1,2,4-triazol-3-yl)phenyl)-3,6-dihydropyridin-1(2H)-yl)-2-oxoethyl)-2-(3-(2-methylpyridin-4-yl)-1H-indazol-5-yl)-2,7-diazaspiro[4.4]nonan-1-one

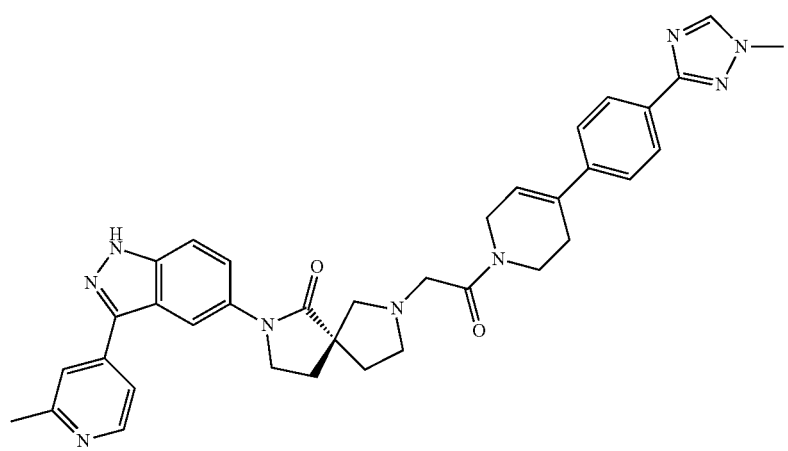

The title compound was prepared following General Procedures A and B using (R)-2-(3-(2-methylpyridin-4-yl)-1-trityl-1H-indazol-5-yl)-2,7-diazaspiro[4.4]nonan-1-one (Intermediate 22) and 2-chloro-1-(4-(4-(1-methyl-1H-1,2,4-triazol-3-yl)phenyl)-3,6-dihydropyridin-1(2H)-yl)ethan-1-one (Intermediate 31). LCMS: 628.30 [M+H]⁺.

Example 10

(S)-2-(3-(6-Isopropoxypyridin-3-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one

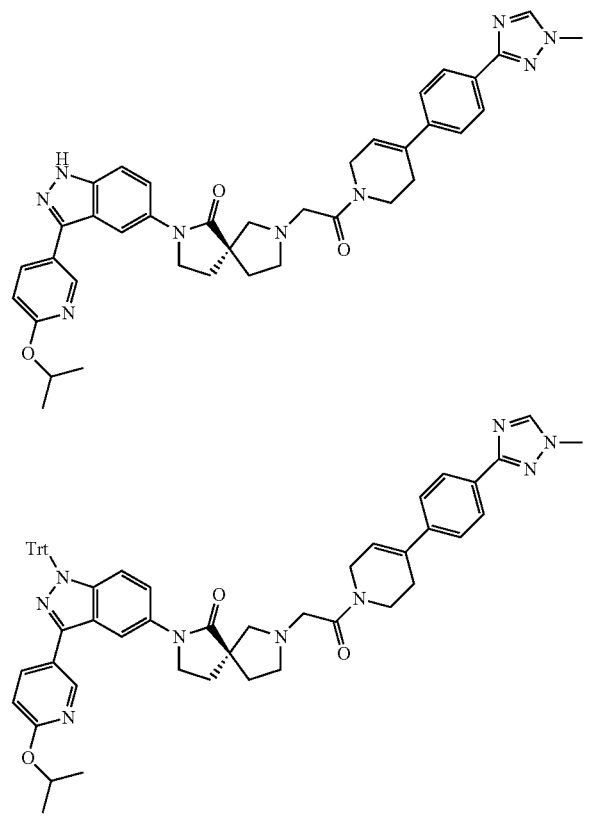

Step 1: (S)-2-(3-(6-isopropoxypyridin-3-yl)-1-trityl-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one To a stirred solution of (S)-2-(3-(6-isopropoxypyridin-3-yl)-1-trityl-1H-indazol-5-yl)-2,7-diazaspiro[4.4]nonan-1-one (Intermediate 5) (5 g, 7.898 mmol) in DMF, DIPEA (8.16 mL, 47.393 mmol) was added followed by 2-chloro-1-(4-(4-(1-methyl-1H-1,2,4-triazol-3-yl)phenyl)-5,6-dihydropyridin-1(2H)-yl)ethanone (Intermediate 31) (2.49 g, 7.898 mmol) at rt. The mixture was stirred at rt for 16 h. After completion of the reaction, the mixture was diluted with cold water (250 mL) and extracted with ethyl acetate (3×250 mL). The organic layers were combined, washed with water (500 mL) and brine (500 mL), dried over sodium sulphate, filtered and concentrated. The residue was purified by combi-column chromatography to afford (5 g, 5.47 mmol, 70% yield) (S)-2-(3-(6-isopropoxypyridin-3-yl)-1-trityl-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one as an off white solid. ¹H NMR (400 MHz, DMSO-d₆) δ 8.65 (d, J=1.6 Hz, 1H), 8.50 (s, 1H), 8.22 (s, 1H), 8.06 (dd, J=8.8, 2.8 Hz, 1H), 7.95-7.93 (m, 2H), 7.54-7.52 (m, 2H), 7.43-7.40 (m, 1H), 7.35-7.27 (m, 9H), 7.22-7.20 (m, 6H), 6.87 (d, J=8.8 Hz, 1H), 6.42 (d, J=9.6 Hz, 1H), 6.26 (s, 1H), 5.32-5.27 (m, 1H), 4.31-4.02 (m, 2H), 3.91 (s, 3H), 3.84-3.65 (m, 4H), 3.45-3.33 (m, 2H), 2.95-2.73 (m, 2H), 2.66-2.56 (m, 4H), 2.18-1.99 (m, 3H), 1.81-1.73 (m, 1H), 1.31 (d, J=6.4 Hz, 6H). LCMS: 914.52 [M+H]⁺.

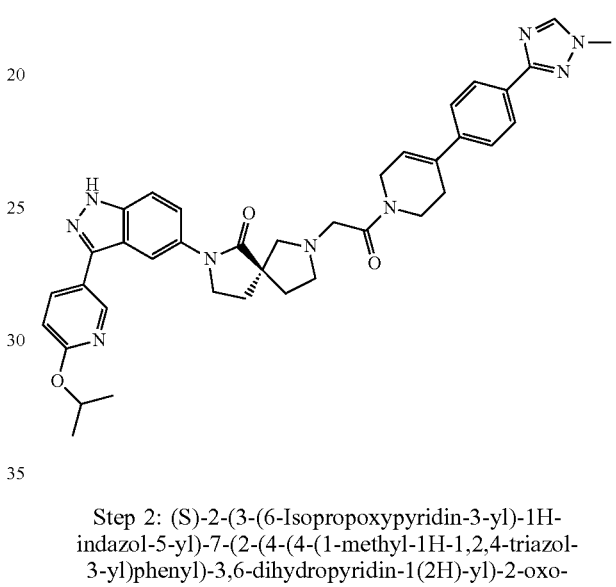

Step 2: (S)-2-(3-(6-Isopropoxypyridin-3-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one To a stirred solution of (S)-2-(3-(6-isopropoxypyridin-3-yl)-1-trityl-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one (5 g, 5.47 mmol) in DCM (170 mL) was added TFA (100 mL) at 0° C. The mixture was slowly warmed to rt after 5 mins, and then stirred at rt for 3 h. The reaction was quenched with aqueous sodium bicarbonate and extracted with ethyl acetate (2×250 mL). The organic layers were combined, washed with water (500 mL), dried over sodium sulphate, filtered and concentrated. The residue was purified by combi-column chromatography to afford (S)-2-(3-(6-isopropoxypyridin-3-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one (2.64 g, 3.9 mmol, 73% yield) as an off white solid. ¹H NMR (400 MHz, DMSO-d₆) δ 13.12 (s, 1H), 8.73 (d, J=2.4 Hz, 1H), 8.50 (s, 1H), 8.21 (dd, J=8.8, 2.4 Hz, 1H), 8.15 (s, 1H), 7.95 (d, J=8.0 Hz, 2H), 7.80-7.73 (m, 1H), 7.60-7.51 (m, 3H), 6.89 (d, J=8.4 Hz, 1H), 6.28 (s, 1H), 5.40-5.28 (m, 1H), 4.33-4.29 (m, 1H), 4.14-4.10 (m, 1H), 3.95-3.82 (m, 5H), 3.81-3.66 (m, 2H), 3.47-3.35 (m, 2H), 2.96-2.90 (m, 1H), 2.87-2.80 (m, 1H), 2.70-2.63 (m, 4H), 2.22-2.08 (m, 3H), 1.87-1.76 (m, 1H), 1.33 (d, J=6.4 Hz, 6H). LCMS: 672.47 [M+H]⁺.

Example 11

(R)-2-(3-(6-Isopropoxypyridin-3-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

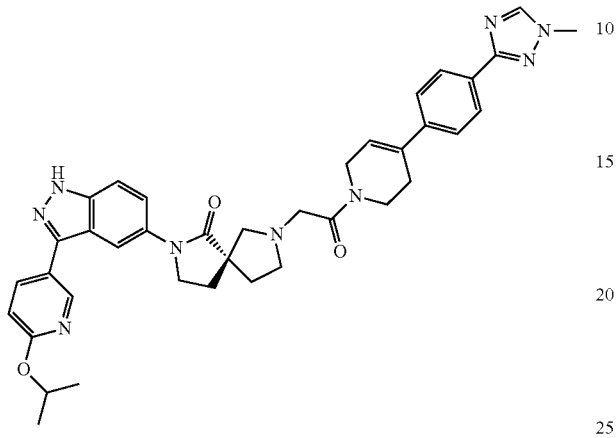

The title compound was prepared following General Procedures A and B using (R)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, CDCl$_3$) δ 10.4-10.3 (br, 1H), 8.74 (d, 1H), 8.15-8.02 (m, 5H), 7.79 (m, 1H), 7.51-7.44 (m, 3H), 6.84 (d, 1H), 6.19 (d, 1H), 5.41-5.38 (m, 1H), 4.27 (br, 1H), 4.00 (s, 3H), 3.90-3.87 (m, 5H), 3.66 (m, 3H), 2.99-2.90 (m, 2H), 2.67-2.61 (m, 2H), 2.46-2.41 (m, 2H), 2.39-2.28 (m, 1H), 2.10-2.00 (m, 1H), 1.42 (d, 6H). LCMS: 672.30 [M+H]$^+$.

Example 12

(5S)-7-(2-(4-(4-(1-Methyl-1H-1,2,4-triazol-3-yl)phenyl)-3,6-dihydropyridin-1(2H)-yl)-2-oxoethyl)-2-(3-(2-(trifluoromethyl)piperidin-4-yl)-1H-indazol-5-yl)-2,7-diazaspiro[4.4]nonan-1-one

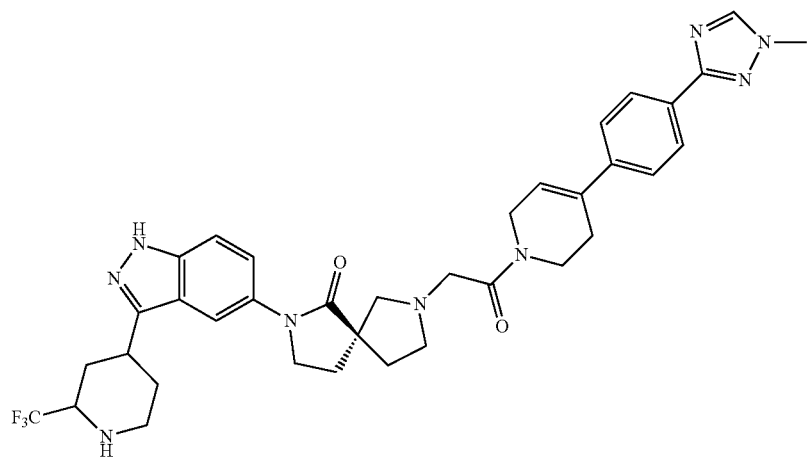 [SMILES: Cn1cnc(-c2ccc(C3=CCN(C(=O)CN4CC[C@]5(CCN(c6ccc7[nH]nc(C8CCNC(C(F)(F)F)C8)c7c6)C5=O)C4)CC3)cc2)n1]

The title compound was prepared following General Procedure A using (5S)-2-(3-(2-(trifluoromethyl)piperidin-4-yl)-1H-indazol-5-yl)-2,7-diazaspiro[4.4]nonan-1-one (Intermediate 10) and 2-chloro-1-(4-(4-(1-methyl-1H-1,2,4-triazol-3-yl)phenyl)-3,6-dihydropyridin-1(2H)-yl)ethan-1-one (Intermediate 31). LCMS: 688.30 [M+H]$^+$.

Example 13

6-(3-(6-Isopropoxypyridin-3-yl)-1H-indazol-5-yl)-2-(2-(4-(4-(1-methyl-1H-1,2,4-triazol-3-yl)phenyl)-3,6-dihydropyridin-1(2H)-yl)-2-oxoethyl)-2,6-diazaspiro[3.4]octan-5-one

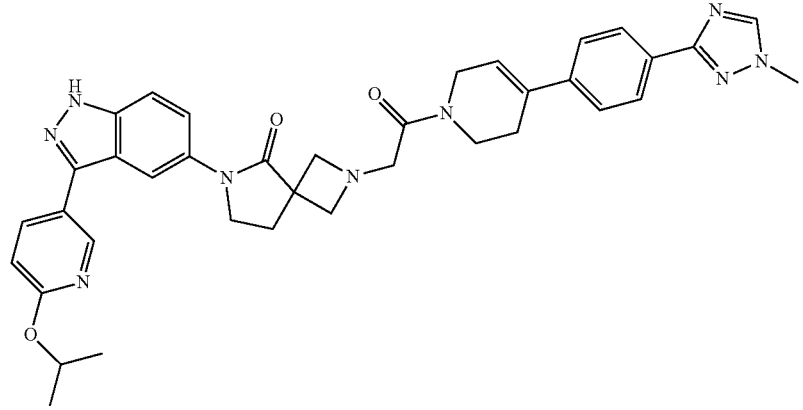 [SMILES: CC(C)Oc1ccc(-c2n[nH]c3ccc(N4CCC5(CN(CC(=O)N6CC=C(c7ccc(-c8ncn(C)n8)cc7)CC6)C5)C4=O)cc23)cn1]

The title compound was prepared following General Procedure A using 6-(3-(6-isopropoxypyridin-3-yl)-1H-indazol-5-yl)-2,6-diazaspiro[3.4]octan-5-one (Intermediate 13) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-d$_6$) δ 13.30 (br, 1H), 8.73 (s, 1H), 8.51 (s, 1H), 8.23-8.21 (dd, 1H), 8.16 (s, 1H), 7.97 (d, 2H), 7.73 (d, 1H), 7.56-7.54 (m, 2H), 6.90 (d, 1H), 6.28 (s, 1H), 6.35-6.32 (m, 1H), 4.19 (s, 2H), 4.10 (s, 2H), 3.92 (s, 3H), 3.92-3.888 (m, 2H), 3.68-3.65 (m, 2H), 3.44-3.36 (m, 3H), 3.36-3.32 (m, 4H), 2.61 (s, 2H), 1.35 (d, 6H). LCMS: 658.30 [M+H]$^+$.

Example 14

(S)-7-(2-(4-(4-(1H-1,2,3-Triazol-1-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

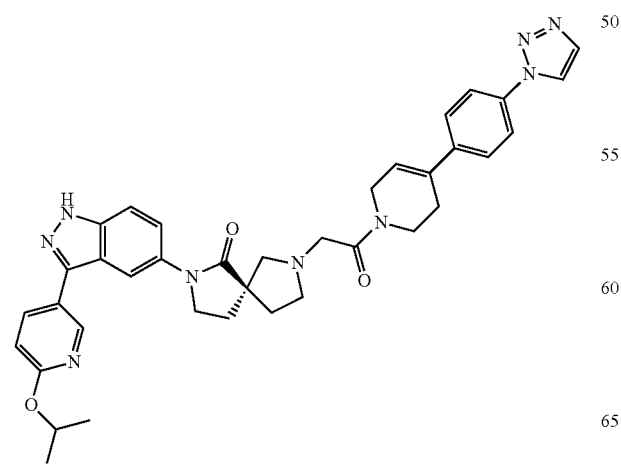

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 1-(4-(4-(1H-1,2,3-Triazol-1-yl)phenyl)-5,6-dihydropyridin-1(2H)-yl)-2-chloroethanone (Intermediate 37). ¹H NMR (400 MHz, DMSO-d₆-HCl salt) δ 13.30-13.2 (br, 1H), 10.60 (br, 0.6H), 10.30 (br, 0.4H), 8.87 (d, 1H), 8.75 (s, 1H), 8.24-8.21 (m, 2H), 7.99 (s, 1H), 7.95-7.91 (m, 2H), 7.70-7.64 (m, 3H), 6.93 (d, 1H), 6.35 (br, 1H), 5.34-5.31 (m, 1H), 4.60-4.50 (m, 2H), 4.22 (br, 2H), 4.10 (br, 2H), 4.10-3.95 (m, 2H), 3.80-3.78 (m, 2H), 3.77 (br, 1H), 3.40-3.37 (m, 2H), 2.51 (br, 1H), 2.50 (br, 1H), 2.40-2.210 (m, 4H), 1.34 (d, 6H). LCMS: 658.30 [M+H]⁺.

Example 15

(S)-2-(3-(6-isopropoxypyridin-3-yl)-1H-indazol-5-yl)-7-(2-(4-(4-(1-methyl-1H-1,2,3-triazol-4-yl)phenyl)-3,6-dihydropyridin-1 (2H)-yl)-2-oxoethyl)-2,7-diazaspiro[4.4]nonan-1-one

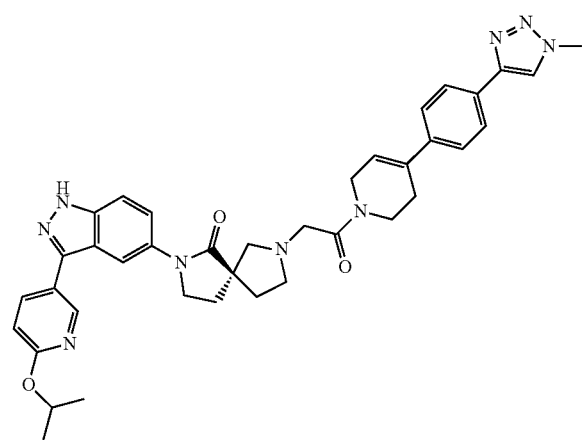 [SMILES: CC(C)Oc1ccc(-c2n[nH]c3ccc(N4CC[C@]5(CCN(CC(=O)N6CC=C(c7ccc(-c8cn(C)nn8)cc7)CC6)C5)C4=O)cc23)cn1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-methyl-1H-1,2,3-triazol-4-yl)phenyl)-5,6-dihydropyridin-1(2H)-yl)ethanone (Intermediate 38). ¹H NMR (400 MHz, DMSO-d₆-HCl salt) δ 13.30 (br, 1H), 10.60 (br, 0.6H), 10.40 (br, 0.4H), 8.75 (s, 1H), 8.54 (d, 1H), 8.24-8.20 (m, 2H), 7.85-7.82 (m, 3H), 7.65-7.54 (m, 3H), 6.92 (dd, 1H), 6.29 (s, 1H), 5.34-5.31 (m, 1H), 4.65-4.50 (m, 2H), 4.10 (s, 1H), 4.09 (s, 3H), 4.09-3.90 (m, 2H), 3.80-3.70 (m, 2H), 3.61-3.60 (m, 1H), 3.45-3.35 (m, 2H), 2.60 (s, 1H), 2.50-2.20 (m, 4H), 1.35 (dd, 6H); LCMS: 672.30 [M+H]⁺.

Example 16

(S)-2-(3-(6-Isopropoxypyridin-3-yl)-1H-indazol-5-yl)-7-(2-(4-(4-(1-methyl-1H-1,2,4-triazol-3-yl)phenyl)piperidin-1-yl)-2-oxoethyl)-2,7-diazaspiro[4.4]nonan-1-one

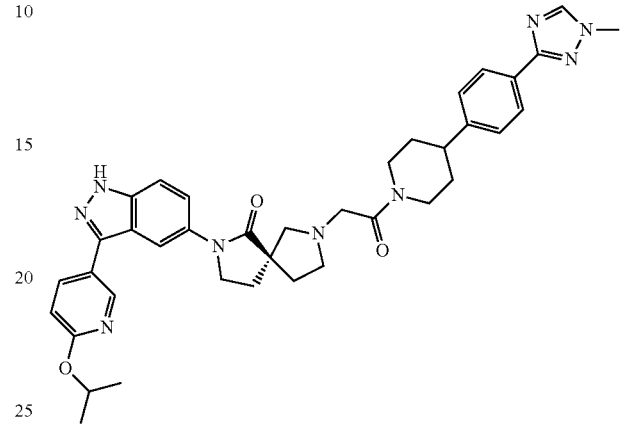

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-methyl-1H-1,2,4-triazol-3-yl)phenyl)piperidin-1-yl)ethanone (Intermediate 33). LCMS: 674.40 [M+H]⁺.

Example 17

(S)-2-(3-(6-Isopropoxypyridin-3-yl)-1H-indazol-5-yl)-7-(2-(4-(4-(5-methyl-1,3,4-oxadiazol-2-yl)phenyl)-3,6-dihydropyridin-1(2H)-yl)-2-oxoethyl)-2,7-diazaspiro[4.4]nonan-1-one

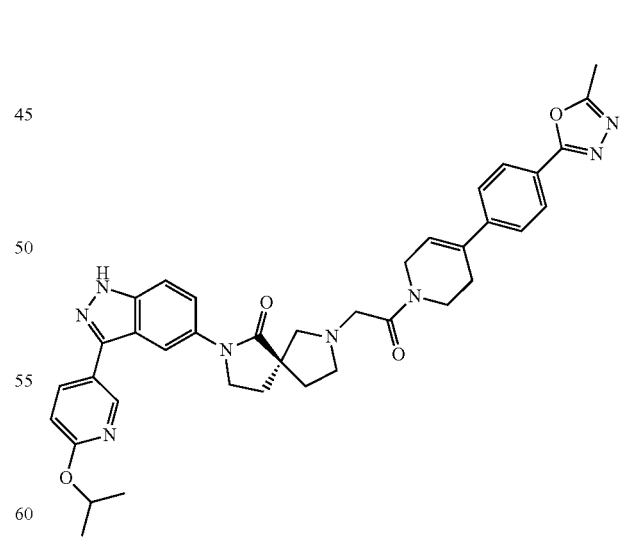

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(5-methyl-1,3,4-oxadiazol-2-yl)phenyl)-5,6-dihydropyridin-1(2H)-yl)

ethanone (Intermediate 36). $^1$H NMR (400 MHz, DMSO-$d_6$-HCl salt) δ 13.35 (br, 1H), 10.50 (br, 0.6H), 10.25 (br, 0.4H), 8.75 (s, 1H), 8.24-8.20 (m, 2H), 7.99-7.96 (m, 2H), 7.73-7.62 (m, 4H), 6.91 (dd, 1H), 6.41 (s, 1H), 5.34-5.32 (m, 1H), 4.65-4.50 (m, 2H), 4.23-4.10 (m, 5H), 3.79-3.78 (m, 2H), 3.61-3.60 (m, 1H), 3.45-3.35 (m, 2H), 2.60 (s, 1H), 2.55 (s, 3H), 2.50-2.40 (m, 4H), 1.35 (dd, 6H). LCMS: 673.30 [M+H]$^+$.

Example 18

(S)-7-(2-(4-(4-(5-(Ethylamino)-1,3,4-oxadiazol-2-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

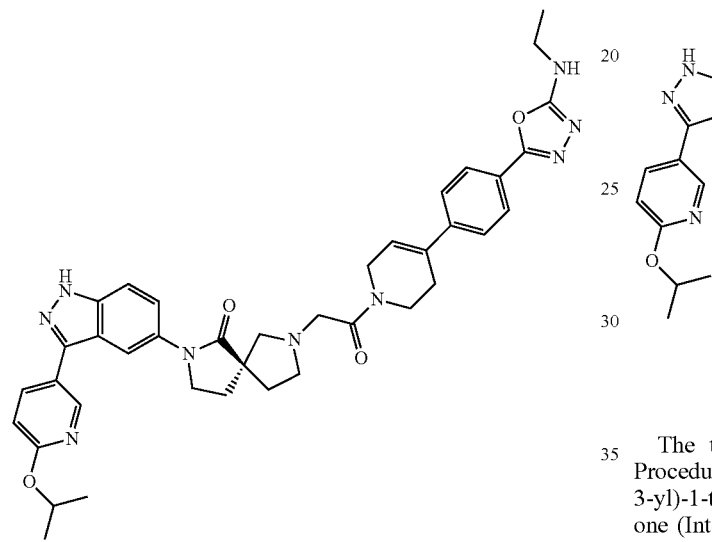

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(5-(ethylamino)-1,3,4-oxadiazol-2-yl)phenyl)-5,6-dihydropyridin-1(2H)-yl)ethanone (Intermediate 35). LCMS: 702.30 [M+H]$^+$.

Example 19

(S)-7-(2-(4-(4-(5-(Ethylamino)-1,3,4-thiadiazol-2-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

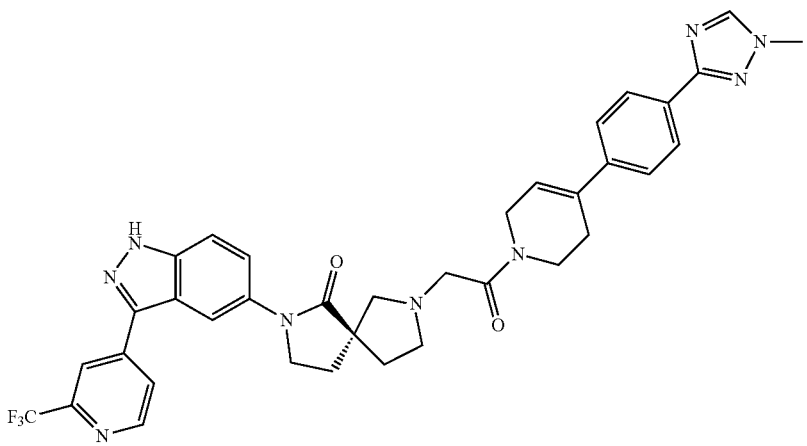 [SMILES: Cn1cnc(-c2ccc(C3=CCN(C(=O)CN4CC[C@]5(CCN(c6ccc7[nH]nc(-c8ccnc(C(F)(F)F)c8)c7c6)C5=O)C4)CC3)cc2)n1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(5-(ethylamino)-1,3,4-thiadiazol-2-yl)phenyl)-5,6-dihydropyridin-1(2H)-yl)ethanone (Intermediate 34). LCMS: 718.30 [M+H]$^+$.

Example 20

(S)-7-(2-(4-(4-(1-Methyl-1H-1,2,4-triazol-3-yl)phenyl)-3,6-dihydropyridin-1 (2H)-yl)-2-oxoethyl)-2-(3-(2-(trifluoromethyl)pyridin-4-yl)-1H-indazol-5-yl)-2,7-diazaspiro[4.4]nonan-1-one The title compound was prepared following General Procedures A, B and C using (S)-2-(3-(2-(trifluoromethyl)pyridin-4-yl)-1-trityl-1H-indazol-5-yl)-2,7-diazaspiro[4.4]nonan-1-one (Intermediate 9) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-d$_6$-HCl salt) δ 14.0 (br, 1H), 10.60 (br, 0.6H), 10.40 (br, 0.4H), 8.90 (dd, 1H), 8.55 (s, 1H), 8.36-8.31 (m, 3H), 7.99 (m, 2H), 7.87-7.85 (m, 1H), 7.76-7.73 (m, 1H), 7.59-7.54 (m, 2H), 6.31 (s, 1H), 4.70-4.60 (m, 2H), 4.21 (br, 2H), 4.14 (br, 2H), 3.93 (s, 3H), 3.82-3.77 (m, 3H), 3.61-3.60 (br, 1H), 3.41-3.39 (m, 2H), 2.70 (br, 1H), 2.60 (br, 1H), 2.40-2.10 (m, 4H). LCMS: 682.30 [M+H]$^+$.

Example 21

7-Benzyl-2-(3-(6-isopropoxypyridin-3-yl)-1H-indazol-5-yl)-2,7-diazaspiro[4.4]nonan-1-one

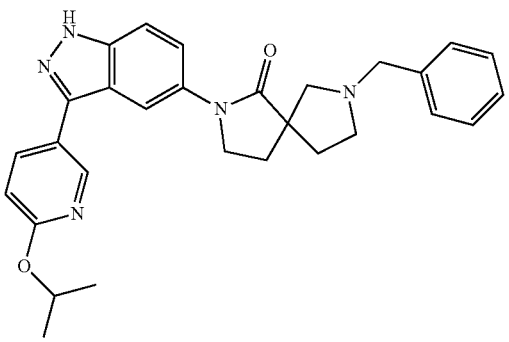 [SMILES: CC(C)Oc1ccc(-c2n[nH]c3ccc(N4CCC5(CCN(Cc6ccccc6)C5)C4=O)cc23)cn1]

The title compound was prepared following General Procedures A using 2-(3-(6-isopropoxypyridin-3-yl)-1H-indazol-5-yl)-2,7-diazaspiro[4.4]nonan-1-one (Intermediate 4) and (bromomethyl)benzene. LCMS: 482.20 [M+H]$^+$.

Example 22

(S)-2-(3-(6-Isopropoxypyridin-3-yl)-1H-indazol-5-yl)-7-(2-oxo-2-(4-(4-(pyrimidin-2-yl)phenyl)-3,6-dihydropyridin-1(2H)-yl)ethyl)-2,7-diazaspiro[4.4]nonan-1-one

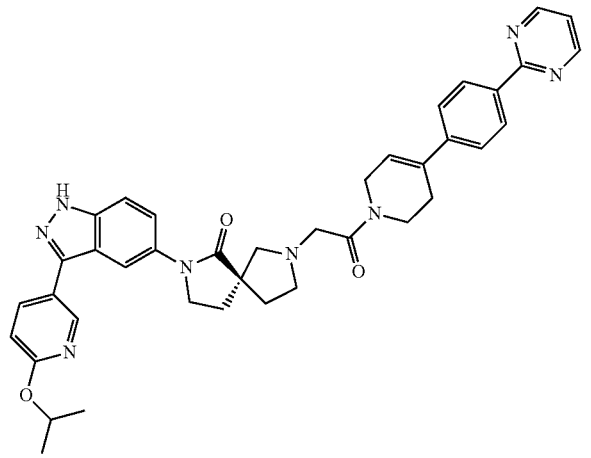 [SMILES: CC(C)Oc1ccc(-c2n[nH]c3ccc(N4CC[C@]5(CCN(CC(=O)N6CC=C(c7ccc(-c8ncccn8)cc7)CC6)C5)C4=O)cc23)cn1]

To a mixture of (S)-2-(7-(3-(6-isopropoxypyridin-3-yl)-1H-indazol-5-yl)-6-oxo-2,7-diazaspiro[4.4]nonan-2-yl)acetic acid (Intermediate 11) (0.2 g, 0.240 mmol) and 2-(4-(1,2,3,6-tetrahydropyridin-4-yl)phenyl)pyrimidine hydrochloride (Intermediate 44) (0.057 g, 0.240 mmol) in DMF (2.403 mL) at 25° C., neat N-ethyl-N-isopropylpropan-2-amine (0.126 mL, 0.721 mmol) was added followed by an addition of 2-(3H-[1,2,3]triazolo[4,5-b]pyridin-3-yl)-1,1,3,3-tetramethyluronium (HATU) (0.085 g, 0.360 mmol). The mixture was stirred at rt overnight. Upon completion by LCMS, the solvent was removed on a rotary evaporator to give the crude material that was directly purified on a RP C18 Luna column eluted with 0-50% acetonitrile/water in the presence of 0.1% formic acid. The fractions were pooled and concentrated to give the formate salt. This salt was dissolved in dichloromethane (0.1 M) and cooled to 0° C. To this solution, 2M HCl (3 eq. 2.0 M in ether) was added. The mixture was concentrated on a rotary evaporator and dried to afford the title compound as hydrochloride salt (0.15 g, 93%). $^1$H NMR (400 MHz, DMSO-d$_6$-HCl salt) δ 13.30 (br, 1H), 10.50 (br, 0.6H), 10.40 (br, 0.4H), 8.91 (d, 2H), 8.75 (s, 1H), 8.40 (dd, 2H), 8.24-8.20 (m, 2H), 7.73 (m, 1H), 7.67-7.62 (m, 3H), 7.46-7.44 (m, 1H), 6.92 (dd, 1H), 6.40 (br, 1H), 5.34-5.32 (m, 1H), 4.60-4.50 (m, 2H), 4.23 (br, 1H), 4.15 (br, 1H), 4.10-3.99 (m, 2H), 3.78 (br, 3H), 3.40-3.30 (m, 2H), 2.70 (br, 1H), 2.59 (br, 1H), 2.34-2.20 (m, 4H), 1.34 (d, 6H). CMS: 669.30 [M+H]$^+$.

Example 23

(S)-7-(2-(4-(4-(5-Fluoropyrimidin-2-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

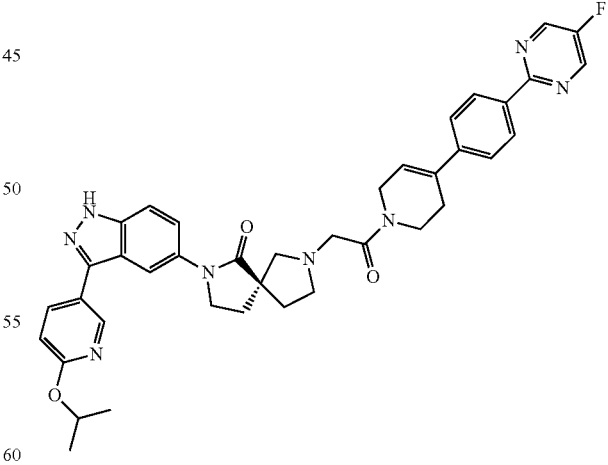

The title compound was prepared following the procedure described for Example 22 using (S)-2-(7-(3-(6-isopropoxypyridin-3-yl)-1H-indazol-5-yl)-6-oxo-2,7-diazaspiro[4.4]nonan-2-yl)acetic acid (Intermediate 11) and 5-fluoro-2-(4-(1,2,3,6-tetrahydropyridin-4-yl)phenyl)pyrimidine hydrochloride (Intermediate 45). LCMS: 687.30 [M+H]$^+$.

Example 24

(S)-2-(3-(6-Isopropoxypyridin-3-yl)-1H-indazol-5-yl)-7-(2-(4-(3-(1-methyl-1H-1,2,4-triazol-3-yl)bicyclo[1.1.1]pentan-1-yl)piperidin-1-yl)-2-oxoethyl)-2,7-diazaspiro[4.4]nonan-1-one

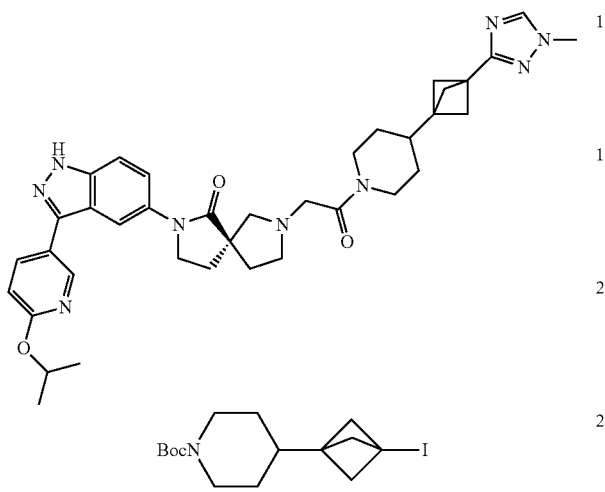

Step 1: tert-Butyl 4-(3-iodobicyclo[1.1.1]pentan-1-yl)piperidine-1-carboxylate A solution of propellane (0.23M in Et$_2$O, 85 mL, 19.44 mmol, 0.23M) and tert-butyl 4-iodopiperidine-1-carboxylate (5.5 g, 17.68 mmol) at −50° C. was treated with methyllithium (1.6M in Et$_2$O, 12.15 mL, 19.44 mmol) using a syringe pump. After the addition was complete the mixture was warmed to rt gradually and reacted overnight. After 23 h the reaction was cooled to −40° C. and treated with MeOH (20 mL). The mixture was then warmed to 0° C. and added to cold H$_2$O (150 mL). The aqueous layer was extracted with Et$_2$O (3×). The combined organic layers were dried over Na$_2$SO$_4$, filtered and concentrated in vacuo to provide a light yellow/orange colored oil (2.15 g, 89% crude yield) which solidified on standing. The crude iodide was used in the subsequent reaction without a further purification. $^1$H NMR (400 MHz, CDCl$_3$) δ 4.13 (s, 2H), 2.63 (t, J=12.8 Hz, 2H), 2.18 (s, 6H), 1.61-1.49 (m, 3H), 1.47 (s, 9H), 1.14-1.03 (m, 2H).

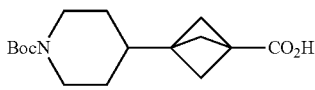

Step 2: 3-(1-(tert-butoxycarbonyl)piperidin-4-yl)bicyclo[1.1.1]pentane-1-carboxylic acid A solution of tert-butyl 4-(3-iodobicyclo[1.1.1]pentan-1-yl)piperidine-1-carboxylate (1.26 g, 3.34 mmol) in THF (16.70 mL) was cooled to −78° C. and treated with tert-butyllithium (1.7 M in Et$_2$O, 4.13 mL, 7.01 mmol) dropwise. After 30 mins at −78° C., the mixture was treated with CO$_2$ for 5 mins and then warmed to rt. After 20 mins at rt, the reaction was quenched with H$_2$O. Ethyl acetate was added, and the organic layer was separated. The aqueous layer was cooled in an ice bath and carefully acidified with 1M aqueous HCl and extracted with DCM (3×). The combined organic layer following acidification were dried over Na$_2$SO$_4$, filtered and concentrated in vacuo to provide the desired compound (0.90 g 91%) as a yellow oil. $^1$H NMR (400 MHz, CDCl$_3$) δ 4.14 (br s, 2H), 2.68-2.59 (m, 2H), 1.90 (s, 6H), 1.60-1.48 (m, 3H), 1.45 (s, 9H), 1.11-1.02 (m, 2H). LCMS: 196.10 [M+H]$^+$.

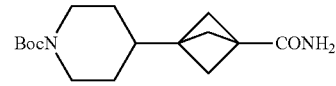 [SMILES: CC(C)(C)OC(=O)N1CCC(C23CC(C(N)=O)(C2)C3)CC1]

Step 3: tert-butyl 4-(3-carbamoylbicyclo[1.1.1]pentan-1-yl)piperidine-1-carboxylate A solution of 3-(1-(tert-butoxycarbonyl)piperidin-4-yl)bicyclo[1.1.1]pentane-1-carboxylic acid (1 g, 3.39 mmol) in DMF (22.57 mL) was treated with DIPEA (2.54 mL, 14.56 mmol), and HATU (1.931 g, 5.08 mmol). After 20 mins, solid ammonium chloride (0.362 g, 6.77 mmol) was added, and the mixture was stirred at rt. After 3 h, water was added, and the mixture was extracted with DCM (3×). The combined organic extracts were dried over Na$_2$SO$_4$, filtered, and concentrated in vacuo. The product was purified by flash column chromatography to afford the desired product (299.0 mg, 30%) as a yellow colored solid. $^1$H NMR (400 MHz, CDCl$_3$) δ 5.50 (s, 1H), 5.31 (s, 1H), 4.14 (d, J=13.2 Hz, 2H), 2.63 (t, J=12.8 Hz, 2H), 1.86 (s, 6H), 1.61-1.45 (m, 3H), 1.45 (s, 9H), 1.12-1.02 (m, 2H). LCMS: 195.10 [M+H]$^+$.

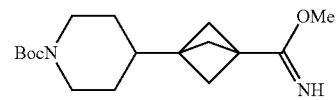 [SMILES: COC(=N)C12CC(C3CCN(C(=O)OC(C)(C)C)CC3)(C1)C2]

Step 4: tert-butyl 4-(3-(imino(methoxy)methyl)bicyclo[1.1.1]pentan-1-yl)piperidine-1-carboxylate A solution of tert-butyl 4-(3-carbamoylbicyclo[1.1.1]pentan-1-yl)piperidine-1-carboxylate (150 mg, 0.510 mmol) was treated with trimethyloxonium tetrafluoroborate (83 mg, 0.560 mmol) at rt. The reaction was heated to 65° C. After 45 mins, the reaction appeared to be ~50% complete by $^1$H NMR analysis (as noted by disappearance of starting amide). An additional trimethyloxonium tetrafluoroborate (0.5, eq., 83 mg, 0.560 mmol) was added. After 30 mins of stirring at rt, the mixture was concentrated in vacuo to provide the crude product as a yellow oil. The crude imidate was used for subsequent reactions. $^1$H NMR (400 MHz, CDCl$_3$) δ 4.21 (s, 3H), 4.13 (s, 2H), 2.62 (t, J=12.8 Hz, 2H), 2.08 (s, 6H), 1.61-1.49 (m, 3H), 1.45 (s, 9H), 1.07 (qd, J=12.7, 4.1 Hz, 2H).

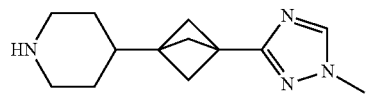 [SMILES: Cn1cnc(C23CC(C4CCNCC4)(C2)C3)n1]

Step 5: 4-(3-(1-methyl-1H-1,2,4-triazol-3-yl)bicyclo[1.1.1]pentan-1-yl)piperidine A solution of tert-butyl 4-(3-(imino(methoxy)methyl)bicyclo[1.1.1]pentan-1-yl)piperidine-1-carboxylate (0.157 g, 0.510 mmol) in pyridine (2.55 mL) at 0° C. was treated with tert-butyl 1-methylhydrazinecarboxylate (0.083 mL, 0.561 mmol), and the mixture warmed to rt. After 75 mins, $^1$H NMR analysis revealed that the starting imidate had been consumed. The mixture was concentrated in vacuo to provide a brown oil. Formic Acid (2.55 mL) was added to the crude product, and the mixture was heated to 105° C. (external temperature). After 90 mins, the mixture was concentrated in vacuo. The crude product was purified via on a RP-C18 column (H$_2$O:CH$_3$CN, 0.1% formic acid), followed by salt exchange with HCl (2M in Et$_2$O) to provide the product as HCl salt (41 mg, 35%) as a white solid. $^1$H NMR (400 MHz, CD$_3$OD) δ 8.30 (s, 1H), 3.87 (s, 3H), 3.43-3.39 (m, 2H), 2.98 (td, J=13.0, 3.0 Hz, 2H), 2.01 (s, 6H), 1.92-1.87 (m, 2H), 1.80 (tt, J=11.9, 3.7 Hz, 1H), 1.47-1.36 (m, 2H). LCMS: 233.10 [M+H]$^+$.

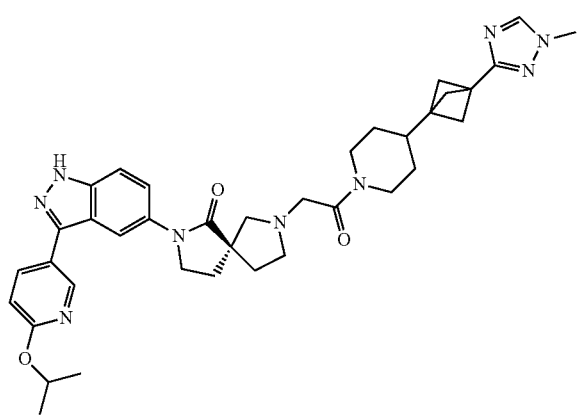 [SMILES: CC(C)Oc1ccc(-c2n[nH]c3ccc(N4CC[C@]5(CCN(CC(=O)N6CCC(C78CC(c9ncn(C)n9)(C7)C8)CC6)C5)C4=O)cc23)cn1]

Step 6: (S)-2-(3-(6-Isopropoxypyridin-3-yl)-1H-indazol-5-yl)-7-(2-(4-(3-(1-methyl-1H-1,2,4-triazol-3-yl)bicyclo[1.1.1]pentan-1-yl)piperidin-1-yl)-2-oxoethyl)-2,7-diazaspiro[4.4]nonan-1-one The title compound was prepared following the procedure described for Example 22 using (S)-2-(7-(3-(6-isopropoxypyridin-3-yl)-1H-indazol-5-yl)-6-oxo-2,7-diazaspiro[4.4]nonan-2-yl)acetic acid (Intermediate 11) and 4-(3-(1-methyl-1H-1,2,4-triazol-3-yl)bicyclo[1.1.1]pentan-1-yl)piperidine from Step 5. LCMS: 664.40 [M+H]$^+$.

Example 25

(S)-2-(3-(6-Isopropoxypyridin-3-yl)-1H-indazol-5-yl)-7-(2-oxo-2-(5-(pyrimidin-2-yl)-3',6'-dihydro-[2,4'-bipyridin]-1'(2'H)-yl)ethyl)-2,7-diazaspiro[4.4]nonan-1-one

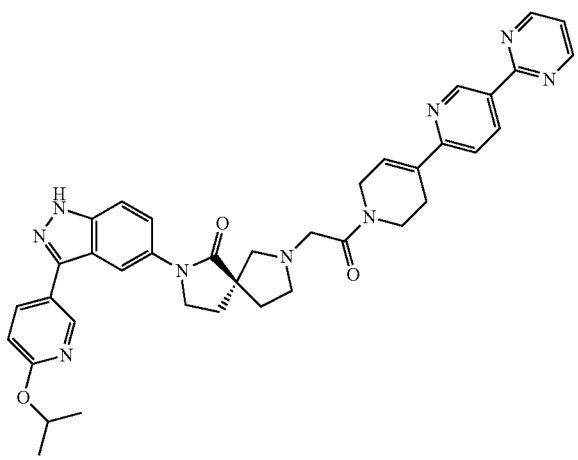 [SMILES: CC(C)Oc1ccc(-c2n[nH]c3ccc(N4CC[C@]5(CCN(CC(=O)N6CC=C(c7ccc(-c8ncccn8)cn7)CC6)C5)C4=O)cc23)cn1]

The title compound was prepared following the procedure described for Example 22 using (S)-2-(7-(3-(6-isopropoxypyridin-3-yl)-1H-indazol-5-yl)-6-oxo-2,7-diazaspiro[4.4]nonan-2-yl)acetic acid (Intermediate 11) and 5-(pyrimidin-2-yl)-1',2',3',6'-tetrahydro-2,4'-bipyridine hydrochloride (Intermediate 43). LCMS: 670.30 [M+H]$^+$.

Example 26

(S)-2-(3-(6-Isopropoxypyridin-3-yl)-1H-indazol-5-yl)-7-(2-(4-(4-(1-methyl-1H-imidazol-4-yl)phenyl)-3,6-dihydropyridin-1(2H)-yl)-2-oxoethyl)-2,7-diazaspiro[4.4]nonan-1-one

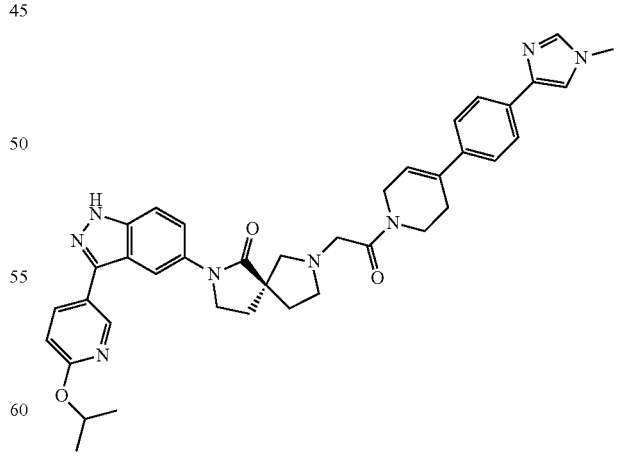

The title compound was prepared following the procedure described for Example 22 using (S)-2-(7-(3-(6-isopropoxypyridin-3-yl)-1H-indazol-5-yl)-6-oxo-2,7-diazaspiro[4.4]nonan-2-yl)acetic acid (Intermediate 11) and 4-(4-(1-

Methyl-1H-imidazol-4-yl)phenyl)-1,2,3,6-tetrahydropyridine dihydrochloride (Intermediate 46). LCMS: 671.40 [M+H]⁺.

Example 27

((S)-7-(2-(4-Fluoro-4-(4-(1-methyl-1H-1,2,4-triazol-3-yl)phenyl)piperidin-1-yl)-2-oxoethyl)-2-(3-(6-isopropoxypyridin-3-yl)-1H-indazol-5-yl)-2,7-diazaspiro[4.4]nonan-1-one

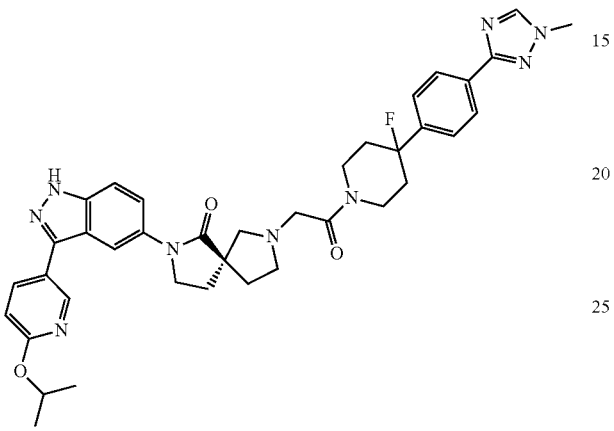

The title compound was prepared following the procedure described for Example 22 using (S)-2-(7-(3-(6-isopropoxypyridin-3-yl)-1H-indazol-5-yl)-6-oxo-2,7-diazaspiro[4.4]nonan-2-yl)acetic acid (Intermediate 11) 4-fluoro-4-(4-(1-methyl-1H-1,2,4-triazol-3-yl)phenyl)piperidine hydrochloride (Intermediate 47). LCMS: 692.30 [M+H]⁺.

Example 28

(S)-7-(2-(4-(4-(5-Fluoropyrimidin-2-yl)phenyl)-3,6-dihydropyridin-1(2H)-yl)-2-oxoethyl)-2-(3-(2-(trifluoromethyl)pyridin-4-yl)-1H-indazol-5-yl)-2,7-diazaspiro[4.4]nonan-1-one

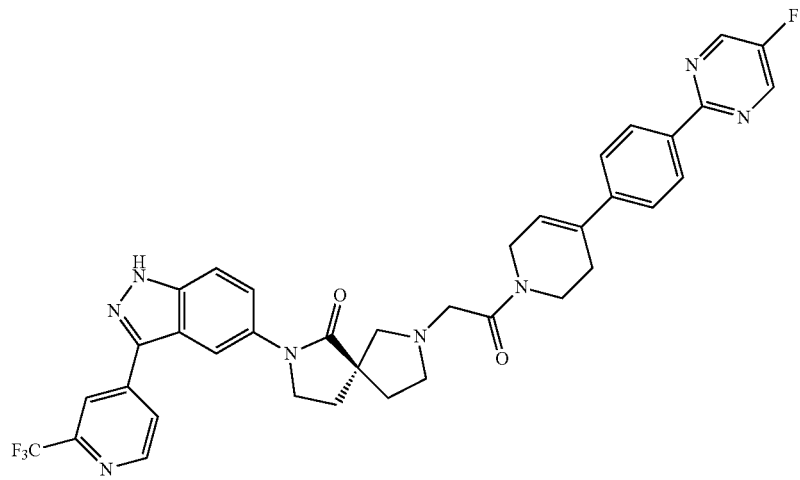 [SMILES: O=C(CN1CC[C@]2(CCN(c3ccc4[nH]nc(-c5ccnc(C(F)(F)F)c5)c4c3)C2=O)C1)N1CC=C(c2ccc(-c3ncc(F)cn3)cc2)CC1]

The title compound was prepared following the procedure described for Example 22 using (S)-2-(6-oxo-7-(3-(2-(trifluoromethyl)pyridin-4-yl)-1H-indazol-5-yl)-2,7-diazaspiro[4.4]nonan-2-yl)acetic acid and 5-fluoro-2-(4-(1,2,3,6-tetrahydropyridin-4-yl)phenyl)pyrimidine hydrochloride (Intermediate 45). LCMS: 697.20 [M+H]⁺.

Example 29

(S)-2-(3-(4-Fluorophenyl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

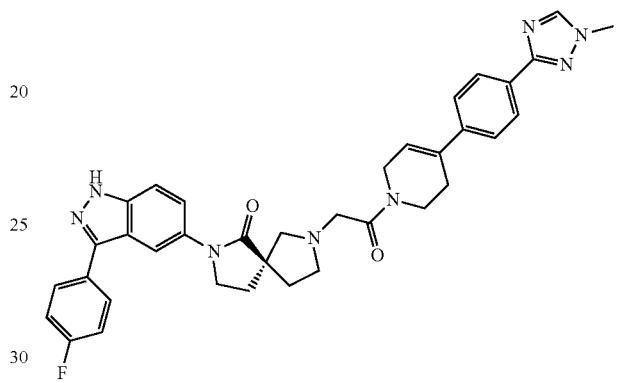

The title compound was prepared following General Procedures A, B, and C using (S)-2-(3-(4-fluorophenyl)-1-trityl-1H-indazol-5-yl)-2,7-diazaspiro[4.4]nonan-1-one (Intermediate 8) and 2-chloro-1-(4-(4-(1-methyl-1H-1,2,4-triazol-3-yl)phenyl)-3,6-dihydropyridin-1(2H)-yl)ethan-1-one (Intermediate 31). ¹H NMR (400 MHz, DMSO-d₆-HCl salt) δ 13.35 (br, 1H), 10.50 (br, 0.6H), 10.30 (br, 0.4H), 8.53 (s, 1H), 8.20 (s, 1H), 8.02-7.97 (m, 4H), 7.76-7.63 (m, 1H), 7.58-7.54 (m, 3H), 7.40-7.35 (m, 2H), 6.31 (s, 1H), 4.64-4.63 (m, 2H), 4.21 (br, 2H), 4.14 (br, 2H), 3.94 (s, 3H), 3.78-3.77 (m, 3H), 3.61-3.60 (br, 1H), 3.41-3.40 (m, 2H), 2.73 (br, 1H), 2.60 (br, 1H), 2.40-2.10 (m, 4H). LCMS: 631.30 [M+H]⁺.

Example 30

(S)-2-(3-(2-Isopropoxypyridin-4-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

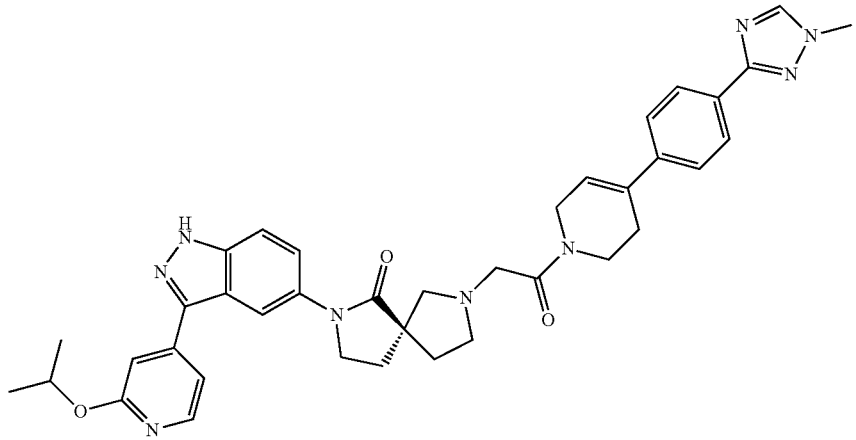 [SMILES: CC(C)Oc1cc(-c2n[nH]c3ccc(N4CC[C@]5(CCN(CC(=O)N6CC=C(c7ccc(-c8ncn(C)n8)cc7)CC6)C5)C4=O)cc23)ccn1]

The title compound was prepared following General Procedures A, B, and C using (S)-2-(3-(2-isopropoxypyridin-4-yl)-1-trityl-1H-indazol-5-yl)-2,7-diazaspiro[4.4]nonan-1-one (Intermediate 15) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-$d_6$-HCl salt) δ 13.70 (br, 1H), 10.55 (br, 0.6H), 10.40 (br, 0.4H), 8.54 (s, 1H), 8.30-8.26 (m, 2H), 8.00-7.97 (m, 2H), 7.77-7.68 (m, 2H), 7.59-7.54 (m, 3H), 7.24-7.23 (m, 1H), 6.31 (s, 1H), 5.35-5.33 (m, 1H), 4.70-4.60 (m, 2H), 4.21 (br, 2H), 4.13 (br, 2H), 3.93 (s, 3H), 3.80-3.77 (m, 2H), 3.61-3.60 (br, 1H), 3.45-3.30 (m, 2H), 2.70 (br, 1H), 2.60 (br, 1H), 2.40-2.10 (m, 4H), 1.35 (dd, 6H). LCMS: 672.30 [M+H]$^+$.

Example 31

(S)-2-(3-(3-Fluoropyridin-4-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

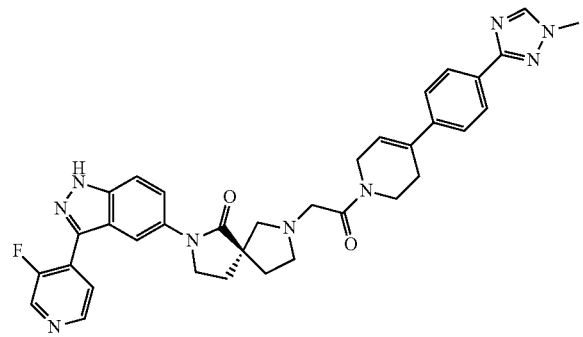 [SMILES: Cn1cnc(-c2ccc(C3=CCN(C(=O)CN4CC[C@]5(CCN(c6ccc7[nH]nc(-c8ccncc8F)c7c6)C5=O)C4)CC3)cc2)n1]

The title compound was prepared following General Procedures A and B using (S)-2-(3-(3-fluoropyridin-4-yl)-1-trityl-1H-indazol-5-yl)-2,7-diazaspiro[4.4]nonan-1-one (Intermediate 14) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, CDCl$_3$) δ 11.10 (br s, 1H), 8.65 (s, 1H), 8.54 (s, 1H), 8.09-8.06 (m, 3H), 7.93-7.83 (m, 3H), 7.53-7.46 (m, 3H), 6.19-6.14 (d, 1H), 4.27 (s, 2H), 4.00 (s, 3H), 3.91-3.81 (m, 4H), 3.55-3.41 (m, 2H), 3.14-3.05 (m, 2H), 2.98-2.61 (m, 4H), 2.44-2.37 (m, 2H), 2.25-2.20 (m, 1H), 1.94-1.92 (m, 1H). LCMS 632.30 [M+H]$^+$.

Example 32

(S)-2-(3-(6-Isopropoxypyridin-3-yl)-1H-indazol-5-yl)-7-(2-(4-(4-(1-methyl-1H-1,2,4-triazol-3-yl)phenyl)piperazin-1-yl)-2-oxoethyl)-2,7-diazaspiro[4.4]nonan-1-one

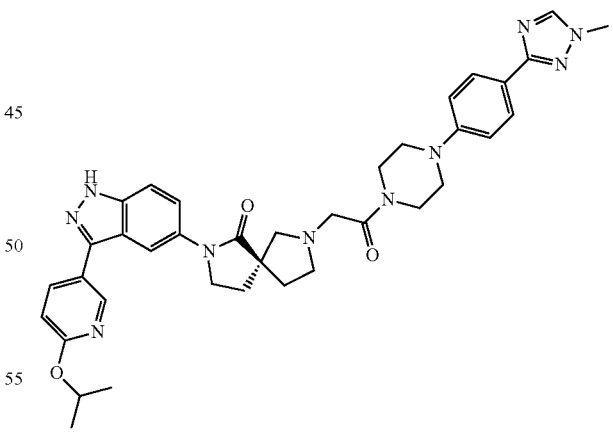

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-methyl-1H-1,2,4-triazol-3-yl)phenyl)piperazin-1-yl)ethan-1-one (Intermediate 32). $^1$H NMR (400 MHz, DMSO-$d_6$-HCl salt) δ 13.30 (s, 1H), 10.80 (br, 0.6H), 10.40 (br, 0.4H), 8.99 (s, 1H), 8.75 (d, 1H), 8.22 (dd, 2H), 7.96-7.93 (m, 2H), 7.65-7.62 (m, 2H), 7.17-7.15 (m, 2H), 6.93 (d, 1H), 5.35-5.20 (m, 1H), 4.60-4.59 (m, 2H), 4.05-3.95 (m, 2H), 3.94 (s, 3H), 3.82-3.77 (m, 1H), 3.70 (br, 2H), 3.57-3.56 (m, 2H), 3.47-3.33 (m, 7H), 2.45-2.33 (m, 2H), 2.29-2.16 (m, 2H), 1.34 (dd, 6H). LCMS: 675.40 [M+H]⁺.

Example 33

(S)-7-(2-(4-(4-(1-Methyl-1H-1,2,4-triazol-3-yl)phenyl)-3,6-dihydropyridin-1(2H)-yl)-2-oxoethyl)-2-(3-morpholino-1H-indazol-5-yl)-2,7-diazaspiro[4.4]nonan-1-one

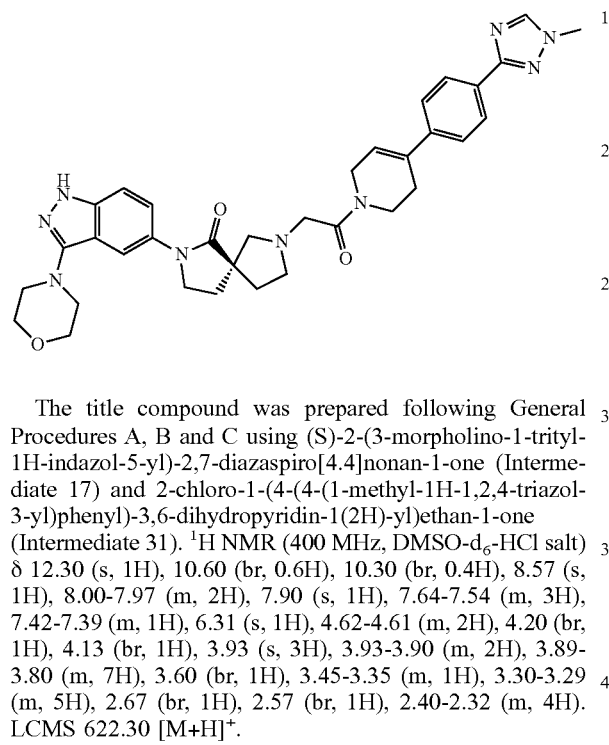

The title compound was prepared following General Procedures A, B and C using (S)-2-(3-morpholino-1-trityl-1H-indazol-5-yl)-2,7-diazaspiro[4.4]nonan-1-one (Intermediate 17) and 2-chloro-1-(4-(4-(1-methyl-1H-1,2,4-triazol-3-yl)phenyl)-3,6-dihydropyridin-1(2H)-yl)ethan-1-one (Intermediate 31). ¹H NMR (400 MHz, DMSO-d₆-HCl salt) δ 12.30 (s, 1H), 10.60 (br, 0.6H), 10.30 (br, 0.4H), 8.57 (s, 1H), 8.00-7.97 (m, 2H), 7.90 (s, 1H), 7.64-7.54 (m, 3H), 7.42-7.39 (m, 1H), 6.31 (s, 1H), 4.62-4.61 (m, 2H), 4.20 (br, 1H), 4.13 (br, 1H), 3.93 (s, 3H), 3.93-3.90 (m, 2H), 3.89-3.80 (m, 7H), 3.60 (br, 1H), 3.45-3.35 (m, 1H), 3.30-3.29 (m, 5H), 2.67 (br, 1H), 2.57 (br, 1H), 2.40-2.32 (m, 4H). LCMS 622.30 [M+H]⁺.

Example 34

(S)-7-(2-(4-(4-(1-Methyl-1H-1,2,4-triazol-3-yl)phenyl)-3,6-dihydropyridin-1(2H)-yl)-2-oxoethyl)-2-(3-(4-(trifluoromethyl)pyridin-3-yl)-1H-indazol-5-yl)-2,7-diazaspiro[4.4]nonan-1-one

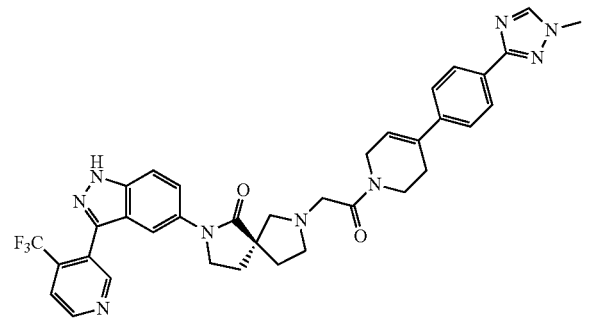 [SMILES: Cn1cnc(-c2ccc(C3=CCN(C(=O)CN4CC[C@]5(CCN(c6ccc7[nH]nc(-c8cnccc8C(F)(F)F)c7c6)C5=O)C4)CC3)cc2)n1]

The title compound was prepared following General Procedures A, B and C using (S)-2-(3-(3-(trifluoromethyl) pyridin-4-yl)-1-trityl-1H-indazol-5-yl)-2,7-diazaspiro[4.4]nonan-1-one (Intermediate 16) and 2-chloro-1-(4-(4-(1-methyl-1H-1,2,4-triazol-3-yl)phenyl)-3,6-dihydropyridin-1(2H)-yl)ethan-1-one (Intermediate 31). LCMS 682.30 [M+H]⁺.

Example 35

(S)-2-(3-(6-isopropoxypyridin-3-yl)-1H-indazol-5-yl)-7-(2-(4-(5-(1-methyl-1H-1,2,4-triazol-3-yl)pyridin-2-yl)piperazin-1-yl)-2-oxoethyl)-2,7-diazaspiro[4.4]nonan-1-one

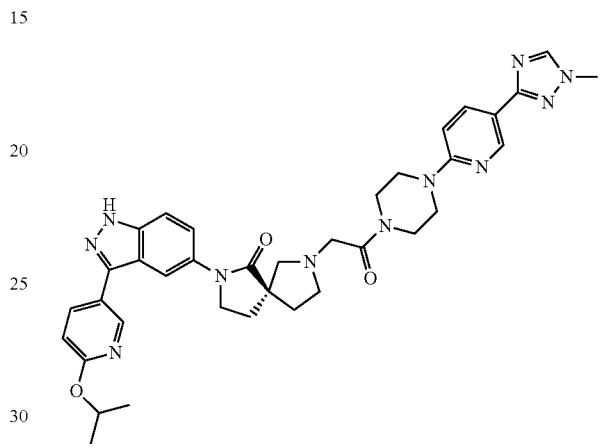

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(5-(1-methyl-1H-1,2,4-triazol-3-yl)pyridin-2-yl)piperazin-1-yl)ethan-1-one (Intermediate 49). ¹H NMR (400 MHz, DMSO-d₆) δ 13.27 (s, 1H), 8.72 (dd, J=6.8, 2.4 Hz, 2H), 8.46 (s, 1H), 8.21 (dd, J=8.8, 2.4 Hz, 1H), 8.14 (s, 1H), 8.05 (dd, J=8.8, 2.4 Hz, 1H), 7.77 (dd, J=9.6, 2.0 Hz, 1H), 7.58 (d, J=8.4 Hz, 1H), 6.96-6.87 (m, 2H), 5.36-5.29 (m, 1H), 3.93-3.89 (m, 5H), 3.68-3.58 (m, 8H), 3.38 (br s, 2H), 2.93 (br s, 1H), 2.86-2.84 (m, 1H), 2.67-2.64 (m, 2H), 2.22-2.09 (m, 3H), 1.82-1.79 (m, 1H), 1.34 (d, J=6.4 Hz, 6H). LCMS: 675.43 [M+H]⁺.

Example 36

(S)-2-(1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

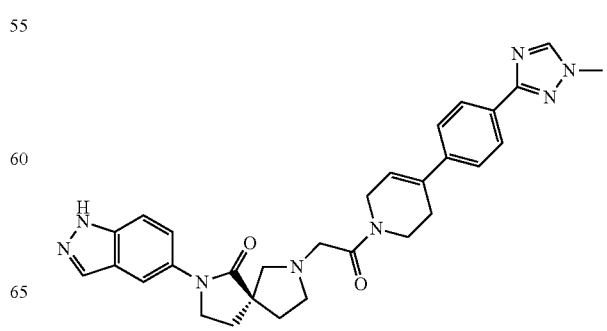

215

-continued

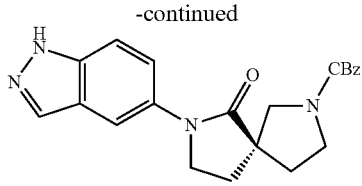

Step 1: Benzyl (R)-7-(1H-indazol-5-yl)-6-oxo-2,7-diazaspiro[4.4]nonane-2-carboxylate To a stirred solution of benzyl (R) 7-(3-iodo-1-trityl-1H-indazol-5-yl)-6-oxo-2,7-diazaspiro[4.4]nonane-2-carboxylate (Intermediate 7) (330 mg, 0.435 mmol) in methanol (10 mL) was added 10% wet Pd/C (100 mg). The mixture was stirred at rt under hydrogen atmosphere (60 psi) for 16 h. The mixture was filtered through Celite, and the organic fractions were concentrated to afford the title compound (150 mg, 0.384 mmol, 88% yield) as an off white solid. LCMS: 391.3 [M+H]$^+$.

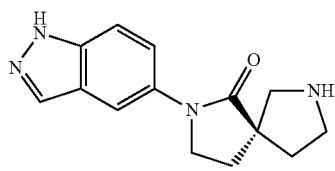 [SMILES: O=C1N(c2ccc3[nH]ncc3c2)CC[C@]12CCNC2]

Step 2: (S)-2-(1H-Indazol-5-yl)-2,7-diazaspiro[4.4]nonan-1-one

To a stirred solution of benzyl (R)-7-(1H-indazol-5-yl)-6-oxo-2,7-diazaspiro[4.4]nonane-2-carboxylate (150 mg, 0.384 mmol) in methanol (10 mL) was added 10% wet Pd/C (100 mg). The mixture was stirred at rt under hydrogen atmosphere (60 psi) for 16 h. The mixture was filtered through Celite, and the organic fractions were concentrated to afford the title compound as an off white solid. $^1$H NMR (300 MHz, DMSO-d$_6$) δ 13.06 (br s, 1H), 8.05 (s, 1H), 7.86 (d, J=1.5 Hz, 1H), 7.77 (dd, J=1.8, 9.2 Hz, 1H), 7.53 (d, J=8.8 Hz, 1H), 3.83 (br t, J=7.2 Hz, 2H), 3.60 (s, 1H), 2.94-2.81 (m, 4H), 2.01-1.99 (m, 3H), 189-1.80 (m, 1H). LCMS: 257.1 [M+H]$^+$.

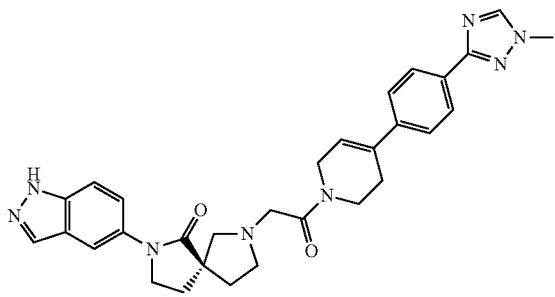 [SMILES: Cn1cnc(-c2ccc(C3=CCN(C(=O)CN4CC[C@]5(CCN(c6ccc7[nH]ncc7c6)C5=O)C4)CC3)cc2)n1]

216

Step 3: (S)-2-(1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one To a stirred solution of (S)-2-(1H-indazol-5-yl)-2,7-diazaspiro[4.4]nonan-1-one (80 mg, 0.312 mmol) in DMF (5 mL) at rt was added 2-chloro-1-(4-(4-(1-methyl-1H-1,2,4-triazol-3-yl)phenyl)-5,6-dihydropyridin-1(2H)-yl)ethanone (Intermediate 31) (99 mg, 0.312 mmol) and DIPEA (241.4 mg, 1.87 mmol). The mixture was stirred at rt for 16 h. After completion of the reaction, water was added. The mixture was extracted with ethyl acetate (3×50 mL). The combined organic layers were washed with water (10 mL) and brine (20 mL), dried over sodium sulfate, filtered and concentrated. The residue obtained was purified by Reveleris C-18 reversed phase column using 40% acetonitrile in aqueous formic acid (0.1%) to afford the title compound (60 mg, 0.111 mmol, 36% yield). $^1$H NMR (400 MHz, DMSO-d$_6$) δ 13.07 (br s, 1H), 8.51 (s, 1H), 8.07 (s, 1H), 7.97 (d, J=8.8 Hz, 2H), 7.88 (br d, J=3.4 Hz, 1H), 7.77-7.72 (m, 1H), 7.58-7.52 (m, 3H), 6.29 (br s, 1H), 4.25-4.13 (m, 2H), 3.93-3.81 (m, 6H), 3.71 (ddd, J=6.1, 12.1, 18.0 Hz, 2H), 3.12 (br s, 4H), 2.68-2.44 (m, 3H), 2.31-2.13 (m, 3H), 1.97 (br s, 1H). LCMS: 537.3 [M+H]$^+$.

Example 37

(S)-5-(7-(2-(4-(4-(1-Methyl-1H-1,2,4-triazol-3-yl)phenyl)piperazin-1-yl)-2-oxoethyl)-1-oxo-2,7-diazaspiro[4.4]nonan-2-yl)-1H-indazole-3-carbonitrile

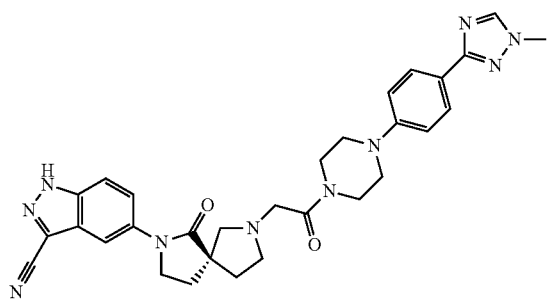 [SMILES: Cn1cnc(-c2ccc(N3CCN(C(=O)CN4CC[C@]5(CCN(c6ccc7[nH]nc(C#N)c7c6)C5=O)C4)CC3)cc2)n1]

The title compound was prepared following General Procedures A, B and C using (S)-5-(1-oxo-2,7-diazaspiro[4.4]nonan-2-yl)-1-trityl-1H-indazole-3-carbonitrile hydrochloride (Intermediate 27) and 2-chloro-1-(4-(4-(1-methyl-1H-1,2,4-triazol-3-yl)phenyl)piperazin-1-yl)ethan-1-one (Intermediate 32). $^1$H NMR (300 MHz, DMSO-d$_6$) δ 14.18 (s, 1H), 8.42 (s, 1H), 8.01-7.97 (m, 2H), 7.85-7.82 (m, 2H), 7.77 (d, J=8.7 Hz, 1H), 7.02 (d, J=8.7 Hz, 1H), 3.95-3.88 (m, 5H), 3.72-3.60 (m, 4H), 3.38-3.20 (m, 6H), 2.96-2.91 (m, 1H), 2.84-2.82 (m, 1H), 2.91-2.81 (m, 1H), 2.65-2.62 (m, 2H), 2.20-2.11 (m, 4H), 1.85-1.75 (m, 1H). LCMS: 565.38 [M+H]$^+$.

Example 38

(S)-7-(2-(4-(4-(1-Methyl-1H-1,2,4-triazol-3-yl)phenyl)-3,6-dihydropyridin-1(2H)-yl)-2-oxoethyl)-2-(3-(2-(1-(trifluoromethyl)cyclopropyl)pyridin-4-yl)-1H-indazol-5-yl)-2,7-diazaspiro[4.4]nonan-1-one

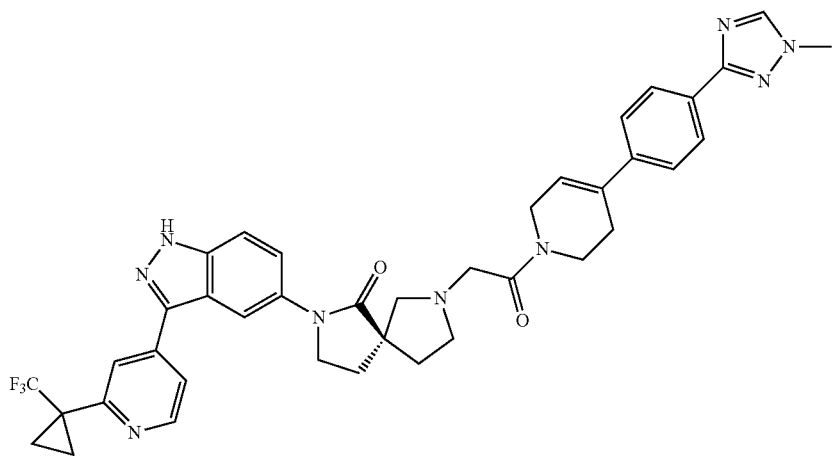 [SMILES: Cn1cnc(-c2ccc(C3=CCN(C(=O)CN4CC[C@]5(CCN(c6ccc7[nH]nc(-c8ccnc(C9(C(F)(F)F)CC9)c8)c7c6)C5=O)C4)CC3)cc2)n1]

The title compound was prepared following General Procedures A and B using (S)-2-(3-(2-(1-(trifluoromethyl)cyclopropyl)pyridin-4-yl)-1-trityl-1H-indazol-5-yl)-2,7-diazaspiro[4.4]nonan-1-one (Intermediate 18) and 2-chloro-1-(4-(4-(1-methyl-1H-1,2,4-triazol-3-yl)phenyl)-3,6-dihydropyridin-1(2H)-yl)ethan-i-one (Intermediate 31). $^1$H NMR (400 MHz, DMSO-d$_6$) δ 13.64 (s, 1H), 8.67 (d, J=4.4 Hz, 1H), 8.50 (s, 1H), 8.22 (s, 1H), 8.12 (s, 1H), 7.99-7.83 (m, 4H), 7.67 (d, J=8.8 Hz, 1H), 7.58-7.51 (m, 2H), 6.28 (br s, 1H), 4.31 (br s, 1H), 4.13 (d, J=4.9 Hz, 1H), 3.98-3.85 (m, 5H), 3.85-3.68 (m, 2H), 3.55-3.35 (br d, J=11.7 Hz, 2H), 3.01-2.82 (m, 2H), 2.76-2.53 (m, 4H), 2.30-2.09 (m, 3H), 1.83 (br s, 1H), 1.52-1.42 (br d, J=5.9 Hz, 4H). LCMS: 722.38 [M+H]$^+$.

Example 39

(S)-2-(3-(2-(1,1-difluoroethyl)pyridin-4-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

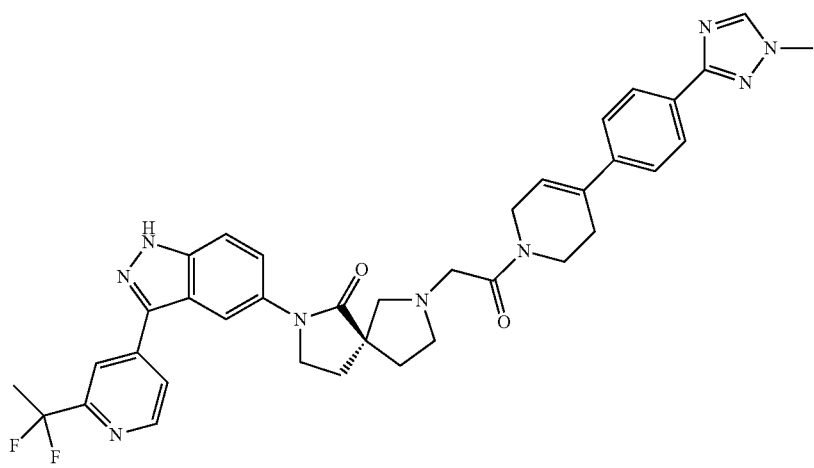 [SMILES: Cn1cnc(-c2ccc(C3=CCN(C(=O)CN4CC[C@]5(CCN(c6ccc7[nH]nc(-c8ccnc(C(C)(F)F)c8)c7c6)C5=O)C4)CC3)cc2)n1]

The title compound was prepared following General Procedures A and B using (S)-2-(3-(2-(1,1-difluoroethyl)pyridin-4-yl)-1-trityl-1H-indazol-5-yl)-2,7-diazaspiro[4.4]nonan-1-one (Intermediate 19) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-$d_6$) δ 13.73 (s, 1H), 8.79 (br d, J=4.4 Hz, 1H), 8.51 (s, 1H), 8.29 (s, 1H), 8.22 (s, 1H), 8.13 (d, J=4.9 Hz, 1H), 7.95 (br d, J=8.3 Hz, 2H), 7.85 (br t, J=7.3 Hz, 1H), 7.68 (d, J=9.3 Hz, 1H), 7.59-7.50 (m, 2H), 6.29 (br s, 1H), 4.38-4.25 (m, 1H), 4.13 (br d, J=6.8 Hz, 1H), 3.92 (s, 5H), 3.81-3.68 (m, 1H), 3.53-3.34 (m, 2H), 3.04-2.79 (m, 3H), 2.73-2.57 (m, 2H), 2.29-1.96 (m, 8H), 1.88-1.74 (m, 1H). LCMS: 678.31 [M+H]$^+$.

Example 40

(S)-2-(3-(2-(Difluoromethyl)pyridin-4-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

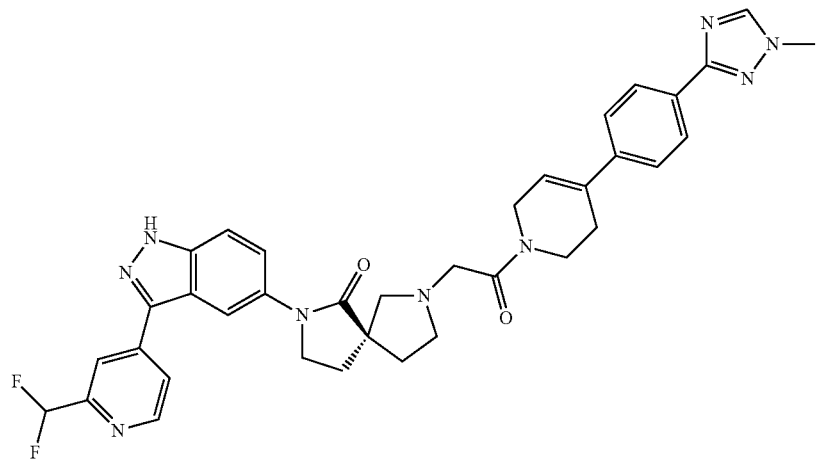 [SMILES: Cn1cnc(-c2ccc(C3=CCN(C(=O)CN4CC[C@]5(CCN(c6ccc7[nH]nc(-c8ccnc(C(F)F)c8)c7c6)C5=O)C4)CC3)cc2)n1]

The title compound was prepared following General Procedures A and B using (S)-2-(3-(2-(difluoromethyl)pyridin-4-yl)-1-trityl-1H-indazol-5-yl)-2,7-diazaspiro[4.4]nonan-1-one (Intermediate 20) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-$d_6$) δ 13.75 (s, 1H), 8.81 (br d, J=4.9 Hz, 1H), 8.51 (s, 1H), 8.32-8.20 (m, 2H), 8.16 (br d, J=4.9 Hz, 1H), 7.96 (br d, J=7.9 Hz, 2H), 7.86 (br t, J=7.9 Hz, 1H), 7.68 (d, J=9.2 Hz, 1H), 7.54 (br d, J=7.9 Hz, 2H), 7.06 (t, J=55 Hz, 1H), 6.29 (br s, 1H), 4.39-4.05 (m, 2H), 4.00-3.85 (br m, 5H), 3.85-3.62 (m, 2H), 3.52-3.36 (m, 2H), 3.02-2.80 (m, 2H), 2.65-2.55 (br m, 4H), 2.30-2.05 (br m, 3H), 1.90-1.62 (br m, 1H). LCMS: 664.38 [M+H]$^+$.

Example 41

(S)-7-(2-(4-(4-(1-methyl-1H-1,2,3-triazol-4-yl)phenyl)-3,6-dihydropyridin-1(2H)-yl)-2-oxoethyl)-2-(3-(2-(trifluoromethyl)pyridin-4-yl)-1H-indazol-5-yl)-2,7-diazaspiro[4.4]nonan-1-one

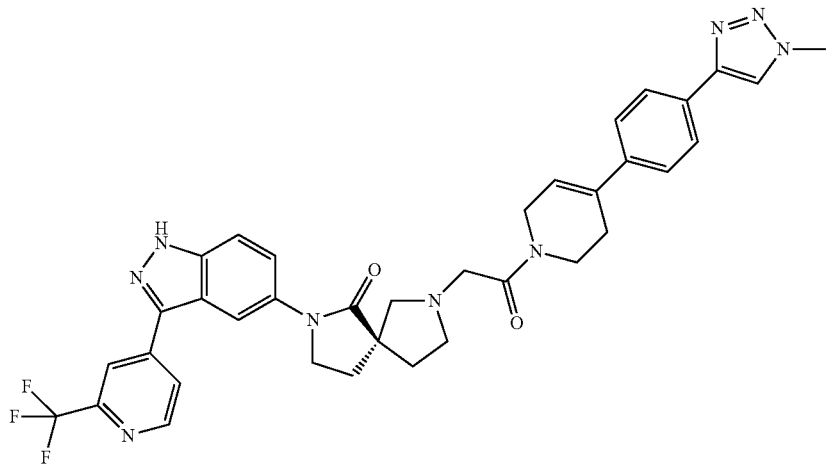 [SMILES: Cn1cc(-c2ccc(C3=CCN(C(=O)CN4CC[C@]5(CCN(c6ccc7[nH]nc(-c8ccnc(C(F)(F)F)c8)c7c6)C5=O)C4)CC3)cc2)nn1]

The title compound was prepared following General Procedures A, B and C using (S)-2-(3-(2-(trifluoromethyl)pyridin-4-yl)-1-trityl-1H-indazol-5-yl)-2,7-diazaspiro[4.4]nonan-1-one (Intermediate 9) and 2-chloro-1-(4-(4-(1-methyl-1H-1,2,3-triazol-4-yl)phenyl)-5,6-dihydropyridin-1(2H)-yl)ethanone (Intermediate 38). LCMS: 682.30 $[M+H]^+$.

Example 42

(S)-7-(2-(4-(4-(5-Methyl-1,3,4-oxadiazol-2-yl)phenyl)-3,6-dihydropyridin-1(2H)-yl)-2-oxoethyl)-2-(3-(2-(trifluoromethyl)pyridin-4-yl)-1H-indazol-5-yl)-2,7-diazaspiro[4.4]nonan-1-one

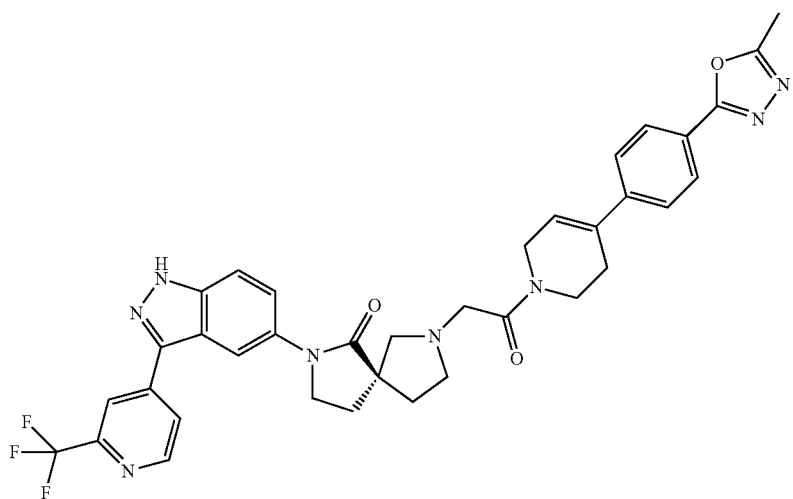 [SMILES: Cc1nnc(-c2ccc(C3=CCN(C(=O)CN4CC[C@]5(CCN(c6ccc7[nH]nc(-c8ccnc(C(F)(F)F)c8)c7c6)C5=O)C4)CC3)cc2)o1]

The title compound was prepared following General Procedures A, B and C using (S)-2-(3-(2-(trifluoromethyl)pyridin-4-yl)-1-trityl-1H-indazol-5-yl)-2,7-diazaspiro[4.4]nonan-1-one (Intermediate 9) and 2-chloro-1-(4-(4-(5-methyl-1,3,4-oxadiazol-2-yl)phenyl)-5,6-dihydropyridin-1(2H)-yl)ethanone (Intermediate 36). LCMS: 683.20 [M+H]⁺.

Example 43

(S)-7-(2-(4-(4-(3-methyl-1,2,4-oxadiazol-5-yl)phenyl)-3,6-dihydropyridin-1(2H)-yl)-2-oxoethyl)-2-(3-(2-(trifluoromethyl)pyridin-4-yl)-1H-indazol-5-yl)-2,7-diazaspiro[4.4]nonan-1-one The title compound was prepared following General Procedures A using (S)-2-(3-cyclopropyl-1H-indazol-5-yl)-2,7-diazaspiro[4.4]nonan-1-one (Intermediate 26) and 2-chloro-1-(4-(4-(1-methyl-1H-1,2,4-triazol-3-yl)phenyl)piperazin-1-yl)ethan-1-one (Intermediate 32). ¹H NMR (400 MHz, DMSO-d₆) δ 12.53 (s, 1H), 8.42 (s, 1H), 7.89-7.81 (m, 3H), 7.66 (dd, J=1.7, 9.0 Hz, 1H), 7.42 (d, J=9.3 Hz, 1H), 7.03 (d, J=8.8 Hz, 2H), 3.88 (s, 3H), 3.86-3.79 (m, 2H), 3.72 (br s, 2H), 3.61 (br s, 2H), 3.39 (br s, 2H), 3.30-3.15 (m, 5H), 2.94 (br d, J=5.4 Hz, 1H), 2.84 (br d, J=8.8 Hz, 1H), 2.69-2.59 (m, 1H), 2.28-2.03 (m, 4H), 1.85-1.75 (m, 1H), 1.02-0.88 (m, 4H). LCMS: 580.40 [M+H]⁺.

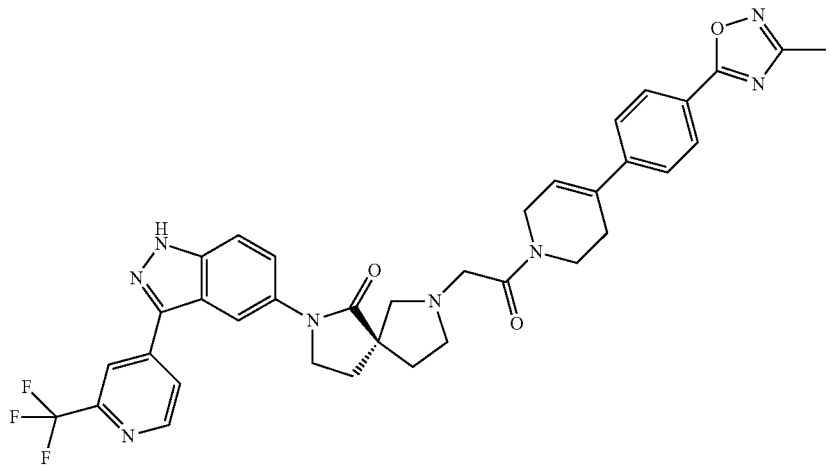 [SMILES: Cc1noc(-c2ccc(C3=CCN(C(=O)CN4CC[C@]5(CCN(c6ccc7[nH]nc(-c8ccnc(C(F)(F)F)c8)c7c6)C5=O)C4)CC3)cc2)n1]

The title compound was prepared following General Procedures A, B and C using (S)-2-(3-(2-(trifluoromethyl)pyridin-4-yl)-1-trityl-1H-indazol-5-yl)-2,7-diazaspiro[4.4]nonan-1-one (Intermediate 9) and 2-Chloro-1-(4-(4-(3-methyl-1,2,4-oxadiazol-5-yl)phenyl)-3,6-dihydropyridin-1(2H)-yl)ethan-1-one (Intermediate 48). LCMS: 683.30 [M+H]⁺.

Example 44

(S)-2-(3-Cyclopropyl-1H-indazol-5-yl)-7-(2-(4-(4-(1-methyl-1H-1,2,4-triazol-3-yl)phenyl)piperazin-1-yl)-2-oxoethyl)-2,7-diazaspiro[4.4]nonan-1-one Example 45

(S)-2-(3-Cyclopropyl-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

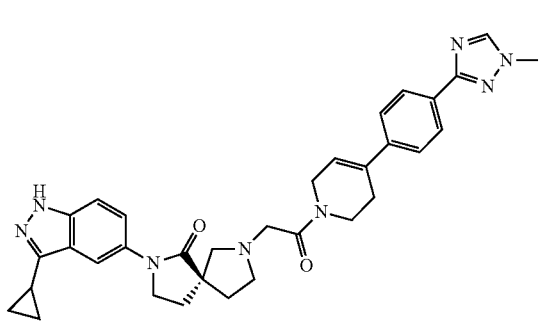

The title compound was prepared following General Procedures A using (S)-2-(3-cyclopropyl-1H-indazol-5-yl)-2,7-diazaspiro[4.4]nonan-1-one (Intermediate 26) and 2-chloro-1-(4-(4-(1-methyl-1H-1,2,4-triazol-3-yl)phenyl)-3,6-dihydropyridin-1(2H)-yl)ethan-1-one (Intermediate 31). ¹H NMR (300 MHz, DMSO-d₆) δ 12.53 (s, 1H), 8.51 (s, 1H), 7.96 (d, J=8.4 Hz, 2H), 7.87 (br d, J=8.4 Hz, 1H), 7.66 (br d, J=9.2 Hz, 1H), 7.55 (br d, J=8.1 Hz, 2H), 7.42 (d, J=8.8 Hz, 1H), 6.29 (br s, 1H), 4.31 (br s, 1H), 4.15 (br s,

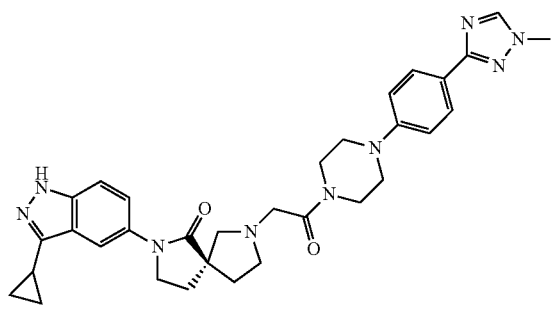 [SMILES: Cn1cnc(-c2ccc(N3CCN(C(=O)CN4CC[C@]5(CCN(c6ccc7[nH]nc(C8CC8)c7c6)C5=O)C4)CC3)cc2)n1]

1H), 3.92 (s, 3H), 3.88-3.69 (m, 4H), 3.52-3.37 (m, 2H), 2.99-2.78 (m, 3H), 2.74-2.56 (m, 3H), 2.30-2.09 (m, 4H), 1.82 (m, 1H), 1.01-0.88 (m, 4H). LCMS: 577.40 [M+H]⁺.

Example 46

(S)-7-(2-(4-(4-(1-Ethyl-1H-1,2,4-triazol-3-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

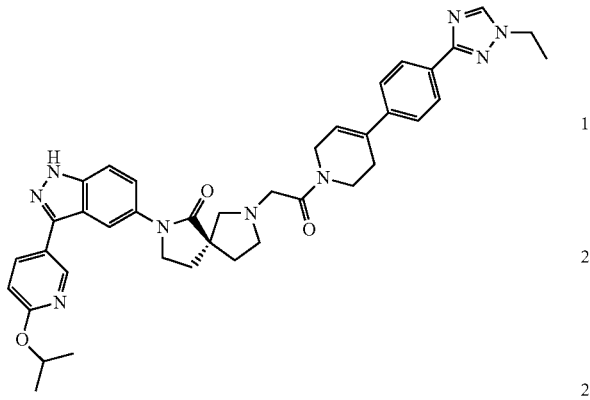

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-ethyl-1H-1,2,4-triazol-3-yl)phenyl)-3,6-dihydropyridin-1(2H)-yl)ethan-1-one (Intermediate 50). ¹H NMR (300 MHz, DMSO-d₆) δ 13.25 (s, 1H), 8.73 (d, J=2.2 Hz, 1H), 8.56 (s, 1H), 8.22 (dd, J=2.6, 8.4 Hz, 1H), 8.15 (s, 1H), 7.97 (br d, J=7.7 Hz, 2H), 7.77 (br d, J=9.2 Hz, 1H), 7.56 (br dd, J=8.8, 12.5 Hz, 3H), 6.90 (d, J=8.4 Hz, 1H), 6.29 (br s, 1H), 5.33 (td, J=6.0, 12.3 Hz, 1H), 4.35-4.08 (m, 4H), 4.00-3.63 (m, 4H), 3.40 (br d, J=11.7 Hz, 2H), 3.02-2.80 (m, 2H), 2.74-2.55 (m, 4H), 2.32-2.03 (m, 3H), 1.81 (br s, 1H), 1.44 (t, J=7.2 Hz, 3H), 1.34 (d, J=6.2 Hz, 6H). LCMS: 686.43 [M+H]⁺.

Example 47

(S)-7-(2-(4-(4-(1-(2-Hydroxyethyl)-1H-1,2,4-triazol-3-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

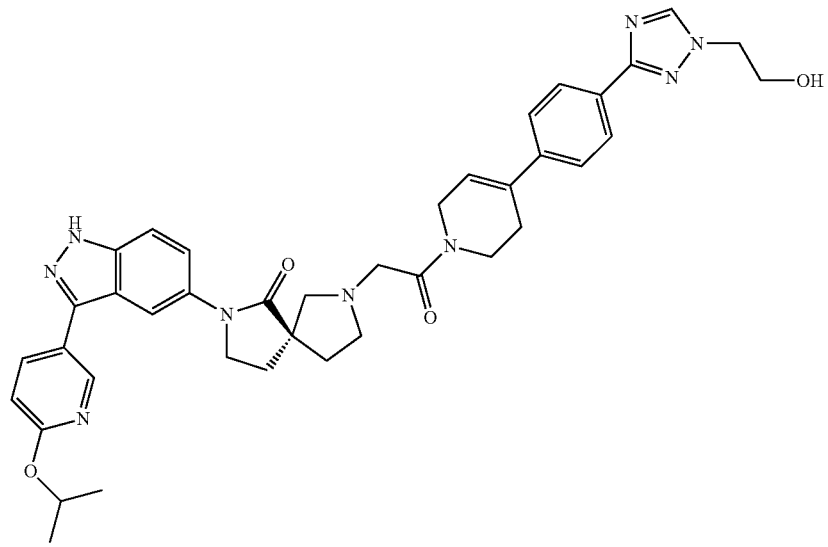 [SMILES: CC(C)Oc1ccc(-c2n[nH]c3ccc(N4CC[C@]5(CCN(CC(=O)N6CC=C(c7ccc(-c8ncn(CCO)n8)cc7)CC6)C5)C4=O)cc23)cn1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-(2-hydroxyethyl)-1H-1,2,4-triazol-3-yl)phenyl)-3,6-dihydropyridin-1(2H)-yl)ethan-1-one (Intermediate 51). $^1$H NMR (400 MHz, DMSO-$d_6$) δ 13.27 (s, 1H), 8.74 (d, J=2.0 Hz, 1H), 8.50 (s, 1H), 8.22 (dd, J=2.4, 8.3 Hz, 1H), 8.16 (s, 1H), 7.97 (br d, J=8.3 Hz, 2H), 7.76 (br t, J=6.8 Hz, 1H), 7.62-7.52 (m, 3H), 6.90 (d, J=8.3 Hz, 1H), 6.29 (br s, 1H), 5.33 (td, J=6.1, 12.2 Hz, 1H), 5.00 (t, J=5.1 Hz, 1H), 4.25 (br t, J=5.4 Hz, 3H), 4.14 (br s, 1H), 3.91 (br d, J=7.3 Hz, 2H), 3.83-3.62 (m, 8H), 3.00 (br s, 3H), 2.73-2.57 (m, 1H), 2.30-2.09 (m, 3H), 1.89 (br d, J=15.7 Hz, 1H), 1.34 (d, J=6.4 Hz, 6H). LCMS: 702.44 [M+H]$^+$.

Example 48

(S)-7-(2-(4-(4-(1-Methyl-1H-1,2,4-triazol-3-yl)phenyl)-3,6-dihydropyridin-1(2H)-yl)-2-oxoethyl)-2-(3-(1-methyl-1H-pyrazol-4-yl)-1H-indazol-5-yl)-2,7-diazaspiro[4.4]nonan-1-one

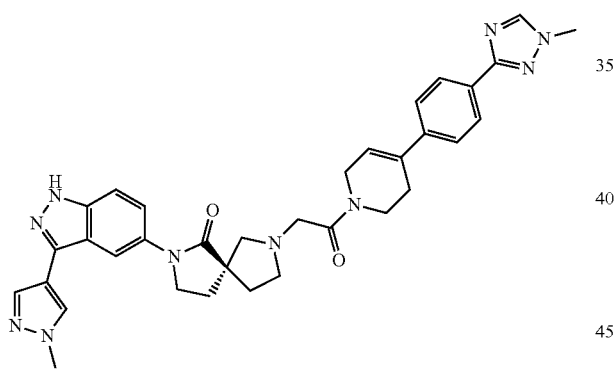

The title compound was prepared following General Procedures A and B using (S)-2-(3-(1-methyl-1H-pyrazol-4-yl)-1-trityl-1H-indazol-5-yl)-2,7-diazaspiro[4.4]nonan-1-one (Intermediate 25) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (300 MHz, DMSO-$d_6$) δ 12.94 (s, 1H), 8.51 (s, 1H), 8.30 (s, 1H), 8.01-7.92 (m, 4H), 7.82-7.73 (m, 1H), 7.53 (br t, J=9.4 Hz, 3H), 6.29 (br s, 1H), 4.30 (br s, 1H), 4.14 (br s, 1H), 3.93 (d, J=5.1 Hz, 8H), 3.80-3.62 (m, 2H), 3.45 (br s, 2H), 3.04-2.81 (m, 2H), 2.76-2.54 (m, 4H), 2.30-2.05 (m, 3H), 1.85 (br d, J=7.0 Hz, 1H). LCMS: 617.41 [M+H]$^+$.

Example 49

(S)-2-(3-(6-Isopropoxypyridin-3-yl)-1H-indazol-5-yl)-7-(2-(4-(4-(1-(2-methoxyethyl)-1H-1,2,4-triazol-3-yl)phenyl)-3,6-dihydropyridin-1(2H)-yl)-2-oxo-ethyl)-2,7-diazaspiro[4.4]nonan-1-one

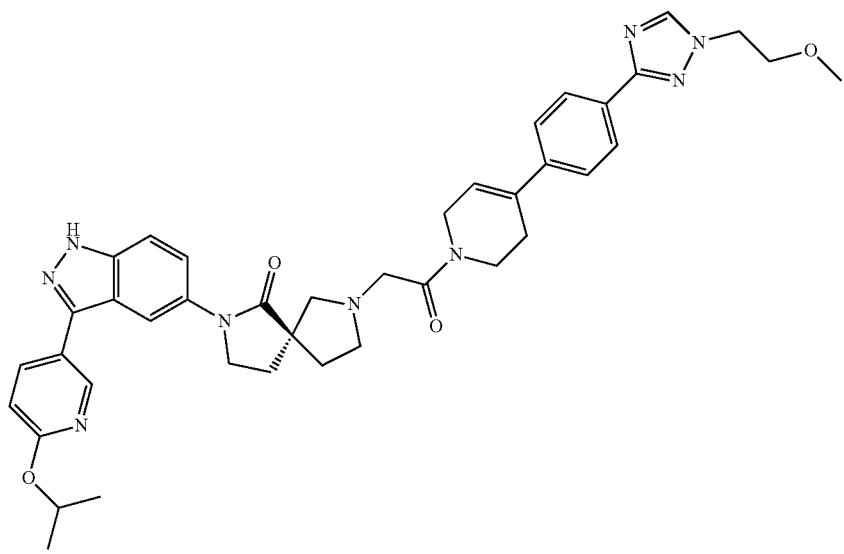 [SMILES: COCCn1cnc(-c2ccc(C3=CCN(C(=O)CN4CC[C@]5(CCN(c6ccc7[nH]nc(-c8ccc(OC(C)C)nc8)c7c6)C5=O)C4)CC3)cc2)n1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-(2-methoxyethyl)-1H-1,2,4-triazol-3-yl)phenyl)-3,6-dihydropyridin-1(2H)-yl)ethan-1-one (Intermediate 52). $^1$H NMR (400 MHz, DMSO-$d_6$) δ 13.24 (s, 1H), 8.73 (d, J=2.0 Hz, 1H), 8.52 (s, 1H), 8.22 (dd, J=2.2, 8.6 Hz, 1H), 8.15 (s, 1H), 7.96 (br d, J=8.3 Hz, 2H), 7.76 (br t, J=6.8 Hz, 1H), 7.56 (br dd, J=8.8, 15.2 Hz, 3H), 6.89 (br d, J=8.8 Hz, 1H), 6.29 (br s, 1H), 5.33 (td, J=5.9, 12.1 Hz, 1H), 4.38 (t, J=5.1 Hz, 2H), 4.31 (br d, J=8.3 Hz, 1H), 4.13 (br s, 1H), 3.97-3.83 (m, 2H), 3.81-3.61 (m, 5H), 3.40 (br d, J=11.7 Hz, 3H), 3.25 (s, 3H), 3.00-2.76 (m, 2H), 2.65 (br d, J=16.6 Hz, 2H), 2.27-2.03 (m, 3H), 1.81 (br dd, J=6.1, 12.0 Hz, 1H), 1.33 (d, J=6.4 Hz, 6H). LCMS: 716.47 [M+H]$^+$.

Example 50

(S)-7-(2-(4-(4-(1-Cyclopropyl-1H-1,2,4-triazol-3-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

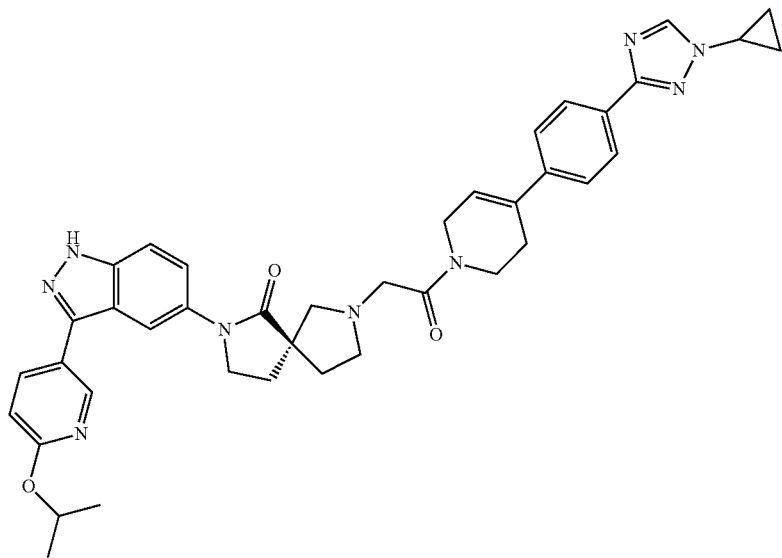 [SMILES: CC(C)Oc1ccc(-c2n[nH]c3ccc(N4CC[C@]5(CCN(CC(=O)N6CC=C(c7ccc(-c8ncn(C9CC9)n8)cc7)CC6)C5)C4=O)cc23)cn1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(1-cyclopropyl-1H-1,2,4-triazol-3-yl)phenyl)-3,6-dihydropyridin-1(2H)-yl)ethan-1-one (Intermediate 53). $^1$H NMR (400 MHz, DMSO-$d_6$) δ 13.21 (s, 1H), 8.73 (d, J=2.4 Hz, 1H), 8.62 (s, 1H), 8.21 (d, J=8.8, 2.4 Hz, 1H), 8.15 (s, 1H), 7.95 (d, J=8.8 Hz, 2H), 7.78-7.74 (m, 1H), 7.56-7.52 (m, 3H), 6.89 (d, J=8.4 Hz, 1H), 6.28 (s, 1H), 5.38-5.30 (m, 1H), 4.30-4.12 (m, 2H), 3.95-3.60 (m, 5H), 3.55-3.40 (m, 2H), 3.00-2.80 (m, 3H), 2.65-2.50 (m, 2H), 2.25-2.10 (m, 4H), 1.85-1.75 (m, 1H), 1.33 (d, 6H), 1.15-1.02 (m, 4H). LCMS: 698.48 [M+H]$^+$.

Example 51

(S)-5-(7-(2-(4-(4-(1-Methyl-1H-1,2,4-triazol-3-yl)phenyl)-3,6-dihydropyridin-1(2H)-yl)-2-oxoethyl)-1-oxo-2,7-diazaspiro[4.4]nonan-2-yl)-1H-indazole-3-carbonitrile The title compound was prepared following General Procedures A, B and C using (S)-5-(1-oxo-2,7-diazaspiro[4.4]nonan-2-yl)-1-trityl-1H-indazole-3-carbonitrile hydrochloride (Intermediate 27) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-$d_6$) δ 14.36 (s, 1H), 8.50 (s, 1H), 8.01-7.95 (m, 4H), 7.77 (d, J=9.2 Hz, 1H), 7.54 (d, J=8.4 Hz, 2H), 6.29 (br s, 1H), 4.35-4.27 (m, 1H), 4.35-4.27 (m, 1H), 4.14-4.10 (m, 1H), 3.92-3.67 (m, 7H), 3.48-3.38 (m, 2H), 2.98-2.80 (m, 3H), 2.72-2.60 (m, 3H), 2.25-2.08 (m, 3H), 1.87-1.76 (m, 1H). LCMS: 562.41 [M+H]$^+$.

Example 52

(S)-2-(3-(Difluoromethyl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

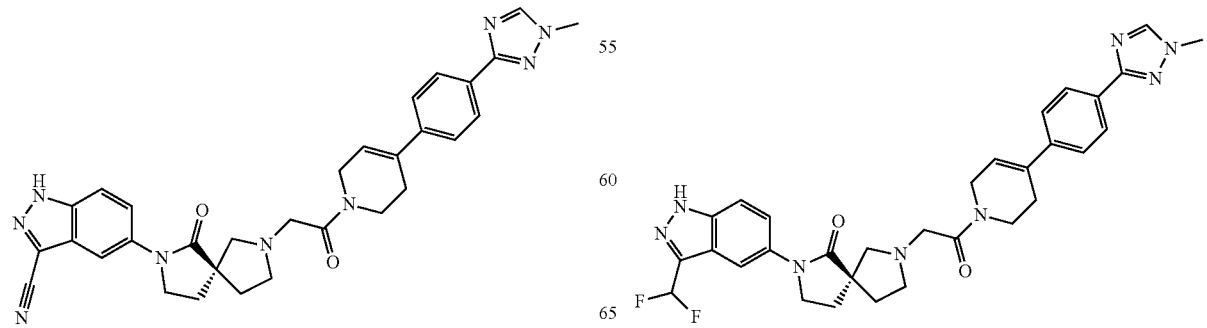

The title compound was prepared following General Procedures A, B and C using (S)-2-(3-(difluoromethyl)-1-trityl-1H-indazol-5-yl)-2,7-diazaspiro[4.4]nonan-1-one (Intermediate 29) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (300 MHz, DMSO-d$_6$) δ 13.60 (br s, 1H), 8.51 (s, 1H), 8.02-7.95 (m, 3H), 7.85-7.75 (m, 1H), 7.64 (d, J=9.0 Hz, 1H), 7.59-7.53 (m, 2H), 7.33 (bt, J=54.0 Hz, 1H), 6.28 (s, 1H), 4.30-4.12 (m, 2H), 3.92 (s, 3H), 3.90-3.70 (m, 4H), 3.45-3.38 (m, 2H), 2.99-2.80 (m, 2H), 2.75-2.55 (m, 3H), 2.28-2.10 (m, 4H), 1.90-1.75 (m, 1H). LCMS: 587.42 [M+H]$^+$.

Example 53

(S)-2-(3-(Ethylamino)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one

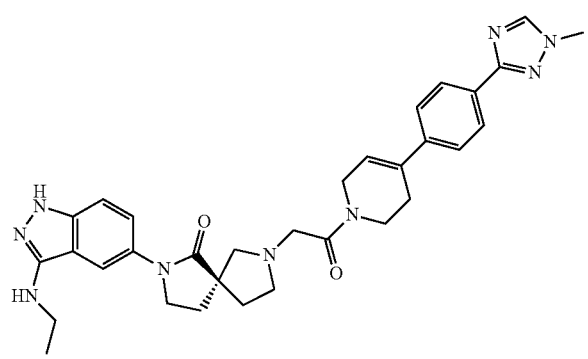 [SMILES: CCNc1n[nH]c2ccc(N3CC[C@]4(CCN(CC(=O)N5CC=C(c6ccc(-c7ncn(C)n7)cc6)CC5)C4)C3=O)cc12]

The title compound was prepared following General Procedures A, B and C using (S)-2-(3-(ethylamino)-1-trityl-1H-indazol-5-yl)-2,7-diazaspiro[4.4]nonan-1-one (Intermediate 28) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-d$_6$) δ 11.34 (s, 1H), 8.51 (s, 1H), 7.96 (d, J=8.3 Hz, 2H), 7.78 (s, 1H), 7.65-7.50 (m, 3H), 7.21 (d, J=9.3 Hz, 1H), 6.28 (br s, 1H), 5.87-5.82 (m, 1H), 4.29 (br s, 1H), 4.13 (br d, J=6.4 Hz, 1H), 3.92 (s, 3H), 3.83-3.67 (m, 5H), 3.57-3.37 (m, 2H), 3.28-3.21 (m, 2H), 3.04-2.80 (m, 3H), 2.64 (br d, J=19.6 Hz, 2H), 2.26-2.04 (m, 3H), 1.81 (br s, 1H), 1.21 (t, J=7.3 Hz, 3H). LCMS: 580.34 [M+H]$^+$.

Example 54

(S)-2-(3-(6-Isopropoxypyridin-3-yl)-1H-indazol-5-yl)-7-(2-(4-(4-(3-methyl-1,2,4-oxadiazol-5-yl)phenyl)-3,6-dihydropyridin-1(2H)-yl)-2-oxoethyl)-2,7-diazaspiro[4.4]nonan-1-one

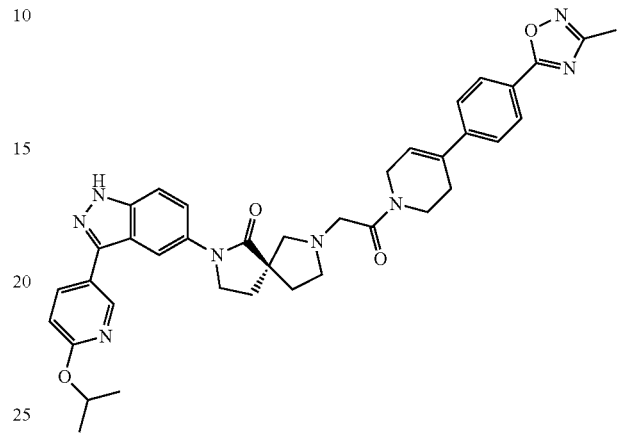

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(4-(3-methyl-1,2,4-oxadiazol-5-yl)phenyl)-3,6-dihydropyridin-1(2H)-yl)ethan-1-one (Intermediate 48). $^1$H NMR (400 MHz, DMSO-d$_6$) δ 13.25 (s, 1H), 8.74 (d, 1H), 8.22 (dd, 1H), 8.16 (d, 1H), 8.07-8.03 (m, 2H), 7.76-7.68 (m, 3H), 7.58 (d, 1H), 6.89 (d, 1H), 6.42 (s, 1H), 5.32 (m, 1H), 4.30 (br, 1H), 4.10 (q, 1H), 3.91-3.89 (m, 3H), 3.75-3.60 (m, 2H), 3.39-3.30 (m, 3H), 2.90-2.80 (m, 2H), 2.70-2.60 (m, 2H), 2.42 (s, 3H), 2.20-2.15 (m, 3H), 1.80-1.75 (m, 1H), 1.34 (d, 6H).

Example 55

(S)-7-(2-(4-(2-Fluoro-4-(1-methyl-1H-1,2,4-triazol-3-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

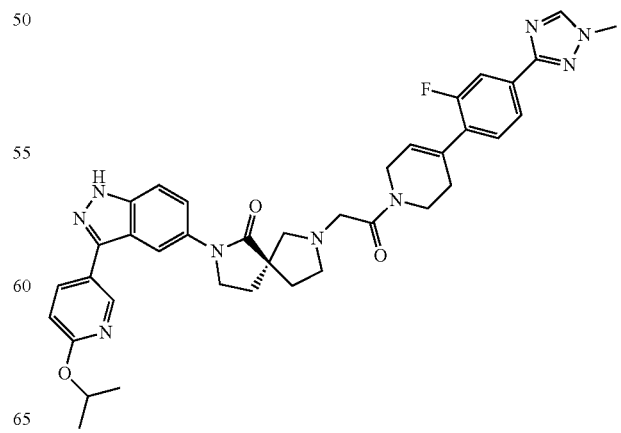

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(2-fluoro-4-(1-methyl-1H-1,2,4-triazol-3-yl)phenyl)-3,6-dihydropyridin-1(2H)-yl)ethan-1-one (Intermediate 39). $^1$H NMR (400 MHz, DMSO-d$_6$) δ 13.26 (s, 1H), 8.74 (d, 1H), 8.55 (s, 1H), 8.22 (dd, 1H), 8.16 (s, 1H), 7.80-7.70 (m, 2H), 7.70-7.66 (m, 1H), 7.60-7.58 (d, 1H), 7.48 (t, 1H), 6.90 (d, 1H), 6.12 (br, 1H), 5.33 (m, 1H), 4.30 (br, 1H), 4.13 (br, 1H), 3.93 (s, 3H), 3.90-3.88 (m, 2H), 3.88 (m, 2H), 3.42-3.40 (m, 2H), 2.95-2.85 (m, 2H), 2.67-2.52 (m, 4H), 2.21-2.19 (m, 3H), 1.85-1.80 (m, 1H), 1.34 (d, 6H).

Example 56

(S)-7-(2-(4-(3-Fluoro-4-(1-methyl-1H-1,2,4-triazol-3-yl)phenyl)-3,6-dihydropyridin-1(2H)-yl)-2-oxoethyl)-2-(3-(6-isopropoxypyridin-3-yl)-1H-indazol-5-yl)-2,7-diazaspiro[4.4]nonan-1-one

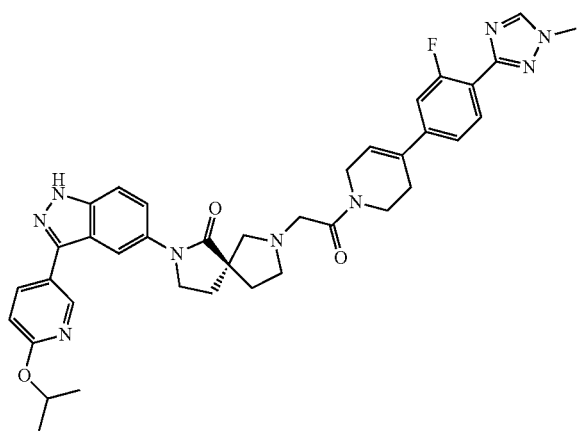 [SMILES: CC(C)Oc1ccc(-c2n[nH]c3ccc(N4CC[C@]5(CCN(CC(=O)N6CC=C(c7ccc(-c8ncn(C)n8)c(F)c7)CC6)C5)C4=O)cc23)cn1]

The title compound was prepared following General Procedures A, B and C using (S)-2-(3-(6-isopropoxypyridin-3-yl)-1-trityl-1H-indazol-5-yl)-2,7-diazaspiro[4.4]nonan-1-one (Intermediate 5) and 2-chloro-1-(4-(3-fluoro-4-(1-methyl-1H-1,2,4-triazol-3-yl)phenyl)-3,6-dihydropyridin-1(2H)-yl)ethan-1-one (Intermediate 40). $^1$H NMR (400 MHz, DMSO-d$_6$) δ 13.25 (s, 1H), 8.74 (d, 1H), 8.56 (s, 1H), 8.22 (dd, 1H), 8.15 (s, 1H), 7.96 (t, 1H), 7.77 (m, 1H), 7.59 (d, 1H), 7.42-7.39 (m, 2H), 6.90 (d, 1H), 6.39 (br, 1H), 5.33 (m, 1H), 4.30 (br, 1H), 4.10 (br, 1H), 3.94 (s, 3H), 3.91-3.88 (m, 2H), 3.80-3.75 (m, 2H), 3.43-3.39 (m, 2H), 2.83-2.81 (m, 2H), 2.62-2.51 (m, 4H), 2.21-2.17 (m, 3H), 1.85-1.80 (m, 1H), 1.34 (d, 6H).

Example 57

(S)-7-(2-(4-(4-(1-Methyl-1H-1,2,4-triazol-3-yl)phenyl)-3,6-dihydropyridin-1(2H)-yl)-2-oxoethyl)-2-(3-(6-methylpyridin-3-yl)-1H-indazol-5-yl)-2,7-diazaspiro[4.4]nonan-1-one

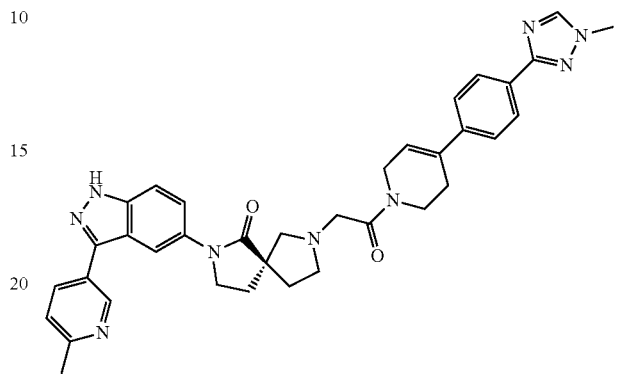

The title compound was prepared following General Procedures A and B using (S)-2-(3-(6-methylpyridin-3-yl)-1-trityl-1H-indazol-5-yl)-2,7-diazaspiro[4.4]nonan-1-one (Intermediate 54) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-d$_6$) δ 13.74 (br s, 1H), 10.53 (br s, 0.60H), 10.30 (br s, 0.40H), 9.14 (s, 1H), 8.68 (br s, 1H), 8.52 (s, 1H), 8.21 (s, 1H), 7.98 (m, 2H), 7.98-7.78 (m, 2H), 7.72-7.69 (m, 1H), 7.60-7.52 (m, 2H), 7.28-7.11 (m, 1H), 6.30 (s, 1H), 4.64-4.53 (m, 2H), 4.20 (s, 1H), 4.13 (s, 1H), 4.12-3.95 (m, 1H), 3.92 (s, 3H), 3.82-3.75 (m, 4H), 3.32-2.83 (m, 4H), 2.71 (s, 3H), 2.68-2.63 (m, 2H), 2.35-2.25 (m, 2H), 2.21-2.06 (m, 1H). LCMS: 628.3 [M+H]$^+$.

Example 58

(S)-7-(2-(4-(4-(1-Methyl-1H-1,2,4-triazol-3-yl)phenyl)-3,6-dihydropyridin-1(2H)-yl)-2-oxoethyl)-2-(3-(4-(methylsulfonyl)phenyl)-1H-indazol-5-yl)-2,7-diazaspiro[4.4]nonan-1-one

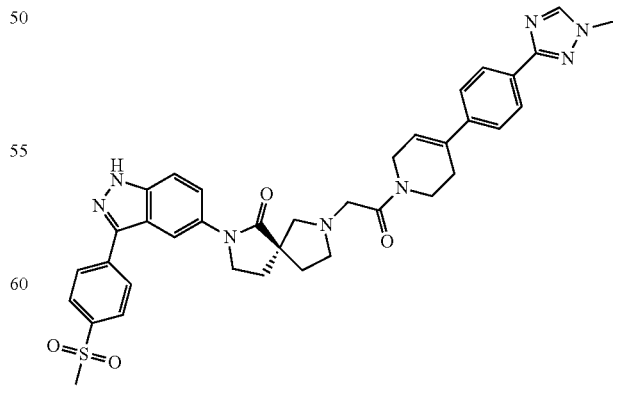

The title compound was prepared following General Procedures A and B using (S)-2-(3-(4-(methylsulfonyl)phenyl)-1-trityl-1H-indazol-5-yl)-2,7-diazaspiro[4.4]nonan-1-one (Intermediate 55) and 2-chloro-1-(4-(4-(1-methyl-1H-1,2,4-triazol-3-yl)phenyl)-3,6-dihydropyridin-1(2H)-yl)ethan-1-one (Intermediate 31). $^1$H NMR (400 MHz, DMSO-d$_6$) δ 13.56 (br s, 1H), 8.51 (s, 1H), 8.25-8.23 (m, 3H), 8.08-8.05 (m, 2H), 7.97-7.95 (m, 2H), 7.83 (m, 1H), 7.65 (d, 1H), 7.57-7.54 (m, 2H), 6.29 (s, 1H), 4.26-4.24 (m, 1H), 4.15-4.11 (m, 1H), 3.92 (s, 3H), 3.92-3.87 (m, 2H), 8.80-8.65 (m, 2H), 3.47-3.37 (m, 2H), 3.28 (s, 3H), 2.99-2.90 (m, 1H), 2.87-2.82 (m, 1H), 2.69-2.55 (m, 2H), 2.23-2.10 (m, 4H), 1.85-1.83 (m, 2H). LCMS: 691.10 [M+H]$^+$.

Example 59

Compounds of Formula (I)

For some compounds, the foregoing syntheses are exemplary and can be used as a starting point to prepare additional compounds of Formula (I). Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

(S)-7-(2-(4-(4-(1-methyl-1H-1,2,4-triazol-3-yl)phenyl)-3,6-dihydropyridin-1 (2H)-yl)-2-oxoethyl)-2-(3-(2-methylbenzo[d]oxazol-5-yl)-1H-indazol-5-yl)-2,7-diazaspiro[4.4]nonan-1-one;

(S)-7-(2-(4-(4-(1-cyclopropyl-1H-1,2,4-triazol-3-yl)phenyl)-3,6-dihydropyridin-1(2H)-yl)-2-oxoethyl)-2-(3-(6-isopropoxypyridin-3-yl)-1H-pyrazolo[4,3-b]pyridin-5-yl)-2,7-diazaspiro[4.4]nonan-1-one;

(S)-7-(2-(4-(4-(1-methyl-1H-1,2,4-triazol-3-yl)phenyl)-3,6-dihydropyridin-1(2H)-yl)-2-oxoethyl)-2-(3-(6-(trifluoromethyl)pyridin-3-yl)-1H-indazol-5-yl)-2,7-diazaspiro[4.4]nonan-1-one;

(S)-2-(3-(6-(difluoromethyl)pyridin-3-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one;

(S)-2-(3-(2-(difluoromethyl)pyrimidin-5-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one;

(5S)-2-(3-(6-(1-hydroxypropan-2-yl)pyridin-3-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one;

(S)-2-(3-(6-isopropoxypyridin-3-yl)-1H-indazol-5-yl)-7-(2-(4-(5-(1-methyl-1H-1,2,4-triazol-3-yl)thiazol-2-yl)-3,6-dihydropyridin-1(2H)-yl)-2-oxoethyl)-2,7-diazaspiro[4.4]nonan-1-one;

(S)-7-(2-(4-(4-(1-methyl-1H-1,2,4-triazol-3-yl)phenyl)-3,6-dihydropyridin-1(2H)-yl)-2-oxoethyl)-2-(3-(tetrahydro-2H-pyran-4-yl)-1H-indazol-5-yl)-2,7-diazaspiro[4.4]nonan-1-one;

(S)-2-(3-(3,6-dihydro-2H-pyran-4-yl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one;

(S)-2-(3-(4-methoxyphenyl)-1H-indazol-5-yl)-7-(2-(4-(4-(1-methyl-1H-1,2,4-triazol-3-yl)phenyl)-3,6-dihydropyridin-1(2H)-yl)-2-oxoethyl)-2,7-diazaspiro[4.4]nonan-1-one;

(S)-4-(5-(7-(2-(4-(4-(1-methyl-1H-1,2,4-triazol-3-yl)phenyl)-3,6-dihydropyridin-1(2H)-yl)-2-oxoethyl)-1-oxo-2,7-diazaspiro[4.4]nonan-2-yl)-1H-indazol-3-yl)benzonitrile;

(S)-2-methoxy-4-(5-(7-(2-(4-(4-(1-methyl-1H-1,2,4-triazol-3-yl)phenyl)-3,6-dihydropyridin-1 (2H)-yl)-2-oxoethyl)-1-oxo-2,7-diazaspiro[4.4]nonan-2-yl)-1H-indazol-3-yl)benzonitrile;

(S)-2-methoxy-5-(5-(7-(2-(4-(4-(1-methyl-1H-1,2,4-triazol-3-yl)phenyl)-3,6-dihydropyridin-1 (2H)-yl)-2-oxoethyl)-1-oxo-2,7-diazaspiro[4.4]nonan-2-yl)-1H-indazol-3-yl)benzonitrile;

(S)-2-(3-(1-acetylpiperidin-4-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one;

(S)-2-(3-(1-(2-hydroxyacetyl)piperidin-4-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one;

(S)-5-(5-(7-(2-(4-(4-(1-methyl-1H-1,2,4-triazol-3-yl)phenyl)-3,6-dihydropyridin-1(2H)-yl)-2-oxoethyl)-1-oxo-2,7-diazaspiro[4.4]nonan-2-yl)-1H-indazol-3-yl)-2-(trifluoromethoxy)benzonitrile;

(S)-5-(5-(7-(2-(4-(4-(1-methyl-1H-1,2,4-triazol-3-yl)phenyl)-3,6-dihydropyridin-1(2H)-yl)-2-oxoethyl)-1-oxo-2,7-diazaspiro[4.4]nonan-2-yl)-1H-indazol-3-yl)-2-(trifluoromethyl)benzonitrile;

(S)-2-(3-(4-methoxypiperidin-1-yl)-1H-indazol-5-yl)-7-(2-(4-(4-(1-methyl-1H-1,2,4-triazol-3-yl)phenyl)-3,6-dihydropyridin-1 (2H)-yl)-2-oxoethyl)-2,7-diazaspiro[4.4]nonan-1-one;

(S)-5-(4-(1-(2-(7-(6-isopropoxypyridin-3-yl)-1H-indazol-5-yl)-6-oxo-2,7-diazaspiro[4.4]nonan-2-yl)acetyl)-1,2,3,6-tetrahydropyridin-4-yl)phenyl)-3-methyl-1,3,4-oxadiazol-2(3H)-one;

(S)-4-(5-(7-(2-(4-(4-(4-methyl-5-oxo-4,5-dihydro-1,3,4-oxadiazol-2-yl)phenyl)-3,6-dihydropyridin-1(2H)-yl)-2-oxoethyl)-1-oxo-2,7-diazaspiro[4.4]nonan-2-yl)-1H-indazol-3-yl)benzonitrile;

(S)-3-(5-(7-(2-(4-(4-(4-methyl-5-oxo-4,5-dihydro-1,3,4-oxadiazol-2-yl)phenyl)-3,6-dihydropyridin-1(2H)-yl)-2-oxoethyl)-1-oxo-2,7-diazaspiro[4.4]nonan-2-yl)-1H-indazol-3-yl)benzonitrile;

(S)-2-methoxy-4-(5-(7-(2-(4-(4-(4-methyl-5-oxo-4,5-dihydro-1,3,4-oxadiazol-2-yl)phenyl)-3,6-dihydropyridin-1(2H)-yl)-2-oxoethyl)-1-oxo-2,7-diazaspiro[4.4]nonan-2-yl)-1H-indazol-3-yl)benzonitrile;

(S)-2-methoxy-5-(5-(7-(2-(4-(4-(4-methyl-5-oxo-4,5-dihydro-1,3,4-oxadiazol-2-yl)phenyl)-3,6-dihydropyridin-1(2H)-yl)-2-oxoethyl)-1-oxo-2,7-diazaspiro[4.4]nonan-2-yl)-1H-indazol-3-yl)benzonitrile;

(S)-3-methyl-5-(4-(1-(2-(7-(3-(2-methylbenzo[d]oxazol-5-yl)-1H-indazol-5-yl)-6-oxo-2,7-diazaspiro[4.4]nonan-2-yl)acetyl)-1,2,3,6-tetrahydropyridin-4-yl)phenyl)-1,3,4-oxadiazol-2(3H)-one;

(S)-3-methyl-5-(4-(1-(2-(7-(3-morpholino-1H-indazol-5-yl)-6-oxo-2,7-diazaspiro[4.4]nonan-2-yl)acetyl)-1,2,3,6-tetrahydropyridin-4-yl)phenyl)-1,3,4-oxadiazol-2(3H)-one;

(S)-3-methyl-5-(4-(1-(2-(6-oxo-7-(3-(tetrahydro-2H-pyran-4-yl)-1H-indazol-5-yl)-2,7-diazaspiro[4.4]nonan-2-yl)acetyl)-1,2,3,6-tetrahydropyridin-4-yl)phenyl)-1,3,4-oxadiazol-2(3H)-one;

(S)-5-(4-(1-(2-(7-(3-(1-acetylpiperidin-4-yl)-1H-indazol-5-yl)-6-oxo-2,7-diazaspiro[4.4]nonan-2-yl)acetyl)-1,2,3,6-tetrahydropyridin-4-yl)phenyl)-3-methyl-1,3,4-oxadiazol-2(3H)-one; and (S)-5-(4-(1-(2-(7-(3-(4-methoxypiperidin-1-yl)-1H-indazol-5-yl)-6-oxo-2,7-diazaspiro[4.4]nonan-2-yl)acetyl)-1,2,3,6-tetrahydropyridin-4-yl)phenyl)-3-methyl-1,3,4-oxadiazol-2(3H)-one.

Example A

Active ERK1 and ERK2 Kinase Assay

Activated ERK1 and ERK2 activity was determined in a Mobility Shift Assay (MSA) format as follows: Compound and kinase solution were prepared with assay buffer (20 mM HEPES, 0.01% Triton X-100, 2 mM DTT, pH7.5) and mixed and incubated in for 30 mins at rt. ERK1 & ERK2 were then activated by the addition of Fl-Substrate, ATP and metal solution and incubated for 1 h at rt. After 1 h, the reaction was terminated by the addition of 70 mL of Termination Buffer (QuickScout Screening Assist MSA; Carna Biosciences) to the well. The reaction mixture was applied to LabChip™ system (PerkinElmer), and the product and substrate peptide peaks were separated, analyzed and quantitated. The kinase reaction is evaluated by the product ratio calculated from peak heights of product (P) and substrate (S) peptides (P/(P+S)).

Compounds of Formula (I) are active in this assay as noted in Table 1, where A=a single $IC_{50} \leq 50$ nM; B=a single $IC_{50} \geq 50$ nM and $\leq 250$ nM; C=a single $IC_{50} \geq 250$ nM.

TABLE 1

| Example # | ERK1 $IC_{50}$ (nM) | ERK2 $IC_{50}$ (nM) |
| --- | --- | --- |
| GDC-0994 | A | A |
| BVD-523 | A | A |
| SCH772984 | A | A |
| 1 | A | A |
| 2 | C | C |
| 3 | A | A |
| 4 | C | C |
| 5 | C | B |
| 6 | A | A |
| 7 | A | A |
| 8 | A | A |
| 9 | B | A |
| 10 | A | A |
| 11 | C | C |
| 12 | A | A |
| 13 | B | B |
| 14 | A | A |
| 15 | A | A |
| 16 | A | A |
| 17 | A | A |
| 18 | A | A |
| 19 | A | A |
| 20 | A | A |
| 21 | C | C |
| 22 | A | A |
| 23 | A | A |
| 24 | B | A |
| 25 | C | B |
| 26 | — | A |
| 27 | C | C |
| 28 | A | A |
| 29 | A | A |
| 30 | A | A |
| 31 | A | A |
| 32 | — | A |
| 33 | — | A |
| 34 | — | C |
| 36 | — | B |
| 38 | — | A |
| 39 | — | A |
| 40 | — | A |
| 41 | — | A |
| 42 | — | A |
| 43 | — | A |
| 44 | — | B |
| 45 | — | A |
| 46 | — | A |
| 47 | — | A |
| 48 | — | A |
| 49 | — | A |
| 50 | — | A |
| 51 | — | A |
| 52 | — | A |
| 53 | — | B |
| 54 | — | A |
| 55 | — | A |
| 56 | — | A |
| 57 | — | A |
| 58 | — | A |

Example B

ERK and RSK Target Engagement Biomarker (pERK and pRSK Western Blot) Protocols

BRAF mutant melanoma cells A375 are plated at approximately 1×106 cells per 10 cm dish in growth media (RPMI 1640, 10% FBS, non-essential amino acids and glutamine). The next day the media is removed and replaced with serum free media (RPMI 1640, 0.1% FBS, non-essential amino acids and glutamine) and allowed to incubate overnight. The following day the serum free media is removed and replaced with fresh serum free media containing compound. Typical concentrations for drug treatments are 300 nM, 100 nM, 30 nM, 10 nM, 3 nM and 1 nM, with a final DMSO concentration of 0.1%. The controls include one plate with DMSO alone at 0.1% final concentration and another plate treated with a compound control at 10 nM final concentration. The cells are treated for 24 h. At the time of harvest, the cells are scraped directly into the media and spun down at 1800 rpm in order to capture the floating dead or dying cells as well. One wash with 5 mL of PBS is done, and the cell pellet are frozen or lysed immediately in lysis buffer. The protein concentrations of the lysates are determined using the Pierce BCA protein assay kit and 50 μg of total cell lysate is loaded per lane of a 15 well, 1.5 mm width Tris glycine gel. The gels are run at 125 Volts constant voltage until the dye just runs off the gel. They are transferred using the Invitrogen transfer apparatus onto nitrocellulose membranes at 25 Volts for 2 h. The nitrocellulose membrane is blocked in 5% (wt/vol) non-fat dried milk protein in TBS/Tween for 30 mins at rt. The blot is incubated with anti-RSK or with anti-ERK antibodies. The nitrocellulose membrane is washed 3 times for 10 minutes with vigorous rocking in 50 mL TBS/Tween then incubated 1 h with HRPx-labeled secondary antibody at rt. The secondary antibodies are diluted in 2% non-fat dried milk protein in TBS/Tween.

The nitrocellulose is washed as above then developed with freshly prepared ECL reagent. The nitrocellulose membranes are incubated for 1 minute with 5 mL ECL reagent. Excess reagent is removed by blotting on a clean paper towel, and the membrane is wrapped in cellophane before exposing to film. Several exposures of film are made for each blot. (The western blots may be developed and/or quantitated by other means if available.) Band densities are quantitated by densitometry, and the scanned densities are plotted using XLfit to give dose response curves.

Example C

Proliferation Assay

A375 (melanoma), Colo-205 (colon cancer), Miapaca (pancreatic), HPAFII (pancreatic), sNF02.0 (neurofibromatosis type 1), sNF96.2 (neurofibromatosis type 1) and 8505 (Thyroid) cells were grown and maintained in RPMI-1640 medium containing 100 U/mL penicillin-streptomycin and 10% fetal bovine serum. Cells were in growth medium in 96-well opaque-walled clear bottom plates and incubated the in the $CO_2$ incubator overnight before treatment. Cells were treated with compounds diluted in DMSO and a 10 point 3-fold serial dilutions were done. Plates were placed in 37° C., 5% $CO_2$ for to incubate for 3 days. Before they were developed by adding 100 μL of CellTiter-Glo reagent (Promega) to the assay plate, plates were shaken briefly for 2 mins and allowed to incubate at rt for 10 mins. The bottom of the plates was pasted with white back seal and luminescence was recorded with Flexstation3 with setting of luminescence, integration time 500 ms.

Compounds of Formula (I) are active in this assay as noted in Tables 2-5. In Table 2: A=a single $IC_{50} \leq 500$ nM; B=a single $IC_{50} \geq 500$ nM and $\leq 1.0$ μM; C=a single $IC_{50} \geq 1.0$ μM. In Table 3: A=a single $IC_{50} \leq 500$ nM; B=a single $IC_{50} \geq 500$ nM and $\leq 1.0$ μM; C=a single $IC_{50} \geq 1.$ μM. In Table 4: A=a single $IC_{50} \leq 500$ nM; B=a single $IC_{50} \geq 500$ nM and $\leq 1.0$ μM; C=a single $IC_{50} \geq 1.$ μM. In Table 5: A=a single $IC_{50} \leq 500$ nM; B=a single $IC_{50} \geq 500$ nM and $\leq 1.0$ μM; C=a single $IC_{50} \geq 1.0$ μM.

TABLE 2

| Example # | A375 $IC_{50}$ (nM) | Colo205 $IC_{50}$ (nM) |
|---|---|---|
| GDC-0994 | B | A |
| BVD-523 | A | A |
| SCH772984 | A | A |
| 7 | A | A |
| 8 | A | A |
| 10 | A | A |
| 12 | B | A |
| 15 | A | A |
| 17 | A | A |
| 18 | A | A |
| 20 | A | A |
| 22 | A | — |
| 23 | B | — |
| 24 | C | — |
| 25 | C | — |
| 26 | A | — |
| 27 | C | — |
| 28 | A | — |
| 29 | A | — |
| 30 | A | — |
| 31 | A | — |
| 32 | A | — |
| 33 | A | — |
| 34 | C | — |
| 36 | C | — |
| 38 | A | — |
| 39 | A | — |

TABLE 2-continued

| Example # | A375 $IC_{50}$ (nM) | Colo205 $IC_{50}$ (nM) |
|---|---|---|
| 40 | A | — |
| 41 | A | — |
| 42 | A | — |
| 43 | C | — |

TABLE 3

| Example # | Mia Paca-2 $IC_{50}$ (μM) | HPAFII $IC_{50}$ (μM) |
|---|---|---|
| BVD-523 | A | A |
| SCH772984 | A | A |
| 8 | A | A |
| 10 | A | A |
| 29 | A | A |
| 38 | A | A |

TABLE 4

| Example # | sNF02.2 $IC_{50}$ (μM) | sNF96.2 $IC_{50}$ (μM) |
|---|---|---|
| BVD-523 | C | B |
| SCH772984 | A | B |
| 8 | A | A |
| 10 | C | B |
| 29 | A | A |
| 38 | C | B |

TABLE 5

| Example # | 8505C $IC_{50}$ (μM) |
|---|---|
| BVD-523 | C |
| SCH772984 | B |
| 8 | A |
| 10 | C |
| 29 | B |
| 38 | C |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound selected from the group consisting of:

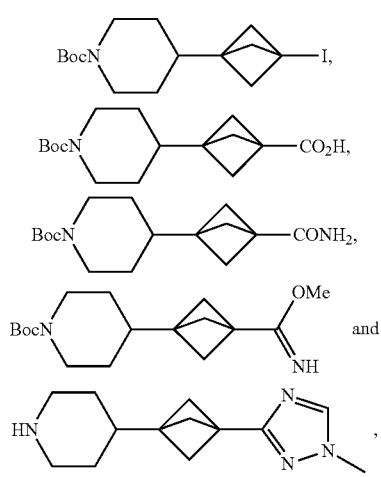

or a pharmaceutically salt of any of the foregoing.

2. The compound of claim 1, wherein the compound is

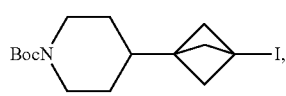

or a pharmaceutically acceptable salt thereof.

3. The compound of claim 1, wherein the compound is

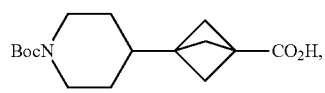 [SMILES: CC(C)(C)OC(=O)N1CCC(C23CC(C(=O)O)(C2)C3)CC1]

or a pharmaceutically acceptable salt thereof.

4. The compound of claim 1, wherein the compound is

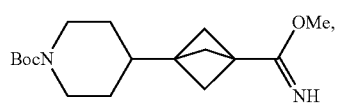

or a pharmaceutically acceptable salt thereof.

5. The compound of claim 1, wherein the compound is

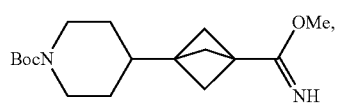

or a pharmaceutically acceptable salt thereof.

6. The compound of claim 1, wherein the compound is
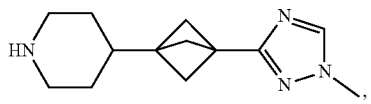
or a pharmaceutically acceptable salt thereof.
7. The compound of claim 1, wherein the compound is
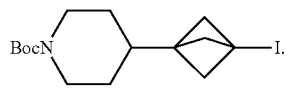
8. The compound of claim 1, wherein the compound is
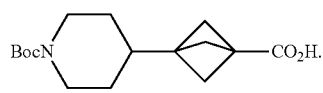
9. The compound of claim 1, wherein the compound is
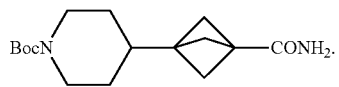 [SMILES: CC(C)(C)OC(=O)N1CCC(C23CC(C(N)=O)(C2)C3)CC1]
10. The compound of claim 1, wherein the compound is
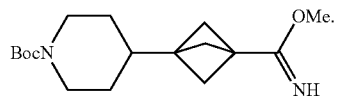
11. The compound of claim 1, wherein the compound is
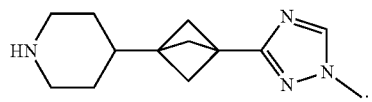
* * * * *